US008685660B2

(12) United States Patent
Vogelstein et al.

(10) Patent No.: US 8,685,660 B2
(45) Date of Patent: Apr. 1, 2014

(54) GENETIC ALTERATIONS IN ISOCITRATE DEHYDROGENASE AND OTHER GENES IN MALIGNANT GLIOMA

(75) Inventors: Bert Vogelstein, Baltimore, MD (US); Kenneth W. Kinzler, Baltimore, MD (US); D. Williams Parsons, Bellaire, TX (US); Xiaosong Zhang, Baltimore, MD (US); Jimmy Cheng-Ho Lin, Baltimore, MD (US); Rebecca J. Leary, Baltimore, MD (US); Philipp Angenendt, Hamburg (DE); Nickolas Papadopoulos, Towson, MD (US); Victor Velculescu, Dayton, MD (US); Giovanni Parmigiani, Boston, MA (US); Rachel Karchin, Towson, MD (US); Sian Jones, Baltimore, MD (US); Hai Yan, Chapel Hill, NC (US); Darell Bigner, Mebane, NC (US); Chien-Tsun Kuan, Cary, NC (US); Gregory J. Riggins, White Hall, MD (US)

(73) Assignees: The Johns Hopkins University, Baltimore, MD (US); Duke University, Durham, NC (US)

( * ) Notice: Subject to any disclaimer, the term of this patent is extended or adjusted under 35 U.S.C. 154(b) by 81 days.

(21) Appl. No.: 13/060,191

(22) PCT Filed: Sep. 3, 2009

(86) PCT No.: PCT/US2009/055803
§ 371 (c)(1),
(2), (4) Date: Jun. 7, 2011

(87) PCT Pub. No.: WO2010/028099

PCT Pub. Date: Mar. 11, 2010

(65) Prior Publication Data

US 2011/0229479 A1 Sep. 22, 2011

Related U.S. Application Data

(60) Provisional application No. 61/093,739, filed on Sep. 3, 2008, provisional application No. 61/110,397, filed on Oct. 31, 2008, provisional application No. 61/162,737, filed on Mar. 24, 2009.

(51) Int. Cl.
*G01N 33/574* (2006.01)

(52) U.S. Cl.
USPC ............................. 435/7.23; 514/1; 424/141.1

(58) Field of Classification Search
None
See application file for complete search history.

(56) References Cited

U.S. PATENT DOCUMENTS

2008/0108061 A1  5/2008  Inazawa et al.
2010/0291590 A1  11/2010 Hartman et al.

FOREIGN PATENT DOCUMENTS

DE       19817948 A1   10/1999

OTHER PUBLICATIONS

Extended European Search Report issued in related Eurpoean Application No. 12188429.0, dated Nov. 14, 2012.
Database EMBL [Online]; Apr. 26, 1996; "Human isocitrate dehydrogenase mRNA, complete cds."; XP002686302, retrieved from EBI accession No. EMBL:U52144 Database accession No. U52144.
Database EMBL [Online[; Sep. 23, 1998; "*Homo sapiens* NADP-dependent isocitrate dehydrogenase (IDH) mRNA, complete cds."; XP002686303, retrieved from EBI accession No. EMBL: AF020038 Database accession No. AF020038.
International Search Report for PCT/US2009/055803 dated Nov. 12, 2009.
Daisuke, Kita et al: "PIK3CA alterations in primary (de novo) and secondary glioblastomas" Acta Neuropathologica, Springer, Berlin DE, vol. 113, No. 3, Jan. 18, 2007, pp. 295-302.
Balakrishnan, Asha et al: Novel somatic and germline mutations in cancer candidate genes in glioblastoma, melanoma, and pancreatic carcinoma Cancer Research, vol. 67, No. 8, Apr. 2007 pp. 3545-3550.
Sjoblom, Tobias et al: "The Consensus Coding Sequences of Human Breast and Colorectal Cancers" Science, American Association for the Advancement of Science, US, Washington, DC, vol. 314, Oct. 13, 2006, pp. 268-274.
Bleeker, Fonnet E et al: "IDH1 Mutations at Residue p. R132 (IDH1(R132)) Occur Frequently in High Grade Gliomas But Not in Other Solid Tumors" Human Mutation, vol. 30, No. 1, Jan. 2009, pp. 7-11.
Yan, Hai et al: "IDH1 and IDH2 Mutations in Gliomas" New England Journal of Medicine, vol. 360, No. 8 Feb. 2009, pp. 765-773.
Parsons, D Williams et al: "An integrated genomic analysis of human glioblastoma Multiforme" Science (Washington D C), vol. 321, No. 5897, Sep. 2008, pp. 1807-1812.
Balss, Joerg et al: "Analysis of the IDH1 codon 132 mutation in brain tumors" Acta Neuropathologica, vol. 116, No. 6, Dec. 2008, pp. 597-602.
Database UniProt [Online] Feb. 1, 1996, RecName:Full=Isocitrate dehydrogenase [NADP], mitochondrial; EBI accession No. Uniprot P48725.
Database UniProt [Online] May 10, 2005, SubName: Full=IDH1 protein; SubName: Full=Isocitrate dehydrogenase 1 (NADP+), soluble isoform CRA_a; Subname: Full=Putative uncharecterized protein IDH1; Flags: Fragment; EBI accession No. Uniprot Q6FHQ6.
Non-Final Office Action issued in related U.S. Appl. No. 13/412,696, mailed Aug. 10, 2012.
Database UniProt [Online Feb. 1, 1996 Isocitrate dehydrogenase [NADP]. mitochondrial; , XP002555014, retrieved from EBI accession No. UniProt:P48735 Database accession No. P48735 * compound *.
Japanese Office action dispatched May 20, 2013, Japanese Patent Application No. 2011-526180.
Extended European Search Report dated May 13, 2013 in Application No. 13160496.9.

*Primary Examiner* — Mark Halvorson

(57) ABSTRACT

We found mutations of the R132 residue of isocitrate dehydrogenase 1 (IDH1) in the majority of grade II and III astrocytomas and oligodendrogliomas as well as in glioblastomas that develop from these lower grade lesions. Those tumors without mutations in IDH1 often had mutations at the analogous R172 residue of the closely related IDH2 gene. These findings have important implications for the pathogenesis and diagnosis of malignant gliomas.

14 Claims, 188 Drawing Sheets

Fig. 7
IDH1
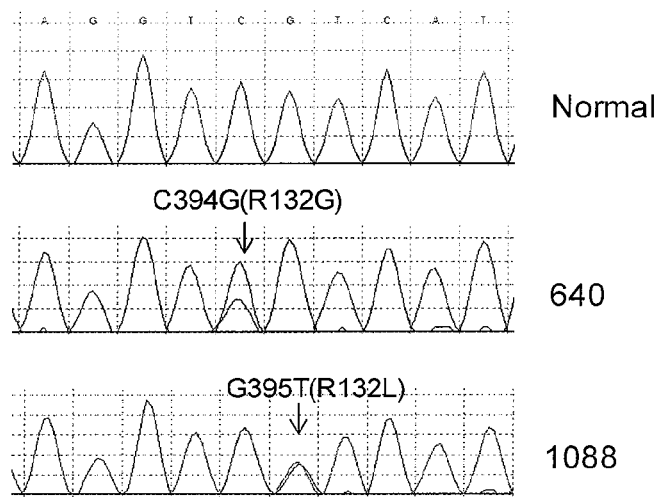
IDH2
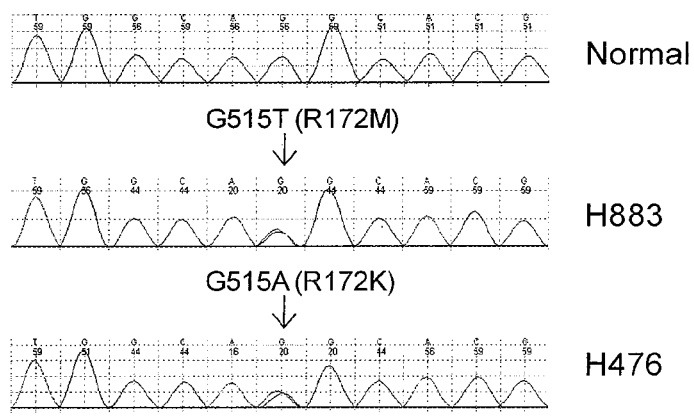

TABLE S3. SOMATIC MUTATIONS IDENTIFIED IN GBM DISCOVERY SCREEN

| GENE | TRANSCRIPT ACCESSION | TUMOR | NUCLEOTIDE (GENOMIC)* |
|---|---|---|---|
| A2M | NM_000014 | Br9PT | g.chr12:9150431C>A |
| A4GALT | CCDS14041.1 | Br08X | g.chr22:41413510G>A |
| A4GNT | CCDS3097.1 | Br13X | g.chr3:139332485T>G |
| AACS | CCDS9263.1 | Br27P | g.chr12:124116625C>T |
| ABCA10 | CCDS11684.1 | Br11P | g.chr17:64701274G>C |
| ABCA12 | NM_015657 | Br27P | g.chr2:215691839G>A |
| ABCA13 | NM_152701 | Br27P | g.chr7:48091360C>T |
| ABCA4 | CCDS747.1 | Br27P | g.chr1:94232842C>T |
| ABCA4 | CCDS747.1 | Br14X | g.chr1:94199521G>T |
| ABCA5 | CCDS11685.1 | Br27P | g.chr17:64781713C>T |
| ABCA7 | CCDS12055.1 | Br25X | g.chr19:994398C>T |
| ABCA9 | CCDS11681.1 | Br05X | g.chr17:64551266G>A |
| ABCB1 | CCDS5608.1 | Br27P | g.chr7:86835309G>A |
| ABCB6 | CCDS2436.1 | Br25X | g.chr2:219902670C>T |
| ABCC10 | CCDS4896.1 | Br27P | g.chr6:43525676C>T |
| ABCC11 | CCDS10732.1 | Br27P | g.chr16:46796828C>T |
| ABCC3 | NM_003786 | Br14X | g.chr17:46123489G>T |
| ABCC5 | NM_005688 | Br04X | g.chr3:185178995C>T |
| ABCD2 | CCDS8734.1 | Br25X | g.chr12:38266275C>A |
| ABCF2 | CCDS5922.1 | Br27P | g.chr7:150349640C>T |
| ABCG2 | CCDS3628.1 | Br27P | g.chr4:89400087G>A |
| ABHD3 | NM_138340 | Br27P | g.chr18:17498193C>T |
| ABHD4 | CCDS9572.1 | Br10P | g.chr14:22148578C>T |
| ABHD7 | CCDS736.1 | Br27P | g.chr1:92230203G>A |
| ABL2 | NM_007314 | Br15X | g.chr1:175815771C>T |
| ABTB2 | CCDS7890.1 | Br26X | g.chr11:34132451C>A |
| ACAD9 | CCDS3053.1 | Br27P | g.chr3:130110513G>A |
| ACADS | CCDS9207.1 | Br15X | g.chr12:119639932G>A |
| ACADS | CCDS9207.1 | Br11P | g.chr12:119637983C>T |
| ACADSB | CCDS7634.1 | Br14X | g.chr10:124800607T>G (HOMOZYGOUS) |
| ACAT2 | CCDS5268.1 | Br27P | g.chr6:160160062G>A |
| ACCN1 | CCDS11276.1 | Br27P | g.chr17:28375101C>T |
| ACCN3 | CCDS5914.1 | Br27P | g.chr7:150185508C>T |
| ACF | CCDS7241.1 | Br27P | g.chr10:52245937G>A |
| ACLY | CCDS11412.1 | Br29P | g.chr17:37302840T>G |
| ACOX3 | CCDS3401.1 | Br27P | g.chr4:8536193G>A |
| ACP5 | CCDS12265.1 | Br27P | g.chr19:11549031G>A |
| ACRBP | CCDS8554.1 | Br14X | g.chr12:6619514C>T |
| ACTG1 | CCDS11782.1 | Br15X | g.chr17:77092864C>T |
| ACTN1 | CCDS9792.1 | Br27P | g.chr14:68446506C>T |
| ACTR10 | NM_018477 | Br27P | g.chr14:57739326G>A |
| ACTR1A | CCDS7536.1 | Br27P | g.chr10:104230676G>A |
| ACTR8 | CCDS2875.1 | Br27P | g.chr3:53881563C>T |
| ACTRT1 | CCDS14611.1 | Br03x | g.chrX:126911559G>A (HOMOZYGOUS) |

FIG. 10

| NUCLEOTIDE (cDNA)*† | AMINO ACID (PROTEIN)*‡ | MUTATION TYPE |
|---|---|---|
| c.917C>A | p.T306N | MISSENSE |
| c.946G>A | p.V316M | MISSENSE |
| c.312T>G | p.A104A | SYNONYMOUS |
| c.846C>T | p.S282S | SYNONYMOUS |
| c.1596G>C | p.Q532H | MISSENSE |
| c.1858G>A | p.E620K | MISSENSE |
| c.4673C>T | p.S1558F | MISSENSE |
| c.2433C>T | p.R811R | SYNONYMOUS |
| c.4675G>T | p.G1559X | NONSENSE |
| c.2746C>T | p.L916F | MISSENSE |
| c.856C>T | p.R286C | MISSENSE |
| c.759G>A | p.T253T | SYNONYMOUS |
| c.748G>A | p.A250T | MISSENSE |
| c.1912C>T | p.R638C | MISSENSE |
| c.4264C>T | p.L1422L | SYNONYMOUS |
| c.1802C>T | p.A601V | MISSENSE |
| c.4513G>T | p.D1505Y | MISSENSE |
| c.1294C>T | p.Q432X | NONSENSE |
| c.1738C>A | p.L580M | MISSENSE |
| c.1707C>T | p.V569V | SYNONYMOUS |
| c.568G>A | p.E190K | MISSENSE |
| IVS4-4C>T | SPLICE SITE | SPLICE SITE |
| c.861C>T | p.Y287Y | SYNONYMOUS |
| c.824G>A | p.S275N | MISSENSE |
| c.1460C>T | p.P487L | MISSENSE |
| c.2259C>A | p.C753X | NONSENSE |
| IVS13-1G>A | SPLICE SITE | SPLICE SITE |
| c.1200G>A | p.L400L | SYNONYMOUS |
| c.465C>T | p.S155S | SYNONYMOUS |
| c.1043T>G | p.L348X | NONSENSE |
| c.481G>A | p.G161S | MISSENSE |
| c.1240C>T | p.P414S | MISSENSE |
| c.829C>T | p.P277S | MISSENSE |
| c.976G>A | p.E326K | MISSENSE |
| c.1573T>G | p.S525A | MISSENSE |
| c.127G>A | p.G43S | MISSENSE |
| c.102G>A | p.W34X | NONSENSE |
| c.1398C>T | p.S466S | SYNONYMOUS |
| c.747C>T | p.T249T | SYNONYMOUS |
| c.434C>T | p.S145L | MISSENSE |
| c.78G>A | p.K26K | SYNONYMOUS |
| c.1065G>A | p.K355K | SYNONYMOUS |
| c.1190C>T | p.T397I | MISSENSE |
| c.162G>A | p.K54K | SYNONYMOUS |

FIG. 10
CONTINUED

| | | | |
|---|---|---|---|
| ACTRT1 | CCDS14611.1 | Br15X | g.chrX:126910589A>T (HOMOZYGOUS) |
| ADAM12 | CCDS7653.1 | Br27P | g.chr10:127796641G>A |
| ADAM15 | CCDS1084.1 | Br27P | g.chr1:151842802G>A |
| ADAM18 | CCDS6113.1 | Br13X | g.chr8:39644808T>C |
| ADAM18 | CCDS6113.1 | Br03X | g.chr8:39656829C>T |
| ADAM28 | NM_014265 | Br26X | g.chr8:24240084C>T |
| ADAM29 | CCDS3823.1 | Br07X | g.chr4:176272525T>C |
| ADAM29 | CCDS3823.1 | Br07x | g.chr4:176273643C>T (HOMOZYGOUS) |
| ADAMTS1 | NM_006988 | Br27P | g.chr21:27132153C>T |
| ADAMTS13 | CCDS6970.1 | Br27P | g.chr9:133337114G>A |
| ADAMTS13 | CCDS6970.1 | Br27P | g.chr9:133349273G>A |
| ADAMTS17 | CCDS10383.1 | Br20P | g.chr15:98512929A>G |
| ADAMTS20 | NM_175851 | Br27P | g.chr12:42134010T>C |
| ADAMTS20 | NM_175851 | Br27P | g.chr12:42132735C>T |
| ADAMTS4 | CCDS1223.1 | Br17X | g.chr1:157974131G>A |
| ADAMTS8 | NM_007037 | Br27P | g.chr11:129783713C>T |
| ADAR | CCDS1071.1 | Br27P | g.chr1:151373693C>T |
| ADARB2 | CCDS7058.1 | Br15X | g.chr10:1395335G>A (HOMOZYGOUS) |
| ADCY1 | NM_021116 | Br27P | g.chr7:45498885C>T |
| ADCY8 | CCDS6363.1 | Br27P | g.chr8:131966156C>T |
| ADRBK2 | CCDS13832.1 | Br27P | g.chr22:24410762G>A |
| AGC1 | NM_001135 | Br27P | g.chr15:87199676G>A |
| AGL | CCDS759.1 | Br27P | g.chr1:100055259G>A |
| AGPAT1 | CCDS4744.1 | Br27P | g.chr6:32247183C>T |
| AGPS | CCDS2275.1 | Br27P | g.chr2:178189966G>A |
| AGRN | NM_198576 | Br15X | g.chr1:1025272G>C |
| AGRN | NM_198576 | Br27P | g.chr1:1030124C>T |
| AHDC1 | NM_001029882 | Br27P | g.chr1:27561935C>T |
| AHI1 | NM_017651 | Br27P | g.chr6:135811225C>T |
| AIM1L | NM_017977 | Br17X | g.chr1:26356608C>T |
| AIM1L | NM_017977 | Br23X | g.chr1:26356352G>A |
| AKAP11 | CCDS9383.1 | Br27P | g.chr13:41775774G>A |
| AKAP13 | NM_007200 | Br27P | g.chr15:83924931C>T |
| AKAP13 | NM_007200 | Br07X | g.chr15:84052299C>T |
| AKAP13 | NM_007200 | Br17X | g.chr15:84085604G>A |
| AKAP4 | CCDS14329.1 | Br27P | g.chrX:49660730C>T |
| AKAP4 | CCDS14329.1 | Br27P | g.chrX:49661935C>T |
| AKAP9 | CCDS5622.1 | Br27P | g.chr7:91318999G>A |
| AKNA | CCDS6805.1 | Br05X | g.chr9:114209494G>A |
| AKNA | CCDS6805.1 | Br27P | g.chr9:114198755G>A |
| AKR7A2 | CCDS194.1 | Br27P | g.chr1:19377861C>T |
| ALDH18A1 | CCDS7443.1 | Br27P | g.chr10:97356610C>T |
| ALDH1A2 | CCDS10163.1 | Br27P | g.chr15:56093392G>A |
| ALDH1L1 | CCDS3034.1 | Br27P | g.chr3:127352019C>T |
| ALDH2 | CCDS9155.1 | Br27P | g.chr12:110700429G>A |
| ALLC | NM_018436 | Br07X | g.chr2:3243411C>T |
| ALOX12 | CCDS11084.1 | Br27P | g.chr17:6840996C>T |
| ALOXE3 | CCDS11130.1 | Br27P | g.chr17:7940771delC |
| ALPI | CCDS2492.1 | Br15X | g.chr2:233148489C>T |
| ALPK2 | CCDS11966.1 | Br16X | g.chr18:54397977G>A |

FIG. 10
CONTINUED

| | | |
|---|---|---|
| UTR+1A>T | 3'UTR | 3'UTR |
| c.568G>A | p.A190T | MISSENSE |
| c.1214G>A | p.G405E | MISSENSE |
| c.1461T>C | p.T487T | SYNONYMOUS |
| c.1748C>T | p.T583I | MISSENSE |
| c.963C>T | p.G321G | SYNONYMOUS |
| c.1119T>C | p.D373D | SYNONYMOUS |
| c.2237C>T | p.T746M | MISSENSE |
| c.2520C>T | p.Y840Y | SYNONYMOUS |
| c.2009G>A | p.R670H | MISSENSE |
| c.3227G>A | p.W1076X | NONSENSE |
| c.1301A>G | p.D434G | MISSENSE |
| c.1727T>C | p.I576T | MISSENSE |
| c.1791C>T | p.G597G | SYNONYMOUS |
| c.2384G>A | p.R795H | MISSENSE |
| c.1955C>T | p.T652I | MISSENSE |
| c.3000C>T | p.L1000L | SYNONYMOUS |
| c.965G>A | p.R322H | MISSENSE |
| c.2158C>T | p.P720S | MISSENSE |
| c.1945C>T | p.L649L | SYNONYMOUS |
| c.1010G>A | p.G337D | MISSENSE |
| c.2856G>A | p.G952G | SYNONYMOUS |
| c.1465G>A | p.D489N | MISSENSE |
| c.69C>T | p.P23P | SYNONYMOUS |
| IVS14+1G>A | SPLICE SITE | SPLICE SITE |
| c.4811G>C | p.R1604P | MISSENSE |
| IVS35-3C>T | SPLICE SITE | SPLICE SITE |
| c.834C>T | p.P278P | SYNONYMOUS |
| c.1522C>T | p.P508S | MISSENSE |
| c.683C>T | p.S228L | MISSENSE |
| c.939G>A | p.P313P | SYNONYMOUS |
| c.4892G>A | p.R1631K | MISSENSE |
| c.2628C>T | p.A876A | SYNONYMOUS |
| c.5510C>T | p.S1837F | MISSENSE |
| c.7932G>A | p.K2644K | SYNONYMOUS |
| c.1670C>T | p.T557I | MISSENSE |
| c.465C>T | p.C155C | SYNONYMOUS |
| c.5189G>A | p.R1730K | MISSENSE |
| c.1611G>A | p.S537S | SYNONYMOUS |
| c.2788G>A | p.E930K | MISSENSE |
| c.875C>T | p.T292I | MISSENSE |
| c.2287C>T | p.L763L | SYNONYMOUS |
| c.319G>A | p.D107N | MISSENSE |
| c.912C>T | p.N304N | SYNONYMOUS |
| IVS10-1G>A | SPLICE SITE | SPLICE SITE |
| c.1065C>T | p.D355D | SYNONYMOUS |
| c.263C>T | p.A88V | MISSENSE |
| c.2035delC | fs | INDEL |
| c.1049C>T | p.A350V | MISSENSE |
| c.300G>A | p.T100T | SYNONYMOUS |

FIG. 10
CONTINUED

| | | | |
|---|---|---|---|
| ALPK2 | CCDS11966.1 | Br27P | g.chr18:54300218C>T |
| ALPK3 | CCDS10333.1 | Br26X | g.chr15:83204060G>A |
| ALPL | CCDS217.1 | Br27P | g.chr1:21649283C>T |
| ALPL | CCDS217.1 | Br27P | g.chr1:21634962C>T |
| ALS2CL | CCDS2743.1 | Br27P | g.chr3:46693184G>A |
| ALS2CL | CCDS2743.1 | Br27P | g.chr3:46703608C>T |
| ALS2CR12 | CCDS2346.1 | Br27P | g.chr2:201997816G>A |
| AMACO | CCDS7589.1 | Br15X | g.chr10:116036087G>A (HOMOZYGOUS) |
| AMID | CCDS7297.1 | Br27P | g.chr10:71544885C>T |
| ANK2 | CCDS3702.1 | Br27P | g.chr4:114632930C>T |
| ANK2 | CCDS3702.1 | Br27P | g.chr4:114515860C>T |
| ANK3 | CCDS7258.1 | Br17X | g.chr10:61538664C>T (HOMOZYGOUS) |
| ANKMY1 | CCDS2536.1 | Br27P | g.chr2:241171315G>A |
| ANKRD10 | CCDS9520.1 | Br27P | g.chr13:110343498A>G |
| ANKRD11 | NM_013275 | Br27P | g.chr16:87874161C>T |
| ANKRD12 | CCDS11843.1 | Br27P | g.chr18:9246519G>A |
| ANKRD15 | CCDS6441.1 | Br27P | g.chr9:701831G>A |
| ANKRD28 | NM_015199 | Br9PT | g.chr3:15753569A>C |
| ANP32D | NM_012404 | Br27P | g.chr12:47152930C>T |
| AP3B1 | CCDS4041.1 | Br27P | g.chr5:77507409G>A |
| APG7L | CCDS2605.1 | Br27P | g.chr3:11329895G>A |
| API5 | NM_006595 | Br27P | g.chr11:43306005G>A |
| APOB | CCDS1703.1 | Br27P | g.chr2:21162905T>C |
| APOB | CCDS1703.1 | Br08X | g.chr2:21146371A>G |
| APOB | CCDS1703.1 | Br07X | g.chr2:21142988G>A |
| APOBEC3G | CCDS13984.1 | Br27P | g.chr22:37802017G>A |
| APRG1 | NM_178339 | Br05X | g.chr3:37433846G>A |
| AQP10 | CCDS1065.1 | Br27P | g.chr1:151108533G>A |
| AR | CCDS14387.1 | Br12P | g.chrX:66720414C>T |
| ARD1B | ENST00000286794 | Br04X | g.chr4:80603788G>A |
| ARHGAP4 | CCDS14736.1 | Br27P | g.chrX:152708075C>T |
| ARHGAP5 | NM_001173 | Br27P | g.chr14:31632997C>T |
| ARHGAP8 | CCDS14058.1 | Br27P | g.chr22:43451484G>A |
| ARHGDIG | CCDS10404.1 | Br27P | g.chr16:272477G>A |
| ARHGEF9 | NM_015185 | Br27P | g.chrX:62646878A>C |
| ARID1A | CCDS285.1 | Br27P | g.chr1:26740387G>A |
| ARID1A | CCDS285.1 | Br27P | g.chr1:26707082C>T |
| ARL1 | NM_001177 | Br14X | g.chr12:100292678C>T |
| ARNT2 | NM_014862 | Br15X | g.chr15:78659938C>A |
| ARNT2 | NM_014862 | Br11P | g.chr15:78549732A>G |
| ARP10 | CCDS13985.1 | Br03x | g.chr22:37821842C>T |
| ARSE | CCDS14122.1 | Br9PT | g.chrX:2871804_2871802delACA |
| ASB4 | CCDS5641.1 | Br27P | g.chr7:94801932C>T |
| ASCL4 | NM_203436 | Br27P | g.chr12:106671712C>T |
| ASCL5 | ENST00000344317 | Br27P | g.chr1:197816276C>T |
| ASGR1 | CCDS11089.1 | Br27P | g.chr17:7017734G>A |
| ASH1L | CCDS1113.1 | Br15X | g.chr1:152262607G>C |
| ASIP | CCDS13232.1 | Br07X | g.chr20:32320560G>A |
| ASTN | CCDS1319.1 | Br9PT | g.chr1:173733563G>A |
| ASTN | CCDS1319.1 | Br04X | g.chr1:173733513A>G |

FIG. 10
CONTINUED

| | | |
|---|---|---|
| c.5619C>T | p.T1873T | SYNONYMOUS |
| c.4621G>A | p.V1541I | MISSENSE |
| c.1411C>T | p.L471L | SYNONYMOUS |
| c.351C>T | p.Y117Y | SYNONYMOUS |
| c.1980G>A | p.E660E | SYNONYMOUS |
| c.403C>T | p.Q135X | NONSENSE |
| c.811G>A | p.G271R | MISSENSE |
| c.1397G>A | p.R466H | MISSENSE |
| IVS6-3C>T | SPLICE SITE | SPLICE SITE |
| c.5552C>T | p.T1851I | MISSENSE |
| c.597C>T | p.A199A | SYNONYMOUS |
| c.3103C>T | p.P1035S | MISSENSE |
| c.1972G>A | p.G658S | MISSENSE |
| c.569A>G | p.N190S | MISSENSE |
| c.6290C>T | p.P2097L | MISSENSE |
| c.3254G>A | p.S1085N | MISSENSE |
| c.591G>A | p.E197E | SYNONYMOUS |
| c.437A>C | p.H146P | MISSENSE |
| c.216C>T | p.S72S | SYNONYMOUS |
| c.1050G>A | p.Q350Q | SYNONYMOUS |
| IVS5+1G>A | SPLICE SITE | SPLICE SITE |
| IVS8+1G>A | SPLICE SITE | SPLICE SITE |
| c.1775T>C | p.F592S | MISSENSE |
| c.5021A>G | p.E1674G | MISSENSE |
| c.8404G>A | p.E2802K | MISSENSE |
| c.508G>A | p.E170K | MISSENSE |
| c.85G>A | p.A29T | MISSENSE |
| c.235G>A | p.A79T | MISSENSE |
| c.2247C>T | p.A749A | SYNONYMOUS |
| c.561G>A | p.G187G | SYNONYMOUS |
| c.102C>T | p.C34C | SYNONYMOUS |
| c.3371C>T | p.S1124L | MISSENSE |
| c.596G>A | p.R199H | MISSENSE |
| c.424G>A | p.E142K | MISSENSE |
| IVS9+3A>C | SPLICE SITE | SPLICE SITE |
| c.1241G>A | p.G414E | MISSENSE |
| c.46C>T | p.P16S | MISSENSE |
| c.482C>T | p.T161I | MISSENSE |
| c.1745C>A | p.P582Q | MISSENSE |
| c.313A>G | p.I105V | MISSENSE |
| c.251C>T | p.P84L | MISSENSE |
| UTR-2_1delACA | UNKNOWN | INDEL |
| c.644C>T | p.A215V | MISSENSE |
| c.250C>T | p.R84W | MISSENSE |
| c.26C>T | p.S9F | MISSENSE |
| c.844G>A | p.D282N | MISSENSE |
| c.3127G>C | p.G1043R | MISSENSE |
| c.325G>A | p.D109N | MISSENSE |
| c.551G>A | p.R184H | MISSENSE |
| c.601A>G | p.I201V | MISSENSE |

FIG. 10
CONTINUED

| | | | |
|---|---|---|---|
| ATAD2B | ENST00000295142 | Br27P | g.chr2:24061283C>T |
| ATP10B | ENST00000327245 | Br03X | g.chr5:159958513T>A |
| ATP12A | NM_001676 | Br27P | g.chr13:24170838C>T |
| ATP12A | NM_001676 | Br13X | g.chr13:24178566C>G |
| ATP13A1 | NM_020410 | Br27P | g.chr19:19626975G>A |
| ATP13A2 | CCDS175.1 | Br27P | g.chr1:17060192C>T |
| ATP1A2 | CCDS1196.1 | Br27P | g.chr1:156918456G>A |
| ATP2A1 | CCDS10643.1 | Br27P | g.chr16:28820696C>T |
| ATP2A3 | CCDS11041.1 | Br9PT | g.chr17:3787662C>T |
| ATP2B1 | CCDS9035.1 | Br12P | g.chr12:88531401T>A |
| ATP2B2 | CCDS2601.1 | Br27P | g.chr3:10392328G>A |
| ATP6V1G3 | CCDS1396.1 | Br26X | g.chr1:195237514A>T |
| ATP7B | NM_000053 | Br27P | g.chr13:51407782G>A |
| ATP8A1 | CCDS3466.1 | Br27P | g.chr4:42421311G>A |
| ATP8B1 | CCDS11965.1 | Br27P | g.chr18:53503330C>T |
| ATP8B1 | CCDS11965.1 | Br16X | g.chr18:53512891C>A |
| ATRNL1 | CCDS7592.1 | Br27P | g.chr10:117476771G>A |
| ATXN1 | NM_000332 | Br27P | g.chr6:16436254G>A |
| AUTS2 | CCDS5539.1 | Br27P | g.chr7:69699995C>T |
| AXIN2 | CCDS11662.1 | Br27P | g.chr17:60962242C>T |
| AZI1 | NM_001009811 | Br27P | g.chr17:76790689G>A |
| B3Gn-T6 | NM_138706 | Br27P | g.chr11:76429072C>T |
| BAD | CCDS8065.1 | Br27P | g.chr11:63795668C>T |
| BAI2 | CCDS346.1 | Br25X | g.chr1:31865600C>T |
| BAMBI | CCDS7162.1 | Br06X | g.chr10:29011167dupA |
| BAT2D1 | CCDS1296.1 | Br27P | g.chr1:168241275G>A |
| BAZ1A | CCDS9651.1 | Br27P | g.chr14:34333728G>A |
| BCAR3 | CCDS745.1 | Br17X | g.chr1:93760355C>T |
| BCL2L1 | CCDS13188.1 | Br27P | g.chr20:29717517G>A |
| BCL2L12 | CCDS12776.1 | Br27P | g.chr19:54865490C>T |
| BCL2L2 | CCDS9591.1 | Br9PT | g.chr14:22847208A>G |
| BCL6 | CCDS3289.1 | Br27P | g.chr3:188930420G>A |
| BCOR | CCDS14250.1 | Br08X | g.chrX:39670947C>T |
| BFSP1 | CCDS13126.1 | Br27P | g.chr20:17423130G>A |
| BIN1 | CCDS2137.1 | Br07X | g.chr2:127524280C>G |
| BIN1 | CCDS2137.1 | Br27P | g.chr2:127537450G>A |
| BIRC1 | CCDS4009.1 | Br26X | g.chr5:70344085C>T |
| BIRC6 | NM_016252 | Br27P | g.chr2:32565957G>A |
| BMP3 | CCDS3588.1 | Br08X | g.chr4:82324498C>G |
| BMPER | CCDS5442.1 | Br17X | g.chr7:33965986C>T |
| BNC2 | CCDS6482.1 | Br27P | g.chr9:16572987G>A |
| BOC | CCDS2971.1 | Br27P | g.chr3:114474608C>T |
| BPY2IP1 | NM_018174 | Br08X | g.chr19:17698128G>A |
| BRAF | CCDS5863.1 | Br27P | g.chr7:139953397C>T |
| BRF1 | CCDS10001.1 | Br20P | g.chr14:104756379G>A |
| BRP44L | CCDS5293.1 | Br27P | g.chr6:166749339G>A |
| BRPF1 | CCDS2575.1 | Br27P | g.chr3:9760305C>T |
| BSN | CCDS2800.1 | Br27P | g.chr3:49673702C>T |
| BST1 | CCDS3416.1 | Br04X | g.chr4:15409723A>C |
| BTAF1 | CCDS7419.1 | Br27P | g.chr10:93776485G>A |

FIG. 10
CONTINUED

| | | |
|---|---|---|
| c.9C>T | p.N3N | SYNONYMOUS |
| c.3406T>A | p.F1136I | MISSENSE |
| c.1555C>T | p.L519F | MISSENSE |
| c.2134C>G | p.Q712E | MISSENSE |
| c.1254G>A | p.G418G | SYNONYMOUS |
| c.2693C>T | p.A898V | MISSENSE |
| c.2275G>A | p.V759M | MISSENSE |
| c.2112C>T | p.G704G | SYNONYMOUS |
| c.2118C>T | p.N706N | SYNONYMOUS |
| c.502T>A | p.L168I | MISSENSE |
| c.1067G>A | p.G356D | MISSENSE |
| IVS1-3A>T | SPLICE SITE | SPLICE SITE |
| c.4072G>A | p.A1358T | MISSENSE |
| c.1022G>A | p.G341E | MISSENSE |
| c.1445C>T | p.A482V | MISSENSE |
| c.950C>A | p.T317N | MISSENSE |
| c.3819G>A | p.Q1273Q | SYNONYMOUS |
| c.267G>A | p.P89P | SYNONYMOUS |
| c.3142C>T | p.P1048S | MISSENSE |
| c.2201C>T | p.A734V | MISSENSE |
| c.734G>A | p.G245E | MISSENSE |
| c.829C>T | p.P277S | MISSENSE |
| c.371C>T | p.S124F | MISSENSE |
| c.4238C>T | p.P1413L | MISSENSE |
| c.614dupA | fs | INDEL |
| c.3006G>A | p.R1002R | SYNONYMOUS |
| c.1341G>A | p.E447E | SYNONYMOUS |
| c.1210C>T | p.P404S | MISSENSE |
| c.409G>A | p.A137T | MISSENSE |
| c.887C>T | p.T296I | MISSENSE |
| c.392A>G | p.E131G | MISSENSE |
| c.475G>A | p.G159S | MISSENSE |
| c.4537C>T | p.R1513X | NONSENSE |
| c.1587G>A | p.Q529Q | SYNONYMOUS |
| c.1204C>G | p.L402V | MISSENSE |
| c.608G>A | p.R203H | MISSENSE |
| c.414C>T | p.Y138Y | SYNONYMOUS |
| c.2881G>A | p.E961K | MISSENSE |
| c.744C>G | p.A248A | SYNONYMOUS |
| c.1919C>T | p.P640L | MISSENSE |
| c.193G>A | p.A65T | MISSENSE |
| c.964C>T | p.P322S | MISSENSE |
| c.935G>A | p.R312H | MISSENSE |
| c.929C>T | p.T310I | MISSENSE |
| IVS14+1G>A | SPLICE SITE | SPLICE SITE |
| c.319G>A | p.A107T | MISSENSE |
| c.2337C>T | p.H779H | SYNONYMOUS |
| c.9420C>T | p.A3140A | SYNONYMOUS |
| c.943A>C | p.R315R | SYNONYMOUS |
| c.5232G>A | p.G1744G | SYNONYMOUS |

FIG. 10
CONTINUED

| | | | |
|---|---|---|---|
| BTBD1 | CCDS10322.1 | Br27P | g.chr15:81489969G>A |
| BTBD3 | CCDS13113.1 | Br27P | g.chr20:11851652G>A |
| BTC | CCDS3566.1 | Br27P | g.chr4:76033011G>A |
| BTK | CCDS14482.1 | Br27P | g.chrX:100417280C>T |
| BTNL2 | CCDS4749.1 | Br27P | g.chr6:32471943G>A |
| BTNL9 | CCDS4460.1 | Br07X | g.chr5:180407717G>A (HOMOZYGOUS) |
| BUCS1 | CCDS10587.1 | Br27P | g.chr16:20609893G>A |
| C10orf18 | ENST00000263123 | Br05X | g.chr10:5843371G>A |
| C10orf26 | CCDS7540.1 | Br27P | g.chr10:104562539C>T |
| C10orf33 | CCDS7474.1 | Br27P | g.chr10:100133609G>T |
| C10orf47 | CCDS7085.1 | Br04X | g.chr10:11948752G>T |
| C10orf64 | ENST00000265453 | Br14X | g.chr10:49710728C>T (HOMOZYGOUS) |
| C10orf71 | ENST00000323868 | Br27P | g.chr10:50203424G>A |
| C10orf80 | NM_001008723 | Br27P | g.chr10:106118299G>A |
| C10orf81 | CCDS7583.1 | Br27P | g.chr10:115516387C>T |
| C11orf11 | NM_006133 | Br27P | g.chr11:61264574G>A |
| C11ORF4 | CCDS8066.1 | Br27P | g.chr11:63812220G>A |
| C12orf11 | CCDS8708.1 | Br27P | g.chr12:26955452C>T |
| C12orf42 | NM_198521 | Br27P | g.chr12:102297915C>T |
| C14orf115 | CCDS9830.1 | Br9PT | g.chr14:73894110G>A |
| C14orf131 | NM_018335 | Br27P | g.chr14:101878133C>T |
| C14orf133 | CCDS9862.1 | Br26X | g.chr14:76965843G>C |
| C14orf145 | NM_152446 | Br26X | g.chr14:80398895C>T |
| C14orf155 | CCDS9679.1 | Br17X | g.chr14:44045852G>A |
| C14orf159 | NM_024952 | Br27P | g.chr14:90725215C>T |
| C14orf159 | NM_024952 | Br27P | g.chr14:90735956C>T |
| C14orf31 | CCDS9704.1 | Br02X | g.chr14:51264389C>T |
| C14orf43 | CCDS9819.1 | Br05X | g.chr14:73276371C>T |
| C14orf49 | CCDS9935.1 | Br27P | g.chr14:94991706G>A |
| C15orf2 | CCDS10015.1 | Br23X | g.chr15:22472605G>A |
| C15orf42 | ENST00000268138 | Br17X | g.chr15:87920396T>C |
| C15orf42 | ENST00000268138 | Br27P | g.chr15:87920406G>A |
| C16orf9 | CCDS10402.1 | Br11P | g.chr16:254837G>A |
| C17orf27 | NM_020914 | Br27P | g.chr17:75961478G>A |
| C17orf31 | CCDS11016.1 | Br27P | g.chr17:2086668C>T |
| C17orf31 | CCDS11016.1 | Br27P | g.chr17:2149981C>T |
| C18orf25 | NM_001008239 | Br07X | g.chr18:42087709C>T |
| C18orf4 | CCDS11995.1 | Br25X | g.chr18:63330753C>G |
| C19orf29 | ENST00000221899 | Br04X | g.chr19:3569902G>C |
| C1orf147 | NM_001025592 | Br27P | g.chr1:203059417C>T |
| C1orf151 | NM_001032363 | Br27P | g.chr1:19695301C>T |
| C1orf16 | CCDS1355.1 | Br15X | g.chr1:180234495G>A |
| C1orf173 | NM_001002912 | Br27P | g.chr1:74750303G>A |
| C1orf84 | NM_015284 | Br27P | g.chr1:43582385C>T |
| C1orf84 | NM_015284 | Br27P | g.chr1:43577029T>A |
| C1QDC1 | CCDS8720.1 | Br27P | g.chr12:30754328G>A |
| C20orf10 | CCDS13352.1 | Br27P | g.chr20:43435985G>A |
| C20orf102 | CCDS13299.1 | Br27P | g.chr20:35965280C>T |
| C20orf114 | CCDS13218.1 | Br27P | g.chr20:31355429C>T |
| C20orf114 | CCDS13218.1 | Br27P | g.chr20:31355490C>T |

FIG. 10
CONTINUED

| | | |
|---|---|---|
| c.978G>A | p.R326R | SYNONYMOUS |
| c.907G>A | p.A303T | MISSENSE |
| c.379G>A | p.V127I | MISSENSE |
| c.1471C>T | p.H491Y | MISSENSE |
| c.929G>A | p.G310E | MISSENSE |
| c.294G>A | p.P98P | SYNONYMOUS |
| c.119G>A | p.W40X | NONSENSE |
| c.3784G>A | p.E1262K | MISSENSE |
| c.490C>T | p.P164S | MISSENSE |
| c.1682G>T | p.G561V | MISSENSE |
| c.355G>T | p.E119X | NONSENSE |
| c.889C>T | p.R297W | MISSENSE |
| c.215G>A | p.S72N | MISSENSE |
| c.921G>A | p.L307L | SYNONYMOUS |
| c.144C>T | p.I48I | SYNONYMOUS |
| c.1917G>A | p.E639E | SYNONYMOUS |
| c.741G>A | p.R247R | SYNONYMOUS |
| c.1871C>T | p.P624L | MISSENSE |
| c.84C>T | p.S28S | SYNONYMOUS |
| c.871G>A | p.V291I | MISSENSE |
| c.1151C>T | p.S384F | MISSENSE |
| c.1200G>C | p.K400N | MISSENSE |
| c.721C>T | p.R241C | MISSENSE |
| c.89G>A | p.R30H | MISSENSE |
| c.1128C>T | p.D376D | SYNONYMOUS |
| c.1383C>T | p.D461D | SYNONYMOUS |
| c.1737C>T | p.C579C | SYNONYMOUS |
| c.94C>T | p.L32L | SYNONYMOUS |
| c.898G>A | p.G300R | MISSENSE |
| c.498G>A | p.P166P | SYNONYMOUS |
| c.575T>C | p.L192S | MISSENSE |
| c.585G>A | p.K195K | SYNONYMOUS |
| c.1474G>A | p.A492T | MISSENSE |
| c.7079G>A | p.R2360Q | MISSENSE |
| c.2737C>T | p.P913S | MISSENSE |
| c.816C>T | p.G272G | SYNONYMOUS |
| c.764C>T | p.A255V | MISSENSE |
| c.2103C>G | p.S701R | MISSENSE |
| c.929G>C | p.R310P | MISSENSE |
| c.29C>T | p.S10F | MISSENSE |
| c.140C>T | p.S47F | MISSENSE |
| c.1034G>A | p.C345Y | MISSENSE |
| c.3112G>A | p.A1038T | MISSENSE |
| c.6666C>T | p.Y2222Y | SYNONYMOUS |
| IVS39-3T>A | SPLICE SITE | SPLICE SITE |
| c.3009G>A | p.K1003K | SYNONYMOUS |
| c.849G>A | p.W283X | NONSENSE |
| c.114C>T | p.S38S | SYNONYMOUS |
| c.1145C>T | p.A382V | MISSENSE |
| c.1206C>T | p.I402I | SYNONYMOUS |

FIG. 10
CONTINUED

| | | | |
|---|---|---|---|
| C20orf23 | CCDS13122.1 | Br27P | g.chr20:16307605G>A |
| C20orf78 | ENST00000278779 | Br08X | g.chr20:18753915delA |
| C21orf29 | CCDS13712.1 | Br17X | g.chr21:44771612C>T |
| C21orf29 | CCDS13712.1 | Br9PT | g.chr21:44749134T>A |
| C21orf29 | CCDS13712.1 | Br05X | g.chr21:44772876C>T |
| C21orf5 | CCDS13643.1 | Br29P | g.chr21:36508719A>T |
| C21orf69 | NM_058189 | Br27P | g.chr21:45178476C>T |
| C2orf17 | CCDS2434.1 | Br02X | g.chr2:219872581C>T |
| C2orf29 | CCDS2050.1 | Br27P | g.chr2:101332905G>A |
| C2orf3 | CCDS1961.1 | Br27P | g.chr2:75845376G>A |
| C3orf14 | CCDS2896.1 | Br27P | g.chr3:62292081C>T |
| C4orf7 | CCDS3537.1 | Br03X | g.chr4:71277680A>T |
| C5AR1 | NM_001736 | Br9PT | g.chr19:52515442G>A |
| C6 | CCDS3936.1 | Br27P | g.chr5:41189823C>T |
| C6 | CCDS3936.1 | Br13X | g.chr5:41189744G>T |
| C6orf103 | ENST00000326929 | Br9PT | g.chr6:147063896T>C |
| C6orf150 | CCDS4978.1 | Br27P | g.chr6:74191797G>A |
| C6orf163 | NM_001010868 | Br27P | g.chr6:88131789C>T |
| C6orf165 | CCDS5009.1 | Br27P | g.chr6:88180261G>A |
| C6orf168 | NM_032511 | Br27P | g.chr6:99878221C>T |
| C6orf170 | NM_152730 | Br04X | g.chr6:121680381C>T (HOMOZYGOUS) |
| C6orf170 | NM_152730 | Br04X | g.chr6:121680365C>T (HOMOZYGOUS) |
| C6orf21 | NM_001003693 | Br27P | g.chr6:31786174G>A |
| C6orf213 | NM_001010852 | Br27P | g.chr6:123373937C>T |
| C6orf29 | CCDS4724.1 | Br27P | g.chr6:31940771G>A |
| C6orf4 | CCDS5092.1 | Br27P | g.chr6:111987373G>A |
| C6orf68 | CCDS5118.1 | Br27P | g.chr6:118103684G>A |
| C7orf16 | CCDS5436.1 | Br20P | g.chr7:31508388G>A |
| C8A | CCDS606.1 | Br03X | g.chr1:57090167G>A |
| C8B | NM_000066 | Br27P | g.chr1:57107246C>T |
| C8B | NM_000066 | Br27P | g.chr1:57137786C>T |
| C8orf77 | NM_001039382 | Br29P | g.chr8:146199285_146199288delGAAG |
| C8ORFK23 | NM_001039112 | Br9PT | g.chr8:125037438A>C |
| C9orf126 | NM_173690 | Br07x | g.chr9:124813204G>A (HOMOZYGOUS) |
| C9orf19 | CCDS6598.1 | Br27P | g.chr9:36152520C>T |
| C9orf5 | NM_032012 | Br04X | g.chr9:108878134C>T |
| C9orf50 | NM_199350 | Br27P | g.chr9:129462058G>A |
| CA2 | CCDS6239.1 | Br15X | g.chr8:86564771A>C |
| CAB39 | CCDS2478.1 | Br27P | g.chr2:231450239G>A |
| CABIN1 | CCDS13823.1 | Br27P | g.chr22:22785070C>T |
| CABP1 | CCDS9204.1 | Br27P | g.chr12:119561719G>A |
| CACNA1A | NM_000068 | Br15X | g.chr19:13184518C>T |
| CACNA1C | NM_000719 | Br17X | g.chr12:2094747C>A |
| CACNA1C | NM_000719 | Br27P | g.chr12:2585197G>A |
| CACNA1E | NM_000721 | Br27P | g.chr1:178439999C>T |
| CACNA1E | NM_000721 | Br27P | g.chr1:178476959C>T |
| CACNA1H | NM_021098 | Br15X | g.chr16:1199144C>T |
| CACNA1H | NM_021098 | Br05X | g.chr16:1201735G>A |
| CACNA1I | NM_001003406 | Br27P | g.chr22:38321132C>T |
| CACNA1S | CCDS1407.1 | Br27P | g.chr1:197748332C>T |

FIG. 10
CONTINUED

| | | |
|---|---|---|
| c.3042G>A | p.R1014R | SYNONYMOUS |
| c.111delA | fs | INDEL |
| c.1140C>T | p.I380I | SYNONYMOUS |
| c.1813T>A | p.S605T | MISSENSE |
| c.809C>T | p.T270M | MISSENSE |
| c.1124A>T | p.E375V | MISSENSE |
| c.51C>T | p.A17A | SYNONYMOUS |
| c.1357C>T | p.L453F | MISSENSE |
| c.649G>A | p.D217N | MISSENSE |
| c.322G>A | p.E108K | MISSENSE |
| c.219C>T | p.H73H | SYNONYMOUS |
| c.9A>T | p.K3N | MISSENSE |
| c.568G>A | p.V190M | MISSENSE |
| c.2136C>T | p.V712V | SYNONYMOUS |
| c.2215G>T | p.A739S | MISSENSE |
| c.1704T>C | p.S568S | SYNONYMOUS |
| c.1443G>A | p.E481E | SYNONYMOUS |
| c.568C>T | p.P190S | MISSENSE |
| c.207G>A | p.R69R | SYNONYMOUS |
| c.643C>T | p.R215W | MISSENSE |
| c.454C>T | p.R152C | MISSENSE |
| c.470C>T | p.S157F | MISSENSE |
| c.869G>A | p.G290D | MISSENSE |
| c.498C>T | p.N166N | SYNONYMOUS |
| c.1832G>A | p.G611D | MISSENSE |
| c.1653G>A | p.R551R | SYNONYMOUS |
| c.158G>A | p.G53D | MISSENSE |
| c.148G>A | p.V50I | MISSENSE |
| c.1451G>A | p.R484H | MISSENSE |
| c.1628C>T | p.P543L | MISSENSE |
| c.177C>T | p.T59T | SYNONYMOUS |
| c.109_112delGAAG | fs | INDEL |
| c.19A>C | p.K7Q | MISSENSE |
| c.1742G>A | p.R581Q | MISSENSE |
| UTR+1C>T | 3'UTR | 3'UTR |
| c.2306C>T | p.T769I | MISSENSE |
| c.350G>A | p.R117K | MISSENSE |
| c.53A>C | p.K18T | MISSENSE |
| c.18G>A | p.G6G | SYNONYMOUS |
| c.1903C>T | p.L635L | SYNONYMOUS |
| c.456G>A | p.G152G | SYNONYMOUS |
| c.5980C>T | p.P1994S | MISSENSE |
| c.146C>A | p.A49D | MISSENSE |
| c.3140G>A | p.G1047E | MISSENSE |
| c.3672C>T | p.I1224I | SYNONYMOUS |
| c.5205C>T | p.I1735I | SYNONYMOUS |
| c.3475C>T | p.Q1159X | NONSENSE |
| c.4495G>A | p.V1499M | MISSENSE |
| c.456C>T | p.R152R | SYNONYMOUS |
| c.4521C>T | p.D1507D | SYNONYMOUS |

FIG. 10
CONTINUED

| | | | |
|---|---|---|---|
| CACNA2D3 | NM_018398 | Br07X | g.chr3:54905889G>A |
| CACNB2 | CCDS7125.1 | Br27P | g.chr10:18730945G>A |
| CACNG4 | CCDS11667.1 | Br05X | g.chr17:62451481C>A |
| CADPS | CCDS2898.1 | Br27P | g.chr3:62553378G>A |
| CADPS | CCDS2898.1 | Br08X | g.chr3:62360136C>T |
| CADPS2 | NM_017954 | Br23X | g.chr7:121627314C>T |
| CALM1 | CCDS9892.1 | Br27P | g.chr14:89937439C>T |
| CAMSAP1 | NM_015447 | Br27P | g.chr9:135939001G>A |
| CAPN12 | CCDS12519.1 | Br27P | g.chr19:43920121C>T |
| CAPN3 | CCDS10084.1 | Br08X | g.chr15:40419220T>C (HOMOZYGOUS) |
| CAPN3 | CCDS10084.1 | Br08X | g.chr15:40419268G>A (HOMOZYGOUS) |
| CAPZA3 | CCDS8681.1 | Br12P | g.chr12:18782589T>C |
| CARD11 | CCDS5336.1 | Br27P | g.chr7:2719519G>A |
| CART1 | CCDS9028.1 | Br02X | g.chr12:84197515G>C |
| CASC5 | NM_170589 | Br27P | g.chr15:38702625C>T |
| CASQ1 | CCDS1198.1 | Br27P | g.chr1:156978791A>G |
| CCDC15 | NM_025004 | Br27P | g.chr11:124352627G>A |
| CCNF | CCDS10467.1 | BR27P | g.chr16:2438947C>G |
| CCNL2 | ENST00000321423 | Br05x | g.chr1:1419932G>T |
| CCNYL1 | ENST00000339882 | Br27P | g.chr19:33166187C>T |
| CD19 | CCDS10644.1 | Br27P | g.chr16:28855877G>A |
| CD84 | CCDS1206.1 | Br27P | g.chr1:157348537C>T |
| CD96 | CCDS2958.1 | Br15X | g.chr3:112802268T>C |
| CDA08 | CCDS10728.1 | Br27P | g.chr16:46042831C>T |
| CDC2L6 | CCDS5085.1 | Br04X | g.chr6:111049193C>T (HOMOZYGOUS) |
| CDC7 | CCDS734.1 | Br27P | g.chr1:91689195G>A |
| CDCA8 | CCDS424.1 | Br27P | g.chr1:37843121C>T |
| CDH23 | NM_022124 | Br27P | g.chr10:73120311G>A |
| CDH23 | NM_022124 | Br27P | g.chr10:73134729C>T |
| CDH24 | CCDS9585.1 | Br27P | g.chr14:225594316G>A |
| CDH26 | CCDS13485.1 | Br27P | g.chr20:58009809C>T |
| CDH5 | CCDS10804.1 | Br27P | g.chr16:64980825T>A |
| CDK5 | NM_004935 | Br27P | g.chr7:150191887G>A |
| CDK6 | CCDS5628.1 | Br27P | g.chr7:91889102C>T |
| CDT1 | NM_030928 | Br27P | g.chr16:87399960C>T |
| CDX1 | CCDS4304.1 | Br9PT | g.chr5:149527044C>T |
| CDYL2 | NM_152342 | Br25X | g.chr16:79212311C>A |
| CEACAM1 | CCDS12609.1 | Br02X | g.chr19:47717317C>T |
| CELSR3 | CCDS2775.1 | Br27P | g.chr3:48671847G>A |
| CELSR3 | CCDS2775.1 | Br25X | g.chr3:48655321G>A |
| CENPF | NM_016343 | Br27P | g.chr1:211204488G>A |
| CENTG3 | NM_031946 | Br27P | g.chr7:150258594G>A |
| CENTG3 | NM_031946 | Br27P | g.chr7:150278288C>T |
| CEP135 | NM_025009 | Br11P | g.chr4:56678377G>A |
| Cep164 | NM_014956 | Br27P | g.chr11:116737794C>T |
| CEP2 | CCDS13255.1 | Br27P | g.chr20:33530983C>T |
| CETP | CCDS10772.1 | Br27P | g.chr16:55569609G>A |
| CFTR | CCDS5773.1 | Br20P | g.chr7:116844526_116844528delGTT |
| CGI-38 | CCDS10835.1 | Br17X | g.chr16:65981979G>A |
| CGI-96 | CCDS14036.1 | Br27P | g.chr22:41235186G>A |

FIG. 10
CONTINUED

| | | |
|---|---|---|
| c.2320G>A | p.A774T | MISSENSE |
| c.300G>A | p.E100E | SYNONYMOUS |
| c.348C>A | p.I116I | SYNONYMOUS |
| c.1411G>A | p.A471T | MISSENSE |
| c.3810C>T | p.D1270D | SYNONYMOUS |
| c.2796C>T | p.I932I | SYNONYMOUS |
| c.118C>T | p.L40L | SYNONYMOUS |
| c.2617G>A | p.D873N | MISSENSE |
| IVS8-3C>T | SPLICE SITE | SPLICE SITE |
| c.1905T>C | p.A635A | SYNONYMOUS |
| c.1953G>A | p.K651K | SYNONYMOUS |
| c.120T>C | p.D40D | SYNONYMOUS |
| c.3438G>A | p.Q1146Q | SYNONYMOUS |
| c.775G>C | p.D259H | MISSENSE |
| c.2949C>T | p.S983S | SYNONYMOUS |
| c.665A>G | p.E222G | MISSENSE |
| c.674G>A | p.G225E | MISSENSE |
| c.1185C>G | p.G395G | SYNONYMOUS |
| c.22G>T | p.A8S | MISSENSE |
| c.634C>T | p.L212L | SYNONYMOUS |
| c.1117G>A | p.G373S | MISSENSE |
| c.118C>T | p.P40S | MISSENSE |
| c.904T>C | p.Y302H | MISSENSE |
| c.537C>T | p.N179N | SYNONYMOUS |
| c.1184C>T | p.A395V | MISSENSE |
| c.356G>A | p.G119E | MISSENSE |
| c.833C>T | p.T278I | MISSENSE |
| c.2140G>A | p.E714K | MISSENSE |
| c.2789C>T | p.P930L | MISSENSE |
| c.288G>A | p.E96E | SYNONYMOUS |
| c.2114C>T | p.P705L | MISSENSE |
| c.680T>A | p.V227E | MISSENSE |
| c.46G>A | p.G16R | MISSENSE |
| UTR+3C>T | 3'UTR | 3'UTR |
| c.863C>T | p.A288V | MISSENSE |
| c.412C>T | p.R138C | MISSENSE |
| c.857C>A | p.A286E | MISSENSE |
| c.900C>T | p.H300H | SYNONYMOUS |
| c.3225G>A | p.R1075R | SYNONYMOUS |
| c.8407G>A | p.G2803R | MISSENSE |
| c.4412G>A | p.G1471E | MISSENSE |
| c.1086G>A | p.G362G | SYNONYMOUS |
| c.2378C>T | p.S793F | MISSENSE |
| c.1124G>A | p.C375Y | MISSENSE |
| c.427C>T | p.P143S | MISSENSE |
| c.2387C>T | p.T796I | MISSENSE |
| c.1087G>A | p.V363M | MISSENSE |
| c.2991_2993delGTT | p.L997del | INDEL |
| c.246G>A | p.L82L | SYNONYMOUS |
| c.558G>A | p.E186E | SYNONYMOUS |

FIG. 10
CONTINUED

| | | | |
|---|---|---|---|
| CGNL1 | CCDS10161.1 | Br27P | g.chr15:55518870C>T |
| CHAD | CCDS11568.1 | Br20P | g.chr17:45898161C>G |
| CHD4 | CCDS8552.1 | Br27P | g.chr12:6575522G>A |
| CHD4 | CCDS8552.1 | Br27P | g.chr12:6561156G>A |
| CHD5 | CCDS57.1 | Br05X | g.chr1:6106151C>T |
| CHD6 | CCDS13317.1 | Br27P | g.chr20:39574945G>A |
| CHD9 | NM_025134 | Br11P | g.chr16:51906311delA |
| CHDH | CCDS2873.1 | Br29P | g.chr3:53832926G>A |
| CHEK1 | CCDS8459.1 | Br27P | g.chr11:125019230G>A |
| ChGn | CCDS6010.1 | Br27P | g.chr8:19320489A>G |
| ChGn | CCDS6010.1 | Br27P | g.chr8:19320471A>C |
| CHKA | CCDS8178.1 | Br27P | g.chr11:67589923G>A |
| CHL1 | CCDS2556.1 | Br14X | g.chr3:342738C>A (HOMOZYGOUS) |
| CHL1 | CCDS2556.1 | Br27P | g.chr3:336466C>T |
| CHRM2 | CCDS5843.1 | Br27P | g.chr7:136156899G>A |
| CHRM5 | CCDS10031.1 | Br07X | g.chr15:32143031C>T |
| CHRNA3 | CCDS10305.1 | Br14X | g.chr15:76681620T>C |
| CHRNA4 | CCDS13517.1 | Br16X | g.chr20:61452004G>C |
| CHRNA9 | CCDS3459.1 | Br15X | g.chr4:40197220C>T |
| CHST13 | CCDS3039.1 | Br07X | g.chr3:127743526G>A |
| CIDEA | CCDS11856.1 | Br27P | g.chr18:12267216G>A |
| CIDEC | CCDS2587.1 | Br27P | g.chr3:9883918C>T |
| CIZ1 | CCDS6894.1 | Br27P | g.chr9:128011331C>T |
| CIZ1 | CCDS6894.1 | Br04X | g.chr9:128010960C>A |
| CKLFSF5 | CCDS9599.1 | Br27P | g.chr14:22916453C>T |
| CLASP1 | NM_015282 | Br27P | g.chr2:122079677C>T |
| CLASP2 | NM_015097 | Br27P | g.chr3:33700903G>A |
| CLCN1 | CCDS5881.1 | Br02X | g.chr7:142560556A>G |
| CLCN5 | CCDS14328.1 | Br27P | g.chrX:49554214G>A |
| CLDN11 | CCDS3213.1 | Br27P | g.chr3:171623728C>T |
| CLEC1A | CCDS8612.1 | Br08X | g.chr12:10125204C>G |
| CLEC4E | CCDS8594.1 | Br29P | g.chr12:8578507T>C |
| CLEC7A | CCDS8613.1 | Br27P | g.chr12:10169201G>A |
| CLIC6 | CCDS13638.1 | Br27P | g.chr21:34963705G>A |
| CLN8 | CCDS5956.1 | Br27P | g.chr8:1706692G>A |
| CLSPN | CCDS396.1 | Br15X | g.chr1:35895144C>T |
| CLSTN2 | CCDS3112.1 | Br27P | g.chr3:141748193C>T |
| CLTA | CCDS6600.1 | Br27P | g.chr9:36181248C>T |
| CMIP | NM_198390 | Br27P | g.chr16:80290889G>A |
| CMYA1 | CCDS2683.1 | Br10P | g.chr3:39205833G>A |
| CMYA4 | CCDS11292.1 | Br27P | g.chr17:30521366G>A |
| CMYA4 | CCDS11292.1 | Br27P | g.chr17:30522577C>T |
| CNNM2 | CCDS7543.1 | Br27P | g.chr10:104668323C>T |
| CNOT1 | CCDS10799.1 | Br27P | g.chr16:57172165C>T |
| CNOT1 | CCDS10799.1 | Br27P | g.chr16:57137819G>A |
| CNOT10 | CCDS2655.1 | Br27P | g.chr3:32789963G>A |
| CNOT7 | CCDS6000.1 | Br27P | g.chr8:17134378C>T |
| CNR2 | CCDS245.1 | Br12P | g.chr1:23946683C>G |
| CNTN4 | CCDS2558.1 | Br27P | g.chr3:2942424C>T |
| CNTNAP2 | CCDS5889.1 | Br02X | g.chr7:147038402C>T |

FIG. 10
CONTINUED

| | | |
|---|---|---|
| c.1381C>T | p.P461S | MISSENSE |
| c.844C>G | p.Q282E | MISSENSE |
| c.1935G>A | p.R645R | SYNONYMOUS |
| c.4601G>A | p.G1534E | MISSENSE |
| c.5199C>T | p.Y1733Y | SYNONYMOUS |
| c.806G>A | p.G269D | MISSENSE |
| c.7441delA | fs | INDEL |
| c.150G>A | p.S50S | SYNONYMOUS |
| c.958G>A | p.E320K | MISSENSE |
| c.1185A>G | p.I395M | MISSENSE |
| c.1203A>C | p.A401A | SYNONYMOUS |
| c.1031G>A | p.G344E | MISSENSE |
| c.188C>A | p.P63Q | MISSENSE |
| c.7C>T | p.P3S | MISSENSE |
| c.32G>A | p.S11N | MISSENSE |
| c.821C>T | p.S274F | MISSENSE |
| c.419T>C | p.L140S | MISSENSE |
| c.1203G>C | p.L401L | SYNONYMOUS |
| c.1195C>T | p.R399C | MISSENSE |
| c.433G>A | p.A145T | MISSENSE |
| c.607G>A | p.E203K | MISSENSE |
| c.617C>T | p.S206F | MISSENSE |
| c.2053C>T | p.P685S | MISSENSE |
| c.2220C>A | p.F740L | MISSENSE |
| c.153C>T | p.A51A | SYNONYMOUS |
| c.25C>T | p.L9L | SYNONYMOUS |
| c.596G>A | p.G199E | MISSENSE |
| c.2332A>G | p.R778G | MISSENSE |
| c.998G>A | p.G333E | MISSENSE |
| c.302C>T | p.T101I | MISSENSE |
| c.290C>G | p.S97C | MISSENSE |
| c.654T>C | p.S218S | SYNONYMOUS |
| c.316G>A | p.G106S | MISSENSE |
| c.148G>A | p.A50T | MISSENSE |
| c.65G>A | p.G22E | MISSENSE |
| c.1471C>T | p.R491W | MISSENSE |
| c.1646C>T | p.S549F | MISSENSE |
| c.195C>T | p.H65H | SYNONYMOUS |
| c.1635G>A | p.G545G | SYNONYMOUS |
| c.108G>A | p.P36P | SYNONYMOUS |
| c.1668G>A | p.Q556Q | SYNONYMOUS |
| c.1819C>T | p.P607S | MISSENSE |
| c.96C>T | p.S32S | SYNONYMOUS |
| c.1216C>T | p.L406F | MISSENSE |
| c.3913G>A | p.D1305N | MISSENSE |
| c.2091G>A | p.Q697Q | SYNONYMOUS |
| c.589C>T | p.R197W | MISSENSE |
| c.731C>G | p.A244G | MISSENSE |
| c.335C>T | p.T112I | MISSENSE |
| c.2196C>T | p.I732I | SYNONYMOUS |

FIG. 10
CONTINUED

| | | | |
|---|---|---|---|
| COCH | CCDS9640.1 | Br27P | g.chr14:30424416C>T |
| COG5 | CCDS5742.1 | Br27P | g.chr7:106798271G>A |
| COG5 | CCDS5742.1 | Br15X | g.chr7:106515735A>G |
| COH1 | CCDS6280.1 | Br27P | g.chr8:100229314C>T |
| COH1 | CCDS6280.1 | Br11P | g.chr8:100916970A>C |
| COL14A1 | NM_021110 | Br07X | g.chr8:121391472C>T (HOMOZYGOUS) |
| COL18A1 | NM_030582 | Br27P | g.chr21:45724863G>A |
| COL23A1 | CCDS4436.1 | Br10P | g.chr5:177605917C>G |
| COL24A1 | NM_152890 | Br27P | g.chr1:85964126G>A |
| COL3A1 | CCDS2297.1 | Br9PT | g.chr2:189684824C>T |
| COL3A1 | CCDS2297.1 | Br11P | g.chr2:189693990C>T |
| COL3A1 | CCDS2297.1 | Br25X | g.chr2:189693991G>A |
| COL4A2 | NM_001846 | Br27P | g.chr13:109941590G>A |
| COL4A2 | NM_001846 | Br27P | g.chr13:109889015G>A |
| COL4A4 | NM_000092 | Br15X | g.chr2:227772380G>A |
| COL4A4 | NM_000092 | Br27P | g.chr2:227746289C>T |
| COL4A4 | NM_000092 | Br13X | g.chr2:227698287A>G |
| COL4A5 | CCDS14543.1 | Br04X | g.chrX:107656189C>T |
| COL5A3 | CCDS12222.1 | Br27P | g.chr19:9941335C>T |
| COL6A3 | NM_004369 | Br15X | g.chr2:238071893C>T |
| COL6A3 | NM_057167 | Br27P | g.chr2:238062591G>T |
| COL8A2 | CCDS403.1 | Br27P | g.chr1:36233584G>A |
| COPB | CCDS7815.1 | Br17X | g.chr11:14444432G>A |
| COQ2 | NM_015697 | Br27P | g.chr4:84551918C>T |
| CPB1 | NM_001871 | Br27P | g.chr3:150060415C>T |
| CPN1 | CCDS7486.1 | Br04X | g.chr10:101831232G>A (HOMOZYGOUS) |
| CPN1 | CCDS7486.1 | Br14X | g.chr10:101825715G>A (HOMOZYGOUS) |
| CPNE2 | CCDS10774.1 | Br27P | g.chr16:55710629C>T |
| CPNE4 | CCDS3072.1 | Br27P | g.chr3:132751540C>T |
| CPS1 | CCDS2393.1 | Br04X | g.chr2:211266579C>T |
| CPS1 | CCDS2393.1 | Br25X | g.chr2:211281096G>C |
| CPS1 | CCDS2393.1 | Br27P | g.chr2:211358515G>A |
| CPSF4 | CCDS5664.1 | Br27P | g.chr7:98696339G>A |
| CPT1B | CCDS14098.1 | Br27P | g.chr22:49298869C>T |
| CPT1C | CCDS12779.1 | Br27P | g.chr19:54905550C>T |
| CRA | CCDS942.1 | Br27P | g.chr1:146718400C>T |
| CRAT | CCDS6919.1 | Br27P | g.chr9:128942508G>A |
| CREB1 | CCDS2374.1 | Br27P | g.chr2:208265665C>T |
| CRIM2 | ENST00000257704 | Br27P | g.chr7:128124271C>T |
| CRISPLD1 | CCDS6219.1 | Br27P | g.chr8:76087316C>T |
| CRR9 | CCDS3862.1 | Br20P | g.chr5:1371499G>A |
| CRX | CCDS12706.1 | Br10P | g.chr19:53034727G>A |
| CRY2 | CCDS7915.1 | Br27P | g.chr11:45847672C>T |
| CRYAA | CCDS13695.1 | Br27P | g.chr21:43463779C>T |
| CSK | CCDS10269.1 | Br27P | g.chr15:72878223C>T |
| CSMD1 | NM_033225 | Br27P | g.chr8:3032853C>T |
| CSN3 | CCDS3538.1 | Br13X | g.chr4:71295569A>G |
| CSNK2A2 | CCDS10794.1 | Br27P | g.chr16:56758648G>A |
| CSPG2 | CCDS4060.1 | Br27P | g.chr5:82869679G>A |
| CSPG5 | CCDS2757.1 | Br27P | g.chr3:47594194G>A |

FIG. 10
CONTINUED

| | | |
|---|---|---|
| c.799C>T | p.P267S | MISSENSE |
| c.115G>A | p.V39I | MISSENSE |
| c.1629A>G | p.A543A | SYNONYMOUS |
| c.1913C>T | p.T638I | MISSENSE |
| c.9845A>C | p.K3282T | MISSENSE |
| c.4445C>T | p.P1482L | MISSENSE |
| IVS11+1G>A | SPLICE SITE | SPLICE SITE |
| IVS23-3C>G | SPLICE SITE | SPLICE SITE |
| c.3991G>A | p.A1331T | MISSENSE |
| c.1345C>T | p.R449C | MISSENSE |
| c.2632C>T | p.R878C | MISSENSE |
| c.2633G>A | p.R878H | MISSENSE |
| c.3356G>A | p.G1119E | MISSENSE |
| c.911G>A | p.R304K | MISSENSE |
| c.1652G>A | p.G551D | MISSENSE |
| c.2593C>T | p.P865S | MISSENSE |
| c.4761A>G | p.P1587P | SYNONYMOUS |
| c.2317C>T | p.P773S | MISSENSE |
| c.4014C>T | p.P1338P | SYNONYMOUS |
| c.1562C>T | p.S521L | MISSENSE |
| c.3451G>T | p.V1151L | MISSENSE |
| c.791G>A | p.G264E | MISSENSE |
| c.2262G>A | p.Q754Q | SYNONYMOUS |
| c.602C>T | p.A201V | MISSENSE |
| c.1182C>T | p.I394I | SYNONYMOUS |
| c.141G>A | p.R47R | SYNONYMOUS |
| c.363G>A | p.T121T | SYNONYMOUS |
| c.529C>T | p.P177S | MISSENSE |
| c.1251C>T | p.I417I | SYNONYMOUS |
| c.240C>T | p.Y80Y | SYNONYMOUS |
| c.907G>C | p.A303P | MISSENSE |
| IVS34+1G>A | SPLICE SITE | SPLICE SITE |
| c.670G>A | p.V224I | MISSENSE |
| c.2139C>T | p.G713G | SYNONYMOUS |
| c.1728C>T | p.F576F | SYNONYMOUS |
| c.741C>T | p.H247H | SYNONYMOUS |
| c.820G>A | p.D274N | MISSENSE |
| c.669C>T | p.S223S | SYNONYMOUS |
| c.2406C>T | p.C802C | SYNONYMOUS |
| c.352C>T | p.Q118X | NONSENSE |
| c.1602G>A | p.A534A | SYNONYMOUS |
| c.591G>A | p.P197P | SYNONYMOUS |
| c.922C>T | p.Q308X | NONSENSE |
| c.273C>T | p.D91D | SYNONYMOUS |
| c.133C>T | p.P45S | MISSENSE |
| c.5568C>T | p.S1856S | SYNONYMOUS |
| c.182A>G | p.N61S | MISSENSE |
| c.690G>A | p.R230R | SYNONYMOUS |
| c.5101G>A | p.V1701M | MISSENSE |
| c.326G>A | p.G109E | MISSENSE |

FIG. 10
CONTINUED

| | | | |
|---|---|---|---|
| CSPG6 | NM_005445 | Br20P | g.chr10:112325084C>T |
| CSTF1 | CCDS13452.1 | Br27P | g.chr20:54404114C>T |
| CTEN | CCDS11368.1 | Br05X | g.chr17:35896828C>A |
| CTNNA2 | NM_004389 | Br07X | g.chr2:80747066G>A |
| CTNNA3 | CCDS7269.1 | Br27P | g.chr10:68610122C>T |
| CTSW | CCDS8117.1 | Br27P | g.chr11:65407132G>A |
| CUBN | CCDS7113.1 | Br12P | g.chr10:17123136A>T |
| CUGBP1 | CCDS7938.1 | Br27P | g.chr11:47462615C>T |
| CUGBP1 | CCDS7939.1 | Br27P | g.chr11:47455001G>A |
| CUL4B | NM_003588 | Br27P | g.chrX:119476321G>A |
| CUTL1 | CCDS5721.1 | Br27P | g.chr7:101438232C>T |
| CX40.1 | CCDS7191.1 | Br27P | g.chr10:35937292C>T |
| CXCR3 | CCDS14416.1 | Br05X | g.chrX:70619233C>T (HOMOZYGOUS) |
| CXorf17 | CCDS14356.1 | Br27P | g.chrX:54069008C>T |
| CXorf20 | CCDS14184.1 | Br23X | g.chrX:17955368G>A |
| CXorf27 | ENST00000341016 | Br02X | g.chrX:37606403G>A (HOMOZYGOUS) |
| CXorf37 | CCDS14322.1 | Br25X | g.chrX:48856200G>A (HOMOZYGOUS) |
| CXXC5 | NM_016463 | Br27P | g.chr5:139041147G>A |
| CYBB | CCDS14242.1 | Br27P | g.chrX:37414473G>C |
| CYP26C1 | CCDS7425.1 | Br03X | g.chr10:94818111G>A (HOMOZYGOUS) |
| CYP2C19 | CCDS7436.1 | Br07x | g.chr10:96592767C>T |
| CYP2R1 | CCDS7818.1 | Br27P | g.chr11:14858371C>T |
| CYP4F12 | NM_023944 | Br05X | g.chr19:15667782C>T |
| CYP4F12 | NM_023944 | Br9PT | g.chr19:15650138C>T |
| DAB2IP | CCDS6832.1 | Br11P | g.chr9:121614666G>A |
| DCBLD2 | NM_080927 | Br27P | g.chr3:100001354G>C |
| DCC | CCDS11952.1 | Br27P | g.chr18:48937844C>T |
| DCT | CCDS9470.1 | Br27P | g.chr13:93912394G>A |
| DCTN4 | CCDS4310.1 | Br06X | g.chr5:150078134G>T |
| DDB1 | NM_001923 | Br27P | g.chr11:60853576C>T |
| DDR1 | CCDS4690.1 | Br27P | g.chr6:30972618G>A |
| DDX1 | CCDS1686.1 | Br27P | g.chr2:15711008G>A |
| DDX1 | CCDS1686.1 | Br27P | g.chr2:15693314G>A |
| DDX31 | CCDS6951.1 | Br27P | g.chr9:132574954G>A |
| DDX54 | NM_024072 | Br25X | g.chr12:112063803C>G |
| DEFB112 | NM_001037498 | Br14X | g.chr6:50124236C>T (HOMOZYGOUS) |
| DEFB125 | CCDS12989.1 | Br14X | g.chr20:24953G>T |
| DELGEF | CCDS7828.1 | Br27P | g.chr11:17973973C>T |
| DEPDC5 | NM_014662 | Br13X | g.chr22:30567431G>T |
| DFNB31 | CCDS6806.1 | Br27P | g.chr9:114320539G>A |
| DGCR6 | CCDS13753.1 | Br27P | g.chr22:17273070G>A |
| DGKD | CCDS2504.1 | Br27P | g.chr2:234140016G>A |
| DHPS | CCDS12276.1 | Br14X | g.chr19:12653377C>T (HOMOZYGOUS) |
| DHX29 | NM_019030 | Br27P | g.chr5:54601040G>A |
| DIO3 | NM_001362 | Br27P | g.chr14:101097940G>A |
| DKFZp434I099 | CCDS10787.1 | Br17X | g.chr16:56314542C>T |
| DKFZp547A023 | CCDS845.1 | Br27P | g.chr1:112711988C>T |
| DKFZp547A023 | CCDS845.1 | Br27P | g.chr1:112711154C>T |
| DKFZp547B1713 | CCDS1591.1 | Br27P | g.chr1:227683603C>T |
| DKFZP564B1023 | CCDS1403.1 | Br05X | g.chr1:197364814G>C |

FIG. 10
CONTINUED

| | | |
|---|---|---|
| c.131C>T | p.A44V | MISSENSE |
| c.99C>T | p.G33G | SYNONYMOUS |
| c.1274C>A | p.T425N | MISSENSE |
| c.2398G>A | p.V800M | MISSENSE |
| c.1006C>T | p.R336C | MISSENSE |
| c.762G>A | p.L254L | SYNONYMOUS |
| c.3919A>T | p.N1307Y | MISSENSE |
| c.347C>T | p.S116F | MISSENSE |
| c.967G>A | p.A323T | MISSENSE |
| c.109G>A | p.E37K | MISSENSE |
| c.2220C>T | p.I740I | SYNONYMOUS |
| c.845C>T | p.S282F | MISSENSE |
| UTR+3C>T | 3'UTR | 3'UTR |
| c.762C>T | p.F254F | SYNONYMOUS |
| c.1608G>A | p.P536P | SYNONYMOUS |
| c.94G>A | p.V32M | MISSENSE |
| c.615G>A | p.S205S | SYNONYMOUS |
| c.570G>A | p.K190K | SYNONYMOUS |
| c.727G>C | p.V243L | MISSENSE |
| c.1236G>A | p.R412R | SYNONYMOUS |
| c.1145C>T | p.P382L | MISSENSE |
| c.887C>T | p.S296F | MISSENSE |
| c.1152C>T | p.C384C | SYNONYMOUS |
| c.266C>T | p.T89M | MISSENSE |
| c.1933G>A | p.V645I | MISSENSE |
| c.1880G>C | p.G627A | MISSENSE |
| c.1382C>T | p.T461I | MISSENSE |
| c.914G>A | p.G305D | MISSENSE |
| c.968G>T | p.S323I | MISSENSE |
| c.384C>T | p.C128C | SYNONYMOUS |
| c.1755G>A | p.G585G | SYNONYMOUS |
| c.1285G>A | p.V429I | MISSENSE |
| c.352G>A | p.E118K | MISSENSE |
| c.237G>A | p.S79S | SYNONYMOUS |
| IVS15-4C>G | SPLICE SITE | SPLICE SITE |
| c.88C>T | p.R30X | NONSENSE |
| c.354G>T | p.M118I | MISSENSE |
| c.568C>T | p.P190S | MISSENSE |
| c.3052G>T | p.E1018X | NONSENSE |
| c.685G>A | p.V229I | MISSENSE |
| c.488G>A | p.G163D | MISSENSE |
| c.1882G>A | p.E628K | MISSENSE |
| c.204C>T | p.A68A | SYNONYMOUS |
| c.3252G>A | p.K1084K | SYNONYMOUS |
| c.276G>A | p.W92X | NONSENSE |
| c.1536C>T | p.R512R | SYNONYMOUS |
| c.1832C>T | p.T611I | MISSENSE |
| c.998C>T | p.T333I | MISSENSE |
| c.20C>T | p.A7V | MISSENSE |
| c.862G>C | p.E288Q | MISSENSE |

FIG. 10 CONTINUED

| | | | |
|---|---|---|---|
| DKFZp564I1922 | CCDS14124.1 | Br07x | g.chrX:3234086C>T |
| DKFZp761L1417 | CCDS5658.1 | Br08X | g.chr7:98090906T>C |
| DKFZp761N1114 | CCDS1455.1 | Br27P | g.chr1:202293007G>A |
| DLD | CCDS5749.1 | Br27P | g.chr7:107152438G>A |
| DLEC1 | ENST00000337335 | Br27P | g.chr3:38114268C>T |
| DLEC1 | ENST00000337335 | Br27P | g.chr3:38114287C>T |
| DLGAP2 | NM_004745 | Br27P | g.chr8:1612130A>G |
| DLGAP2 | NM_004745 | Br26X | g.chr8:1632768T>A |
| DLGAP2 | NM_004745 | Br27P | g.chr8:1636761G>A |
| DLGAP2 | NM_004745 | Br27P | g.chr8:1485167G>A |
| DMN | NM_015286 | Br08X | g.chr15:97487568G>A |
| DMTF1 | CCDS5601.1 | Br27P | g.chr7:86458488C>T |
| DNAH1 | NM_015512 | Br27P | g.chr3:52372148C>T |
| DNAH10 | CCDS9255.1 | Br27P | g.chr12:122799405G>A |
| DNAH11 | NM_003777 | Br27P | g.chr7:21713926C>T |
| DNAH3 | CCDS10594.1 | Br27P | g.chr16:20867333C>T |
| DNAH3 | CCDS10594.1 | Br11P | g.chr16:209960912G>A |
| DNAH5 | CCDS3882.1 | Br27P | g.chr5:13864853G>A |
| DNAH8 | CCDS4838.1 | Br17X | g.chr6:38810301G>A |
| DNAH9 | CCDS11160.1 | Br03X | g.chr17:11781538G>A |
| DNAH9 | CCDS11160.1 | Br27P | g.chr17:11786432C>T |
| DNAI2 | CCDS11697.1 | Br27P | g.chr17:69789555G>A |
| DNCH1 | CCDS9966.1 | Br27P | g.chr14:101511876G>A |
| DNCH1 | CCDS9966.1 | Br20P | g.chr14:101558902C>T |
| DNCLI2 | CCDS10818.1 | Br17X | 4032_65334009dupGTACCACAAAGGCCT |
| DNHD3 | NM_020877 | Br25X | g.chr17:7635980G>A |
| DNTTIP1 | CCDS13369.1 | Br27P | g.chr20:43863128G>A |
| DOCK4 | NM_014705 | Br27P | g.chr7:110999193C>T |
| DOCK8 | CCDS6440.1 | Br27P | g.chr9:404942G>A |
| DOCK9 | NM_015296 | Br27P | g.chr13:98281996G>A |
| DOK6 | NM_152721 | Br25X | g.chr18:65576033C>T |
| DONSON | CCDS13632.1 | Br23X | g.chr21:33882755C>G |
| DRCTNNB1A | CCDS5377.1 | Br16X | g.chr7:22758535C>T |
| DRD3 | CCDS2978.1 | Br05X | g.chr3:115332900G>A |
| DRG1 | CCDS13897.1 | Br15X | g.chr22:30143902G>A |
| DSG1 | CCDS11896.1 | Br27P | g.chr18:27170353T>C |
| DSG2 | NM_001943 | Br26X | g.chr18:27332233C>T |
| DSG3 | CCDS11898.1 | Br27P | g.chr18:27303304C>T |
| DSG4 | CCDS11897.1 | Br16X | g.chr18:27240203C>T |
| DSG4 | CCDS11897.1 | Br26X | g.chr18:27225138G>A |
| DSPP | NM_014208 | Br27P | g.chr4:88892193G>A |
| DST | CCDS4959.1 | Br27P | g.chr6:56604068G>A |
| DST | CCDS4959.1 | Br27P | g.chr6:56613211C>T |
| DTX1 | CCDS9164.1 | Br27P | g.chr12:111978112C>T |
| DTX4 | ENST00000227451 | Br27P | g.chr11:58706180G>A |
| DULLARD | CCDS11093.1 | Br27P | g.chr17:7088593G>A |
| DUSP22 | CCDS4468.1 | Br07X | g.chr6:293155G>A |
| DUSP3 | CCDS11469.1 | Br9PT | g.chr17:39202506delC |
| DYRK3 | NM_001004023 | Br27P | g.chr1:203209612G>A |
| DZIP3 | CCDS2952.1 | Br27P | g.chr3:109874107G>A |

FIG. 10
CONTINUED

| | | |
|---|---|---|
| c.3001C>T | p.L1001F | MISSENSE |
| c.1070T>C | p.I357T | MISSENSE |
| c.1232G>A | p.G411D | MISSENSE |
| c.1355G>A | p.G452E | MISSENSE |
| c.560C>T | p.P187L | MISSENSE |
| c.579C>T | p.S193S | SYNONYMOUS |
| c.1987A>G | p.T663A | MISSENSE |
| c.2605T>A | p.W869R | MISSENSE |
| c.2710G>A | p.E904K | MISSENSE |
| c.901G>A | p.E301K | MISSENSE |
| c.1480G>A | p.V494I | MISSENSE |
| c.945C>T | p.T315T | SYNONYMOUS |
| c.5192C>T | p.A1731V | MISSENSE |
| c.943G>A | p.G315R | MISSENSE |
| c.13386C>T | p.C4462C | SYNONYMOUS |
| c.11316C>T | p.Y3772Y | SYNONYMOUS |
| c.4576G>A | p.A1526T | MISSENSE |
| c.7310G>A | p.R2437H | MISSENSE |
| c.33G>A | p.P11P | SYNONYMOUS |
| c.12634G>A | p.G4212R | MISSENSE |
| c.12748C>T | p.P4250S | MISSENSE |
| c.4G>A | p.E2K | MISSENSE |
| c.331G>A | p.V111I | MISSENSE |
| c.8569C>T | p.H2857Y | MISSENSE |
| c.339_362dupGTACCACAAAGGCCTGCTGAAATT | INDEL | INDEL |
| c.6921G>A | p.E2307E | SYNONYMOUS |
| c.381G>A | p.L127L | SYNONYMOUS |
| c.3925C>T | p.Q1309X | NONSENSE |
| c.3487G>A | p.D1163N | MISSENSE |
| c.4294G>A | p.V1432I | MISSENSE |
| c.800C>T | p.A267V | MISSENSE |
| c.63C>G | p.L21L | SYNONYMOUS |
| c.1479C>T | p.Y493Y | SYNONYMOUS |
| c.761G>A | p.R254H | MISSENSE |
| c.665G>A | p.R222H | MISSENSE |
| c.1044T>C | p.S348S | SYNONYMOUS |
| c.21C>T | p.R7R | SYNONYMOUS |
| c.1891C>T | p.L631L | SYNONYMOUS |
| c.1802C>T | p.A601V | MISSENSE |
| c.784G>A | p.V262I | MISSENSE |
| c.1200G>A | p.E400E | SYNONYMOUS |
| c.2431G>A | p.A811T | MISSENSE |
| c.568C>T | p.P190S | MISSENSE |
| c.423C>T | p.D141D | SYNONYMOUS |
| c.96G>A | p.A286T | MISSENSE |
| IVS7+1G>A | SPLICE SITE | SPLICE SITE |
| c.316G>A | p.V106I | MISSENSE |
| c.555delC | fs | INDEL |
| c.614G>A | p.R205K | MISSENSE |
| c.2503G>A | p.E835K | MISSENSE |

FIG. 10
CONTINUED

| Gene | Accession | Sample | Variant |
|---|---|---|---|
| E2F4 | NM_001950 | Br04X | g.chr16:65784512C>T |
| EAF1 | CCDS2626.1 | Br08X | g.chr3:15453048G>T |
| EBF | CCDS4343.1 | Br08X | g.chr5:158071816C>T |
| EBF3 | NM_001005463 | Br27P | g.chr10:131556126G>T |
| ECEL1 | CCDS2493.1 | Br13X | g.chr2:233174379C>T |
| ECEL1 | CCDS2493.1 | Br27P | g.chr2:233171842G>A |
| ECHDC2 | CCDS571.1 | Br07X | g.chr1:53085564A>G |
| ECOP | NM_030796 | Br05X | g.chr7:55334248G>A |
| EDD1 | NM_015902 | Br23X | g.chr8:103354043G>A |
| EDG3 | CCDS6680.1 | Br27P | g.chr9:88846179C>T |
| EDG8 | CCDS12240.1 | Br17X | g.chr19:10486558C>T |
| EEF1A1 | ENST00000331523 | Br26X | g.chr5:99360721A>G |
| EFCBP1 | NM_022351 | Br27P | g.chr8:92032543C>T |
| EFHC2 | NM_025184 | Br27P | g.chrX:43857775G>A |
| EGF | CCDS3689.1 | Br27P | g.chr4:111192180C>T |
| EGFR | CCDS5514.1 | Br02X | g.chr7:55007252G>T (HOMOZYGOUS) |
| EGFR | CCDS5514.1 | Br20P | g.chr7:54994474T>G |
| EHBP1L1 | ENST00000309295 | Br14X | g.chr11:65106679C>T |
| EIF2A | NM_032025 | Br27P | g.chr3:151782223C>T |
| EIF3S12 | CCDS12517.1 | Br27P | g.chr19:43806626C>T |
| EIF4G1 | CCDS3259.1 | Br04X | g.chr3:185525375A>T |
| EIF4G2 | NM_001418 | Br27P | g.chr11:10784151C>T |
| EME2 | NM_001010865 | Br26X | g.chr16:1766094C>T |
| EML4 | CCDS1807.1 | Br15X | g.chr2:42456214C>A |
| EMR4 | ENST00000359590 | Br06X | g.chr19:6932130G>A |
| EN2 | CCDS5940.1 | Br03X | g.chr7:154754861C>T |
| ENO1 | CCDS97.1 | Br27P | g.chr1:8859757G>A |
| ENPP2 | CCDS6329.1 | Br14X | g.chr8:120677325A>G |
| ENPP2 | CCDS6329.1 | Br13X | g.chr8:120667672C>G |
| ENPP6 | CCDS3834.1 | Br05X | g.chr4:185413167A>G (HOMOZYGOUS) |
| ENPP7 | CCDS11763.1 | Br27P | g.chr17:75323463C>T |
| ENPP7 | CCDS11763.1 | Br27P | g.chr17:75323749C>T |
| ENSA | CCDS958.1 | Br27P | g.chr1:147413099G>A |
| ENST00000294635 | ENST00000294635 | Br27P | g.chr1:74657904C>T |
| ENST00000310882 | ENST00000310882 | Br17X | g.chr19:22112927G>A |
| ENST00000326382 | ENST00000326382 | Br27P | g.chr7:75509139C>T |
| ENST00000328067 | ENST00000328067 | Br08X | g.chr7:143292764G>A |
| ENST00000331583 | ENST00000331583 | Br27P | g.chr1:209990554G>A |
| ENST00000334627 | ENST00000334627 | Br03X | g.chr2:106363959C>T |
| ENST00000336168 | ENST00000336168 | Br27P | g.chr22:23607224G>A |
| ENST00000336168 | ENST00000336168 | Br27P | g.chr22:23576119C>T |
| ENST00000355177 | ENST00000355177 | Br07X | g.chr8:27261015G>A (HOMOZYGOUS) |
| ENST00000355324 | ENST00000355324 | Br14X | g.chr6:32535582C>A |
| ENST00000355324 | ENST00000355324 | Br13X | g.chr6:32535582C>G (HOMOZYGOUS) |
| ENST00000355607 | ENST00000355607 | Br27P | g.chr11:4867746G>A |
| ENST00000357689 | ENST00000357689 | Br02X | g.chr18:3124161dupA |
| ENST00000358347 | ENST00000358347 | Br27P | g.chr19:53875256C>T |
| ENST00000359736 | ENST00000359736 | Br27P | g.chr14:69108537G>A |
| EPB41L2 | CCDS5141.1 | Br27P | g.chr6:131232577C>T |
| EPB41L4B | NM_019114 | Br07X | g.chr9:109055589G>A (HOMOZYGOUS) |

FIG. 10 CONTINUED

| | | |
|---|---|---|
| c.345C>T | p.D115D | SYNONYMOUS |
| c.722G>T | p.S241I | MISSENSE |
| c.1473C>T | p.Y491Y | SYNONYMOUS |
| c.795G>T | p.W265C | MISSENSE |
| c.1244C>T | p.P415L | MISSENSE |
| c.1868G>A | p.G623D | MISSENSE |
| c.361A>G | p.I121V | MISSENSE |
| c.264G>A | p.P88P | SYNONYMOUS |
| c.6863G>A | p.G2288D | MISSENSE |
| c.510C>T | p.A170A | SYNONYMOUS |
| c.130C>T | p.L44L | SYNONYMOUS |
| c.551A>G | p.Y184C | MISSENSE |
| c.965C>T | p.T322I | MISSENSE |
| c.1126G>A | p.V376I | MISSENSE |
| c.85C>T | p.P29S | MISSENSE |
| c.1793G>T | p.G598V | MISSENSE |
| c.655T>G | p.C219G | MISSENSE |
| c.1921C>T | p.Q641X | NONSENSE |
| c.1618C>T | p.L540L | SYNONYMOUS |
| c.228C>T | p.N76N | SYNONYMOUS |
| c.2627A>T | p.E876V | MISSENSE |
| c.127C>T | p.P43S | MISSENSE |
| c.1189C>T | p.R397W | MISSENSE |
| IVS18-4C>A | SPLICE SITE | SPLICE SITE |
| c.502G>A | p.A168T | MISSENSE |
| UTR+3C>T | 3'UTR | 3'UTR |
| c.718G>A | p.V240M | MISSENSE |
| c.1071A>G | p.K357K | SYNONYMOUS |
| c.1458C>G | p.H486Q | MISSENSE |
| c.846A>G | p.K282K | SYNONYMOUS |
| c.426C>T | p.Y142Y | SYNONYMOUS |
| c.712C>T | p.R238C | MISSENSE |
| c.100G>A | p.E34K | MISSENSE |
| c.858C>T | p.L286L | SYNONYMOUS |
| c.178G>A | p.E60K | MISSENSE |
| c.104C>T | p.A35V | MISSENSE |
| c.752G>A | p.R251Q | MISSENSE |
| c.261G>A | p.R87R | SYNONYMOUS |
| c.69C>T | p.I23I | SYNONYMOUS |
| c.2297G>A | p.G766E | MISSENSE |
| c.848C>T | p.S283F | MISSENSE |
| c.327G>A | p.W109X | NONSENSE |
| c.261C>A | p.H87Q | MISSENSE |
| c.261C>G | p.H87Q | MISSENSE |
| c.608G>A | p.G203D | MISSENSE |
| c.108dupA | fs | INDEL |
| c.164C>T | p.P55L | MISSENSE |
| c.1508G>A | p.R503Q | MISSENSE |
| c.2426C>T | p.T809I | MISSENSE |
| c.1698G>A | p.L566L | SYNONYMOUS |

FIG. 10
CONTINUED

| | | | |
|---|---|---|---|
| EPB49 | CCDS6020.1 | Br27P | g.chr8:21983345C>T |
| EPC1 | CCDS7172.1 | Br27P | g.chr10:32600999G>A |
| EPHA2 | CCDS169.1 | Br27P | g.chr1:16203547C>T |
| EPHA5 | CCDS3513.1 | Br07X | g.chr4:66042690delT |
| EPHA6 | ENST00000334709 | Br05X | g.chr3:98839497G>C |
| EPHA8 | CCDS225.1 | Br04X | g.chr1:22670819C>T (HOMOZYGOUS) |
| EPO | CCDS5705.1 | Br26X | g.chr7:99964998C>T |
| ERCC5 | NM_000123 | Br11P | g.chr13:102313361C>G |
| ERF | CCDS12600.1 | Br27P | g.chr19:47444614G>A |
| ERN1 | NM_001433 | Br27P | g.chr17:59495158C>T |
| ESCO2 | NM_001017420 | Br27P | g.chr8:27706167C>T |
| ESPNP | ENST00000270691 | Br27P | g.chr1:16771684C>T |
| ESR1 | CCDS5234.1 | Br07X | g.chr6:152357683C>T |
| ESR2 | CCDS9762.1 | Br17X | g.chr14:63786151delG |
| ETV1 | NM_004956 | Br27P | g.chr7:13744503C>G |
| EVI1 | CCDS3205.1 | Br27P | g.chr3:170290545G>A |
| EVPL | CCDS11737.1 | Br27P | g.chr17:71523187C>T |
| EXOC6B | ENST00000272427 | Br15X | g.chr2:72318160G>T |
| EXOC6B | ENST00000272427 | Br27P | g.chr2:72518562C>T |
| EXTL1 | CCDS271.1 | Br27P | g.chr1:26045806G>T |
| F13B | CCDS1388.1 | Br16X | g.chr1:193756636T>C |
| F2RL1 | CCDS4033.1 | Br14X | g.chr5:76164865G>C |
| F3 | CCDS750.1 | Br27P | g.chr1:94713672G>A |
| F5 | CCDS1281.1 | Br07X | g.chr1:166251632G>A |
| FAD158 | CCDS725.1 | Br27P | g.chr1:89891718G>A |
| FADS1 | CCDS8011.1 | Br27P | g.chr11:61340759C>T |
| FAM43A | NM_153690 | Br27P | g.chr3:195889463G>A |
| FAM46B | CCDS294.1 | Br27P | g.chr1:27017291C>T |
| FAM47A | NM_203408 | Br27P | g.chrX:33908975T>A |
| FAM48A | ENST00000360252 | Br27P | g.chr13:36510638C>G |
| FAM63B | NM_019092 | Br27P | g.chr15:56850904G>A |
| FAM78B | NM_001017961 | Br27P | g.chr1:162867048G>A |
| FAM92B | NM_198491 | Br27P | g.chr16:83696470G>A |
| FANCA | NM_000135 | Br27P | g.chr16:88352505C>T |
| FANCD2 | CCDS2595.1 | Br02X | g.chr3:10091272dupT |
| FASN | CCDS11801.1 | Br27P | g.chr17:77644540G>A |
| FAT | NM_005245 | Br15X | g.chr4:187885152A>G |
| FBN3 | CCDS12196.1 | Br14X | g.chr19:8044008G>A |
| FBXO40 | NM_016298 | Br03X | g.chr3:122823199G>A |
| FBXW7 | CCDS3777.1 | Br27P | g.chr4:153604789C>T |
| FCGBP | CCDS12546.1 | Br15X | g.chr19:45100663C>A |
| FCHSD1 | NM_033449 | Br27P | g.chr5:141004098G>A |
| FECH | CCDS11964.1 | Br27P | g.chr18:53372525C>T |
| FEZ1 | NM_005103 | Br04X | g.chr11:124864772dupC |
| FGD1 | CCDS14359.1 | Br27P | g.chrX:54356791G>A |
| FGD4 | CCDS8727.1 | Br02X | g.chr12:32669913G>A |
| FGF2 | NM_002006 | Br14X | g.chr4:124155122A>G |
| FGFR3 | CCDS3353.1 | Br08X | g.chr4:1773911G>A |
| FGIF | CCDS8300.1 | Br27P | g.chr11:93870897C>T |
| FIGF | CCDS14166.1 | Br23X | g.chrX:15130895A>G |

FIG. 10
CONTINUED

| | | |
|---|---|---|
| c.402C>T | p.S134S | SYNONYMOUS |
| c.2035G>A | p.V679M | MISSENSE |
| c.2450C>T | p.P817L | MISSENSE |
| IVS14-3delT | SPLICE SITE | INDEL |
| c.838G>C | p.V280L | MISSENSE |
| c.2361C>T | p.D787D | SYNONYMOUS |
| c.307C>T | p.R103W | MISSENSE |
| c.1861C>G | p.Q621E | MISSENSE |
| c.1490G>A | p.G497D | MISSENSE |
| c.1007C>T | p.P336L | MISSENSE |
| c.1417C>T | p.P473S | MISSENSE |
| c.1308C>T | p.R436R | SYNONYMOUS |
| c.1022C>T | p.S341L | MISSENSE |
| c.1091delG | fs | INDEL |
| c.666C>G | p.F222L | MISSENSE |
| c.2782G>A | p.D928N | MISSENSE |
| c.1828C>T | p.L610F | MISSENSE |
| c.1006G>T | p.A336S | MISSENSE |
| c.684C>T | p.L228L | SYNONYMOUS |
| c.1857G>T | p.G619G | SYNONYMOUS |
| c.1220T>C | p.V407A | MISSENSE |
| c.677G>C | p.C226S | MISSENSE |
| c.282G>A | p.E94E | SYNONYMOUS |
| c.1300G>A | p.V434M | MISSENSE |
| c.1568G>A | p.G523D | MISSENSE |
| c.48C>T | p.T16T | SYNONYMOUS |
| c.611G>A | p.R204Q | MISSENSE |
| c.561C>T | p.S187S | SYNONYMOUS |
| c.1078T>A | p.S360T | MISSENSE |
| c.104C>G | p.T35R | MISSENSE |
| c.18G>A | p.E6E | SYNONYMOUS |
| c.96G>A | p.T32T | SYNONYMOUS |
| c.501G>A | p.V167V | SYNONYMOUS |
| c.2962C>T | p.L988L | SYNONYMOUS |
| c.2774dupT | fs | INDEL |
| c.499G>A | p.A167T | MISSENSE |
| c.13510A>G | p.K4504E | MISSENSE |
| c.7876G>A | p.A2626T | MISSENSE |
| c.233G>A | p.R78H | MISSENSE |
| c.1618C>T | p.H540Y | MISSENSE |
| c.4016C>A | p.P1339H | MISSENSE |
| c.1734G>A | p.R578R | SYNONYMOUS |
| c.1042C>T | p.L348L | SYNONYMOUS |
| c.112dupC | fs | INDEL |
| c.2554G>A | p.V852M | MISSENSE |
| c.1694G>A | p.C565Y | MISSENSE |
| c.619A>G | p.I207V | MISSENSE |
| c.1396G>A | p.E466K | MISSENSE |
| c.271C>T | p.R91W | MISSENSE |
| c.694A>G | p.K232E | MISSENSE |

FIG. 10
CONTINUED

| | | | |
|---|---|---|---|
| FLII | CCDS11192.1 | Br27P | g.chr17:18091971G>A |
| FLJ10276 | CCDS363.1 | Br05X | g.chr1:32513483A>G |
| FLJ10514 | CCDS1311.1 | Br27P | g.chr1:170554272G>A |
| FLJ10514 | CCDS1311.1 | Br17X | g.chr1:170539044A>G |
| FLJ11088 | CCDS8716.1 | Br27P | g.chr12:28351015G>A |
| FLJ11535 | CCDS12043.1 | Br27P | g.chr19:772530C>T |
| FLJ12529 | CCDS8006.1 | Br27P | g.chr11:60940424C>T |
| FLJ12644 | CCDS12843.1 | Br27P | g.chr19:57086230G>A |
| FLJ12671 | CCDS1153.1 | Br27P | g.chr1:153510252G>A |
| FLJ12700 | CCDS5898.1 | Br27P | g.chr7:148756207C>T |
| FLJ13273 | CCDS3672.1 | Br27P | g.chr4:106996452C>T |
| FLJ13576 | CCDS5757.1 | Br13X | g.chr7:112018093T>A |
| FLJ13725 | CCDS10840.1 | Br27P | g.chr16:66136884G>A |
| FLJ13841 | CCDS11819.1 | Br27P | g.chr17:78381727G>A |
| FLJ13941 | CCDS40.1 | Br26X | g.chr1:2349494C>T |
| FLJ14397 | CCDS1945.1 | Br27P | g.chr2:74620958G>A |
| FLJ16165 | NM_001004318 | Br27P | g.chr19:44289446C>T |
| FLJ16331 | NM_001004326 | Br27P | g.chr11:64738196G>A |
| FLJ16478 | NM_001004341 | Br27P | g.chr1:153875934C>T |
| FLJ20035 | NM_017631 | Br11P | g.chr4:169571321C>T |
| FLJ20097 | ENST00000317751 | Br27P | g.chr7:92565717C>T |
| FLJ20186 | CCDS10989.1 | Br04X | g.chr16:88548186C>T |
| FLJ20232 | CCDS13995.1 | Br27P | g.chr22:38234449G>A |
| FLJ20272 | NM_017735 | Br25X | g.chr2:32895125G>A |
| FLJ20294 | NM_017749 | Br11P | g.chr11:46411689C>T |
| FLJ20298 | CCDS14522.1 | Br13X | g.chrX:105890141G>A |
| FLJ21159 | CCDS3792.1 | Br27P | g.chr4:156639161G>A |
| FLJ21963 | CCDS9022.1 | Br27P | g.chr12:80149797G>A |
| FLJ22709 | CCDS12351.1 | Br27P | g.chr19:17198552G>A |
| FLJ23049 | CCDS3199.1 | Br27P | g.chr3:168489411G>A |
| FLJ23447 | CCDS12300.1 | Br27P | g.chr19:13905800C>T |
| FLJ23577 | ENST00000303168 | Br27P | g.chr5:35775790delT |
| FLJ23577 | CCDS3910.1 | Br17X | g.chr5:35690509C>G |
| FLJ23790 | CCDS6346.1 | Br05X | g.chr8:124887510G>A |
| FLJ25715 | NM_182570 | Br27P | g.chr18:75540448C>T |
| FLJ25715 | NM_182570 | Br27P | g.chr18:75503080G>A |
| FLJ25715 | NM_182570 | Br27P | g.chr18:75502987G>A |
| FLJ25801 | CCDS3850.1 | Br08X | g.chr4:189401232T>A |
| FLJ25801 | CCDS3850.1 | Br17X | g.chr4:189388102G>A |
| FLJ27465 | NM_001039843 | Br26X | g.chr15:99346452C>T |
| FLJ27465 | NM_001039843 | Br26X | g.chr15:99282375G>A |
| FLJ30525 | CCDS787.1 | Br04X | g.chr1:108905031C>T |
| FLJ30655 | CCDS3740.1 | Br27P | g.chr4:130235848G>A |
| FLJ30707 | CCDS9427.1 | Br27P | g.chr13:50753176C>T |
| FLJ31438 | NM_152385 | Br17X | g.chr2:55316398G>A |
| FLJ32796 | CCDS1507.1 | Br27P | g.chr1:209187813G>A |
| FLJ32934 | CCDS1082.1 | Br27P | g.chr1:151819045G>A |
| FLJ33167 | CCDS3837.1 | Br27P | g.chr4:185978613G>A |
| FLJ33387 | CCDS9783.1 | Br27P | g.chr14:67010125C>T |
| FLJ34512 | CCDS10424.1 | Br27P | g.chr16:714935C>T |

FIG. 10
CONTINUED

| | | |
|---|---|---|
| c.2292G>A | p.R764R | SYNONYMOUS |
| c.514A>G | p.K172E | MISSENSE |
| c.1473G>A | p.E491E | SYNONYMOUS |
| c.830A>G | p.E277G | MISSENSE |
| c.341G>A | p.G114E | MISSENSE |
| c.30C>T | p.I10I | SYNONYMOUS |
| c.694C>T | p.L232F | MISSENSE |
| c.971G>A | p.G324E | MISSENSE |
| c.266G>A | p.G89E | MISSENSE |
| c.116C>T | p.T39I | MISSENSE |
| c.78C>T | p.I26I | SYNONYMOUS |
| c.739T>A | p.S247T | MISSENSE |
| c.3136G>A | p.E1046K | MISSENSE |
| c.1752G>A | p.K584K | SYNONYMOUS |
| c.363C>T | p.H121H | SYNONYMOUS |
| c.662G>A | p.S221N | MISSENSE |
| c.1133C>T | p.T378M | MISSENSE |
| c.277G>A | p.A93T | MISSENSE |
| c.666C>T | p.V222V | SYNONYMOUS |
| c.2209C>T | p.R737W | MISSENSE |
| c.187C>T | p.L63L | SYNONYMOUS |
| c.208C>T | p.R70C | MISSENSE |
| c.1013G>A | p.R338Q | MISSENSE |
| c.1568G>A | p.R523Q | MISSENSE |
| c.2617C>T | p.R873X | NONSENSE |
| c.1601G>A | p.R534H | MISSENSE |
| c.814G>A | p.E272K | MISSENSE |
| c.1875G>A | p.Q625Q | SYNONYMOUS |
| c.120G>A | p.R40R | SYNONYMOUS |
| c.991G>A | p.G331S | MISSENSE |
| c.679C>T | p.L227F | MISSENSE |
| c.1534delT | fs | INDEL |
| c.902C>G | p.A301G | MISSENSE |
| c.1166G>A | p.R389H | MISSENSE |
| c.157C>T | p.Q53X | NONSENSE |
| c.437G>A | p.R146K | MISSENSE |
| c.530G>A | p.R177K | MISSENSE |
| c.43T>A | p.L15I | MISSENSE |
| c.738G>A | p.A246A | SYNONYMOUS |
| c.515C>T | p.T172M | MISSENSE |
| c.6G>A | p.S2S | SYNONYMOUS |
| c.600C>T | p.R200R | SYNONYMOUS |
| c.1084G>A | p.E362K | MISSENSE |
| c.1532C>T | p.A511V | MISSENSE |
| c.1555G>A | p.G519S | MISSENSE |
| c.1199G>A | p.S400N | MISSENSE |
| c.206G>A | p.G69D | MISSENSE |
| c.1070G>A | p.G357E | MISSENSE |
| c.269C>T | p.T90I | MISSENSE |
| c.1017C>T | p.G339G | SYNONYMOUS |

FIG. 10
CONTINUED

| | | | |
|---|---|---|---|
| FLJ34658 | CCDS3913.1 | Br27P | g.chr5:35990085G>A |
| FLJ35709 | CCDS7767.1 | Br27P | g.chr11:6476395A>G |
| FLJ35728 | CCDS1537.1 | Br13X | g.chr1:219939893C>T |
| FLJ36004 | CCDS8704.1 | Br11P | g.chr12:25590734C>T |
| FLJ36208 | NM_145270 | Br20P | g.chr16:554064C>T |
| FLJ36601 | CCDS14238.1 | Br03x | g.chrX:35851101G>T |
| FLJ37440 | CCDS2095.1 | Br27P | g.chr2:112659027G>A |
| FLJ38964 | NM_173527 | Br27P | g.chr14:22425960C>T |
| FLJ38973 | NM_153689 | Br27P | g.chr2:200615404G>A |
| FLJ39058 | CCDS8489.1 | Br27P | g.chr11:130048243G>A |
| FLJ39198 | NM_001039769 | Br27P | g.chr8:64053832G>A |
| FLJ39873 | CCDS2980.1 | Br27P | g.chr3:115501183C>T |
| FLJ40243 | NM_173489 | Br23X | g.chr5:41040284T>C |
| FLJ40243 | NM_173489 | Br17X | g.chr5:41040244C>T |
| FLJ40342 | CCDS11512.1 | Br14X | g.chr17:42793835C>T |
| FLJ40869 | CCDS1691.1 | Br27P | g.chr2:177875627C>T |
| FLJ41170 | NM_001004332 | Br11P | g.chr14:100542038T>C |
| FLJ41766 | ENST00000338573 | Br26X | g.chr16:21235757G>A |
| FLJ43706 | NM_001039774 | Br27P | g.chr4:62122281G>A |
| FLJ44186 | CCDS5854.1 | Br07X | g.chr7:138595683C>T |
| FLJ44861 | CCDS11778.1 | Br27P | g.chr17:76755104C>T |
| FLJ45300 | NM_001001681 | Br27P | g.chr11:119007338C>T |
| FLJ45744 | CCDS12424.1 | Br27P | g.chr19:37859283G>A |
| FLJ45964 | CCDS2530.1 | Br27P | g.chr2:240236539C>T |
| FLJ45974 | NM_001001707 | Br07X | g.chr7:53653463C>T |
| FLJ46072 | CCDS6410.1 | Br08x | g.chr8:144882513C>T |
| FLJ90650 | CCDS4124.1 | Br23X | g.chr5:115374362G>A |
| FLT1 | CCDS9330.1 | Br26X | g.chr13:27899451A>T |
| FLT1 | CCDS9330.1 | Br27P | g.chr13:27811340G>A |
| FMN2 | NM_020066 | Br27P | g.chr1:236581393G>A |
| FMNL2 | NM_001004417 | Br27P | g.chr2:153301602C>T |
| FMNL2 | NM_001004417 | Br27P | g.chr2:153314055G>A |
| FN1 | CCDS2399.1 | Br05X | g.chr2:216123657A>G |
| FNBP1 | NM_015033 | Br26X | g.chr9:129769094G>C |
| FNDC1 | NM_032532 | Br13X | g.chr6:159625258G>A |
| FOXA2 | CCDS13147.1 | Br07X | g.chr20:22510578G>A |
| FOXB1 | NM_012182 | Br17X | g.chr15:58084861G>A |
| FOXI1 | CCDS4372.1 | Br20P | g.chr5:169465925C>T |
| FOXM1 | CCDS8515.1 | Br27P | g.chr12:2838919G>A |
| FOXR2 | NM_198451 | Br26X | g.chrX:55533654C>T |
| FRAS1 | NM_025074 | Br26X | g.chr4:79710934C>T |
| FREM2 | NM_207361 | Br27P | g.chr13:38163333G>A |
| FRMD3 | NM_174938 | Br27P | g.chr9:83194176C>T |
| FRMD4B | ENST00000264546 | Br27P | g.chr3:69434212G>A |
| FRMPD1 | CCDS6612.1 | Br27P | g.chr9:37730100C>T |
| FRMPD1 | CCDS6612.1 | Br17X | g.chr9:37719830G>A (HOMOZYGOUS) |
| FRMPD4 | NM_014728 | Br15X | g.chrX:12479743G>A (HOMOZYGOUS) |
| FRMPD4 | NM_014728 | Br9PT | g.chrX:12493874C>T |
| FSD2 | NM_001007122 | Br27P | g.chr15:81244621G>A |
| FSTL1 | CCDS2998.1 | Br11P | g.chr3:121613429G>C |

FIG. 10
CONTINUED

| | | |
|---|---|---|
| c.1548G>A | p.G516G | SYNONYMOUS |
| c.374A>G | p.D125G | MISSENSE |
| c.1297C>T | p.R433W | MISSENSE |
| c.269C>T | p.P90L | MISSENSE |
| c.769C>T | p.R257C | MISSENSE |
| c.379G>T | p.G127X | NONSENSE |
| c.827G>A | p.G276D | MISSENSE |
| UTR+2C>T | 3'UTR | 3'UTR |
| c.99G>A | p.V33V | SYNONYMOUS |
| c.160G>A | p.V54I | MISSENSE |
| c.173G>A | p.S58N | MISSENSE |
| c.441C>T | p.A147A | SYNONYMOUS |
| c.4115T>C | p.I1372T | MISSENSE |
| c.4155C>T | p.F1385F | SYNONYMOUS |
| c.754C>T | p.P252S | MISSENSE |
| c.901C>T | p.H301Y | MISSENSE |
| c.112T>C | p.W38R | MISSENSE |
| c.134G>A | p.R45H | MISSENSE |
| c.409G>A | p.G137S | MISSENSE |
| c.1135C>T | p.L379L | SYNONYMOUS |
| c.214C>T | p.P72S | MISSENSE |
| c.41C>T | p.A14V | MISSENSE |
| c.274G>A | p.D92N | MISSENSE |
| c.166C>T | p.Q56X | NONSENSE |
| c.363C>T | p.Y121Y | SYNONYMOUS |
| c.227C>T | p.P76L | MISSENSE |
| c.2119G>A | p.A707T | MISSENSE |
| c.1281A>T | p.K427N | MISSENSE |
| c.2453G>A | p.S818N | MISSENSE |
| c.372G>A | p.E124E | SYNONYMOUS |
| c.1699C>T | p.P567S | MISSENSE |
| c.2576G>A | p.R859K | MISSENSE |
| c.311A>G | p.N104S | MISSENSE |
| c.723G>C | p.V241V | SYNONYMOUS |
| c.3147G>A | p.K1049K | SYNONYMOUS |
| c.1284G>A | p.T428T | SYNONYMOUS |
| c.407G>A | p.R136Q | MISSENSE |
| c.386C>T | p.S129L | MISSENSE |
| c.1438G>A | p.E480K | MISSENSE |
| c.489C>T | p.D163D | SYNONYMOUS |
| c.5211C>T | p.Y1737Y | SYNONYMOUS |
| c.3852G>A | p.G1284G | SYNONYMOUS |
| c.346C>T | p.P116S | MISSENSE |
| c.472G>A | p.G158S | MISSENSE |
| c.1575C>T | p.D525D | SYNONYMOUS |
| c.718G>A | p.E240K | MISSENSE |
| c.1027G>A | p.V343I | MISSENSE |
| c.1639C>T | p.L547F | MISSENSE |
| c.1062G>A | p.L354L | SYNONYMOUS |
| c.260G>C | p.G87A | MISSENSE |

FIG. 10
CONTINUED

| | | | |
|---|---|---|---|
| FSTL4 | NM_015082 | Br27P | g.chr5:132562801T>A |
| FSTL5 | CCDS3802.1 | Br03X | g.chr4:163390100G>A |
| FUBP1 | CCDS683.1 | Br27P | g.chr1:78127001G>A |
| FUBP1 | CCDS683.1 | Br27P | g.chr1:78142058C>T |
| FUT2 | NM_000511 | Br27P | g.chr19:53898686C>T |
| FXYD6 | CCDS8387.1 | Br27P | g.chr11:117217109G>A |
| FYCO1 | CCDS2734.1 | Br27P | g.chr3:45984943C>T |
| FZD10 | CCDS9267.1 | Br14X | g.chr12:129172394G>T |
| FZD3 | CCDS6069.1 | Br07x | g.chr8:28441140C>A |
| FZD6 | CCDS6298.1 | Br27P | g.chr8:104409743C>T |
| FZD9 | CCDS5548.1 | Br27P | g.chr7:72294706C>T |
| G3BP2 | CCDS3571.1 | Br27P | g.chr4:76927904G>A |
| GABPA | CCDS13575.1 | Br27P | g.chr21:26058805G>A |
| GABRA6 | CCDS4356.1 | Br15X | g.chr5:161048645C>T |
| GABRD | CCDS36.1 | BR14X | g.chr1:1993815G>A |
| GAD2 | CCDS7149.1 | Br06X | g.chr10:26615288G>A |
| GALNT13 | CCDS2199.1 | Br27P | g.chr2:154626633G>A |
| GALNT3 | CCDS2226.1 | Br27P | g.chr2:166446952C>T |
| GALNT3 | CCDS2226.1 | Br27P | g.chr2:166441475C>T |
| GALNT7 | CCDS3815.1 | Br27P | g.chr4:174597947G>A |
| GALNTL1 | NM_020692 | Br27P | g.chr14:68883523G>A |
| GANAB | CCDS8026.1 | Br27P | g.chr11:62152974G>A |
| GAPVD1 | NM_015635 | Br27P | g.chr9:125154427G>A |
| GAS6 | CCDS9540.1 | Br27P | g.chr13:113583934C>T |
| GAS6 | CCDS9540.1 | Br12P | g.chr13:113588931G>A |
| GATA4 | CCDS5983.1 | Br17X | g.chr8:11653376G>A |
| GATA6 | CCDS11872.1 | Br02X | g.chr18:18005370G>T |
| GBF1 | CCDS7533.1 | Br27P | g.chr10:104125238G>A |
| GCGR | NM_000160 | Br27P | g.chr17_random:1868957C>T |
| GCGR | NM_000160 | Br27P | g.chr17_random:1869577G>A |
| GCM1 | CCDS4950.1 | Br15X | g.chr6:53101613C>T |
| GCM2 | CCDS4517.1 | Br11P | g.chr6:10982864C>G |
| GCNT3 | CCDS10172.1 | Br20P | g.chr15:57698490C>T |
| GDF3 | CCDS8581.1 | Br27P | g.chr12:7739324G>A |
| GEFT | CCDS8947.1 | Br27P | g.chr12:56294613G>A |
| GFI1B | CCDS6957.1 | Br27P | g.chr9:132894043C>T |
| GFM1 | NM_024996 | Br27P | g.chr3:159846698G>A |
| GGA2 | CCDS10611.1 | Br08X | g.chr16:23412191G>A |
| GGPS1 | CCDS1604.1 | Br27P | g.chr1:231831786G>A |
| GHSR | CCDS3218.1 | Br08X | g.chr3:173648161G>A |
| GIMAP1 | CCDS5906.1 | Br27P | g.chr7:149855143G>A |
| GIMAP5 | CCDS5907.1 | Br20P | g.chr7:149877039C>A |
| GIMAP8 | NM_175571 | Br27P | g.chr7:149612139G>A |
| GIT2 | CCDS9138.1 | Br27P | g.chr12:108860392G>A |
| GJA4 | NM_002060 | Br27P | g.chr1:34929843C>T |
| GJB4 | CCDS383.1 | Br27P | g.chr1:34896194C>T |
| GK | CCDS14225.1 | Br04X | g.chrX:30497838C>T |
| GLRA1 | CCDS4320.1 | Br15X | g.chr5:151211320C>T |
| GMCL1L | CCDS4433.1 | Br27P | g.chr5:177545346C>T |
| GMDS | CCDS4474.1 | Br27P | g.chr6:2062772G>A |

FIG. 10
CONTINUED

| | | |
|---|---|---|
| c.2414T>A | p.L805H | MISSENSE |
| c.54G>A | p.S18S | SYNONYMOUS |
| c.1786G>A | p.A596T | MISSENSE |
| c.842C>T | p.P281L | MISSENSE |
| c.661C>T | p.R221X | NONSENSE |
| c.173G>A | p.S58N | MISSENSE |
| c.887C>T | p.A296V | MISSENSE |
| c.27G>T | p.W9C | MISSENSE |
| c.944C>A | p.A315D | MISSENSE |
| c.1464C>T | p.I488I | SYNONYMOUS |
| c.1718C>T | p.T573I | MISSENSE |
| c.1338G>A | p.M446I | MISSENSE |
| c.972G>A | p.Q324Q | SYNONYMOUS |
| c.338C>T | p.T113M | MISSENSE |
| c.1291G>A | p.A431T | MISSENSE |
| c.1245G>A | p.M415I | MISSENSE |
| c.115G>A | p.E39K | MISSENSE |
| c.637C>T | p.P213S | MISSENSE |
| c.951C>T | p.N317N | SYNONYMOUS |
| c.1168G>A | p.G390R | MISSENSE |
| c.1285G>A | p.E429K | MISSENSE |
| c.2023G>A | p.A675T | MISSENSE |
| c.1584G>A | p.G528G | SYNONYMOUS |
| c.1437C>T | p.F479F | SYNONYMOUS |
| c.1801G>A | p.A601T | MISSENSE |
| c.1312G>A | p.D438N | MISSENSE |
| c.267G>T | p.G89G | SYNONYMOUS |
| c.3790G>A | p.A1264T | MISSENSE |
| c.1101C>T | p.V367L | MISSENSE |
| c.1228G>A | p.E410K | MISSENSE |
| c.661C>T | p.H221Y | MISSENSE |
| c.871C>G | p.L291V | MISSENSE |
| c.761C>T | p.S254L | MISSENSE |
| c.268G>A | p.G90S | MISSENSE |
| c.774G>A | p.K258K | SYNONYMOUS |
| c.552C>T | p.R184R | SYNONYMOUS |
| c.277G>A | p.E93K | MISSENSE |
| c.342G>A | p.L114L | SYNONYMOUS |
| c.561G>A | p.R187R | SYNONYMOUS |
| c.745G>A | p.V249M | MISSENSE |
| c.403G>A | p.V135M | MISSENSE |
| c.164C>A | p.S55Y | MISSENSE |
| c.1621G>A | p.D541N | MISSENSE |
| c.1079G>A | p.S360N | MISSENSE |
| c.936C>T | p.P312P | SYNONYMOUS |
| c.246C>T | p.I82I | SYNONYMOUS |
| c.1205C>T | p.A402V | MISSENSE |
| c.736C>T | p.R246W | MISSENSE |
| c.1561C>T | p.P521S | MISSENSE |
| c.165G>A | p.R55R | SYNONYMOUS |

FIG. 10
CONTINUED

| | | | |
|---|---|---|---|
| GML | CCDS6391.1 | Br07X | g.chr8:143919589C>G (HOMOZYGOUS) |
| GNAI2 | CCDS2813.1 | Br04X | g.chr3:50269450C>T |
| GNAT1 | CCDS2812.1 | Br27P | g.chr3:50205604G>A |
| GNL2 | CCDS421.1 | Br10P | g.chr1:37709400T>A |
| GNPTG | CCDS10436.1 | Br27P | g.chr16:1352223G>A |
| GNS | CCDS8970.1 | Br27P | g.chr12:63424926C>T |
| GOLGA3 | CCDS9281.1 | Br27P | g.chr12:131994862G>A |
| GOLGA3 | CCDS9281.1 | Br27P | g.chr12:131995273G>A |
| GOLGA4 | CCDS2666.1 | Br27P | g.chr3:37331992G>A |
| GORASP2 | NM_015530 | Br23X | g.chr2:171633368C>G |
| GOT2 | CCDS10801.1 | Br27P | g.chr16:57309940G>A |
| GP6 | NM_016363 | Br26X | g.chr19:60218165G>A |
| GPBP1 | NM_022913 | Br27P | g.chr5:56577880G>A |
| GPI7 | CCDS3336.1 | Br04X | g.chr4:517677T>C |
| GPR114 | CCDS10785.1 | Br27P | g.chr16:56156501C>T |
| GPR116 | CCDS4919.1 | Br03X | g.chr6:46944735delT |
| GPR132 | CCDS9997.1 | Br14X | g.chr14:104589052G>A |
| GPR142 | CCDS11698.1 | Br27P | g.chr17:69879732C>T |
| GPR144 | NM_182611 | Br27P | g.chr9:124295843G>A |
| GPR145 | CCDS5044.1 | Br27P | g.chr6:100475803G>A |
| GPR174 | CCDS14443.1 | Br9PT | g.chrX:78233393C>A |
| GPR37 | CCDS5792.1 | Br27P | g.chr7:123998902C>T |
| GPR37L1 | CCDS1420.1 | Br27P | g.chr1:198828929G>A |
| GPR40 | CCDS12458.1 | Br26X | g.chr19:40534646C>T |
| GPR43 | CCDS12461.1 | Br27P | g.chr19:40633189G>A |
| GPR61 | CCDS801.1 | Br27P | g.chr1:109797705C>T |
| GPR61 | CCDS801.1 | Br27P | g.chr1:109798263C>T |
| GPR73L1 | CCDS13089.1 | Br27P | g.chr20:5231346G>A |
| GPR74 | CCDS3551.1 | Br17X | g.chr4:73378053T>C |
| GPR78 | CCDS3403.1 | Br08X | g.chr4:8700870C>T |
| GPR83 | CCDS8297.1 | Br27P | g.chr11:93773974G>A |
| GPR83 | CCDS8297.1 | Br27P | g.chr11:93766298G>A |
| GPR85 | CCDS5758.1 | Br23X | g.chr7:112317674A>C |
| GPRC5C | CCDS11699.1 | Br14X | g.chr17:69948219C>T |
| GPS1 | CCDS11800.1 | Br11P | g.chr17:77604512T>C |
| GPS2 | NM_032442 | Br27P | g.chr17:7164907G>A |
| GPSM2 | CCDS792.1 | Br27P | g.chr1:109156547C>T |
| GPT | CCDS6430.1 | Br27P | g.chr8:145702560C>T |
| GRAP2 | CCDS13999.1 | Br13X | g.chr22:38691505T>C (HOMOZYGOUS) |
| GRASP | CCDS8817.1 | Br27P | g.chr12:50694842G>A |
| GRCA | CCDS8563.1 | Br04X | g.chr12:6805701C>T |
| GREB1 | NM_014668 | Br15X | g.chr2:11689443C>T |
| GRIA4 | CCDS8333.1 | Br27P | g.chr11:105302713G>A |
| GRIK4 | CCDS8433.1 | Br17X | g.chr11:120343207G>A |
| GRIN2B | CCDS8662.1 | Br04X | g.chr12:13910212C>A |
| GRIN2B | CCDS8662.1 | Br13X | g.chr12:13608123G>A |
| GRIN2B | CCDS8662.1 | Br27P | g.chr12:13607612C>T |
| GRIN3A | CCDS6758.1 | Br29P | g.chr9:101512338A>G |
| GRINA | NM_001009184 | Br27P | g.chr8:145138181C>T |
| GRM1 | CCDS5209.1 | Br15X | g.chr6:146761918C>T |

FIG. 10
CONTINUED

| | | |
|---|---|---|
| c.127C>G | p.P43A | MISSENSE |
| c.801C>T | p.L267L | SYNONYMOUS |
| c.141G>A | p.K47K | SYNONYMOUS |
| c.1261T>A | p.F421I | MISSENSE |
| c.427G>A | p.G143R | MISSENSE |
| c.554C>T | p.T185I | MISSENSE |
| c.1143G>A | p.G381G | SYNONYMOUS |
| c.732G>A | p.R244R | SYNONYMOUS |
| c.1312G>A | p.D438N | MISSENSE |
| c.459C>G | p.I153M | MISSENSE |
| c.589G>A | p.D197N | MISSENSE |
| c.956G>A | p.R319Q | MISSENSE |
| IVS4-4G>A | SPLICE SITE | SPLICE SITE |
| c.2618T>C | p.I873T | MISSENSE |
| c.484C>T | p.H162Y | MISSENSE |
| c.1465delT | fs | INDEL |
| c.467G>A | p.R156Q | MISSENSE |
| c.787C>T | p.P263S | MISSENSE |
| c.991G>A | p.E331K | MISSENSE |
| c.757G>A | p.V253M | MISSENSE |
| c.744C>A | p.F248L | MISSENSE |
| c.80C>T | p.A27V | MISSENSE |
| c.1034G>A | p.C345Y | MISSENSE |
| c.352C>T | p.R118W | MISSENSE |
| c.733G>A | p.G245R | MISSENSE |
| c.19C>T | p.P7S | MISSENSE |
| c.577C>T | p.P193S | MISSENSE |
| c.495G>A | p.M165I | MISSENSE |
| c.1058T>C | p.V353A | MISSENSE |
| c.90C>T | p.C30C | SYNONYMOUS |
| c.88G>A | p.E30K | MISSENSE |
| IVS3+1G>A | SPLICE SITE | SPLICE SITE |
| c.1054A>C | p.T352P | MISSENSE |
| c.844C>T | p.R282C | MISSENSE |
| c.227T>C | p.V76A | MISSENSE |
| c.3420G>A | p.K1140K | SYNONYMOUS |
| c.870C>T | p.D290D | SYNONYMOUS |
| c.1094C>T | p.P365L | MISSENSE |
| c.910T>C | p.S304P | MISSENSE |
| c.780G>A | p.G260G | SYNONYMOUS |
| c.1137C>T | p.S379S | SYNONYMOUS |
| c.2192C>T | p.T731M | MISSENSE |
| c.1884G>A | p.W628X | NONSENSE |
| c.2360G>A | p.G787E | MISSENSE |
| c.198C>A | p.P66P | SYNONYMOUS |
| c.3316G>A | p.E1106K | MISSENSE |
| c.3827C>T | p.A1276V | MISSENSE |
| c.1911A>G | p.A637A | SYNONYMOUS |
| c.640C>T | p.L214F | MISSENSE |
| c.2050C>T | p.R684C | MISSENSE |

FIG. 10
CONTINUED

| | | | |
|---|---|---|---|
| GRM3 | CCDS5600.1 | Br08X | g.chr7:86113754C>T |
| GRM3 | CCDS5600.1 | Br15X | g.chr7:86060570G>A |
| GSR | NM_000637 | Br27P | g.chr8:30656684G>A |
| GSTO2 | CCDS7556.1 | Br27P | g.chr10:106029187G>A |
| GTF2A2 | CCDS10173.1 | Br27P | g.chr15:57718645C>T |
| GTF2H4 | NM_020442 | Br20P | g.chr6:31001736G>C |
| GTF3C4 | CCDS6953.1 | Br27P | g.chr9:132584539G>A |
| GUCY1A3 | NM_000856 | Br08X | g.chr4:156989502dupG |
| GUCY1B2 | CCDS9426.1 | Br27P | g.chr13:50500400G>A |
| GZMH | CCDS9632.1 | Br17X | g.chr14:24145771G>A |
| HAMP | CCDS12454.1 | Br27P | g.chr19:40467743C>T |
| HBB | NM_000519 | Br07X | g.chr11:5211942G>C |
| HBXAP | CCDS8253.1 | Br27P | g.chr11:77063772T>C |
| HBXAP | CCDS8253.1 | Br27P | g.chr11:77091173G>A |
| HCFC2 | CCDS9097.1 | Br06X | g.chr12:102977024G>A |
| HDAC2 | NM_001527 | Br03X | g.chr6:114381275G>C |
| HDAC9 | NM_178425 | Br27P | g.chr7:18398170G>A |
| HDAC9 | NM_178425 | Br25X | g.chr7:18447540A>G |
| HDC | CCDS10134.1 | Br27P | g.chr15:48333110C>T |
| HECW2 | NM_020760 | Br27P | g.chr2:196982979G>A |
| HERC1 | NM_003922 | Br27P | g.chr15:61754010C>T |
| HERC1 | NM_003922 | Br06X | g.chr15:61748950G>A |
| HERC2 | CCDS10021.1 | Br15X | g.chr15:26088302C>T |
| HGSNAT | ENST00000332689 | Br27P | g.chr8:43114876G>A |
| HHIP | CCDS3762.1 | Br11P | g.chr4:146013538delG |
| HIF3A | CCDS12681.1 | Br27P | g.chr19:51524515G>A |
| HIP1 | NM_005338 | Br27P | g.chr7:74832210G>A |
| HIVEP1 | NM_002114 | Br23X | g.chr6:12232178C>A |
| HIVEP2 | NM_006734 | Br9PT | g.chr6:143137172G>A |
| HIVEP3 | CCDS463.1 | Br27P | g.chr1:41719464C>T |
| HMG20A | CCDS10295.1 | Br02X | g.chr15:75558704G>A |
| HMGCL | CCDS243.1 | Br27P | g.chr1:23888551G>A |
| HMP19 | CCDS4391.1 | Br27P | g.chr5:173423841G>A |
| HNT | CCDS8491.1 | Br27P | g.chr11:131710194G>A |
| HORMAD1 | CCDS967.1 | Br27P | g.chr1:147493950C>T |
| HOXA6 | CCDS5407.1 | Br07X | g.chr7:26958628C>T |
| HP | NM_005143 | Br14X | g.chr16:70651895G>A |
| HP1BP3 | NM_016287 | Br17X | g.chr1:20829004_20829000delAGAAC |
| HPCAL4 | CCDS441.1 | Br04X | g.chr1:39819340C>A |
| HRB | CCDS2467.1 | Br26X | g.chr2:228243952_228243955delCAAA |
| HRBL | CCDS5697.1 | Br27P | g.chr7:99792782G>A |
| HRG | CCDS3280.1 | Br27P | g.chr3:187878168G>A |
| HS2ST1 | CCDS712.1 | Br27P | g.chr1:87310212C>T |
| HS2ST1 | CCDS711.1 | Br27P | g.chr1:87282172A>T |
| HSA9761 | CCDS3981.1 | Br23X | g.chr5:61730453G>A |
| HSD17B2 | CCDS10936.1 | Br15X | g.chr16:80659286C>T |
| HSD17B8 | CCDS4769.1 | Br27P | g.chr6:33281662G>A |
| HSPA4L | CCDS3734.1 | Br9PT | g.chr4:129086786T>C |
| HSPC111 | NM_016391 | Br27P | g.chr5:175743906C>T |
| HSPG2 | NM_005529 | Br27P | g.chr1:21936825C>T |

FIG. 10
CONTINUED

| | | |
|---|---|---|
| c.2273C>T | p.T758M | MISSENSE |
| c.811G>A | p.V271I | MISSENSE |
| c.1464G>A | p.L488L | SYNONYMOUS |
| c.436G>A | p.A146T | MISSENSE |
| c.308C>T | p.T103I | MISSENSE |
| c.3062G>C | p.G1021A | MISSENSE |
| c.1979G>A | p.G660E | MISSENSE |
| c.580dupG | fs | INDEL |
| c.344G>A | p.R115K | MISSENSE |
| c.619G>A | p.V207M | MISSENSE |
| c.213C>T | p.G71G | SYNONYMOUS |
| c.170G>C | p.G57A | MISSENSE |
| c.3519T>C | p.D1173D | SYNONYMOUS |
| c.749G>A | p.S250N | MISSENSE |
| c.716G>A | p.G239E | MISSENSE |
| c.498G>C | p.K166N | MISSENSE |
| c.49G>A | p.G17S | MISSENSE |
| c.847A>G | p.N283D | MISSENSE |
| c.766C>T | p.L256L | SYNONYMOUS |
| c.2816G>A | p.S939N | MISSENSE |
| c.7430C>T | p.S2477F | MISSENSE |
| c.8046G>A | p.R2682R | SYNONYMOUS |
| c.10152C>T | p.L3384L | SYNONYMOUS |
| c.68G>A | p.G23D | MISSENSE |
| c.1801delG | fs | INDEL |
| c.1652G>A | p.C551Y | MISSENSE |
| c.1376G>A | p.R459K | MISSENSE |
| c.4164C>A | p.F1388L | MISSENSE |
| c.397G>A | p.V133I | MISSENSE |
| c.98C>T | p.S33F | MISSENSE |
| c.1036G>A | p.D346N | MISSENSE |
| c.268G>A | p.E90K | MISSENSE |
| c.130G>A | p.V44M | MISSENSE |
| c.979G>A | p.A327T | MISSENSE |
| c.402C>T | p.N134N | SYNONYMOUS |
| c.591C>T | p.R197R | SYNONYMOUS |
| c.826G>A | p.G276R | MISSENSE |
| c.942_946delAGAAC | fs | INDEL |
| c.29C>A | p.P10H | MISSENSE |
| c.1565_1568delCAAA | fs | INDEL |
| c.428G>A | p.R143K | MISSENSE |
| c.1372G>A | p.V458M | MISSENSE |
| c.423C>T | p.G141G | SYNONYMOUS |
| IVS6-2A>T | SPLICE SITE | SPLICE SITE |
| c.253G>A | p.E85K | MISSENSE |
| c.276C>T | p.C92C | SYNONYMOUS |
| c.646G>A | p.D216N | MISSENSE |
| c.1275T>C | p.P425P | SYNONYMOUS |
| c.469C>T | p.R157C | MISSENSE |
| c.4443C>T | p.L1481L | SYNONYMOUS |

FIG. 10
CONTINUED

| | | | |
|---|---|---|---|
| HTR3C | CCDS3250.1 | Br26X | g.chr3:185256780C>T |
| HTR3E | CCDS3251.1 | Br10P | g.chr3:185300897G>A |
| HXMA | CCDS10586.1 | Br14X | g.chr16:20461790C>T |
| HYPB | CCDS2749.1 | Br27P | g.chr3:47133202T>G |
| IBTK | NM_015525 | Br02X | g.chr6:82979143G>C |
| IBTK | NM_015525 | Br27P | g.chr6:82939856C>T |
| ICAM3 | CCDS12235.1 | Br17X | g.chr19:10310614G>A |
| ICEBERG | NM_021571 | Br26X | g.chr11:104514773G>A |
| IDE | CCDS7421.1 | Br27P | g.chr10:94281604G>A |
| IDH1 | CCDS2381.1 | Br10P | g.chr2:208938618G>A |
| IDH1 | CCDS2381.1 | Br11P | g.chr2:208938618G>A |
| IDH1 | CCDS2381.1 | Br12P | g.chr2:208938618G>A |
| IDH1 | CCDS2381.1 | Br27P | g.chr2:208938618G>A |
| IDH1 | CCDS2381.1 | Br29P | g.chr2:208938618G>A |
| IFI44 | CCDS688.1 | Br26X | g.chr1:78833091C>T |
| IFIT3 | CCDS7402.1 | Br27P | g.chr10:91089032G>A |
| IFNAR1 | CCDS13624.1 | Br17X | g.chr21:33639513G>A |
| IFRD1 | NM_001007245 | Br27P | g.chr7:111684744G>A |
| IGF1 | CCDS9091.1 | Br27P | g.chr12:101372044G>A |
| IGF2 | CCDS7728.1 | Br27P | g.chr11:2110805C>T |
| IGFBP7 | CCDS3512.1 | Br27P | g.chr4:57739618G>A |
| IGSF1 | CCDS14629.1 | Br03X | g.chrX:130135064A>G (HOMOZYGOUS) |
| IGSF10 | CCDS3160.1 | Br03X | g.chr3:152646824C>G |
| IGSF9 | CCDS1190.1 | Br27P | g.chr1:156713171G>A |
| IGSF9 | CCDS1190.1 | Br27P | g.chr1:156720567G>A |
| IKBKE | NM_014002 | Br27P | g.chr1:203054848G>A |
| IL12RB2 | CCDS638.1 | Br23X | g.chr1:67498069G>T |
| IL17B | CCDS4297.1 | Br17X | g.chr5:148734262C>T |
| IL17RE | CCDS2589.1 | Br27P | g.chr3:9920722C>T |
| IL1F9 | CCDS2108.1 | Br9PT | g.chr2:113452488C>T |
| IL1RL1 | CCDS2057.1 | Br27P | g.chr2:102418056G>A |
| IL3 | CCDS4149.1 | Br27P | g.chr5:131424345C>T |
| ILT7 | CCDS12890.1 | Br03X | g.chr19:59541295G>A (HOMOZYGOUS) |
| IMP4 | CCDS2160.1 | Br03X | g.chr2:130816898G>A |
| IMP4 | CCDS2160.1 | Br29P | g.chr2:130819902T>C |
| IMPDH1 | NM_183243 | Br27P | g.chr7:127643797G>A |
| INDO | NM_002164 | Br27P | g.chr8:39904750C>T |
| INDO | NM_002164 | Br27P | g.chr8:39896791G>A |
| INSIG2 | CCDS2122.1 | Br27P | g.chr2:118570375G>A |
| IPO13 | CCDS503.1 | Br08X | g.chr1:44091688_44091690delTGA |
| IPO8 | CCDS8719.1 | Br27P | g.chr12:30683785C>T |
| IQGAP2 | NM_006633 | Br27P | g.chr5:76003350G>A |
| IQWD1 | CCDS1267.1 | Br27P | g.chr1:164745940G>A |
| IRS1 | CCDS2463.1 | Br02X | g.chr2:227488820A>G |
| IRTA2 | CCDS1165.1 | Br26X | g.chr1:154327353C>A |
| IRX6 | NM_024335 | Br14X | g.chr16:53917924C>A |
| IRX6 | NM_024335 | Br27P | g.chr16:53920286G>A |
| IRX6 | NM_024335 | Br04X | chr16:53917796_53917806delACGCTCTGT |
| ISL1 | NM_002202 | Br27P | g.chr5:50721259G>A |
| ITGA4 | NM_000885 | Br25X | g.chr2:182224557C>A |

FIG. 10
CONTINUED

| | | |
|---|---|---|
| IVS4+4C>T | SPLICE SITE | SPLICE SITE |
| c.35G>A | p.R12H | MISSENSE |
| c.1456C>T | p.P486S | MISSENSE |
| c.2992T>G | p.C998G | MISSENSE |
| c.2291G>C | p.C764S | MISSENSE |
| c.3744C>T | p.T1248T | SYNONYMOUS |
| c.87G>A | p.G29G | SYNONYMOUS |
| c.250G>A | p.A84T | MISSENSE |
| c.542G>A | p.R181K | MISSENSE |
| c.395G>A | p.R132H | MISSENSE |
| c.395G>A | p.R132H | MISSENSE |
| c.395G>A | p.R132H | MISSENSE |
| c.395G>A | p.R132H | MISSENSE |
| c.395G>A | p.R132H | MISSENSE |
| c.714C>T | p.D238D | SYNONYMOUS |
| c.640G>A | p.G214S | MISSENSE |
| c.765G>A | p.M255I | MISSENSE |
| c.50G>A | p.G17D | MISSENSE |
| c.64G>A | p.V22M | MISSENSE |
| c.531C>T | p.S177S | SYNONYMOUS |
| c.731G>A | p.G244E | MISSENSE |
| c.3107A>G | p.Y1036C | MISSENSE |
| c.3643C>G | p.P1215A | MISSENSE |
| c.1897G>A | p.V633I | MISSENSE |
| c.382G>A | p.V128M | MISSENSE |
| IVS17+1G>A | SPLICE SITE | SPLICE SITE |
| UTR-4G>T | 5'UTR | 5'UTR |
| c.406C>T | p.R136C | MISSENSE |
| c.155C>T | p.S52F | MISSENSE |
| c.42C>T | p.A14A | SYNONYMOUS |
| c.725G>A | p.G242D | MISSENSE |
| c.47C>T | p.P16L | MISSENSE |
| c.379G>A | p.A127T | MISSENSE |
| c.13G>A | p.E5K | MISSENSE |
| c.676T>C | p.Y226H | MISSENSE |
| c.110G>A | p.S37N | MISSENSE |
| c.1101C>T | p.T367T | SYNONYMOUS |
| IVS5+1G>A | SPLICE SITE | SPLICE SITE |
| c.13G>A | p.E5K | MISSENSE |
| c.1218_1220delTGA | p.D406del | INDEL |
| c.2420C>T | p.P807L | MISSENSE |
| c.2854G>A | p.D952N | MISSENSE |
| c.863G>A | p.S288N | MISSENSE |
| c.140A>G | p.Y47C | MISSENSE |
| c.616C>A | p.P206T | MISSENSE |
| c.221C>A | p.P74H | MISSENSE |
| c.895G>A | p.A299T | MISSENSE |
| c.93_103delACGCTCTGTCT | fs | INDEL |
| c.492G>A | p.Q164Q | SYNONYMOUS |
| c.2837C>A | p.P946Q | MISSENSE |

FIG. 10
CONTINUED

| | | | |
|---|---|---|---|
| ITGA7 | CCDS8888.1 | Br27P | g.chr12:54383206C>T |
| ITGAL | NM_002209 | Br04X | g.chr16:30436684G>T |
| ITGAL | NM_002209 | Br26X | g.chr16:30398277G>A |
| ITGAX | CCDS10711.1 | Br17X | g.chr16:31282136G>T |
| ITIH5 | NM_032817 | Br12P | g.chr10:7645217G>T |
| ITIH5 | NM_032817 | Br27P | g.chr10:7661978G>A |
| ITLN1 | CCDS1211.1 | Br05X | g.chr1:157666290G>A |
| ITPKB | CCDS1555.1 | Br27P | g.chr1:223132114G>A |
| ITPR3 | CCDS4783.1 | Br16X | g.chr6:33761264G>A |
| IVNS1ABP | CCDS1368.1 | Br05X | g.chr1:181999070_181999067delGTTT |
| JMJD1A | CCDS1990.1 | Br27P | g.chr2:86605545G>A |
| JMJD1B | NM_016604 | Br27P | g.chr5:137736306G>A |
| JUNB | CCDS12280.1 | Br27P | g.chr19:12763638C>T |
| K0574_HUMAN | ENST00000261275 | Br27P | g.chr15:27205831G>A |
| KATNAL2 | NM_031303 | Br27P | g.chr18:42849857G>T |
| KBTBD3 | CCDS8334.1 | Br27P | g.chr11:105429606C>T |
| KBTBD4 | CCDS7940.1 | Br27P | g.chr11:47551919G>A |
| KCNA4 | NM_002233 | Br29P | g.chr11:29990620C>T |
| KCNA7 | CCDS12755.1 | Br02X | g.chr19:54265675C>T |
| KCNB2 | CCDS6209.1 | Br11P | g.chr8:74011087G>A |
| KCNC4 | CCDS821.1 | Br20P | g.chr1:110478374C>T |
| KCND2 | CCDS5776.1 | Br27P | g.chr7:119976568C>T |
| KCND2 | CCDS5776.1 | Br03X | g.chr7:119979914C>T |
| KCNG3 | CCDS1809.1 | Br26X | g.chr2:42631881G>A |
| KCNH1 | CCDS1496.1 | Br9PT | g.chr1:207365704G>T |
| KCNH5 | CCDS9756.1 | Br08X | g.chr14:623162O1C>T |
| KCNJ15 | CCDS13656.1 | Br03X | g.chr21:38593138G>A |
| KCNK1 | CCDS1599.1 | Br26X | g.chr1:230109198G>A |
| KCNK5 | CCDS4841.1 | Br27P | g.chr6:39304718C>T |
| KCNN1 | NM_002248 | Br27P | g.chr19:17946067G>A |
| KCNQ3 | NM_004519 | Br27P | g.chr8:133211412G>A |
| KCNQ4 | CCDS456.1 | Br27P | g.chr1:40954145G>A |
| KCTD7 | CCDS5534.1 | Br27P | g.chr7:65538336G>A |
| KCTD8 | CCDS3467.1 | Br27P | g.chr4:44291341C>T |
| KCTD8 | CCDS3467.1 | Br27P | g.chr4:44291181C>T |
| KDELR2 | CCDS5351.1 | Br27P | g.chr7:6276044C>T |
| KDR | CCDS3497.1 | Br03X | g.chr4:55797122G>A |
| KEL | NM_000420 | Br27P | g.chr7:142158572G>A |
| KIAA0082 | CCDS4835.1 | Br16X | g.chr6:37555001C>T |
| KIAA0101 | CCDS10193.1 | Br27P | g.chr15:62456131C>T |
| KIAA0103 | CCDS6309.1 | Br20P | g.chr8:109551279G>A |
| KIAA0133 | NM_014777 | Br07X | g.chr1:226080304T>A |
| KIAA0133 | NM_014777 | Br17X | g.chr1:226077736G>A |
| KIAA0143 | NM_015137 | Br17X | g.chr8:133065700G>C |
| KIAA0153 | CCDS14047.1 | Br27P | g.chr22:41901418C>T |
| KIAA0317 | NM_001039479 | Br27P | g.chr14:74206524G>A |
| KIAA0329 | NM_014844 | Br27P | g.chr14:101970983C>T |
| KIAA0350 | NM_015226 | Br17X | g.chr16:11052915C>G |
| KIAA0367 | NM_015225 | Br03X | g.chr9:76552682G>A |
| KIAA0404 | NM_015104 | Br27P | g.chr11:64434704C>T |

FIG. 10 CONTINUED

| | | |
|---|---|---|
| c.230C>T | p.A77V | MISSENSE |
| c.3099G>T | p.V1033V | SYNONYMOUS |
| c.570G>A | p.S190S | SYNONYMOUS |
| c.1650G>T | p.R550R | SYNONYMOUS |
| c.2022G>T | p.V674V | SYNONYMOUS |
| c.522G>A | p.V174V | SYNONYMOUS |
| IVS2+1G>A | SPLICE SITE | SPLICE SITE |
| IVS6+1G>A | SPLICE SITE | SPLICE SITE |
| c.5458G>A | p.E1820K | MISSENSE |
| c.1683_1686delGTTT | fs | INDEL |
| c.1400G>A | p.C467Y | MISSENSE |
| c.237G>A | p.W79X | NONSENSE |
| c.53C>T | p.T18M | MISSENSE |
| c.757G>A | p.V253M | MISSENSE |
| c.680G>T | p.G227V | MISSENSE |
| c.1020C>T | p.Y340Y | SYNONYMOUS |
| IVS2-1G>A | SPLICE SITE | SPLICE SITE |
| c.182C>T | p.S61F | MISSENSE |
| c.828C>T | p.I276I | SYNONYMOUS |
| c.943G>A | p.A315T | MISSENSE |
| c.1425C>T | p.F475F | SYNONYMOUS |
| c.1428C>T | p.T476T | SYNONYMOUS |
| c.1597C>T | p.R533X | NONSENSE |
| c.412G>A | p.D138N | MISSENSE |
| c.1662G>T | p.K554N | MISSENSE |
| c.2017C>T | p.R673W | MISSENSE |
| c.85G>A | p.V29I | MISSENSE |
| c.478G>A | p.V160I | MISSENSE |
| c.148C>T | p.P50S | MISSENSE |
| c.370G>A | p.E124K | MISSENSE |
| c.1898G>A | p.G633E | MISSENSE |
| c.742G>A | p.V248M | MISSENSE |
| c.135G>A | p.L45L | SYNONYMOUS |
| c.128C>T | p.P43L | MISSENSE |
| c.288C>T | p.R96R | SYNONYMOUS |
| c.607C>T | p.L203F | MISSENSE |
| c.3121G>A | p.V1041M | MISSENSE |
| c.1408G>A | p.D470N | MISSENSE |
| c.2367C>T | p.A789A | SYNONYMOUS |
| c.154C>T | p.P52S | MISSENSE |
| c.412G>A | p.V138M | MISSENSE |
| c.3209T>A | p.F1070Y | MISSENSE |
| c.641G>A | p.G214E | MISSENSE |
| c.1600G>C | p.D534H | MISSENSE |
| c.374C>T | p.T125M | MISSENSE |
| c.1667G>A | p.G556E | MISSENSE |
| c.2076C>T | p.H692H | SYNONYMOUS |
| c.1911C>G | p.I637M | MISSENSE |
| c.2985G>A | p.G995G | SYNONYMOUS |
| c.1667C>T | p.A556V | MISSENSE |

FIG. 10
CONTINUED

| Gene | Accession | Sample | Variant |
|---|---|---|---|
| KIAA0406 | CCDS13300.1 | Br27P | g.chr20:36068178C>T |
| KIAA0528 | NM_014802 | Br27P | g.chr12:22557563G>A |
| KIAA0649 | CCDS6988.1 | Br23X | g.chr9:135605495G>A |
| KIAA0652 | CCDS7921.1 | Br05X | g.chr11:46627297_46627301delAAATG |
| KIAA0664 | NM_015229 | Br27P | g.chr17:2542135C>T |
| KIAA0664 | NM_015229 | Br27P | g.chr17:2544166G>A |
| KIAA0672 | NM_014859 | Br15X | g.chr17:12802872G>A |
| KIAA0672 | NM_014859 | Br27P | g.chr17:12740531G>A |
| KIAA0690 | CCDS7457.1 | Br06X | g.chr10:99113648G>A |
| KIAA0701 | NM_001006947 | Br27P | g.chr12:98979356C>T |
| KIAA0703 | NM_014861 | Br20P | g.chr16:83006699G>A |
| KIAA0748 | ENST00000316577 | Br27P | g.chr12:53643162G>A |
| KIAA0759 | CCDS9852.1 | Br27P | g.chr14:76345743C>T |
| KIAA0774 | NM_001033602 | Br15X | g.chr13:28506145C>T (HOMOZYGOUS) |
| KIAA0774 | NM_001033602 | Br05X | g.chr13:28497704C>T |
| KIAA0802 | CCDS11841.1 | Br9PT | g.chr18:8774394C>T |
| KIAA0831 | NM_014924 | Br9PT | g.chr14:54918591C>A |
| KIAA0863 | NM_014913 | Br27P | g.chr18:75996793G>A |
| KIAA0980 | NM_025176 | Br27P | g.chr20:25404789G>A |
| KIAA1024 | NM_015206 | Br27P | g.chr15:77547735C>T |
| KIAA1033 | NM_015275 | Br27P | g.chr12:104011475G>A |
| KIAA1086 | ENST00000262961 | Br04X | g.chr19:3771285G>C |
| KIAA1109 | ENST00000264501 | Br27P | g.chr4:123583744G>A |
| KIAA1223 | NM_020337 | Br25X | g.chr4:125947835A>T |
| KIAA1274 | NM_014431 | Br27P | g.chr10:71962517G>A |
| KIAA1328 | NM_020776 | Br27P | g.chr18:32901211G>A |
| KIAA1377 | NM_020802 | Br13X | g.chr11:101338494A>T |
| KIAA1411 | NM_020819 | Br27P | g.chr6:71247348C>T |
| KIAA1441 | CCDS992.1 | Br04X | g.chr1:148073883G>C |
| KIAA1441 | CCDS992.1 | Br04X | g.chr1:148073884T>A |
| KIAA1441 | CCDS992.1 | Br27P | g.chr1:148076695C>T |
| KIAA1467 | NM_020853 | Br11P | 2:13124806_13124822delCGATAACTCTTT |
| KIAA1505 | NM_020879 | Br27P | g.chr7:76530454_76530455delTT |
| KIAA1524 | NM_020890 | Br17X | g.chr3:109766959_109766955delTTGAT |
| KIAA1576 | NM_020927 | Br27P | g.chr16:76416695G>A |
| KIAA1618 | CCDS11772.1 | Br27P | g.chr17:75876486G>A |
| KIAA1754L | NM_178495 | Br26X | g.chr2:96415170C>T |
| KIAA1804 | CCDS1598.1 | Br07X | g.chr1:229822156A>C |
| KIAA1804 | CCDS1598.1 | Br07X | g.chr1:229822168T>C |
| KIAA1862 | NM_032534 | Br27P | g.chr7:148857534G>A |
| KIAA1909 | NM_052909 | Br27P | g.chr5:216616C>T |
| KIAA1909 | NM_052909 | Br26X | g.chr5:196353G>A |
| KIAA1946 | NM_177454 | Br06X | g.chr2:187452911C>T |
| KIAA1967 | NM_021174 | Br07X | g.chr8:22529222C>T (HOMOZYGOUS) |
| KIAA2022 | NM_001008537 | Br05X | g.chrX:73746128C>G |
| KIAA2026 | NM_001017969 | Br12P | g.chr9:5912152G>T |
| KIDINS220 | NM_020738 | Br27P | g.chr2:8840972G>A |
| KIFC2 | CCDS6427.1 | Br27P | g.chr8:145668629C>T |
| KIFC3 | CCDS10789.1 | Br27P | g.chr16:56362003G>A |
| KIRREL2 | CCDS12479.1 | Br27P | g.chr19:41049219C>T |

FIG. 10 CONTINUED

| | | |
|---|---|---|
| c.2338C>T | p.L780F | MISSENSE |
| c.970G>A | p.A324T | MISSENSE |
| c.3194G>A | p.G1065D | MISSENSE |
| c.305_309delAAATG | fs | INDEL |
| c.3450C>T | p.H1150H | SYNONYMOUS |
| IVS17+1G>A | SPLICE SITE | SPLICE SITE |
| c.1456G>A | p.E486K | MISSENSE |
| c.176G>A | p.G59E | MISSENSE |
| c.3520G>A | p.E1174K | MISSENSE |
| c.1313C>T | p.T438I | MISSENSE |
| IVS5+1G>A | SPLICE SITE | SPLICE SITE |
| c.373G>A | p.D125N | MISSENSE |
| IVS1-4C>T | SPLICE SITE | SPLICE SITE |
| c.2359C>T | p.R787C | MISSENSE |
| c.899C>T | p.S300L | MISSENSE |
| c.1284C>T | p.F428F | SYNONYMOUS |
| c.719C>A | p.A240D | MISSENSE |
| c.2506G>A | p.E836K | MISSENSE |
| c.3138G>A | p.E1046E | SYNONYMOUS |
| c.2705C>T | p.T902I | MISSENSE |
| IVS5+1G>A | SPLICE SITE | SPLICE SITE |
| c.1524G>C | p.R508R | SYNONYMOUS |
| IVS20+1G>A | SPLICE SITE | SPLICE SITE |
| c.4202A>T | p.E1401V | MISSENSE |
| c.768G>A | p.R256R | SYNONYMOUS |
| c.937G>A | p.D313N | MISSENSE |
| c.1518A>T | p.K506N | MISSENSE |
| c.437C>T | p.T146I | MISSENSE |
| c.2043G>C | p.Q681H | MISSENSE |
| c.2044T>A | p.C682S | MISSENSE |
| c.3651C>T | p.T1217T | SYNONYMOUS |
| IVS12-20_IVS12-4delCGATAACTCTTTTTCC | SPLICE SITE | INDEL |
| c.661_662delTT | fs | INDEL |
| c.1448_1452delTTGAT | fs | INDEL |
| c.415G>A | p.V139I | MISSENSE |
| c.539G>A | p.G180E | MISSENSE |
| c.951C>T | p.T317T | SYNONYMOUS |
| c.2669A>C | p.H890P | MISSENSE |
| c.2681T>C | p.M894T | MISSENSE |
| c.611G>A | p.G204E | MISSENSE |
| c.2361C>T | p.P787P | SYNONYMOUS |
| c.601G>A | p.G201R | MISSENSE |
| c.2336C>T | p.S779L | MISSENSE |
| c.1460C>T | p.A487V | MISSENSE |
| c.1285C>G | p.L429V | MISSENSE |
| c.1369G>T | p.V457F | MISSENSE |
| c.3282G>A | p.G1094G | SYNONYMOUS |
| c.1685C>T | p.A562V | MISSENSE |
| c.459G>A | p.V153V | SYNONYMOUS |
| c.1843C>T | p.P615S | MISSENSE |

FIG. 10
CONTINUED

| | | | |
|---|---|---|---|
| KIRREL3 | NM_032531 | Br27P | g.chr11:125800102C>T |
| KLHDC5 | NM_020782 | Br02X | g.chr12:27825052A>G |
| KLHL10 | NM_152467 | Br04X | g.chr17:37257996G>A |
| KLHL4 | CCDS14456.1 | Br27P | g.chrX:86695014C>T |
| KLK9 | CCDS12816.1 | Br11P | g.chr19:56198214T>G |
| KLP1 | CCDS12926.1 | Br29P | g.chr19:60689674G>A |
| KLRG1 | CCDS8599.1 | Br07X | g.chr12:9039068G>A (HOMOZYGOUS) |
| KNTC1 | NM_014708 | Br06X | g.chr12:121580488A>G |
| KREMEN2 | CCDS10484.1 | Br27P | g.chr16:2957845G>A |
| KREMEN2 | CCDS10483.1 | Br27P | g.chr16:2955005G>A |
| KRT9 | NM_000226 | Br27P | g.chr17:36978068G>A |
| KRTAP12-3 | NM_198697 | Br27P | g.chr21:44902470C>T |
| KRTAP20-2 | CCDS13604.1 | Br27P | g.chr21:30929456G>A |
| KRTHA4 | CCDS11390.1 | Br04X | g.chr17:36787862C>A |
| KSR1 | NM_014238 | Br27P | g.chr17:22956841C>T |
| L1CAM | CCDS14733.1 | Br20P | g.chrX:152654161C>T |
| L3MBTL2 | CCDS14011.1 | Br27P | g.chr22:39944621C>T |
| LACE1 | CCDS5067.1 | Br9PT | g.chr6:108784598delC |
| LACRT | CCDS8883.1 | Br27P | g.chr12:53313235G>A |
| LAMA1 | NM_005559 | Br12P | g.chr18:6967742G>A |
| LAMA3 | CCDS11880.1 | Br14X | g.chr18:19738532G>A |
| LAMA4 | NM_002290 | Br20P | g.chr6:112558910C>T |
| LAMB3 | CCDS1487.1 | Br27P | g.chr1:206188654G>A |
| LAMB3 | CCDS1487.1 | Br17X | g.chr1:206180232G>A |
| LAMP3 | CCDS3242.1 | Br15X | g.chr3:184354455C>A |
| LAP1B | CCDS1335.1 | Br27P | g.chr1:176618341C>T |
| LARGE | CCDS13912.1 | Br27P | g.chr22:31994964C>T |
| LARP5 | NM_015155 | Br17X | g.chr10:848909G>A |
| LATS1 | NM_004690 | Br27P | g.chr6:150093563G>A |
| LATS2 | CCDS9294.1 | Br27P | g.chr13:20451877G>A |
| LAX | CCDS1441.1 | Br27P | g.chr1:200475255G>A |
| LBP | CCDS13304.1 | Br04X | g.chr20:36431158G>A |
| LCA10 | NM_001039768 | Br27P | g.chrX:152673310C>T |
| LCT | CCDS2178.1 | Br04X | g.chr2:136408656T>A |
| LCT | CCDS2178.1 | Br03x | g.chr2:136400046C>T |
| LDLRAD3 | NM_174902 | Br27P | g.chr11:36059887G>A |
| LEMD2 | CCDS4785.1 | Br27P | g.chr6:33864496C>T |
| LENG8 | CCDS12894.1 | Br12P | g.chr19:59657433G>A |
| LETM1 | CCDS3355.1 | Br27P | g.chr4:1791230G>A |
| LETMD1 | CCDS8806.1 | Br27P | g.chr12:49739469G>A |
| LETMD1 | CCDS8806.1 | Br04X | g.chr12:49735994A>G |
| LIP8 | CCDS11126.1 | Br20P | g.chr17:7784239C>G |
| LIPM | ENST00000282673 | Br26X | g.chr10:90569974T>C (HOMOZYGOUS) |
| LMNB1 | CCDS4140.1 | Br27P | g.chr5:126141304G>A |
| LMX1A | CCDS1247.1 | Br23X | g.chr1:162054049G>A |
| LMX1A | CCDS1247.1 | Br16X | g.chr1:161911626G>A |
| LMX1A | CCDS1247.1 | Br15X | g.chr1:161904931C>T |
| LNX | CCDS3492.1 | Br27P | g.chr4:54188918C>T |
| LNX | CCDS3492.1 | Br27P | g.chr4:54185756G>A |
| LNX2 | CCDS9323.1 | Br27P | g.chr13:27022629G>A |

FIG. 10
CONTINUED

| | | |
|---|---|---|
| c.1920C>T | p.V640V | SYNONYMOUS |
| c.522A>G | p.Q174Q | SYNONYMOUS |
| c.1738G>A | p.E580K | MISSENSE |
| c.1670C>T | p.S557L | MISSENSE |
| c.718T>G | p.Y240D | MISSENSE |
| c.160G>A | p.G54S | MISSENSE |
| c.274G>A | p.E92K | MISSENSE |
| c.1954A>G | p.I652V | MISSENSE |
| c.1133G>A | p.R378Q | MISSENSE |
| c.239G>A | p.R80H | MISSENSE |
| c.1266G>A | p.Q422Q | SYNONYMOUS |
| c.146C>T | p.S49F | MISSENSE |
| c.3G>A | p.M1I | MISSENSE |
| c.1286C>A | p.T429N | MISSENSE |
| c.1524C>T | p.G508G | SYNONYMOUS |
| c.1880C>T | p.T627M | MISSENSE |
| c.1040C>T | p.T347I | MISSENSE |
| c.529delC | fs | INDEL |
| c.108G>A | p.G36G | SYNONYMOUS |
| c.6329G>A | p.R2110H | MISSENSE |
| c.1664G>A | p.S555N | MISSENSE |
| c.3900C>T | p.Y1300Y | SYNONYMOUS |
| c.1550G>A | p.R517H | MISSENSE |
| c.2869G>A | p.A957T | MISSENSE |
| c.476C>A | p.T159N | MISSENSE |
| c.1062C>T | p.F354F | SYNONYMOUS |
| UTR+3C>T | 3'UTR | 3'UTR |
| c.2174G>A | p.R725H | MISSENSE |
| c.2155G>A | p.V719I | MISSENSE |
| c.2725G>A | p.G909R | MISSENSE |
| c.758G>A | p.G253E | MISSENSE |
| c.1087G>A | p.E363K | MISSENSE |
| c.343C>T | p.P115S | MISSENSE |
| c.1694T>A | p.V565E | MISSENSE |
| c.3603C>T | p.A1201A | SYNONYMOUS |
| c.302G>A | p.S101N | MISSENSE |
| c.376C>T | p.P126S | MISSENSE |
| c.439G>A | p.G147S | MISSENSE |
| c.1517G>A | p.R506K | MISSENSE |
| c.1071G>A | p.G357G | SYNONYMOUS |
| c.583A>G | p.I195V | MISSENSE |
| c.1265C>G | p.A422G | MISSENSE |
| c.861T>C | p.T287T | SYNONYMOUS |
| c.205G>A | p.E69K | MISSENSE |
| c.185G>A | p.C62Y | MISSENSE |
| c.715G>A | p.V239I | MISSENSE |
| c.993C>T | p.A331A | SYNONYMOUS |
| c.1094C>T | p.S365F | MISSENSE |
| c.1279G>A | p.A427T | MISSENSE |
| IVS7-1G>A | SPLICE SITE | SPLICE SITE |

FIG. 10
CONTINUED

| | | | |
|---|---|---|---|
| LOC113655 | CCDS6431.1 | Br27P | g.chr8:145705898A>C |
| LOC113655 | CCDS6431.1 | Br27P | g.chr8:145705899G>T |
| LOC124842 | CCDS11283.1 | Br27P | g.chr17:29984030C>T |
| LOC126248 | CCDS12429.1 | Br27P | g.chr19:38343191G>A |
| LOC131368 | CCDS2947.1 | Br16X | g.chr3:103657744A>T |
| LOC131873 | ENST00000358511 | Br05X | g.chr3:131767096C>T |
| LOC134145 | NM_199133 | Br27P | g.chr5:10289727G>A |
| LOC146562 | CCDS10521.1 | BR27P | g.chr16:4730662G>A |
| LOC158830 | NM_001025265 | Br27P | g.chrX:70106912C>T |
| LOC200312 | NM_001017981 | Br27P | g.chr22:29106470C>T |
| LOC221955 | CCDS5350.1 | Br27P | g.chr7:6229509G>A |
| LOC257106 | CCDS1215.1 | Br27P | g.chr1:157831186C>T |
| LOC257106 | CCDS1215.1 | Br27P | g.chr1:157839375G>A |
| LOC283537 | CCDS9332.1 | Br15X | g.chr13:28189947G>C |
| LOC284912 | CCDS13918.1 | Br11P | g.chr22:34348002C>T |
| LOC284948 | CCDS1976.1 | Br07X | g.chr2:85573774C>T |
| LOC339977 | NM_001024611 | Br27P | g.chr4:52703222G>A |
| LOC374768 | NM_199339 | Br27P | g.chr17:7267592C>T |
| LOC387755 | NM_001031853 | Br16X | g.chr11:15213745A>T |
| LOC387856 | NM_001013635 | Br27P | g.chr12:46864265G>A |
| LOC388595 | NM_001013641 | Br27P | g.chr1:15814859C>T |
| LOC388969 | NM_001013649 | Br15X | g.chr2:85748258C>T |
| LOC391123 | NM_001013661 | Br27P | g.chr1:156641726C>T |
| LOC392617 | ENST00000333066 | Br03X | g.chr7:1559311C>T |
| LOC392617 | ENST00000333066 | Br16X | g.chr7:1557860C>T |
| LOC400707 | NM_001013673 | Br27P | g.chr19:51690107C>T |
| LOC441136 | NM_001013719 | Br27P | g.chr6:27465110G>A |
| LOC441233 | NM_001013724 | Br15X | g.chr7:57282870G>A |
| LOC442213 | NM_001013732 | Br27P | g.chr6:47954784C>T |
| LOC494115 | NM_001008662 | Br27P | g.chr1:89126934C>T |
| LOC51058 | CCDS476.1 | Br27P | g.chr1:42985811G>A |
| LOC54103 | NM_017439 | Br27P | g.chr7:76636587G>A |
| LOC54499 | CCDS1251.1 | Br27P | g.chr1:162469112A>G |
| LOC550631 | NM_001017437 | Br27P | g.chr22:29094218C>T |
| LOC63928 | CCDS10617.1 | Br27P | g.chr16:23674524G>A |
| LOC643866 | NM_001039771 | Br02X | g.chr14:23967927G>A |
| LOC648272 | ENST00000343945 | Br27P | g.chr19:14054377G>A |
| LOC651746 | ENST00000296657 | BR02X | g.chr5:10702532G>A |
| LOC651863 | ENST00000333744 | Br26X | g.chr5:17688134C>T |
| LOC90379 | NM_138353 | Br27P | g.chr19:13932775G>A |
| LOC90826 | CCDS3771.1 | Br15X | g.chr4:148932669G>A |
| LOC92154 | NM_138383 | Br27P | g.chr16:69256483C>T |
| LOC93349 | NM_138402 | Br27P | g.chr2:231082415G>A |
| LPAL2 | ENST00000342479 | Br9PT | g.chr6:160858400C>T |
| LPHN1 | CCDS12307.1 | Br27P | g.chr19:14122991G>A |
| LPHN2 | CCDS689.1 | Br15X | g.chr1:82133746A>G |
| LPHN3 | NM_015236 | Br07X | g.chr4:62604044T>A (HOMOZYGOUS) |
| LPIN3 | NM_022896 | Br27P | g.chr20:39414891C>T |
| LPL | CCDS6012.1 | Br04X | g.chr8:19853707C>A |
| LRAT | CCDS3789.1 | Br02X | g.chr4:156023524G>C |

FIG. 10
CONTINUED

| | | |
|---|---|---|
| c.374A>C | p.Q125P | MISSENSE |
| c.375G>T | p.Q125H | MISSENSE |
| c.1407C>T | p.L469L | SYNONYMOUS |
| c.1029G>A | p.R343R | SYNONYMOUS |
| c.393A>T | p.G131G | SYNONYMOUS |
| c.1147C>T | p.R383W | MISSENSE |
| c.307G>A | p.V103I | MISSENSE |
| IVS3+1G>A | SPLICE SITE | SPLICE SITE |
| c.498C>T | p.D166D | SYNONYMOUS |
| c.564C>T | p.T188T | SYNONYMOUS |
| c.1416G>A | p.R472R | SYNONYMOUS |
| c.2065C>T | p.P689S | MISSENSE |
| c.221G>A | p.R74Q | MISSENSE |
| c.189G>C | p.E63D | MISSENSE |
| c.230C>T | p.A77V | MISSENSE |
| c.38C>T | p.S13F | MISSENSE |
| c.894G>A | p.R298R | SYNONYMOUS |
| c.461C>T | p.A154V | MISSENSE |
| c.1333A>T | p.M445L | MISSENSE |
| c.93G>A | p.V31V | SYNONYMOUS |
| c.200C>T | p.A67V | MISSENSE |
| c.336C>T | p.Y112Y | SYNONYMOUS |
| c.99C>T | p.Y33Y | SYNONYMOUS |
| c.1796C>T | p.A599V | MISSENSE |
| c.387C>T | p.R129R | SYNONYMOUS |
| c.378C>T | p.A126A | SYNONYMOUS |
| c.498G>A | p.R166R | SYNONYMOUS |
| c.170G>A | p.R57H | MISSENSE |
| c.1704C>T | p.F568F | SYNONYMOUS |
| c.900C>T | p.D300D | SYNONYMOUS |
| c.89G>A | p.G30D | MISSENSE |
| c.268G>A | p.G90R | MISSENSE |
| c.123A>G | p.A41A | SYNONYMOUS |
| c.1261C>T | p.L421L | SYNONYMOUS |
| c.109G>A | p.A37T | MISSENSE |
| c.174G>A | p.G58G | SYNONYMOUS |
| c.548G>A | p.G183D | MISSENSE |
| c.792G>A | p.P264P | SYNONYMOUS |
| c.230C>T | p.A77V | MISSENSE |
| c.1771G>A | p.D591N | MISSENSE |
| c.1984G>A | p.D662N | MISSENSE |
| c.1146C>T | p.G382G | SYNONYMOUS |
| c.812G>A | p.R271H | MISSENSE |
| c.299C>T | p.T100M | MISSENSE |
| c.4104G>A | p.R1368R | SYNONYMOUS |
| c.1947A>G | p.S649S | SYNONYMOUS |
| c.1684T>A | p.L562M | MISSENSE |
| c.1497C>T | p.S499S | SYNONYMOUS |
| c.397C>A | p.Q133K | MISSENSE |
| c.441G>C | p.K147N | MISSENSE |

FIG. 10
CONTINUED

| Gene | Accession | Sample | Variant |
|---|---|---|---|
| LRCH1 | NM_015116 | Br14X | g.chr13:46177267C>G |
| LRFN5 | CCDS9678.1 | Br26X | g.chr14:41425765G>A |
| LRP1 | CCDS8932.1 | Br17X | g.chr12:55857636C>T |
| LRP10 | CCDS9578.1 | Br27P | g.chr14:22414270G>A |
| LRP1B | CCDS2182.1 | Br27P | g.chr2:141405026G>A |
| LRP1B | CCDS2182.1 | Br27P | g.chr2:141047846C>T |
| LRP2 | CCDS2232.1 | Br27P | g.chr2:169928866G>A |
| LRP2 | CCDS2232.1 | Br03x | g.chr2:169926886G>A |
| LRP2 | CCDS2232.1 | Br05X | g.chr2:169886257G>A |
| LRP2 | CCDS2232.1 | Br17X | g.chr2:169870167G>A |
| LRRC16 | NM_017640 | Br27P | g.chr6:25689597C>T |
| LRRC4 | CCDS5799.1 | Br27P | g.chr7:127264318C>T |
| LRRC4B | ENST00000253728 | Br03X | g.chr19:55713328C>T |
| LRRC7 | CCDS645.1 | Br16X | g.chr1:70214215_70214218delCTCA |
| LRRC7 | CCDS645.1 | Br04X | g.chr1:70216830G>C |
| LRRIQ1 | NM_032165 | Br20P | g.chr12:84018016C>T |
| LRRK1 | NM_024652 | Br9PT | g.chr15:99410752C>A |
| LRRK1 | NM_024652 | Br11P | g.chr15:99424368delG |
| LRRN1 | NM_020873 | Br27P | g.chr3:3862281C>T |
| LRRN3 | CCDS5754.1 | Br26X | g.chr7:110357189C>T |
| LRRN5 | CCDS1448.1 | Br27P | g.chr1:201319504C>T |
| LTB4R2 | CCDS9624.1 | Br14X | g.chr14:23843301G>A |
| LTBP1 | NM_000627 | Br27P | g.chr2:33502134G>A |
| LTBP3 | CCDS8103.1 | Br27P | g.chr11:65065753C>T |
| LTBP4 | NM_003573 | Br03X | g.chr19:45824922G>T |
| LTK | CCDS10077.1 | Br13X | g.chr15:39590689C>T |
| LUC7L | CCDS10401.1 | Br27P | g.chr16:198077G>A |
| LY6K | CCDS6385.1 | Br10P | g.chr8:143778899C>T |
| LYNX1 | ENST00000317543 | Br04X | g.chr8:143848208_143848207delCT |
| LYPLA1 | CCDS6157.1 | Br08X | g.chr8:55127795G>T |
| LYRIC | CCDS6274.1 | Br27P | g.chr8:98800512C>T |
| LYST | NM_000081 | Br27P | g.chr1:232176318C>T |
| LYST | NM_000081 | Br27P | g.chr1:232282899G>A |
| LYZL4 | CCDS2697.1 | Br20P | g.chr3:42413815G>A |
| LZTR2 | NM_033127 | Br27P | g.chr1:174652727G>A |
| M160 | CCDS8577.1 | Br27P | g.chr12:7413219G>A |
| MACF1 | CCDS435.1 | Br27P | g.chr1:39570389C>T |
| MACF1 | CCDS435.1 | Br27P | g.chr1:39583523G>A |
| MACF1 | CCDS435.1 | Br17X | g.chr1:39493468C>T |
| MAEA | NM_001017405 | Br27P | g.chr4:1322210C>T |
| MAGEA4 | CCDS14702.1 | Br27P | g.chrX:150763365G>A |
| MAGEB10 | NM_182506 | Br9PT | g.chrX:27599243G>T |
| MAGEC1 | NM_005462 | Br02X | g.chrX:140721711A>T (HOMOZYGOUS) |
| MAGEH1 | CCDS14369.1 | Br23X | g.chrX:55361867G>A |
| MAGI-3 | CCDS859.1 | Br27P | g.chr1:113905733G>T |
| MAK10 | CCDS6673.1 | Br27P | g.chr9:85854359G>A |
| MALT1 | CCDS11967.1 | Br27P | g.chr18:54565995G>A |
| MAMDC2 | CCDS6631.1 | Br27P | g.chr9:70070265G>A |
| MAN1B1 | CCDS7029.1 | Br27P | g.chr9:137277846G>A |
| MAN2A1 | NM_002372 | Br27P | g.chr5:109148487G>A |

FIG. 10
CONTINUED

| | | |
|---|---|---|
| c.1464C>G | p.A488A | SYNONYMOUS |
| c.187G>A | p.V63I | MISSENSE |
| c.4356C>T | p.D1452D | SYNONYMOUS |
| c.382G>A | p.G128S | MISSENSE |
| c.5291G>A | p.G1764D | MISSENSE |
| c.9873C>T | p.A3291A | SYNONYMOUS |
| c.3046G>A | p.D1016N | MISSENSE |
| c.3254G>A | p.R1085H | MISSENSE |
| c.7747G>A | p.V2583M | MISSENSE |
| c.9148G>A | p.V3050I | MISSENSE |
| c.2957C>T | p.T986I | MISSENSE |
| c.327C>T | p.N109N | SYNONYMOUS |
| c.809C>T | p.T270I | MISSENSE |
| c.2061_2064delCTCA | fs | INDEL |
| c.3188G>C | p.S1063T | MISSENSE |
| c.3451C>T | p.R1151C | MISSENSE |
| c.1677C>A | p.G559G | SYNONYMOUS |
| c.3654delG | fs | INDEL |
| c.956C>T | p.A319V | MISSENSE |
| c.410C>T | p.S137F | MISSENSE |
| c.1274C>T | p.S425F | MISSENSE |
| c.1625G>A | p.R542H | MISSENSE |
| c.3649G>A | p.G1217S | MISSENSE |
| c.2619C>T | p.D873D | SYNONYMOUS |
| c.4278G>T | p.E1426D | MISSENSE |
| c.962C>T | p.A321V | MISSENSE |
| IVS4+1G>A | SPLICE SITE | SPLICE SITE |
| c.126C>T | p.G42G | SYNONYMOUS |
| c.19_20delCT | fs | INDEL |
| c.435G>T | p.W145C | MISSENSE |
| c.1440C>T | p.T480T | SYNONYMOUS |
| c.10772C>T | p.A3591V | MISSENSE |
| c.4061G>A | p.C1354Y | MISSENSE |
| c.387G>A | p.R129R | SYNONYMOUS |
| c.1524G>A | p.G508G | SYNONYMOUS |
| IVS15+1G>A | SPLICE SITE | SPLICE SITE |
| c.11665C>T | p.L3889L | SYNONYMOUS |
| c.14076G>A | p.V4692V | SYNONYMOUS |
| c.5764C>T | p.R1922X | NONSENSE |
| c.1070C>T | p.P357L | MISSENSE |
| c.661G>A | p.E221K | MISSENSE |
| c.163G>T | p.D55Y | MISSENSE |
| c.3001A>T | p.I1001F | MISSENSE |
| c.39G>A | p.A13A | SYNONYMOUS |
| c.2378G>T | p.R793L | MISSENSE |
| c.1249G>A | p.A417T | MISSENSE |
| c.2416G>A | p.E806K | MISSENSE |
| c.1957G>A | p.A653T | MISSENSE |
| c.1791G>A | p.R597R | SYNONYMOUS |
| c.1721G>A | p.G574E | MISSENSE |

FIG. 10
CONTINUED

| | | | |
|---|---|---|---|
| MAN2B1 | NM_000528 | Br17X | g.chr19:12619121G>A |
| MAN2B1 | NM_000528 | Br27P | g.chr19:12619070G>A |
| MAP1B | CCDS4012.1 | Br27P | g.chr5:71526970G>A |
| MAP3K11 | CCDS8107.1 | Br9PT | g.chr11:65123671G>A |
| MAP3K14 | NM_003954 | Br27P | g.chr17:40719883C>T |
| MAP3K8 | CCDS7166.1 | Br27P | g.chr10:30788322G>A |
| MAP3K9 | NM_033141 | Br14X | g.chr14:70267227G>A |
| MAP4K4 | NM_004834 | Br27P | g.chr2:101944678delC |
| MAP7D3 | ENST00000218318 | Br27P | g.chrX:135039435C>T |
| MARCO | CCDS2124.1 | Br27P | g.chr2:119443935C>T |
| MARK3 | NM_002376 | Br11P | chr14:103039090_103039098delATCCGCA |
| MARS | CCDS8942.1 | Br27P | g.chr12:56180468G>A |
| MARS2 | NM_138395 | Br27P | g.chr2:198396070G>A |
| MASS1 | NM_032119 | Br17X | g.chr5:90172179G>A |
| MASS1 | NM_032119 | Br16X | g.chr5:90017395C>T |
| MASS1 | NM_032119 | Br25X | g.chr5:90048295G>A |
| MAST4 | ENST00000261569 | Br27P | g.chr5:66494362C>T |
| MATN1 | CCDS336.1 | Br27P | g.chr1:30863523C>T |
| MBD1 | CCDS11941.1 | Br15X | g.chr18:46053264G>T |
| MBNL1 | CCDS3163.1 | Br27P | g.chr3:153656050C>T |
| MCCC1 | CCDS3241.1 | Br27P | g.chr3:184223000G>A |
| MCF2L | ENST00000261963 | Br27P | g.chr13:112797752G>A |
| MCFD2 | NM_139279 | Br23X | g.chr2:47047893C>T |
| MCM10 | CCDS7095.1 | Br27P | g.chr10:13254664G>A |
| MCPH1 | NM_024596 | Br15X | g.chr8:6466515G>A |
| MDGA1 | NM_153487 | Br27P | g.chr6:37739725C>T |
| MDGA1 | NM_153487 | Br27P | g.chr6:37731507C>T |
| MDH2 | CCDS55581.1 | Br27P | g.chr7:75338323G>A |
| MEA | CCDS4879.1 | Br27P | g.chr6:43088213C>T |
| MED12 | NM_005120 | Br27P | g.chrX:70140738C>T |
| MEFV | CCDS10498.1 | Br02X | g.chr16:3237215G>A |
| MEFV | CCDS10498.1 | Br20P | g.chr16:3244459C>T |
| MEN1 | CCDS8083.1 | Br27P | g.chr11:64331062C>T |
| METTL5 | NM_014168 | Br27P | g.chr2:170504002G>A |
| MGAM | NM_004668 | Br14X | g.chr7:141211268A>G |
| MGC16635 | CCDS14097.1 | Br27P | g.chr22:49277907C>T |
| MGC19764 | NM_144975 | Br27P | g.chr17:30616547C>T |
| MGC20419 | CCDS562.1 | Br27P | g.chr1:52211229G>A |
| MGC20419 | CCDS562.1 | Br27P | g.chr1:52211110G>A |
| MGC20741 | CCDS4861.1 | Br27P | g.chr6:41882523G>A |
| MGC21830 | CCDS10463.1 | Br27P | g.chr16:2199693G>A |
| MGC24039 | NM_144973 | Br27P | g.chr12:31468870G>A |
| MGC2655 | CCDS10491.1 | BR15X | g.chr16:3016079G>A |
| MGC26598 | CCDS9036.1 | Br05x | g.chr12:89850557G>A |
| MGC26818 | CCDS44.1 | Br27P | g.chr1:2552544A>T |
| MGC27016 | CCDS3790.1 | Br27P | g.chr4:156076585C>T |
| MGC29814 | CCDS11742.1 | Br27P | g.chr17:71778171G>A |
| MGC29875 | CCDS1493.1 | Br27P | g.chr1:206398540G>A |
| MGC33367 | CCDS10738.1 | Br11P | g.chr16:47969907A>G |
| MGC33414 | CCDS279.1 | Br07X | g.chr1:26378279C>T |

FIG. 10
CONTINUED

| | | |
|---|---|---|
| c.2849G>A | p.R950H | MISSENSE |
| c.2900G>A | p.R967K | MISSENSE |
| c.2032G>A | p.E678K | MISSENSE |
| c.1976G>A | p.R659H | MISSENSE |
| c.850C>T | p.L284L | SYNONYMOUS |
| c.1159G>A | p.A387T | MISSENSE |
| c.2980G>A | p.D994N | MISSENSE |
| c.2054delC | fs | INDEL |
| c.796C>T | p.L266L | SYNONYMOUS |
| c.215C>T | p.A72V | MISSENSE |
| c.1963_1971delATCCGCAAA | p.I655_K657del | INDEL |
| c.1189G>A | p.A397T | MISSENSE |
| c.435G>A | p.V145V | SYNONYMOUS |
| c.16640G>A | p.R5547H | MISSENSE |
| c.6317C>T | p.A2106V | MISSENSE |
| c.9440G>A | p.R3147Q | MISSENSE |
| c.2799C>T | p.D933D | SYNONYMOUS |
| c.263C>T | p.T88I | MISSENSE |
| c.1338G>T | p.K446N | MISSENSE |
| c.983C>T | p.P328L | MISSENSE |
| c.1776G>A | p.E592E | SYNONYMOUS |
| c.184G>A | p.E62K | MISSENSE |
| c.69C>T | p.G23G | SYNONYMOUS |
| c.485G>A | p.R162K | MISSENSE |
| c.2062G>A | p.G688R | MISSENSE |
| c.203C>T | p.P68L | MISSENSE |
| c.526C>T | p.L176L | SYNONYMOUS |
| c.649G>A | p.D217N | MISSENSE |
| c.531C>T | p.A177A | SYNONYMOUS |
| c.5968C>T | p.H1990Y | MISSENSE |
| c.1389G>A | p.Q463Q | SYNONYMOUS |
| c.610C>T | p.R204C | MISSENSE |
| c.924C>T | p.H308H | SYNONYMOUS |
| c.182G>A | p.G61D | MISSENSE |
| c.3775A>G | p.I1259V | MISSENSE |
| c.871C>T | p.P291S | MISSENSE |
| c.2203C>T | p.P735S | MISSENSE |
| c.226G>A | p.V76I | MISSENSE |
| c.345G>A | p.A115A | SYNONYMOUS |
| c.177G>A | p.E59E | SYNONYMOUS |
| c.454G>A | p.V152I | MISSENSE |
| c.2149G>A | p.E717K | MISSENSE |
| c.235G>A | p.V79I | MISSENSE |
| c.431G>A | p.G144D | MISSENSE |
| c.482A>T | p.H161L | MISSENSE |
| c.169C>T | p.P57S | MISSENSE |
| c.485G>A | p.G162D | MISSENSE |
| IVS5-1G>A | SPLICE SITE | SPLICE SITE |
| c.296A>G | p.D99G | MISSENSE |
| c.221C>T | p.P74L | MISSENSE |

FIG. 10
CONTINUED

| | | | |
|---|---|---|---|
| MGC33486 | CCDS8133.1 | Br27P | g.chr11:65819120C>T |
| MGC33889 | CCDS14216.1 | Br14X | g.chrX:25917303C>T |
| MGC34647 | CCDS10895.1 | Br27P | g.chr16:69251453G>A |
| MGC35118 | CCDS10046.1 | Br15X | g.chr15:36016860G>T |
| MGC35194 | CCDS147.1 | Br03X | g.chr1:12755075G>A |
| MGC35366 | CCDS9057.1 | Br14X | g.chr12:94853185C>A |
| MGC39581 | CCDS12149.1 | Br12P | g.chr19:5714257G>T |
| MGC42174 | NM_152383 | Br27P | g.chr2:232705195G>A |
| MGC4251 | CCDS11474.1 | Br20P | g.chr17:39447383C>T |
| MGC4268 | CCDS2152.1 | Br23X | g.chr2:128343293C>T |
| MGC45562 | CCDS11371.1 | Br14X | g.chr17:36071741C>T |
| MGC45780 | CCDS6064.1 | Br27P | g.chr8:27900983C>T |
| MGC47869 | CCDS8667.1 | Br16X | g.chr12:14867397T>A |
| MHC2TA | CCDS10544.1 | Br02X | g.chr16:10908851G>C |
| MIA3 | ENST00000320831 | Br27P | g.chr1:219191115G>A |
| MICAL-L2 | CCDS5324.1 | Br27P | g.chr7:1251179C>T |
| MINK1 | NM_170663 | Br27P | g.chr17:4734784C>T |
| MINK1 | NM_170663 | Br27P | g.chr17:4735122C>T |
| MIPEP | CCDS9303.1 | Br27P | g.chr13:23232352G>A |
| MIR16 | CCDS10578.1 | BR27P | g.chr16:19423783C>T |
| MKI67 | CCDS7659.1 | Br27P | g.chr10:129803650C>T |
| MLL | NM_005933 | Br27P | g.chr11:117877759G>A |
| MLL3 | CCDS5931.1 | Br08X | g.chr7:151283619G>A |
| MLL4 | NM_014727 | Br27P | g.chr19:40909940C>T |
| MLL4 | NM_014727 | Br27P | g.chr19:40903018G>A |
| MLLT4 | CCDS5303.1 | Br08X | g.chr6:168130361G>A (HOMOZYGOUS) |
| MLLT7 | NM_005938 | Br10P | g.chrX:70103911G>A |
| MME | CCDS3172.1 | Br17X | g.chr3:156342495T>A |
| MMP10 | CCDS8321.1 | Br27P | g.chr11:102146779G>A |
| MMP16 | CCDS6246.1 | Br27P | g.chr8:89155969G>A |
| MOCS1 | CCDS4845.1 | Br27P | g.chr6:39985589C>T |
| MON2 | NM_015026 | Br14X | g.chr12:61233048C>T |
| MON2 | NM_015026 | Br27P | g.chr12:61147262G>A |
| MPDU1 | CCDS11115.1 | Br17X | g.chr17:7431513C>T |
| MPDZ | NM_003829 | Br27P | g.chr9:13182159G>A |
| MPP1 | CCDS14762.1 | Br27P | g.chrX:153573680G>A |
| MPZ | CCDS1229.1 | Br23X | g.chr1:158089246A>G |
| MRC2 | CCDS11634.1 | Br27P | g.chr17:58121092G>A |
| MRGX1 | CCDS7846.1 | Br13X | g.chr11:18912677C>T |
| MRPL13 | CCDS6332.1 | Br05X | g.chr8:121524697C>G |
| MRPL16 | CCDS7976.1 | Br16X | g.chr11:59330577G>A |
| MRPL37 | ENST00000329505 | Br07X | g.chr18:54508739C>T |
| MRPL44 | CCDS2459.1 | Br27P | g.chr2:224654081C>T |
| MRPL46 | CCDS10341.1 | Br27P | g.chr15:86803844G>A |
| MRPL55 | CCDS1567.1 | Br11P | g.chr1:224602692C>T |
| MRPS5 | CCDS2010.1 | Br27P | g.chr2:95175109C>T |
| MRPS7 | CCDS11718.1 | Br27P | g.chr17:70770272G>A |
| MRVI1 | NM_006069 | Br27P | g.chr11:106030214G>A |
| MS4A | CCDS7985. | Br27P | hr11:59916824_59916835delAACAACCCTG |
| MSI2 | CCDS11596.1 | Br27P | g.chr17:52833756G>A |

FIG. 10
CONTINUED

| | | |
|---|---|---|
| c.827C>T | p.P276L | MISSENSE |
| c.544C>T | p.L182F | MISSENSE |
| c.591G>A | p.Q197Q | SYNONYMOUS |
| c.286G>T | p.V96F | MISSENSE |
| c.510G>A | p.P170P | SYNONYMOUS |
| c.564C>A | p.Y188X | NONSENSE |
| c.1237G>T | p.V413L | MISSENSE |
| IVS1+1G>A | SPLICE SITE | SPLICE SITE |
| c.186C>T | p.A62A | SYNONYMOUS |
| c.689C>T | p.T230I | MISSENSE |
| c.178C>T | p.R60C | MISSENSE |
| c.69C>T | p.S23S | SYNONYMOUS |
| c.261T>A | p.C87X | NONSENSE |
| c.2001G>C | p.L667L | SYNONYMOUS |
| c.682G>A | p.V228I | MISSENSE |
| c.2174C>T | p.T725I | MISSENSE |
| c.1538C>T | p.P513L | MISSENSE |
| c.1661C>T | p.A554V | MISSENSE |
| c.1853G>A | p.W618X | NONSENSE |
| c.769C>T | p.L257F | MISSENSE |
| c.1012C>T | p.P338S | MISSENSE |
| c.6473G>A | p.G2158D | MISSENSE |
| c.13041G>A | p.P4347P | SYNONYMOUS |
| c.4047C>T | p.D1349D | SYNONYMOUS |
| c.929G>A | p.R310K | MISSENSE |
| c.1746G>A | p.E582E | SYNONYMOUS |
| c.810G>A | p.R270R | SYNONYMOUS |
| c.971T>A | p.L324X | NONSENSE |
| c.1386G>A | p.R462R | SYNONYMOUS |
| c.1202G>A | p.G401E | MISSENSE |
| c.1070C>T | p.A357V | MISSENSE |
| c.3037C>T | p.H1013Y | MISSENSE |
| c.8G>A | p.G3D | MISSENSE |
| c.664C>T | p.L222F | MISSENSE |
| c.1939G>A | p.D647N | MISSENSE |
| c.1048G>A | p.E350K | MISSENSE |
| c.560A>G | p.Y187C | MISSENSE |
| c.3679G>A | p.G1227R | MISSENSE |
| c.231C>T | p.S77S | SYNONYMOUS |
| c.60C>G | p.L20L | SYNONYMOUS |
| c.575G>A | p.R192H | MISSENSE |
| c.160C>T | p.P54S | MISSENSE |
| c.752C>T | p.S251L | MISSENSE |
| UTR+4G>A | 3'UTR | 3'UTR |
| c.5C>T | p.A2V | MISSENSE |
| c.1160C>T | p.P387L | MISSENSE |
| c.183G>A | p.E61E | SYNONYMOUS |
| c.155G>A | p.C52Y | MISSENSE |
| c.637_648delAACAACCCTGG | p.N213_G216de | INDEL |
| c.330G>A | p.K110K | SYNONYMOUS |

FIG. 10
CONTINUED

| Gene | Accession | Sample | Variant |
|---|---|---|---|
| MSL2L1 | NM_018133 | Br04X | g.chr3:137353846A>G |
| MSRB3 | CCDS8973.1 | Br23X | g.chr12:64143316G>A |
| MTA1 | NM_004689 | Br27P | g.chr14:105001442G>A |
| MTHFD2L | NM_001004346 | Br03X | g.chr4:75430698G>T |
| MTNR1B | CCDS8290.1 | Br9PT | g.chr11:92354586C>T |
| MTP | CCDS3651.1 | Br02X | g.chr4:100885100G>A |
| MTR | CCDS1614.1 | Br27P | g.chr1:233341895C>T |
| MTX2 | CCDS2272.1 | Br05X | g.chr2:177019633T>A |
| MUC15 | CCDS7859.1 | Br15X | g.chr11:26541255C>T |
| MUC16 | NM_024690 | Br27P | g.chr19:8951078G>A |
| MUC16 | NM_024690 | Br27P | g.chr19:8910153G>A |
| MUC16 | NM_024690 | Br15X | g.chr19:8908401T>C |
| MUC16 | NM_024690 | Br27P | g.chr19:8948685C>T |
| MUC16 | NM_024690 | Br26X | g.chr19:8947573A>G |
| MUC5AC | ENST00000349637 | Br27P | g.chr11:1229470C>T |
| MUC7 | CCDS3541.1 | Br14X | g.chr4:71527580C>A |
| MVP | CCDS10656.1 | Br27P | g.chr16:29755686C>T |
| MYBPC3 | NM_000256 | Br27P | g.chr11:47321680G>A |
| MYBPHL | NM_001010985 | Br14X | g.chr1:109549781G>A |
| MYF6 | CCDS9019.1 | Br27P | g.chr12:79604235C>T |
| MYH14 | NM_024729 | Br15X | g.chr19:55475105G>A |
| MYH15 | ENST00000273353 | Br27P | g.chr3:109707262G>A |
| MYH15 | ENST00000273353 | Br13X | g.chr3:109639116C>T |
| MYH3 | CCDS11157.1 | Br27P | g.chr17:10477729T>C |
| MYH4 | CCDS11154.1 | Br27P | g.chr17:10291219G>A |
| MYO15A | NM_016239 | Br27P | g.chr17:17999185C>T |
| MYO18B | NM_032608 | Br27P | g.chr22:24518509C>T |
| MYO18B | NM_032608 | Br27P | g.chr22:24596841C>T |
| MYO18B | NM_032608 | Br27P | g.chr22:24747854C>T |
| MYO1B | CCDS2311.1 | Br08X | g.chr2:192077579G>A |
| MYO1B | CCDS2311.1 | Br17X | g.chr2:192104887G>A |
| MYO1D | NM_015194 | Br03X | g.chr17:28072304G>A |
| MYO1E | NM_004998 | Br27P | g.chr15:57307050G>C |
| MYO3A | CCDS7148.1 | Br14X | g.chr10:26476369delT(HOMOZYGOUS) |
| MYO3B | NM_138995 | Br17X | g.chr2:171074457G>A |
| MYO5A | NM_000259 | Br27P | g.chr15:50439471C>T |
| MYO5C | NM_018728 | Br27P | g.chr15:50275882A>T |
| MYO5C | NM_018728 | Br27P | g.chr15:50355051G>A |
| MYO5C | NM_018728 | Br23X | g.chr15:50352205G>T |
| MYO9B | NM_004145 | Br27P | g.chr19:17144142C>T |
| MYOCD | CCDS11163.1 | Br16X | g.chr17:12590006G>A |
| MYOCD | CCDS11163.1 | Br27P | g.chr17:12607551C>T |
| MYOM1 | NM_003803 | Br27P | g.chr18:3178881G>A |
| MYOM2 | CCDS5957.1 | Br27P | g.chr8:1993210G>A |
| MYR8 | NM_015011 | Br04X | g.chr13:108273608C>A |
| MYRIP | CCDS2689.1 | Br17X | g.chr3:40198763C>T |
| MYST3 | CCDS6124.1 | Br27P | g.chr8:41931994C>T |
| MYT1L | NM_015025 | Br27P | g.chr2:1866304C>T |
| NAGA | CCDS14030.1 | Br27P | g.chr22:40787285C>T |
| NALP1 | NM_014922 | Br27P | g.chr17:5403560C>T |

FIG. 10 CONTINUED

| | | |
|---|---|---|
| c.575A>G | p.N192S | MISSENSE |
| c.526G>A | p.E176K | MISSENSE |
| c.1105G>A | p.V369I | MISSENSE |
| c.430G>T | p.G144X | NONSENSE |
| c.549C>T | p.Y183Y | SYNONYMOUS |
| c.1362G>A | p.K454K | SYNONYMOUS |
| c.1729C>T | p.L577F | MISSENSE |
| c.515T>A | p.I172N | MISSENSE |
| c.828C>T | p.D276D | SYNONYMOUS |
| c.1737G>A | p.G579G | SYNONYMOUS |
| c.32478G>A | p.T10826T | SYNONYMOUS |
| c.34230T>C | p.S11410S | SYNONYMOUS |
| c.4130C>T | p.T1377I | MISSENSE |
| c.5242A>G | p.S1748G | MISSENSE |
| c.14619C>T | p.T4873T | SYNONYMOUS |
| c.359C>A | p.S120Y | MISSENSE |
| c.815C>T | p.P272L | MISSENSE |
| c.1162G>A | p.A388T | MISSENSE |
| c.1048G>A | p.V350M | MISSENSE |
| c.269C>T | p.A90V | MISSENSE |
| IVS27-1G>A | SPLICE SITE | SPLICE SITE |
| c.253G>A | p.E85K | MISSENSE |
| c.3256C>T | p.R1086X | NONSENSE |
| c.4551T>C | p.I1517I | SYNONYMOUS |
| c.5005G>A | p.D1669N | MISSENSE |
| c.8261C>T | p.T2754M | MISSENSE |
| c.2412C>T | p.A804A | SYNONYMOUS |
| c.4212C>T | p.L1404L | SYNONYMOUS |
| c.7360C>T | p.P2454S | MISSENSE |
| c.1678G>A | p.A560T | MISSENSE |
| c.2971G>A | p.V991I | MISSENSE |
| c.1763G>A | p.R588H | MISSENSE |
| c.542G>C | p.G181A | MISSENSE |
| c.2510delT | fs | INDEL |
| c.1736G>A | p.R579K | MISSENSE |
| c.3409C>T | p.P1137S | MISSENSE |
| c.4911A>T | p.A1637A | SYNONYMOUS |
| c.606G>A | p.E202E | SYNONYMOUS |
| c.614G>T | p.G205V | MISSENSE |
| IVS10-4C>T | SPLICE SITE | SPLICE SITE |
| c.1017G>A | p.T339T | SYNONYMOUS |
| c.2682C>T | p.D894D | SYNONYMOUS |
| c.636G>A | p.R212R | SYNONYMOUS |
| c.465G>A | p.E155E | SYNONYMOUS |
| c.1012C>A | p.P338T | MISSENSE |
| c.922C>T | p.P308S | MISSENSE |
| c.1575C>T | p.S525S | SYNONYMOUS |
| c.2079C>T | p.Y693Y | SYNONYMOUS |
| c.526C>T | p.L176L | SYNONYMOUS |
| c.1180C>T | p.P394S | MISSENSE |

FIG. 10
CONTINUED

| | | | |
|---|---|---|---|
| NALP11 | CCDS12935.1 | Br27P | g.chr19:61011060G>A |
| NALP7 | CCDS12912.1 | Br20P | g.chr19:60126916G>A |
| NAPSB | ENST00000253720 | Br13X | g.chr19:55528981G>A (HOMOZYGOUS) |
| NARG1L | CCDS9379.1 | Br27P | g.chr13:40839646C>T |
| NAV1 | CCDS1414.1 | Br27P | g.chr1:198481871C>T |
| NAV1 | CCDS1414.1 | Br27P | g.chr1:198350039G>A |
| NCBP1 | CCDS6728.1 | Br27P | g.chr9:97497920G>A |
| NCKAP1L | NM_005337 | Br27P | g.chr12:53189757G>A |
| NCOA5 | CCDS13392.1 | Br27P | g.chr20:44132330G>A |
| NCOA6 | CCDS13241.1 | Br27P | g.chr20:32809387G>A |
| NDUFA11 | CCDS12155.1 | Br27P | g.chr19:5847519C>T |
| NDUFB2 | CCDS5862.1 | Br17X | g.chr7:139855878C>T |
| NDUFS6 | CCDS3866.1 | Br04X | g.chr5:1854528C>A |
| NEB | NM_004543 | Br27P | g.chr2:152347499C>T |
| NEIL3 | CCDS3828.1 | Br16X | g.chr4:178658657G>T |
| NEUROG2 | CCDS3698.1 | BR27P | g.chr4:113793867C>T |
| NF1 | CCDS11264.1 | Br23X | g.chr17:26570198T>G (HOMOZYGOUS) |
| NF1 | CCDS11264.1 | Br27P | g.chr17:26677066C>T |
| NF1 | CCDS11264.1 | Br16X | g.chr17:26678862C>T |
| NF1 | CCDS11264.1 | Br04X | g.chr17:26707634C>G (HOMOZYGOUS) |
| NFATC3 | CCDS10862.1 | Br27P | g.chr16:66749293G>A |
| NFATC4 | CCDS9629.1 | Br27P | g.chr14:23909514G>A |
| NGEF | CCDS2500.1 | Br20P | g.chr2:233660448C>T |
| NGEF | CCDS2500.1 | Br9PT | g.chr2:233610551G>A |
| NHS | CCDS14181.1 | Br29P | g.chrX:17509864C>T |
| NIF3L1BP1 | CCDS2900.1 | Br27P | g.chr3:63799130C>T |
| NIN | NM_182944 | Br14X | g.chr14:50309444A>G |
| NISCH | NM_007184 | Br15X | g.chr3:52497091G>T |
| NKG7 | CCDS12830.1 | Br27P | g.chr19:56567585C>T |
| NKRF | NM_017544 | Br13X | g.chrX:118506348C>A |
| NKX2-5 | CCDS4387.1 | Br27P | g.chr5:172594371G>A |
| NLGN1 | CCDS3222.1 | Br27P | g.chr3:174805443C>T |
| NLGN2 | CCDS11103.1 | Br02X | g.chr17:7261063G>A (HOMOZYGOUS) |
| NLN | CCDS3989.1 | Br27P | g.chr5:65124210G>A |
| NM_001080470.1 | ENST00000271263 | Br27P | g.chr1:119877458G>A |
| NMBR | CCDS5196.1 | Br27P | g.chr6:142451323G>A |
| NMUR1 | CCDS2486.1 | Br20P | g.chr2:232219206C>T |
| NNT | CCDS3949.1 | Br27P | g.chr5:43685112G>A |
| NOD3 | NM_178844 | Br27P | g.chr16:3553329G>A |
| NOR1 | CCDS409.1 | Br27P | g.chr1:36573473C>T |
| NOS3 | CCDS5912.1 | Br27P | g.chr7:150141911C>T |
| NOTCH1 | NM_017617 | Br07X | g.chr9:136679184A>T |
| NOTCH1 | NM_017617 | Br06X | g.chr9:136673514G>T |
| NOTCH2 | CCDS908.1 | Br27P | g.chr1:120218353G>T |
| NOTCH2 | CCDS908.1 | Br27P | g.chr1:120176905C>T |
| NOTCH3 | CCDS12326.1 | Br27P | g.chr19:15151091G>A |
| NOTCH4 | NM_004557 | Br27P | g.chr6:32298278C>T |
| NOX4 | CCDS8285.1 | Br27P | g.chr11:88817033C>T |
| NP_001073909.1 | ENST00000327928 | Br27P | g.chr3:162703860G>A |
| NP_001073931.1 | ENST00000341689 | Br27P | g.chr15:70486147G>A |

FIG. 10
CONTINUED

| | | |
|---|---|---|
| c.1974G>A | p.E658E | SYNONYMOUS |
| UTR+4G>A | 3'UTR | 3'UTR |
| c.1225G>A | p.G409R | MISSENSE |
| c.1611C>T | p.A537A | SYNONYMOUS |
| c.1440C>T | p.A480A | SYNONYMOUS |
| c.586G>A | p.D196N | MISSENSE |
| c.1371G>A | p.M457I | MISSENSE |
| c.544G>A | p.E182K | MISSENSE |
| c.291G>A | p.R97R | SYNONYMOUS |
| c.825G>A | p.Q275Q | SYNONYMOUS |
| c.258C>T | p.D86D | SYNONYMOUS |
| c.127C>T | p.R43W | MISSENSE |
| UTR-4C>A | 5'UTR | 5'UTR |
| c.5094C>T | p.S1698S | SYNONYMOUS |
| c.1701G>T | p.K567N | MISSENSE |
| c.369C>T | p.N123N | SYNONYMOUS |
| c.1577T>G | p.I526S | MISSENSE |
| c.4875C>T | p.T1625T | SYNONYMOUS |
| c.5425C>T | p.R1809C | MISSENSE |
| c.7583C>G | p.S2528X | NONSENSE |
| c.1422G>A | p.K474K | SYNONYMOUS |
| c.1070G>A | p.G357E | MISSENSE |
| c.364C>T | p.P122S | MISSENSE |
| c.776G>A | p.R259Q | MISSENSE |
| c.4516C>T | p.R1506C | MISSENSE |
| c.223C>T | p.L75F | MISSENSE |
| c.786A>G | p.R262R | SYNONYMOUS |
| c.2543G>T | p.C848F | MISSENSE |
| c.17C>T | p.S6F | MISSENSE |
| c.922C>A | p.P308T | MISSENSE |
| c.322G>A | p.A108T | MISSENSE |
| c.353C>T | p.P118L | MISSENSE |
| c.1729G>A | p.E577K | MISSENSE |
| c.1499G>A | p.G500D | MISSENSE |
| c.605G>A | p.G202D | MISSENSE |
| c.166G>A | p.V56M | MISSENSE |
| c.31C>T | p.L11F | MISSENSE |
| c.1551G>A | p.W517X | NONSENSE |
| c.1610G>A | p.G537D | MISSENSE |
| c.274C>T | p.L92L | SYNONYMOUS |
| c.2011C>T | p.L671L | SYNONYMOUS |
| c.3149A>T | p.Q1050L | MISSENSE |
| c.5127G>T | p.S1709S | SYNONYMOUS |
| c.1801G>T | p.G601C | MISSENSE |
| c.5209C>T | p.L1737L | SYNONYMOUS |
| c.3463G>A | p.V1155M | MISSENSE |
| c.439C>T | p.P147S | MISSENSE |
| c.365C>T | p.A122V | MISSENSE |
| c.862G>A | p.D288N | MISSENSE |
| IVS3+1G>A | SPLICE SITE | SPLICE SITE |

FIG. 10
CONTINUED

| | | | |
|---|---|---|---|
| NP_001073940.1 | ENST00000292357 | Br07X | g.chr1:153695670C>T |
| NP_001073948.1 | ENST00000296794 | Br27P | g.chr5:73108187C>T |
| NP_001073961.1 | ENST00000219301 | Br27P | g.chr16:56872074G>A |
| NP_001073971.1 | ENST00000266524 | Br15X | g.chr12:31180262G>A |
| NP_001074294.1 | ENST00000342607 | Br27P | g.chr12:120613521C>T |
| NPC1L1 | CCDS5491.1 | Br9PT | g.chr7:44349148C>T |
| NPL | CCDS1350.1 | Br27P | g.chr1:179519388G>A |
| NPLOC4 | NM_017921 | Br27P | g.chr17:771186221C>T |
| NPPA | CCDS139.1 | Br27P | g.chr1:11841655C>T |
| NPR3 | NM_000908 | Br27P | g.chr5:32774866G>A |
| NPTXR | NM_014293 | Br27P | g.chr22:37543669G>A |
| NPTXR | NM_014293 | Br27P | g.chr22:37543668G>A |
| NR_002781.1 | ENST00000246203 | Br27P | g.chr20:30241272G>A |
| NR2E1 | CCDS5063.1 | Br27P | g.chr6:108604438C>T |
| NRAP | CCDS7578.1 | Br12P | g.chr10:115413102G>A |
| NRBP2 | NM_178564 | Br26X | g.chr8:144992873C>T |
| NRK | NM_198465 | Br20P | g.chrX:104996069C>T |
| NRP1 | CCDS7177.1 | Br27P | g.chr10:33542636G>A |
| NRP1 | CCDS7177.1 | Br27P | g.chr10:33592695G>A |
| NRP2 | CCDS2364.1 | Br27P | g.chr2:206418180G>A |
| NRXN2 | CCDS8077.1 | Br27P | g.chr11:64184928C>T |
| NS3TP2 | CCDS4136.1 | Br27P | g.chr5:125850557C>T |
| NT5E | CCDS5002.1 | Br27P | g.chr6:86251702G>A |
| NTN2L | CCDS10469.1 | BR27P | g.chr16:2463320G>A |
| NTRK3 | CCDS10340.1 | Br27P | g.chr15:86472961G>A |
| NUAK1 | NM_014840 | Br08X | g.chr12:104963998C>T |
| NUP160 | NM_015231 | Br17X | g.chr11:47776510G>A |
| NUP188 | NM_015354 | Br04X | g.chr9:128848466T>A |
| NUP205 | NM_015135 | Br27P | g.chr7:134742962G>A |
| NUP210L | NM_207308 | Br27P | g.chr1:150885659G>A |
| NUP98 | CCDS7746.1 | Br27P | hr11:3701100_3701087delCCATTGTTGCAT |
| NURIT | CCDS9399.1 | Br27P | g.chr13:45174589G>A |
| NXF3 | CCDS14503.1 | Br27P | g.chrX:102144135C>T |
| NXF5 | CCDS14491.1 | Br15X | g.chrX:100902882G>A (HOMOZYGOUS) |
| NXPH1 | NM_152745 | Br23X | g.chr7:8564335C>T |
| OAS3 | NM_006187 | Br02X | g.chr12:111870246G>A |
| OBSCN | CCDS1570.1 | Br27P | g.chr1:224782705G>A |
| ODZ2 | ENST00000314238 | Br27P | g.chr5:167559701C>T |
| ODZ2 | ENST00000314238 | Br27P | g.chr5:167484534G>A |
| ODZ2 | ENST00000314238 | Br08X | g.chr5:167606953C>A |
| ODZ2 | ENST00000314238 | Br27P | g.chr5:167607933G>C |
| OLIG | CCDS13620. | Br27 | g.chr21:33321336_33321338dupAGC |
| OPRD1 | CCDS329.1 | Br20P | g.chr1:29006099C>T |
| OPRL1 | CCDS13556.1 | Br05X | g.chr20:62200248C>T |
| OR10G3 | NM_001005465 | Br27P | g.chr14:211107895C>T |
| OR10G4 | NM_001004462 | Br27P | g.chr11:123392034G>A |
| OR10H2 | CCDS12333.1 | Br27P | g.chr19:15700209G>A |
| OR10P1 | NM_206899 | Br27P | g.chr12:54317845C>T |
| OR10T2 | NM_001004475 | Br25X | g.chr1:155182089C>A |
| OR13J1 | NM_001004487 | Br04X | g.chr9:35860164C>T |

FIG. 10
CONTINUED

| | | |
|---|---|---|
| c.2245C>T | p.P749S | MISSENSE |
| c.750C>T | p.T250T | SYNONYMOUS |
| c.743G>A | p.C248Y | MISSENSE |
| c.2293G>A | p.V765I | MISSENSE |
| c.96C>T | p.I32I | SYNONYMOUS |
| c.1801C>T | p.R601X | NONSENSE |
| c.513G>A | p.G171G | SYNONYMOUS |
| c.505C>T | p.R169W | MISSENSE |
| c.231C>T | p.L77L | SYNONYMOUS |
| c.1032G>A | p.E344E | SYNONYMOUS |
| c.1197G>A | p.G399G | SYNONYMOUS |
| c.1198G>A | p.E400K | MISSENSE |
| c.462G>A | p.W154X | NONSENSE |
| c.298C>T | p.R100C | MISSENSE |
| c.166G>A | p.A56T | MISSENSE |
| c.78C>T | p.R26R | SYNONYMOUS |
| c.4120C>T | p.R1374X | NONSENSE |
| c.1298G>A | p.G433E | MISSENSE |
| c.543G>A | p.K181K | SYNONYMOUS |
| c.1050G>A | p.R350R | SYNONYMOUS |
| c.2058C>T | p.C686C | SYNONYMOUS |
| c.1152C>T | p.T384T | SYNONYMOUS |
| c.782G>A | p.G261E | MISSENSE |
| c.1318G>A | p.D440N | MISSENSE |
| c.1213G>A | p.D405N | MISSENSE |
| c.1035C>T | p.T345T | SYNONYMOUS |
| c.2977G>A | p.D993N | MISSENSE |
| c.5205T>A | p.P1735P | SYNONYMOUS |
| c.2364G>A | p.V788V | SYNONYMOUS |
| c.1025G>A | p.S342N | MISSENSE |
| c.2009_2022delCCATTGTTGCATTA | fs | INDEL |
| c.63G>A | p.W21X | NONSENSE |
| c.633C>T | p.N211N | SYNONYMOUS |
| c.149G>A | p.R50Q | MISSENSE |
| c.512C>T | p.T171I | MISSENSE |
| c.3218G>A | p.R1073Q | MISSENSE |
| c.10020G>A | p.A3340A | SYNONYMOUS |
| c.1554C>T | p.L518L | SYNONYMOUS |
| c.220G>A | p.V74I | MISSENSE |
| c.4565C>A | p.T1522N | MISSENSE |
| c.5545G>C | p.D1849H | MISSENSE |
| c.296_298dupAGC | p.Q100de | INDEL |
| c.245C>T | p.T82M | MISSENSE |
| c.765C>T | p.D255D | SYNONYMOUS |
| c.821C>T | p.A274V | MISSENSE |
| c.543G>A | p.P181P | SYNONYMOUS |
| c.356G>A | p.G119D | MISSENSE |
| c.903C>T | p.A301A | SYNONYMOUS |
| c.241C>A | p.Q81K | MISSENSE |
| c.235C>T | p.P79S | MISSENSE |

FIG. 10
CONTINUED

| | | | |
|---|---|---|---|
| OR1L8 | NM_001004454 | Br04X | g.chr9:122410060T>G |
| OR2A12 | NM_001004135 | Br14X | g.chr7:143230447C>T |
| OR2AG1 | NM_001004489 | Br02X | g.chr11:6763740G>A |
| OR2AG2 | NM_001004490 | Br27P | g.chr11:6746632C>T |
| OR2D2 | NM_003700 | Br26X | g.chr11:6869599G>A |
| OR2G3 | NM_001001914 | Br05X | g.chr1:244094933G>T |
| OR2L13 | CCDS1637.1 | Br03x | g.chr1:244589038C>T |
| OR2L13 | CCDS1637.1 | Br17X | g.chr1:244589283A>G |
| OR2L2 | NM_001004686 | Br17X | g.chr1:244527924C>A |
| OR2S2 | CCDS6596.1 | Br27P | g.chr9:35947789G>A |
| OR2T4 | NM_001004696 | Br20P | g.chr1:244851039C>G |
| OR2V2 | CCDS4461.1 | Br27P | g.chr5:180514912G>A |
| OR2Y1 | NM_001001657 | Br27P | g.chr5:180099334G>A |
| OR2Z1 | NM_001004699 | Br27P | g.chr19:8702563C>T |
| OR3A1 | CCDS11023.1 | Br17X | g.chr17:3142552G>A |
| OR4A5 | NM_001005272 | Br12P | g.chr11:51268333C>A |
| OR4L1 | NM_001004717 | Br07X | g.chr14:19598334C>T (HOMOZYGOUS) |
| OR4N2 | NM_001004723 | Br27P | g.chr14:19365489C>T |
| OR4P4 | NM_001004124 | Br9PT | g.chr11:55162451delG |
| OR52A5 | NM_001005160 | Br05x | g.chr11:5109517delT |
| OR52B2 | NM_001004052 | Br17X | g.chr11:6147331C>T |
| OR52D1 | NM_001005163 | Br27P | g.chr11:5466584G>A |
| OR52E6 | NM_001005167 | Br27P | g.chr11:5819151G>A |
| OR52I1 | NM_001005169 | Br27P | g.chr11:4572398A>G |
| OR52N4 | NM_001005175 | Br12P | g.chr11:5732981G>T |
| OR56A4 | NM_001005179 | Br13X | g.chr11:5980580C>T |
| OR56B1 | NM_001005180 | Br27P | g.chr11:5714584C>T |
| OR56B4 | NM_001005181 | Br27P | g.chr11:6086389G>A |
| OR5A1 | NM_001004728 | Br27P | g.chr11:59967301C>T |
| OR5AP2 | NM_001002925 | Br27P | g.chr11:56166004C>T |
| OR5AU1 | NM_001004731 | Br27P | g.chr14:20693728G>A |
| OR5B17 | ENST00000357377 | Br27P | g.chr11:57890665G>A |
| OR5BF1 | NM_001001918 | Br07X | g.chr1:244838450G>A |
| OR5D14 | NM_001004735 | Br26X | g.chr11:55319814T>C |
| OR5K4 | NM_001005517 | Br17X | g.chr3:99556305C>T |
| OR5M1 | ENST00000303005 | Br29P | g.chr11:56066764G>A |
| OR5M8 | NM_001005282 | Br07x | g.chr11:56014968C>T |
| OR5M9 | NM_001004743 | Br15X | g.chr11:55987439G>A |
| OR6C74 | NM_001005490 | Br17X | g.chr12:53927523G>A |
| OR6K3 | NM_001005327 | Br14X | g.chr1:155500526C>T |
| OR6W1P | ENST00000340373 | Br27P | g.chr7:142276589G>A |
| OR7A5 | CCDS12318.1 | Br27P | g.chr19:14799350A>T |
| OR7D4 | NM_001005191 | Br27P | g.chr19:9185711C>T |
| OR8D2 | NM_001002918 | Br11P | g.chr11:123694585C>G |
| OR8K3 | NM_001005202 | Br27P | g.chr11:55843094G>A |
| OR9K2 | NM_001005243 | Br27P | g.chr12:53810025G>A |
| OR9Q2 | NM_001005283 | Br27P | g.chr11:57714754C>T |
| OSAP | NM_032623 | Br27P | g.chr4:140545427G>A |
| OSBPL2 | CCDS13494.1 | Br13X | g.chr20:60292518C>T |
| OSBPL5 | NM_145638 | Br20P | g.chr11:3067734C>T |

FIG. 10
CONTINUED

| | | |
|---|---|---|
| c.251T>G | p.M84R | MISSENSE |
| c.599C>T | p.A200V | MISSENSE |
| c.896G>A | p.R299Q | MISSENSE |
| c.133C>T | p.L45L | SYNONYMOUS |
| c.709G>A | p.A237T | MISSENSE |
| c.5G>T | p.G2V | MISSENSE |
| c.320C>T | p.A107V | MISSENSE |
| c.565A>G | p.T189A | MISSENSE |
| c.314C>A | p.T105N | MISSENSE |
| c.277G>A | p.A93T | MISSENSE |
| c.116C>G | p.T39S | MISSENSE |
| c.364G>A | p.D122N | MISSENSE |
| c.331G>A | p.E111K | MISSENSE |
| c.173C>T | p.P58L | MISSENSE |
| c.75G>A | p.G25G | SYNONYMOUS |
| c.639C>A | p.I213I | SYNONYMOUS |
| c.291C>T | p.C97C | SYNONYMOUS |
| c.42C>T | p.L14L | SYNONYMOUS |
| c.42delG | fs | INDEL |
| c.932delT | fs | INDEL |
| c.802C>T | p.R268C | MISSENSE |
| c.72G>A | p.E24E | SYNONYMOUS |
| c.553G>A | p.G185S | MISSENSE |
| c.554A>G | p.H185R | MISSENSE |
| c.435G>T | p.K145N | MISSENSE |
| c.375C>T | p.D125D | SYNONYMOUS |
| c.262C>T | p.P88S | MISSENSE |
| c.805G>A | p.A269T | MISSENSE |
| c.84C>T | p.A28A | SYNONYMOUS |
| c.488C>T | p.A163V | MISSENSE |
| c.297G>A | p.L99L | SYNONYMOUS |
| c.148G>A | p.D50N | MISSENSE |
| c.333G>A | p.L111L | SYNONYMOUS |
| c.207T>C | p.S69S | SYNONYMOUS |
| c.918C>T | p.N306N | SYNONYMOUS |
| c.549G>A | p.P183P | SYNONYMOUS |
| c.455C>T | p.A152V | MISSENSE |
| c.15G>A | p.T5T | SYNONYMOUS |
| c.185G>A | p.R62Q | MISSENSE |
| c.501C>T | p.F167F | SYNONYMOUS |
| c.774G>A | p.R258R | SYNONYMOUS |
| c.704A>T | p.Y235F | MISSENSE |
| c.803C>T | p.S268F | MISSENSE |
| c.719C>G | p.T240S | MISSENSE |
| c.736G>A | p.V246M | MISSENSE |
| c.206G>A | p.G69E | MISSENSE |
| c.216C>T | p.C72C | SYNONYMOUS |
| c.654G>A | p.E218E | SYNONYMOUS |
| c.858C>T | p.I286I | SYNONYMOUS |
| c.2215C>T | p.R739W | MISSENSE |

FIG. 10
CONTINUED

| | | | |
|---|---|---|---|
| OSBPL9 | CCDS558.1 | Br27P | g.chr1:51939596C>T |
| OSR2 | NM_053001 | Br10P | g.chr8:100030880A>G |
| OSTM1 | CCDS5062.1 | Br27P | g.chr6:108477150C>T |
| OTOF | CCDS1725.1 | Br07X | g.chr2:26629590C>T |
| OTOG | ENST00000342528 | Br27P | g.chr11:17564682G>A |
| OTOR | CCDS13124.1 | Br27P | g.chr20:16678646T>G |
| OTUD1 | ENST00000298035 | Br03X | g.chr10:23769412G>A |
| OVCH1 | NM_183378 | Br27P | g.chr12:29495725C>T |
| OVCH1 | NM_183378 | Br20P | g.chr12:29495715G>A |
| OVCH1 | NM_183378 | Br27P | g.chr12:29539614C>T |
| OVOL1 | CCDS8112.1 | Br27P | g.chr11:65318668C>T |
| OXA1L | CCDS9573.1 | Br27P | g.chr14:22308982G>A |
| p44S10 | CCDS2901.1 | Br03X | g.chr3:63983090G>A |
| PADI2 | CCDS177.1 | Br27P | g.chr1:17174839G>A |
| PAPLN | NM_173462 | Br27P | g.chr14:72791442G>A |
| PAPOLG | CCDS1863.1 | Br15X | g.chr2:60926307G>A |
| PAPPA2 | NM_020318 | Br25X | g.chr1:173257746G>A |
| PARC | CCDS4890.1 | Br27P | g.chr6:43260574G>A |
| PARP11 | CCDS8523.1 | Br17X | g.chr12:3801413_3801410delTCAA |
| PAX9 | CCDS9662.1 | Br9PT | g.chr14:36201924C>T |
| PCAF | CCDS2634.1 | Br27P | g.chr3:20139274G>A |
| PCDH11X | CCDS14463.1 | BR02X | g.chrX:90944096C>A |
| PCDHA10 | NM_031859 | Br26X | g.chr5:140217718G>A (HOMOZYGOUS) |
| PCDHA13 | CCDS4240.1 | Br04X | g.chr5:140242246G>C |
| PCDHB7 | CCDS4249.1 | Br04X | g.chr5:140533518A>G |
| PCDHGA4 | NM_032053 | Br27P | g.chr5:140716538G>A |
| PCDHGA4 | NM_032053 | Br27P | g.chr5:140716717C>T |
| PCDHGA9 | NM_032089 | Br27P | g.chr5:140764920C>T |
| PCDHGB7 | NM_032101 | Br23X | g.chr5:140779284C>T |
| PCDHGC4 | CCDS4260.1 | Br27P | g.chr5:140791568C>T |
| PCDHGC4 | CCDS4261.1 | Br27P | g.chr5:140837868C>T |
| PCDHGC4 | CCDS4263.1 | Br27P | g.chr5:140849287G>A |
| PCGF2 | NM_007144 | Br08X | g.chr17:34149384C>T |
| PCNXL2 | ENST00000344698 | Br27P | g.chr1:229428818C>T |
| PCSK2 | CCDS13125.1 | Br08X | g.chr20:17382530C>T |
| PCSK2 | CCDS13125.1 | Br02X | g.chr20:17365459A>T |
| PCYOX1 | CCDS1902.1 | Br27P | g.chr2:70397047C>T |
| PDCD10 | CCDS3202.1 | Br27P | g.chr3:168888183G>A |
| PDCD11 | NM_014976 | Br03X | g.chr10:105194320C>T (HOMOZYGOUS) |
| PDE1C | CCDS5437.1 | Br02X | g.chr7:31692010T>G |
| PDE4A | CCDS12238.1 | Br27P | g.chr19:10439192C>T |
| PDE4B | CCDS632.1 | Br27P | g.chr1:66435499C>T |
| PDE4C | CCDS12373.1 | Br27P | g.chr19:18194052G>A |
| PDE4D | NM_006203 | Br27P | g.chr5:58320177G>A |
| PDGFB | CCDS13987.1 | Br02X | g.chr22:37946297C>A (HOMOZYGOUS) |
| PDGFRA | CCDS3495.1 | Br15X | g.chr4:55002246T>C |
| PDGFRB | CCDS4303.1 | Br27P | g.chr5:149492589C>T |
| PDHA2 | CCDS3644.1 | Br06X | g.chr4:97119398G>A |
| PDHB | CCDS2890.1 | Br27P | g.chr3:58394545C>T |
| PDIA2 | NM_006849 | Br23X | g.chr16:275424C>T |

FIG. 10
CONTINUED

| | | |
|---|---|---|
| c.380C>T | p.S127F | MISSENSE |
| c.524A>G | p.K175R | MISSENSE |
| c.949C>T | p.P317S | MISSENSE |
| c.768C>T | p.V256V | SYNONYMOUS |
| c.65G>A | p.G22D | MISSENSE |
| c.354T>G | p.V118V | SYNONYMOUS |
| c.234G>A | p.R78R | SYNONYMOUS |
| c.2575C>T | p.P859S | MISSENSE |
| c.2585G>A | p.R862Q | MISSENSE |
| c.325C>T | p.L109F | MISSENSE |
| c.402C>T | p.N134N | SYNONYMOUS |
| c.762G>A | p.E254E | SYNONYMOUS |
| c.295G>A | p.E99K | MISSENSE |
| c.298G>A | p.E100K | MISSENSE |
| c.1509G>A | p.V503V | SYNONYMOUS |
| c.1297G>A | p.V433I | MISSENSE |
| c.628G>A | p.G210R | MISSENSE |
| c.548G>A | p.R183H | MISSENSE |
| c.414_417delTCAA | fs | INDEL |
| c.76C>T | p.R26W | MISSENSE |
| c.1387G>A | p.D463N | MISSENSE |
| UTR+1C>A | 3'UTR | 3'UTR |
| c.1901G>A | p.R634H | MISSENSE |
| c.209G>C | p.R70T | MISSENSE |
| c.918A>G | p.Q306Q | SYNONYMOUS |
| c.1587G>A | p.Q529Q | SYNONYMOUS |
| c.1766C>T | p.T589I | MISSENSE |
| c.2217C>T | p.H739H | SYNONYMOUS |
| c.1674C>T | p.N558N | SYNONYMOUS |
| c.1058C>T | p.A353V | MISSENSE |
| c.2001C>T | p.T667T | SYNONYMOUS |
| c.296G>A | p.S99N | MISSENSE |
| c.190C>T | p.R64W | MISSENSE |
| c.1951C>T | p.P651S | MISSENSE |
| c.1029C>T | p.Y343Y | SYNONYMOUS |
| c.816A>T | p.T272T | SYNONYMOUS |
| c.100C>T | p.P34S | MISSENSE |
| c.396G>A | p.K132K | SYNONYMOUS |
| c.5335C>T | p.R1779W | MISSENSE |
| c.264T>G | p.D88E | MISSENSE |
| c.1839C>T | p.H613H | SYNONYMOUS |
| c.516C>T | p.V172V | SYNONYMOUS |
| c.324G>A | p.Q108Q | SYNONYMOUS |
| IVS10-1G>A | SPLICE SITE | SPLICE SITE |
| c.657C>A | p.P219P | SYNONYMOUS |
| c.3149T>C | p.I1050T | MISSENSE |
| c.1044C>T | p.V348V | SYNONYMOUS |
| c.919G>A | p.E307K | MISSENSE |
| c.32C>T | p.P11L | MISSENSE |
| c.907C>T | p.R303C | MISSENSE |

FIG. 10
CONTINUED

| | | | |
|---|---|---|---|
| PDK1 | CCDS2250.1 | Br27P | g.chr2:173261008C>T |
| PDLIM4 | CCDS4152.1 | Br27P | g.chr5:131634592G>A |
| PDZD2 | NM_178140 | Br27P | g.chr5:32124299C>G |
| PDZD2 | NM_178140 | Br08X | g.chr5:32126540T>G |
| PDZD7 | NM_024895 | Br27P | g.chr10:102773736C>T |
| PEG10 | ENST00000362013 | Br27P | g.chr7:93938352G>A |
| PELP1 | NM_014389 | Br27P | g.chr17:4523466G>A |
| PENK | CCDS6168.1 | Br27P | g.chr8:57521016G>A |
| PERQ1 | NM_022574 | Br27P | g.chr7:99925593G>A |
| PEX1 | CCDS5627.1 | Br12P | g.chr7:91793015T>C |
| PEX10 | CCDS41.1 | Br27P | g.chr1:2372259G>A |
| PFAS | CCDS11136.1 | Br27P | g.chr17:8107654C>T |
| PFAS | CCDS11136.1 | Br27P | g.chr17:8099715G>A |
| PFKFB3 | CCDS7078.1 | Br27P | g.chr10:6297219G>A |
| PGAP1 | CCDS2318.1 | Br27P | g.chr2:197603144C>T |
| PGBD5 | CCDS1583.1 | Br17X | g.chr1:226793553C>T |
| PHC3 | NM_024947 | Br20P | g.chr3:171329309G>A |
| PHEMX | CCDS7733.1 | Br26X | g.chr11:2294472C>T |
| PHF2 | ENST00000298216 | Br26X | g.chr13:18523321G>A |
| PHF21A | NM_016621 | Br27P | g.chr11:45949455C>T |
| PHIP | CCDS4987.1 | Br04X | g.chr6:79721272C>T (HOMOZYGOUS) |
| PHIP | CCDS4987.1 | Br9PT | g.chr6:79792464A>G |
| PHKA2 | CCDS14190.1 | Br27P | g.chrX:18674973G>A |
| PHLPP | NM_194449 | Br27P | g.chr18:58657123G>A |
| PHLPPL | NM_015020 | Br04X | g.chr16:70263693G>T |
| PHOX2B | CCDS3463.1 | Br07X | g.chr4:41590408C>T |
| PIGN | NM_176787 | Br27P | g.chr18:57972836T>C |
| PIGQ | CCDS10411.1 | Br27P | g.chr16:564229G>A |
| PIGR | CCDS1474.1 | Br08X | g.chr1:203502259G>A |
| PIK3C2G | NM_004570 | Br17X | g.chr12:18415448delA |
| PIK3CA | NM_006218 | Br27P | g.chr3:180404246C>T |
| PIK3CA | NM_006218 | Br26X | g.chr3:180429864G>C |
| PIK3CA | NM_006218 | Br05X | g.chr3:180434792G>A |
| PIK3CG | CCDS5739.1 | Br27P | g.chr7:106103291C>T |
| PIK3CG | CCDS5739.1 | Br08X | g.chr7:106102464C>T |
| PIK3R1 | CCDS3993. | Br14X | g.chr5:67624906_67624908delTTA |
| PIK3R1 | CCDS3993. | Br12P | g.chr5:67625341_67625346delCATGAA |
| PIK3R1 | CCDS3993.1 | Br27P | g.chr5:67626876C>T |
| PIK3R4 | CCDS3067.1 | Br27P | g.chr3:131892162G>A |
| PIK3R5 | CCDS11147.1 | Br17X | g.chr17:8755455C>T |
| PIP5K1A | CCDS990.1 | Br27P | g.chr1:148027705G>A |
| PIP5K3 | CCDS2382.1 | Br02X | g.chr2:208988927C>A |
| PISD | CCDS13899.1 | Br27P | g.chr22:30341678G>A |
| PITPNM1 | NM_004910 | Br13X | g.chr11:67023775C>T |
| PITPNM2 | CCDS9242.1 | Br27P | g.chr12:122014890G>A |
| PITPNM3 | CCDS11076.1 | Br23X | g.chr17:6382100C>T (HOMOZYGOUS) |
| PITPNM3 | CCDS11076.1 | Br27P | g.chr17:6322610G>A |
| PIWIL3 | NM_001008496 | Br27P | g.chr22:23440063C>T |
| PKD1 | NM_000296 | Br27P | g.chr16:2083676C>T |
| PKD1L2 | NM_182740 | Br14X | g.chr16:79765857G>T |

FIG. 10
CONTINUED

| | | |
|---|---|---|
| c.894C>T | p.Y298Y | SYNONYMOUS |
| c.413G>A | p.G138E | MISSENSE |
| c.4988C>G | p.S1663C | MISSENSE |
| c.7229T>G | p.L2410R | MISSENSE |
| c.306C>T | p.R102R | SYNONYMOUS |
| c.884G>A | p.R295H | MISSENSE |
| c.1673G>A | p.G558D | MISSENSE |
| c.51G>A | p.G17G | SYNONYMOUS |
| c.1628G>A | p.C543Y | MISSENSE |
| c.302T>C | p.V101A | MISSENSE |
| c.394G>A | p.G132R | MISSENSE |
| c.1604C>T | p.A535V | MISSENSE |
| c.555G>A | p.E185E | SYNONYMOUS |
| c.232G>A | p.A78T | MISSENSE |
| c.617C>T | p.A206V | MISSENSE |
| c.870C>T | p.I290I | SYNONYMOUS |
| c.1560G>A | p.Q520Q | SYNONYMOUS |
| c.718C>T | p.R240X | NONSENSE |
| c.595G>A | p.A199T | MISSENSE |
| c.400C>T | p.L134L | SYNONYMOUS |
| c.4031C>T | p.P1344L | MISSENSE |
| c.737A>G | p.D246G | MISSENSE |
| c.3247G>A | p.G1083R | MISSENSE |
| IVS3+1G>A | SPLICE SITE | SPLICE SITE |
| c.1505G>T | p.S502I | MISSENSE |
| c.315C>T | p.F105F | SYNONYMOUS |
| c.471T>C | p.Y157Y | SYNONYMOUS |
| c.154G>A | p.V52M | MISSENSE |
| c.13G>A | p.V5M | MISSENSE |
| c.1693delA | fs | INDEL |
| c.1026C>T | p.T342T | SYNONYMOUS |
| c.2598G>C | p.L866F | MISSENSE |
| c.3145G>A | p.G1049S | MISSENSE |
| c.1334C>T | p.A445V | MISSENSE |
| c.507C>T | p.H169H | SYNONYMOUS |
| c.1138_1140delTTA | p.I380del | INDEL |
| c.1348_1350delCATGAA | p.H450_E451del | INDEL |
| c.1713C>T | p.I571I | SYNONYMOUS |
| c.3133G>A | p.V1045I | MISSENSE |
| c.82C>T | p.R28C | MISSENSE |
| c.1358G>A | p.G453D | MISSENSE |
| c.968C>A | p.S323X | NONSENSE |
| c.600G>A | p.A200A | SYNONYMOUS |
| c.1166C>T | p.T389M | MISSENSE |
| c.729G>A | p.R243R | SYNONYMOUS |
| c.49C>T | p.P17S | MISSENSE |
| c.758G>A | p.G253E | MISSENSE |
| c.2579C>T | p.A860V | MISSENSE |
| c.10883C>T | p.T3628I | MISSENSE |
| c.2747G>T | p.G916V | MISSENSE |

FIG. 10
CONTINUED

| | | | |
|---|---|---|---|
| PKD1L2 | NM_182740 | Br27P | g.chr16:79755806C>T |
| PKHD1 | CCDS4935.1 | Br05X | g.chr6:52028414G>A |
| PKHD1 | CCDS4935.1 | Br13X | g.chr6:51855963C>T (HOMOZYGOUS) |
| PKHD1 | CCDS4935.1 | Br15X | g.chr6:52038789C>A |
| PKHD1L1 | NM_177531 | Br10P | g.chr8:110508510C>T |
| PKHD1L1 | NM_177531 | Br13X | g.chr8:110543250C>T |
| PKIA | CCDS6222.1 | Br27P | g.chr8:79676585G>A |
| PLA1A | CCDS2991.1 | Br27P | g.chr3:120799463C>T |
| PLCH2 | NM_014638 | Br27P | g.chr1:2460260G>A |
| PLCH2 | NM_014638 | Br27P | g.chr1:2462173G>A |
| PLCH2 | NM_014638 | Br27P | g.chr1:2443787G>A |
| PLCXD3 | NM_001005473 | Br27P | g.chr5:41546381C>T |
| PLD2 | CCDS11057.1 | Br27P | g.chr17:4659769C>T |
| PLEC1 | NM_201378 | Br07X | g.chr8:145069023G>A (HOMOZYGOUS) |
| PLEKHA4 | CCDS12737.1 | Br02X | g.chr19:54047346G>A |
| PLEKHH2 | CCDS1812.1 | Br27P | g.chr2:43838666C>T |
| PLIN | CCDS10353.1 | Br27P | g.chr15:88011246G>A |
| PLSCR3 | NM_020360 | Br27P | g.chr17:7234727G>A |
| PLXDC2 | CCDS7132.1 | Br27P | g.chr10:20397169C>T |
| PLXNA3 | CCDS14752.1 | Br03X | hrX:153259847_153259848insT (HOMOZYGOUS) |
| PLXNB2 | ENST00000359337 | Br03X | g.chr22:49026886G>C |
| PLXNC1 | CCDS9049.1 | Br27P | g.chr12:93122909C>T |
| PMS1 | CCDS2302.1 | Br17X | g.chr2:190508255C>A |
| PMS2L4 | ENST00000275546 | Br27P | g.chr7:66211539G>C |
| PNLIP | CCDS7594.1 | Br26X | g.chr10:118308785C>T (HOMOZYGOUS) |
| PNOC | CCDS6066.1 | Br27P | g.chr8:28252730G>A |
| PODXL2 | CCDS3044.1 | Br14X | g.chr3:128862487G>A (HOMOZYGOUS) |
| POLD1 | CCDS12795.1 | Br27P | g.chr19:55610809C>T |
| POLE | CCDS9278.1 | Br03X | g.chr12:131829493G>A |
| POLG2 | NM_007215 | Br27P | g.chr17:59923448C>T |
| POLM | NM_013284 | Br23X | g.chr7:43887015G>T |
| POLR3B | CCDS9105.1 | Br17X | g.chr12:105393000G>A |
| POLR3E | CCDS10605.1 | Br27P | g.chr16:22250989G>A |
| POPDC2 | CCDS2992.1 | Br27P | g.chr3:120861955C>T |
| POR | CCDS5579.1 | Br07X | g.chr7:75259971G>A |
| PORCN | CCDS14296.1 | Br27P | g.chrX:48135017G>A |
| POT1 | CCDS5793.1 | Br20P | g.chr7:124086991G>A |
| POU1F1 | CCDS2919.1 | Br27P | g.chr3:87394002C>T |
| POU2F1 | CCDS1259.1 | Br27P | g.chr1:164112867C>T |
| POU6F2 | NM_007252 | Br15X | g.chr7:39277017C>T |
| PPAP2C | CCDS12023.1 | Br27P | g.chr19:233754G>A |
| PPARA | NM_001001930 | Br27P | g.chr22:44948569A>G |
| PPBP | CCDS3563.1 | Br27P | g.chr4:75218279G>A |
| PPEF2 | NM_006239 | Br27P | g.chr4:77139251delG |
| PPIG | CCDS2235.1 | Br27P | g.chr2:170315217C>T |
| PPL | CCDS10526.1 | BR27P | g.chr16:4889085G>A |
| PPM2C | CCDS6259.1 | Br27P | g.chr8:95003531C>T |
| PPP1CC | CCDS9150.1 | Br27P | g.chr12:109631287C>T |
| PPP1R12A | NM_002480 | Br27P | g.chr12:78769096C>T |
| PPP1R12C | CCDS12916.1 | Br23X | g.chr19:60298771G>A |

FIG. 10
CONTINUED

| | | |
|---|---|---|
| c.3289C>T | p.P1097S | MISSENSE |
| c.1766G>A | p.R589H | MISSENSE |
| c.7237C>T | p.R2413C | MISSENSE |
| c.824C>A | p.T275K | MISSENSE |
| c.2949C>T | p.Y983Y | SYNONYMOUS |
| c.7320C>T | p.C2440C | SYNONYMOUS |
| c.205G>A | p.G69R | MISSENSE |
| c.13C>T | p.P5S | MISSENSE |
| c.1888G>A | p.V630M | MISSENSE |
| c.2274G>A | p.K758K | SYNONYMOUS |
| c.519G>A | p.W173X | NONSENSE |
| c.5C>T | p.A2V | MISSENSE |
| c.573C>T | p.V191V | SYNONYMOUS |
| c.7020G>A | p.A2340A | SYNONYMOUS |
| c.1376G>A | p.G459D | MISSENSE |
| c.918C>T | p.L306L | SYNONYMOUS |
| c.1134G>A | p.G378G | SYNONYMOUS |
| c.781G>A | p.D261N | MISSENSE |
| c.536C>T | p.T179I | MISSENSE |
| c.3619_3620insT | fs | INDEL |
| c.1976G>C | p.R659P | MISSENSE |
| c.1851C>T | p.H617H | SYNONYMOUS |
| c.425C>A | p.T142N | MISSENSE |
| c.11G>C | p.S4T | MISSENSE |
| c.1060C>T | p.R354C | MISSENSE |
| c.381G>A | p.Q127Q | SYNONYMOUS |
| c.918G>A | p.L306L | SYNONYMOUS |
| c.2734C>T | p.P912S | MISSENSE |
| c.4901G>A | p.R1634H | MISSENSE |
| c.101C>T | p.T34M | MISSENSE |
| c.1026G>T | p.Q342H | MISSENSE |
| c.2821G>A | p.G941R | MISSENSE |
| c.2052G>A | p.E684E | SYNONYMOUS |
| c.6C>T | p.S2S | SYNONYMOUS |
| c.1749G>A | p.A583A | SYNONYMOUS |
| c.1252G>A | p.G418S | MISSENSE |
| c.855G>A | p.V285V | SYNONYMOUS |
| c.513C>T | p.C171C | SYNONYMOUS |
| c.1500C>T | p.T500T | SYNONYMOUS |
| IVS8-4C>T | SPLICE SITE | SPLICE SITE |
| c.538G>A | p.A180T | MISSENSE |
| c.1073A>G | p.K358R | MISSENSE |
| c.274G>A | p.V92I | MISSENSE |
| c.2010delG | fs | INDEL |
| c.970C>T | p.L324F | MISSENSE |
| c.806G>A | p.R269K | MISSENSE |
| c.68C>T | p.T23I | MISSENSE |
| IVS2-3C>T | SPLICE SITE | SPLICE SITE |
| c.328C>T | p.L110L | SYNONYMOUS |
| c.1240G>A | p.A414T | MISSENSE |

FIG. 10
CONTINUED

| | | | |
|---|---|---|---|
| PPP2CZ | CCDS855.1 | Br27P | g.chr1:112965510G>A |
| PPP2R2C | CCDS3387.1 | Br15X | g.chr4:6495627G>A |
| PPRC1 | CCDS7529.1 | Br27P | g.chr10:103896443C>T |
| PRCC | CCDS1157.1 | Br27P | g.chr1:153580163G>A |
| PRCC | CCDS1157.1 | Br27P | g.chr1:153550879C>T |
| PRDM16 | NM_199454 | Br10P | g.chr1:3324915A>G |
| PRDM5 | CCDS3716.1 | Br27P | g.chr4:122063793C>T |
| PRELP | CCDS1438.1 | Br27P | g.chr1:200187622G>A |
| PRIC285 | CCDS13527.1 | Br27P | g.chr20:61664927C>T |
| PRIC285 | CCDS13527.1 | Br04X | g.chr20:61661854A>G |
| PRKCBP1 | CCDS13404.1 | Br17X | g.chr20:45308281T>G |
| PRKCBP1 | CCDS13404.1 | Br27P | g.chr20:45308267G>A |
| PRKCZ | CCDS37.1 | Br27P | g.chr1:2114391G>A |
| PRKDC | NM_006904 | Br27P | g.chr8:48934868C>T |
| PRKDC | NM_006904 | Br04X | g.chr8:49009077G>A |
| PRKG2 | CCDS3589.1 | Br27P | g.chr4:82422614G>A |
| PRKG2 | CCDS3589.1 | Br15X | g.chr4:82482975C>A |
| PRKRA | CCDS2279.1 | Br27P | g.chr2:179133564G>A |
| PRO1853 | CCDS1788.1 | Br25X | g.chr2:37380406G>C |
| PRO1855 | CCDS11566.1 | Br27P | g.chr17:45817595C>T |
| PROM1 | NM_006017 | Br15X | g.chr4:15669171C>A |
| PROSC | CCDS6096.1 | Br27P | g.chr8:37743032G>A |
| PRPF18 | CCDS7100.1 | Br04X | g.chr10:13692110C>T |
| PRR12 | ENST00000246798 | Br14X | g.chr19:54794996A>G |
| PRSS16 | CCDS4623.1 | Br27P | g.chr6:27330561G>A |
| PRSS16 | CCDS4623.1 | Br27P | g.chr6:27327000C>T |
| PRSS22 | CCDS10481.1 | Br02X | g.chr16:2846838C>T |
| PSF1 | NM_021067 | Br27P | g.chr20:25345836C>T |
| PSIP1 | CCDS6479.1 | Br27P | g.chr9:15456783G>A |
| PSMD8 | CCDS12515.1 | Br26X | g.chr19:43558671C>T |
| PSRC2 | NM_144982 | Br27P | g.chr12:70327821G>A |
| PTAR1 | ENST00000340434 | Br16X | g.chr9:69595384G>T |
| PTCH2 | CCDS516.1 | Br27P | g.chr1:44962636C>T |
| PTCH2 | CCDS516.1 | Br04X | g.chr1:44976628A>G |
| PTEN | NM_000314 | Br07X | g.chr10:89682890G>A (HOMOZYGOUS) |
| PTEN | NM_000314 | Br04X | g.chr10:89710832C>T (HOMOZYGOUS) |
| PTEN | NM_000314 | Br17X | 10:89715128_89715131delTAGA(HOMOZYGOUS) |
| PTEN | NM_000314 | Br03X | g.chr10:89710630G>A(HOMOZYGOUS) |
| PTEN | NM_000314 | Br25X | g.chr10:89710857T>G(HOMOZYGOUS) |
| PTGDR | CCDS9707.1 | Br27P | g.chr14:51804540C>T |
| PTGFR | CCDS686.1 | Br07X | g.chr1:78714146A>T |
| PTGS2 | CCDS1371.1 | Br27P | g.chr1:183376164C>T |
| PTPLA | CCDS7121.1 | Br27P | g.chr10:17681411G>A |
| PTPN23 | CCDS2754.1 | Br11P | chr3:47428149_47428159delTCATGCTGGT |
| PTPRF | CCDS489.1 | Br27P | g.chr1:43732747G>A |
| PTPRK | CCDS5137.1 | Br27P | g.chr6:128368056C>T |
| PTPRM | CCDS11840.1 | Br15X | g.chr18:8369249A>G |
| PTPRS | CCDS12139.1 | Br27P | g.chr19:5165667C>T |
| PTPRU | CCDS334.1 | Br03X | g.chr1:29402467C>T |
| PTX3 | CCDS3180.1 | Br27P | g.chr3:158637474C>T |

FIG. 10
CONTINUED

| | | |
|---|---|---|
| c.498G>A | p.R166R | SYNONYMOUS |
| c.438G>A | p.T146T | SYNONYMOUS |
| c.3704C>T | p.P1235L | MISSENSE |
| c.1346G>A | p.G449D | MISSENSE |
| c.243C>T | p.P81P | SYNONYMOUS |
| c.481A>G | p.N161D | MISSENSE |
| c.1247C>T | p.P416L | MISSENSE |
| c.1105G>A | p.D369N | MISSENSE |
| c.3985C>T | p.P1329S | MISSENSE |
| c.5989A>G | p.T1997A | MISSENSE |
| c.2162T>G | p.V721G | MISSENSE |
| c.2176G>A | p.D726N | MISSENSE |
| c.688G>A | p.D230N | MISSENSE |
| c.6064C>T | p.P2022S | MISSENSE |
| IVS15+1G>A | SPLICE SITE | SPLICE SITE |
| c.1204G>A | p.E402K | MISSENSE |
| c.406C>A | p.L136M | MISSENSE |
| c.451G>A | p.G151R | MISSENSE |
| c.443G>C | p.C148S | MISSENSE |
| c.559C>T | p.L187L | SYNONYMOUS |
| c.1926C>A | p.P642P | SYNONYMOUS |
| IVS4+1G>A | SPLICE SITE | SPLICE SITE |
| c.429C>T | p.V143V | SYNONYMOUS |
| c.1874A>G | p.N625S | MISSENSE |
| c.1261G>A | p.A421T | MISSENSE |
| c.695C>T | p.T232I | MISSENSE |
| c.95C>T | p.A32V | MISSENSE |
| c.237C>T | p.Y79Y | SYNONYMOUS |
| c.1495G>A | p.D499N | MISSENSE |
| c.113C>T | p.T38I | MISSENSE |
| c.1055G>A | p.S352N | MISSENSE |
| c.123G>T | p.R41S | MISSENSE |
| c.2030C>T | p.A677V | MISSENSE |
| c.249A>G | p.E83E | SYNONYMOUS |
| c.394G>A | p.G132S | MISSENSE |
| c.1003C>T | p.R335X | NONSENSE |
| c.1131_1134delTAGA | fs | INDEL |
| IVS7-1G>A | SPLICE SITE | SPLICE SITE |
| IVS8+2T>G | SPLICE SITE | SPLICE SITE |
| c.258C>T | p.A86A | SYNONYMOUS |
| c.833A>T | p.H278L | MISSENSE |
| c.1279C>T | p.P427S | MISSENSE |
| c.489G>A | p.Q163Q | SYNONYMOUS |
| c.3854_3864delTCATGCTGGTT | fs | INDEL |
| c.2019G>A | p.W673X | NONSENSE |
| c.2360C>T | p.A787V | MISSENSE |
| c.3658A>G | p.M1220V | MISSENSE |
| c.3058C>T | p.P1020S | MISSENSE |
| c.138C>T | p.Y46Y | SYNONYMOUS |
| c.50C>T | p.A17V | MISSENSE |

FIG. 10
CONTINUED

| | | | |
|---|---|---|---|
| PUM1 | CCDS338.1 | Br27P | g.chr1:31147821G>A |
| PYGB | CCDS13171.1 | Br27P | g.chr20:25209674C>T |
| Q13034_HUMAN | ENST00000225928 | Br27P | g.chr17:37953829C>T |
| Q4VXG5_HUMAN | ENST00000327794 | Br27P | g.chr1:221618015G>A |
| Q4VXG5_HUMAN | ENST00000331811 | Br27P | g.chr1:221761194A>T |
| Q5JX50_HUMAN | ENST00000325076 | Br27P | g.chr20:33651159G>A |
| Q5JYU7_HUMAN | ENST00000333418 | Br27P | g.chr22:36707744C>T |
| Q5T740_HUMAN | ENST00000343319 | BR02X | g.chr10:447501111C>T |
| Q5W0A0_HUMAN | ENST00000298738 | Br17X | g.chr13:45022091G>T |
| Q68CJ6_HUMAN | ENST00000341513 | Br25X | g.chr8:27943827G>T |
| Q6IEE8_HUMAN | ENST00000354872 | Br27P | g.chr17:30908947delC |
| Q6PK04_HUMAN | ENST00000329214 | Br27P | g.chr17:77245281G>A |
| Q6RGF6_HUMAN | ENST00000359144 | Br27P | g.chr4:18168367G>A |
| Q6ZRB0_HUMAN | ENST00000297487 | Br27P | g.chr7:1311692G>A |
| Q6ZSY1_HUMAN | ENST00000320930 | Br27P | g.chr15:31232700A>G |
| Q6ZT40_HUMAN | ENST00000296564 | Br27P | g.chr5:5514743C>T |
| Q6ZUG5_HUMAN | ENST00000344062 | Br16X | g.chr3:130134493G>A |
| Q6ZV46_HUMAN | ENST00000341696 | Br27P | g.chr7:1347402G>A |
| Q76B61_HUMAN | ENST00000360022 | Br27P | g.chr7:148919650C>T |
| Q86U37_HUMAN | ENST00000335192 | Br27P | g.chr14:283111812G>A |
| Q86XQ1_HUMAN | ENST00000261673 | Br27P | g.chr12:131770009C>T |
| Q86XQ1_HUMAN | ENST00000261673 | Br27P | g.chr12:131761336G>A |
| Q86YU6_HUMAN | ENST00000330768 | Br27P | g.chr16:69256483G>A |
| Q8IUR1_HUMAN | ENST00000327506 | Br03X | g.chr2:234522856T>C |
| Q8N1R6_HUMAN | ENST00000331014 | Br27P | g.chr13:110066133C>T |
| Q8N646_HUMAN | ENST00000359720 | Br08X | g.chr9:86854631C>T |
| Q8N800_HUMAN | ENST00000322516 | Br03X | g.chr13:102185000G>A (HOMOZYGOUS) |
| Q8N822_HUMAN | ENST00000317280 | Br27P | g.chr1:209187813C>T |
| Q8N8C3_HUMAN | ENST00000319889 | Br20P | g.chr7:70042362G>T |
| Q8N8K0_HUMAN | ENST00000301807 | Br08X | g.chr3:36855185A>G |
| Q8N9H1_HUMAN | ENST00000359503 | Br27P | g.chr22:16818069G>A |
| Q8NBE0_HUMAN | ENST00000297801 | Br04X | g.chr7:128108555G>A |
| Q8NDH2_HUMAN | ENST00000322527 | Br11P | chr13:102180027_102180020delTGAAAGA |
| Q8NDH2_HUMAN | ENST00000322527 | Br11P | g.chr13:102181079_102181078delAA |
| Q8NGK8_HUMAN | ENST00000334020 | Br9PT | g.chr11:55380131C>A |
| Q8NGL5_HUMAN | ENST00000328673 | Br9PT | g.chr11:55279853C>A |
| Q8NH06_HUMAN | ENST00000324144 | Br16X | g.chr17:3004187G>T |
| Q8NHB0_HUMAN | ENST00000315712 | Br9PT | g.chr5:180052803G>A |
| Q8TBR1_HUMAN | ENST00000354206 | Br10P | g.chr7:23303688G>A |
| Q96CH6_HUMAN | ENST00000329920 | Br27P | g.chr22:28967205G>A |
| Q96CK5_HUMAN | ENST00000273582 | Br02X | g.chr3:198919747C>T |
| Q96DR3_HUMAN | ENST00000324748 | Br27P | g.chr1:25831361C>T |
| Q96FF7_HUMAN | ENST00000269720 | Br27P | g.chr19:14046199C>T |
| Q96NE0_HUMAN | ENST00000329922 | Br27P | g.chr4:764982G>A |
| Q96NL2_HUMAN | ENST00000272907 | Br25X | g.chr2:226099141G>A |
| Q96PS2_HUMAN | ENST00000326978 | Br03X | g.chr4:37690920A>T |
| Q9H030_HUMAN | ENST00000237449 | Br27P | g.chr2:84954843G>A |
| Q9H6A9_HUMAN | ENST00000309024 | Br27P | g.chr11:65142913C>T |
| Q9H800_HUMAN | ENST00000357106 | Br27P | g.chr20:51620384G>A |
| Q9H8D1_HUMAN | ENST00000360549 | Br11P | g.chr6:80076998G>A |

FIG. 10
CONTINUED

| | | |
|---|---|---|
| c.692G>A | p.G231D | MISSENSE |
| c.1329C>T | p.A443A | SYNONYMOUS |
| c.620C>T | p.T207I | MISSENSE |
| c.1065G>A | p.W355X | NONSENSE |
| c.3732A>T | p.K1244N | MISSENSE |
| c.1566G>A | p.E522E | SYNONYMOUS |
| c.776C>T | p.P259L | MISSENSE |
| c.351C>T | p.G117G | SYNONYMOUS |
| c.1584G>T | p.R528S | MISSENSE |
| c.139G>T | p.D47Y | MISSENSE |
| c.242delC | fs | INDEL |
| c.252G>A | p.K84K | SYNONYMOUS |
| c.102G>A | p.W34X | NONSENSE |
| c.1175G>A | p.C392Y | MISSENSE |
| c.1708A>G | p.T570A | MISSENSE |
| c.463C>T | p.P155S | MISSENSE |
| c.1137G>A | p.T379T | SYNONYMOUS |
| c.219G>A | p.T73T | SYNONYMOUS |
| c.797C>T | p.P266L | MISSENSE |
| c.57G>A | p.R19R | SYNONYMOUS |
| c.1299C>T | p.G433G | SYNONYMOUS |
| c.532G>A | p.G178R | MISSENSE |
| c.291G>A | p.E97E | SYNONYMOUS |
| c.730T>C | p.L244L | SYNONYMOUS |
| c.495C>T | p.S165S | SYNONYMOUS |
| c.164C>T | p.T55M | MISSENSE |
| c.2161G>A | p.V721I | MISSENSE |
| c.295C>T | p.L99F | MISSENSE |
| c.422G>T | p.C141F | MISSENSE |
| c.3801A>G | p.G1267G | SYNONYMOUS |
| c.281G>A | p.G94E | MISSENSE |
| c.670G>A | p.E224K | MISSENSE |
| c.1104_1111delTGAAAGAA | fs | INDEL |
| c.52_53delAA | fs | INDEL |
| c.83C>A | p.T28N | MISSENSE |
| c.798C>A | p.N266K | MISSENSE |
| c.659G>T | p.R220M | MISSENSE |
| c.460G>A | p.V154M | MISSENSE |
| c.134G>A | p.R45H | MISSENSE |
| c.458G>A | p.G153E | MISSENSE |
| c.550C>T | p.Q184X | NONSENSE |
| c.36C>T | p.A12A | SYNONYMOUS |
| IVS1-3C>T | SPLICE SITE | SPLICE SITE |
| c.72G>A | p.R24R | SYNONYMOUS |
| c.115G>A | p.D39N | MISSENSE |
| c.85A>T | p.R29X | NONSENSE |
| c.3939G>A | p.R1313R | SYNONYMOUS |
| c.1147C>T | p.R383C | MISSENSE |
| c.402G>A | p.L134L | SYNONYMOUS |
| c.487G>A | p.A163T | MISSENSE |

FIG. 10
CONTINUED

| | | | |
|---|---|---|---|
| Q9HAC4_HUMAN | ENST00000206466 | Br27P | g.chr14:23954179G>A |
| Q9P1M5_HUMAN | ENST00000303007 | Br20P | g.chr16:77143863C>T |
| Q9ULE4_HUMAN | ENST00000265018 | Br27P | g.chr4:17325528G>A |
| Q9Y6V0-3 | ENST00000333891 | Br23X | g.chr7:82240015A>T |
| QPCT | CCDS1790.1 | Br27P | g.chr2:37506022C>T |
| QRICH2 | NM_032134 | Br27P | g.chr17:71789568C>T |
| QSCN6 | CCDS1337.1 | Br27P | g.chr1:176897466G>A |
| QSER1 | NM_024774 | Br27P | g.chr11:32912116G>A |
| QSER1 | NM_024774 | Br27P | g.chr11:32913184G>A |
| QTRTD1 | NM_024638 | Br27P | g.chr3:115266805G>A |
| RAB36 | CCDS13805.1 | Br27P | g.chr22:21819859C>T |
| RAB3C | CCDS3976.1 | Br16X | g.chr5:57949348G>A(HOMOZYGOUS) |
| RAB3GAP2 | NM_012414 | Br14X | g.chr1:216732842T>C |
| RAB3IL1 | CCDS8014.1 | Br27P | g.chr11:61422371G>A |
| RAC2 | CCDS13945.1 | Br08X | g.chr22:35953427G>T |
| RAD23A | CCDS12289.1 | Br27P | g.chr19:12920370G>A |
| RAD51L3 | CCDS11287.1 | Br16X | g.chr17:30452129G>T |
| RAD52 | CCDS8507.1 | Br04X | g.chr12:910696G>A |
| RAFTLIN | NM_015150 | Br04X | g.chr3:16386690G>A |
| RAI1 | CCDS11188.1 | Br27P | g.chr17:17640870C>T |
| RALBP1 | CCDS11845.1 | Br08X | g.chr18:9525789G>A |
| RANBP17 | NM_022897 | Br23X | g.chr5:170559307C>T |
| RANP1 | ENST00000333828 | Br27P | g.chr13:20220032C>T |
| RAP140 | CCDS2877.1 | Br27P | g.chr3:56669816C>T |
| RAPGEF4 | NM_007023 | Br27P | g.chr2:173681090G>A |
| RAPGEF6 | NM_016340 | Br9PT | g.chr5:130868963A>T |
| RAPGEFL1 | CCDS11363.1 | Br15X | g.chr17:35603492C>T |
| RAPH1 | CCDS2359.1 | Br27P | g.chr2:204130462G>A |
| RAPH1 | CCDS2359.1 | Br27P | g.chr2:204179828G>A |
| RARSL | CCDS5011.1 | Br27P | g.chr6:88312065G>A |
| RASGRF1 | CCDS10309.1 | Br20P | g.chr15:77097236G>A |
| RASGRF2 | CCDS4052.1 | Br25X | g.chr5:80445480C>T |
| RASL11B | CCDS3490.1 | Br27P | g.chr4:53572619C>T |
| RAX | CCDS11972.1 | Br17X | g.chr18:55091191G>A |
| RB1 | NM_000321 | Br04X | g.chr13:47853551C>T (HOMOZYGOUS) |
| RB1 | NM_000321 | Br15X | g.chr13:47937481delC(HOMOZYGOUS) |
| RBM14 | CCDS8147.1 | Br04X | g.chr11:66149438G>A |
| RBM19 | CCDS9172.1 | Br27P | g.chr12:112846399C>T |
| RBM21 | CCDS8021.1 | Br27P | g.chr11:62099535G>A |
| RBM25 | NM_021239 | Br27P | g.chr14:72645842G>A |
| RBM25 | NM_021239 | Br29P | g.chr14:72633565T>G |
| RBM27 | ENST00000265271 | Br04X | g.chr5:145644445C>A |
| RBM27 | ENST00000265271 | Br04X | g.chr5:145644453T>G |
| RBM34 | ENST00000362051 | Br27P | g.chr1:231627288C>T |
| RBMS3 | NM_001003792 | Br25X | g.chr3:29756314A>G |
| RBP3 | CCDS7218.1 | Br08X | g.chr10:48009668G>A(HOMOZYGOUS) |
| RBPSUH | CCDS3436.1 | Br27P | g.chr4:26084098G>A |
| RC74 | NM_018250 | Br08X | g.chr8:28684457G>A |
| RCD-8 | CCDS10849.1 | Br27P | g.chr16:66471294G>A |
| RCD-8 | CCDS10849.1 | Br13X | g.chr16:66473355C>T |

FIG. 10
CONTINUED

| | | |
|---|---|---|
| c.3147G>A | p.W1049X | NONSENSE |
| c.207C>T | p.D69D | SYNONYMOUS |
| IVS12+1G>A | SPLICE SITE | SPLICE SITE |
| c.3584A>T | p.K1195M | MISSENSE |
| IVS3-4C>T | SPLICE SITE | SPLICE SITE |
| c.3737C>T | p.P1246L | MISSENSE |
| c.1881G>A | p.E627E | SYNONYMOUS |
| c.1632G>A | p.Q544Q | SYNONYMOUS |
| c.2700G>A | p.E900E | SYNONYMOUS |
| c.11G>A | p.S4N | MISSENSE |
| c.511C>T | p.P171S | MISSENSE |
| c.146G>A | p.R49H | MISSENSE |
| c.2593T>C | p.L865L | SYNONYMOUS |
| c.1104G>A | p.K368K | SYNONYMOUS |
| c.139G>T | p.D47Y | MISSENSE |
| IVS4+4G>A | SPLICE SITE | SPLICE SITE |
| c.943G>T | p.G315W | MISSENSE |
| c.137G>A | p.R46K | MISSENSE |
| c.927G>A | p.Q309Q | SYNONYMOUS |
| c.3883C>T | p.P1295S | MISSENSE |
| c.1822G>A | p.D608N | MISSENSE |
| c.2067C>T | p.F689F | SYNONYMOUS |
| c.157C>T | p.P53S | MISSENSE |
| c.163C>T | p.L55L | SYNONYMOUS |
| c.1420G>A | p.V474I | MISSENSE |
| c.1094A>T | p.D365V | MISSENSE |
| c.1297C>T | p.R433C | MISSENSE |
| c.2957G>A | p.G986D | MISSENSE |
| c.717G>A | p.G239G | SYNONYMOUS |
| c.523G>A | p.G175S | MISSENSE |
| c.1674G>A | p.P558P | SYNONYMOUS |
| c.2455C>T | p.R819X | NONSENSE |
| c.466C>T | p.L156L | SYNONYMOUS |
| c.228G>A | p.A76A | SYNONYMOUS |
| c.1666C>T | p.R556X | NONSENSE |
| c.2465delC | fs | INDEL |
| c.1515G>A | p.G505G | SYNONYMOUS |
| c.1580C>T | p.A527V | MISSENSE |
| c.2232G>A | p.E744E | SYNONYMOUS |
| c.1581G>A | p.K527K | SYNONYMOUS |
| IVS6+4T>G | SPLICE SITE | SPLICE SITE |
| c.3056C>A | p.P1019Q | MISSENSE |
| c.3064T>G | p.S1022A | MISSENSE |
| c.794C>T | p.A265V | MISSENSE |
| c.496A>G | p.I166V | MISSENSE |
| c.1216G>A | p.E406K | MISSENSE |
| c.86G>A | p.G29E | MISSENSE |
| c.1623G>A | p.S541S | SYNONYMOUS |
| c.1862G>A | p.S621N | MISSENSE |
| IVS22-3C>T | SPLICE SITE | SPLICE SITE |

FIG. 10
CONTINUED

| | | | |
|---|---|---|---|
| RDHE2 | CCDS6167.1 | Br27P | g.chr8:57391284G>A |
| RDS | CCDS4871.1 | Br20P | g.chr6:42797544C>T |
| REG1B | CCDS1963.1 | Br20P | g.chr2:79225679C>T |
| REN | NM_000537 | Br20P | g.chr1:200862821G>A |
| REPS2 | CCDS14180.1 | Br27P | g.chrX:16855059C>T |
| RET | CCDS7200.1 | Br16X | g.chr10:42921950C>T(HOMOZYGOUS) |
| RFC2 | CCDS5567.1 | Br25X | g.chr7:73113319C>T |
| RFNG | NM_002917 | Br27P | g.chr17:77600984C>T |
| RFX3 | CCDS6450.1 | Br27P | g.chr9:3237930C>T |
| RGS22 | NM_015668 | Br27P | g.chr8:101063523C>T |
| RGSL1 | CCDS1346.1 | Br03X | g.chr1:179249594G>A |
| RHOT1 | NM_001033568 | Br03X | g.chr17:27552098T>A |
| RICTOR | NM_152756 | Br27P | g.chr5:38998885C>T |
| RIMBP2 | NM_015347 | Br17X | g.chr12:129452013G>A |
| RIMBP2 | NM_015347 | Br27P | g.chr12:129423546C>T |
| RIMS2 | NM_014677 | Br27P | g.chr8:104967454G>A |
| RIMS4 | CCDS13338.1 | Br04X | g.chr20:42818210G>T |
| RIPK4 | CCDS13675.1 | Br05X | g.chr21:42042391C>A |
| RLBP1 | NM_000326 | Br27P | g.chr15:87554535G>A |
| RLTPR | NM_001013838 | Br05X | g.chr16:66245596G>A |
| RNASEH2A | CCDS12282.1 | Br27P | g.chr19:12778824C>T |
| RNF103 | NM_005667 | Br27P | g.chr2:86761663G>A |
| RNF127 | CCDS14575.1 | Br29P | g.chrX:117890725G>A |
| RNF128 | CCDS14521.1 | Br27P | g.chrX:105776494G>A |
| RNF19 | CCDS6286.1 | Br27P | g.chr8:101369110G>A |
| RNF25 | CCDS2420.1 | Br27P | g.chr2:219354326G>A |
| RNF40 | CCDS10691.1 | Br27P | g.chr16:30685339G>A |
| RNPC2 | CCDS13265.1 | Br25X | g.chr20:33776054G>A |
| ROBO3 | NM_022370 | Br27P | g.chr11:124252678C>T |
| ROCK1 | CCDS11870.1 | Br03X | 8:16825270_16825265delGAGATA (HOMOZYGOUS) |
| ROM1 | CCDS8024.1 | Br27P | g.chr11:62138672C>T |
| ROS1 | CCDS5116.1 | Br27P | g.chr6:117772120A>G |
| RoXaN | CCDS14013.1 | Br27P | g.chr22:40061588C>T |
| RP1L1 | NM_178857 | Br02X | g.chr8:10517973G>A |
| RPL11 | CCDS238.1 | Br15X | g.chr1:23765668C>T |
| RPS14 | CCDS4307.1 | Br27P | g.chr5:149806617G>A |
| RPS6KA2 | CCDS5294.1 | Br27P | g.chr6:166802208C>T |
| RPS6KB2 | NM_003952 | Br27P | g.chr11:66953040C>T |
| RPUSD3 | CCDS2586.1 | Br10P | g.chr3:9857404C>T |
| RRAGD | CCDS5022.1 | Br27P | g.chr6:90178409C>T |
| RSHL1 | CCDS12675.1 | Br27P | g.chr19:51009812G>A |
| RSU1 | CCDS7112.1 | Br27P | g.chr10:16834645A>G |
| RTN1 | CCDS9740.1 | Br23X | g.chr14:59263427C>T (HOMOZYGOUS) |
| RTTN | NM_173630 | Br27P | g.chr18:66015864C>T |
| RUNX1 | CCDS13639.1 | Br27P | g.chr21:35086533C>T |
| RUNX1T1 | CCDS6256.1 | Br27P | g.chr8:93086672C>T |
| RWDD1 | NM_001007464 | Br27P | g.chr6:117018748A>G |
| RYR2 | NM_001035 | Br27P | g.chr1:234250313C>T |
| RYR2 | NM_001035 | Br23X | g.chr1:234273164C>T |
| RYR2 | NM_001035 | Br27P | g.chr1:233992712C>T |

FIG. 10
CONTINUED

| | | |
|---|---|---|
| c.177G>A | p.Q59Q | SYNONYMOUS |
| c.507C>T | p.N169N | SYNONYMOUS |
| c.97C>T | p.R33X | NONSENSE |
| c.226G>A | p.V76M | MISSENSE |
| c.971C>T | p.S324F | MISSENSE |
| c.988C>T | p.R330W | MISSENSE |
| c.46C>T | p.Q16X | NONSENSE |
| c.686C>T | p.A229V | MISSENSE |
| c.2070C>T | p.N690N | SYNONYMOUS |
| IVS21-3C>T | SPLICE SITE | SPLICE SITE |
| c.1183G>A | p.V395I | MISSENSE |
| c.1111T>A | p.Y371N | MISSENSE |
| c.1416C>T | p.A472A | SYNONYMOUS |
| c.713G>A | p.R238Q | MISSENSE |
| IVS12+4C>T | SPLICE SITE | SPLICE SITE |
| c.875G>A | p.S292N | MISSENSE |
| c.789G>T | p.G263G | SYNONYMOUS |
| c.665C>A | p.P222Q | MISSENSE |
| c.939G>A | p.E313E | SYNONYMOUS |
| c.3164G>A | p.R1055H | MISSENSE |
| c.130C>T | p.P44S | MISSENSE |
| c.5G>A | p.W2X | NONSENSE |
| c.100G>A | p.D34N | MISSENSE |
| c.206G>A | p.G69D | MISSENSE |
| c.469G>A | p.D157N | MISSENSE |
| c.1239G>A | p.R413R | SYNONYMOUS |
| c.1252G>A | p.A418T | MISSENSE |
| c.539G>A | p.R180Q | MISSENSE |
| c.2900C>T | p.P967L | MISSENSE |
| c.2008_2013delGAGATA | p.E670_I671del | INDEL |
| c.841C>T | p.L281L | SYNONYMOUS |
| IVS26-2A>G | SPLICE SITE | SPLICE SITE |
| IVS9-4C>T | SPLICE SITE | SPLICE SITE |
| c.149G>A | p.R50H | MISSENSE |
| c.223C>T | p.R75X | NONSENSE |
| c.252G>A | p.R84R | SYNONYMOUS |
| c.1854C>T | p.T618T | SYNONYMOUS |
| c.90C>T | p.P30P | SYNONYMOUS |
| c.469C>T | p.Q157X | NONSENSE |
| c.23C>T | p.P8L | MISSENSE |
| c.463G>A | p.D155N | MISSENSE |
| c.497A>G | p.D166G | MISSENSE |
| c.1728C>T | p.G576G | SYNONYMOUS |
| c.669C>T | p.F223F | SYNONYMOUS |
| c.1212C>T | p.H404H | SYNONYMOUS |
| c.588C>T | p.L196L | SYNONYMOUS |
| c.264A>G | p.K88K | SYNONYMOUS |
| c.11420C>T | p.A3807V | MISSENSE |
| c.12111C>T | p.P4037P | SYNONYMOUS |
| c.2479C>T | p.L827L | SYNONYMOUS |

FIG. 10
CONTINUED

| | | | |
|---|---|---|---|
| RYR2 | NM_001035 | Br10P | g.chr1:233820306G>A |
| RYR2 | NM_001035 | Br17X | g.chr1:233858930G>A |
| RYR2 | NM_001035 | Br05X | g.chr1:234132736A>G |
| RYR3 | NM_001036 | Br9PT | g.chr15:31893017C>T |
| RYR3 | NM_001036 | Br27P | g.chr15:31837073A>G |
| SALL3 | CCDS12013.1 | BR27P | g.chr18:74854681C>T |
| SAMD11 | ENST00000294573 | Br25X | g.chr2:132034808C>T |
| SAMD9 | NM_017654 | Br05X | g.chr7:92379086C>T |
| SAPS2 | NM_014678 | Br27P | g.chr22:49172490G>A |
| SARG | CCDS1475.1 | Br27P | g.chr1:203584228C>T |
| SARS | CCDS795.1 | Br27P | g.chr1:109468784G>A |
| SASH1 | CCDS5212.1 | Br27P | g.chr6:148906777G>A |
| SCHIP1 | CCDS3186.1 | Br27P | g.chr3:161097235G>A |
| SCN1B | CCDS12441.1 | BR02X | g.chr19:40213563C>T |
| SCN3A | NM_006922 | Br03x | g.chr2:165772558G>A |
| SCN3B | CCDS8442.1 | Br16X | g.chr11:123018465_123018464delCT |
| SCN5A | NM_000335 | Br20P | g.chr3:38579032G>T |
| SCN9A | NM_002977 | Br07X | g.chr2:166881761C>T |
| SCN9A | NM_002977 | Br9PT | g.chr2:166987822G>A |
| SCRIB | CCDS6411.1 | Br27P | g.chr8:144958235G>A |
| SCUBE1 | CCDS14048.1 | Br02X | g.chr22:41959439C>T(HOMOZYGOUS) |
| SCUBE1 | CCDS14048.1 | Br17X | g.chr22:41959381G>A |
| SDC3 | NM_014654 | Br13X | g.chr1:31019055G>A |
| SDR-O | CCDS8926.1 | Br25X | g.chr12:55603976A>G |
| SEC24C | CCDS7332.1 | Br13X | g.chr10:75176601A>G(HOMOZYGOUS) |
| SELO | NM_031454 | Br27P | g.chr22:48958001G>A |
| SEMA5A | CCDS3875.1 | Br27P | g.chr5:9433001G>A |
| SEMA5B | CCDS3019.1 | Br26X | g.chr3:124125250C>G |
| SEMA7A | CCDS10262.1 | Br27P | g.chr15:72496781C>T |
| SEN2L | CCDS2611.1 | Br27P | g.chr3:125533134G>A |
| SENP3 | NM_015670 | Br27P | g.chr17:7409481G>A |
| SEPT2 | CCDS2548.1 | Br27P | g.chr2:241997158C>T |
| SERPINA12 | CCDS9926.1 | Br08X | g.chr14:94034334A>G |
| SERPINA12 | CCDS9926.1 | Br17X | g.chr14:94034441C>T |
| SERPINA9 | NM_175739 | Br26X | g.chr14:94005784C>T |
| SERPINB3 | CCDS11987.1 | Br27P | 475118_59475107delTGGAAATACCAT(HOMOZYGOUS) |
| SERPINB7 | CCDS11988.1 | Br06X | g.chr18:59622650G>A |
| SERPINE2 | CCDS2460.1 | Br27P | g.chr2:224692077C>T |
| SERPING1 | CCDS7962.1 | Br14X | g.chr11:57124012G>A |
| SET7 | CCDS3748.1 | Br27P | g.chr4:140796648G>A |
| SETDB2 | CCDS9417.1 | Br27P | g.chr13:48952406C>T |
| SEZ6 | NM_178860 | Br23X | g.chr17:24308535G>T(HOMOZYGOUS) |
| SEZ6L | CCDS13833.1 | Br07X | g.chr22:25071613C>T |
| SFI1 | NM_001007467 | Br27P | g.chr22:30293732C>T |
| SFMBT2 | NM_001029880 | Br27P | g.chr10:7245754C>T |
| SFRP2 | NM_003013 | Br27P | g.chr4:1550060321G>A |
| SFTPB | CCDS1983.1 | Br04X | g.chr2:85804437C>T |
| SG223_HUMAN | ENST00000330777 | Br27P | g.chr8:8271455G>A |
| SG223_HUMAN | ENST00000330777 | Br27P | g.chr8:8272807C>T |
| SGCZ | CCDS5992.1 | Br16X | g.chr8:14456651C>G |

FIG. 10
CONTINUED

| | | |
|---|---|---|
| c.256G>A | p.V86M | MISSENSE |
| c.365G>A | p.R122H | MISSENSE |
| c.7290A>G | p.G2430G | SYNONYMOUS |
| c.10447C>T | p.R3483W | MISSENSE |
| c.8689A>G | p.K2897E | MISSENSE |
| c.1702C>T | p.P568S | MISSENSE |
| c.1361C>T | p.T454M | MISSENSE |
| c.976C>T | p.Q326X | NONSENSE |
| c.2550G>A | p.K850K | SYNONYMOUS |
| c.1276C>T | p.P426S | MISSENSE |
| c.128G>A | p.W43X | NONSENSE |
| c.2478G>A | p.E826E | SYNONYMOUS |
| c.1434G>A | p.K478K | SYNONYMOUS |
| UTR-2C>T | 5'UTR | 5'UTR |
| c.5612G>A | p.R1871Q | MISSENSE |
| c.344_345delCT | fs | INDEL |
| c.3838G>T | p.V1280F | MISSENSE |
| c.4862C>T | p.T1621M | MISSENSE |
| c.583G>A | p.V195I | MISSENSE |
| c.3089G>A | p.G1030D | MISSENSE |
| c.747C>T | p.N249N | SYNONYMOUS |
| c.805G>A | p.V269I | MISSENSE |
| c.307G>A | p.V103I | MISSENSE |
| c.850A>G | p.K284E | MISSENSE |
| c.5A>G | p.N2S | MISSENSE |
| c.1832G>A | p.G611E | MISSENSE |
| c.58G>A | p.A20T | MISSENSE |
| c.1176C>G | p.L392L | SYNONYMOUS |
| c.609C>T | p.F203F | SYNONYMOUS |
| c.934G>A | p.G312R | MISSENSE |
| c.1068G>A | p.R356R | SYNONYMOUS |
| c.557C>T | p.T186I | MISSENSE |
| c.154A>G | p.N52D | MISSENSE |
| c.47C>T | p.T16M | MISSENSE |
| c.201C>T | p.T67T | SYNONYMOUS |
| c.695_706delTGGAAATACCAT | INDEL | INDEL |
| c.944G>A | p.R315H | MISSENSE |
| c.46C>T | p.P16S | MISSENSE |
| c.136G>A | p.A46T | MISSENSE |
| c.916G>A | p.D306N | MISSENSE |
| c.956C>T | p.P319L | MISSENSE |
| c.2451G>T | p.Q817H | MISSENSE |
| c.2449C>T | p.R817C | MISSENSE |
| c.900C>T | p.R300R | SYNONYMOUS |
| c.2669C>T | p.A890V | MISSENSE |
| c.775G>A | p.V259I | MISSENSE |
| c.532C>T | p.L178F | MISSENSE |
| c.1874G>A | p.R625K | MISSENSE |
| c.522C>T | p.N174N | SYNONYMOUS |
| c.156C>G | p.A52A | SYNONYMOUS |

FIG. 10
CONTINUED

| | | | |
|---|---|---|---|
| SGK2 | CCDS13320.1 | Br14X | g.chr20:41631484C>G |
| SGPP1 | CCDS9760.1 | Br27P | g.chr14:63222958C>T |
| SGPP2 | CCDS2453.1 | Br03X | g.chr2:223212118C>T |
| SGSH | CCDS11770.1 | Br27P | g.chr17:75799257C>T |
| SH3BP1 | CCDS13952.1 | Br27P | g.chr22:36367399C>T |
| SH3BP2 | NM_003023 | Br27P | g.chr4:2863884G>A |
| SH3GL3 | CCDS10325.1 | Br27P | g.chr15:81950638C>T |
| SHANK2 | CCDS8198.1 | Br27P | g.chr11:70183653G>A |
| SHANK3 | ENST00000262795 | Br26X | g.chr22:49449774G>A (HOMOZYGOUS) |
| SHB | NM_003028 | Br27P | g.chr9:38058254C>T |
| SHB | NM_003028 | Br27P | g.chr9:37964796G>A |
| SHE | NM_001010846 | Br27P | g.chr1:151287205G>A |
| SHMT2 | CCDS8934.1 | Br16X | g.chr12:55914414G>A |
| SIGLEC11 | CCDS12790.1 | Br16X | g.chr19:55153383C>T |
| SIGLEC11 | CCDS12790.1 | Br27P | g.chr19:55145101C>T |
| SIGLEC5 | NM_003830 | Br04X | g.chr19:56822806C>T |
| SIGLEC8 | NM_014442 | Br27P | g.chr19:56652596C>T |
| SIM2 | CCDS13646.1 | Br27P | g.chr21:37003376C>T |
| SIPA1L2 | NM_020808 | Br27P | g.chr1:228933357G>A |
| SIPA1L2 | NM_020808 | Br27P | g.chr1:228888104C>T |
| SIPA1L3 | NM_015073 | Br27P | g.chr19:43346959G>A |
| SKIV2L | CCDS4731.1 | Br27P | g.chr6:32043101G>A |
| SKP2 | CCDS3915.1 | Br06X | g.chr5:36202389C>T |
| SKP2 | CCDS3915.1 | Br06X | g.chr5:36202488C>T |
| SLC10A4 | CCDS3482.1 | Br27P | g.chr4:48326769C>T |
| SLC11A1 | CCDS2415.1 | Br25X | g.chr2:219077407G>A |
| SLC12A1 | CCDS10129.1 | Br27P | g.chr15:46287430C>T |
| SLC12A5 | CCDS13391.1 | Br14X | g.chr20:44097883G>A |
| SLC14A1 | CCDS11925.1 | Br07X | g.chr18:41568248C>T |
| SLC14A2 | CCDS11924.1 | Br23X | g.chr18:41477955G>A |
| SLC16A5 | CCDS11713.1 | Br04X | g.chr17:70611797G>T |
| SLC1A2 | NM_004171 | Br03X | g.chr11:35239082_35239081delCT |
| SLC22A11 | CCDS8074.1 | Br27P | hr11:64080137_64080148delGATACCTTCC |
| SLC22A18 | CCDS7740.1 | Br27P | g.chr11:2902956G>A |
| SLC22A18 | CCDS7740.1 | Br27P | g.chr11:2887492G>A |
| SLC22A3 | CCDS5277.1 | Br25X | g.chr6:160828440G>T |
| SLC24A6 | NM_024959 | Br27P | g.chr12:112208284G>A |
| SLC25A13 | CCDS5645.1 | Br17X | g.chr7:95444083C>T |
| SLC26A4 | CCDS5746.1 | Br27P | g.chr7:106923522G>A |
| SLC26A4 | CCDS5746.1 | Br27P | g.chr7:106928845C>T |
| SLC2A1 | CCDS477.1 | Br27P | g.chr1:43062548C>T |
| SLC2A1 | CCDS477.1 | Br27P | g.chr1:43065861G>A |
| SLC30A1 | CCDS1499.1 | Br27P | g.chr1:208140283G>A |
| SLC30A5 | CCDS3996.1 | Br27P | g.chr5:68448005G>A |
| SLC30A9 | CCDS3465.1 | Br27P | g.chr4:41833643C>T |
| SLC30A9 | CCDS3465.1 | Br20P | g.chr4:41905996G>A |
| SLC35B2 | NM_178148 | Br27P | g.chr6:44330964G>A |
| SLC35D3 | NM_001008783 | Br27P | g.chr6:137287138G>A |
| SLC35F2 | NM_017515 | Br20P | g.chr11:107181384_107181381delTTGT |
| SLC38A1 | NM_030674 | Br27P | g.chr12:44877977G>A |

FIG. 10
CONTINUED

| | | |
|---|---|---|
| c.454C>G | p.R152G | MISSENSE |
| c.944C>T | p.S315F | MISSENSE |
| c.506C>T | p.A169V | MISSENSE |
| c.1098C>T | p.S366S | SYNONYMOUS |
| c.759C>T | p.S253S | SYNONYMOUS |
| c.384G>A | p.E128E | SYNONYMOUS |
| c.49C>T | p.L17F | MISSENSE |
| c.225G>A | p.Q75Q | SYNONYMOUS |
| c.567G>A | p.A189A | SYNONYMOUS |
| c.389C>T | p.A130V | MISSENSE |
| c.877G>A | p.G293S | MISSENSE |
| c.371G>A | p.R124Q | MISSENSE |
| UTR+3G>A | 3'UTR | 3'UTR |
| c.1584C>T | p.A528A | SYNONYMOUS |
| c.1999C>T | p.L667L | SYNONYMOUS |
| c.1003C>T | p.P335S | MISSENSE |
| c.664C>T | p.L222F | MISSENSE |
| c.214C>T | p.P72S | MISSENSE |
| c.1132G>A | p.G378R | MISSENSE |
| c.2587C>T | p.P863S | MISSENSE |
| c.3781G>A | p.G1261R | MISSENSE |
| c.2551G>A | p.E851K | MISSENSE |
| c.404C>T | p.S135F | MISSENSE |
| c.503C>T | p.S168L | MISSENSE |
| c.263C>T | p.P88L | MISSENSE |
| c.520G>A | p.V174I | MISSENSE |
| c.222C>T | p.L74L | SYNONYMOUS |
| c.340G>A | p.V114I | MISSENSE |
| c.353C>T | p.A118V | MISSENSE |
| c.1183G>A | p.V395M | MISSENSE |
| c.1291G>T | p.A431S | MISSENSE |
| c.1660_1661delCT | fs | INDEL |
| c.90_101delGATACCTTCCCA | p.I31_Q34del | INDEL |
| c.1228G>A | p.V410I | MISSENSE |
| c.512G>A | p.G171D | MISSENSE |
| c.1074G>T | p.W358C | MISSENSE |
| c.1343G>A | p.G448D | MISSENSE |
| c.1236C>T | p.N412N | SYNONYMOUS |
| c.1075G>A | p.V359M | MISSENSE |
| c.1310C>T | p.A437V | MISSENSE |
| c.1099C>T | p.L367L | SYNONYMOUS |
| c.224G>A | p.G75E | MISSENSE |
| c.67G>A | p.V23M | MISSENSE |
| c.1101G>A | p.K367K | SYNONYMOUS |
| c.47C>T | p.S16F | MISSENSE |
| c.962G>A | p.G321D | MISSENSE |
| c.756G>A | p.M252I | MISSENSE |
| c.862G>A | p.V288M | MISSENSE |
| c.642_645delTTGT | fs | INDEL |
| c.1256G>A | p.G419E | MISSENSE |

FIG. 10
CONTINUED

| | | | |
|---|---|---|---|
| SLC38A4 | CCDS8750.1 | Br03X | g.chr12:45458758A>T |
| SLC38A6 | CCDS9751.1 | Br27P | g.chr14:60517766G>A |
| SLC39A2 | CCDS9563.1 | Br27P | g.chr14:20538978C>T |
| SLC43A3 | CCDS7956.1 | Br27P | g.chr11:56950108G>A |
| SLC4A1 | CCDS11481.1 | Br25X | g.chr17:39695604T>C |
| SLC4A5 | CCDS1936.1 | Br27P | g.chr2:74380808G>A |
| SLC4A7 | NM_003615 | Br27P | g.chr3:27411600C>T |
| SLC5A5 | CCDS12368.1 | Br15X | g.chr19:17855697G>A |
| SLC5A7 | CCDS2074.1 | Br15X | g.chr2:108067164C>A |
| SLC7A10 | CCDS12431.1 | Br27P | g.chr19:38395111C>A |
| SLC7A13 | NM_138817 | Br12P | g.chr8:87298891C>T |
| SLC7A14 | NM_020949 | Br27P | g.chr3:171667699G>A |
| SLC7A6 | NM_003983 | Br13X | g.chr16:66883037C>T |
| SLC8A1 | CCDS1806.1 | Br07X | g.chr2:40568624C>G |
| SLC9A1 | CCDS295.1 | Br07X | g.chr1:27120218C>T |
| SLC9A2 | CCDS2062.1 | Br27P | g.chr2:102758380G>A |
| SLC9A2 | CCDS2062.1 | Br27P | g.chr2:102732565C>T |
| SLC9A2 | CCDS2062.1 | Br23X | g.chr2:102732730G>A |
| SLC9A3R2 | NM_004785 | Br27P | g.chr16:2026853C>T |
| SLC9A4 | NM_001011552 | Br9PT | g.chr2:102583058G>A |
| SLCO1B1 | CCDS8685.1 | Br20P | g.chr12:21244773G>A |
| SLCO2A1 | CCDS3084.1 | Br27P | g.chr3:135144251C>T |
| SLCO4C1 | NM_180991 | Br27P | g.chr5:101654959G>A |
| SLCO6A1 | NM_173488 | Br20P | g.chr5:101752341G>A |
| SLIT2 | CCDS3426.1 | Br11P | g.chr4:20188405A>C |
| SLITRK1 | CCDS9464.1 | Br27P | g.chr13:83352763G>A |
| SLITRK5 | CCDS9465.1 | Br05x | g.chr13:87126216G>A |
| SLITRK6 | ENST00000313206 | Br27P | g.chr13:85268389G>A |
| SMARCA2 | NM_003070 | Br29P | g.chr9:2046831C>T |
| SMARCA4 | CCDS12253.1 | Br27P | g.chr19:10955957G>A |
| SMARCC2 | CCDS8907.1 | Br27P | g.chr12:54845445G>A |
| SMARCC2 | CCDS8907.1 | Br03X | g.chr12:54861124C>T |
| SMC5L1 | CCDS6632.1 | Br27P | g.chr9:70159251G>A |
| SMCR8 | CCDS11195.1 | Br20P | g.chr17:18162194T>A |
| SMF_HUMAN | ENST00000261804 | Br27P | g.chr5:149407502G>A |
| SN | CCDS13060.1 | Br15X | g.chr20:3635219G>T |
| SNED1 | ENST00000310397 | Br27P | g.chr2:241741088C>T |
| SNRPA | CCDS12565.1 | Br23X | g.chr19:45957225G>A |
| SNX13 | NM_015132 | Br27P | g.chr7:17611574C>T |
| SNX27 | CCDS1001.1 | Br27P | g.chr1:148443903G>A |
| SNX4 | CCDS3032.1 | Br15X | g.chr3:126721635C>T |
| SOCS5 | CCDS1830.1 | Br27P | g.chr2:46897685G>A |
| SOHLH1 | NM_001012415 | Br20P | g.chr9:135814487G>A |
| SORCS2 | NM_020777 | Br27P | g.chr4:7787006C>T |
| SORCS3 | CCDS7558.1 | Br27P | g.chr10:106949819G>A |
| SORL1 | CCDS8436.1 | Br08X | g.chr11:120995788C>T |
| SOS1 | CCDS1802.1 | Br17X | g.chr2:39161923G>A |
| SOSTDC1 | CCDS5360.1 | Br17X | g.chr7:16275425C>T |
| SOX13 | NM_005686 | Br27P | g.chr1:200813919G>A |
| SOX30 | CCDS4339.1 | Br27P | g.chr5:156998029G>A |

FIG. 10
CONTINUED

| | | |
|---|---|---|
| c.786A>T | p.S262S | SYNONYMOUS |
| c.18G>A | p.G6G | SYNONYMOUS |
| c.330C>T | p.S110S | SYNONYMOUS |
| c.114G>A | p.K38K | SYNONYMOUS |
| c.32T>C | p.M11T | MISSENSE |
| c.2086G>A | p.A696T | MISSENSE |
| c.2687C>T | p.P896L | MISSENSE |
| c.1368G>A | p.S456S | SYNONYMOUS |
| c.263C>A | p.P88Q | MISSENSE |
| c.715C>A | p.L239I | MISSENSE |
| c.1103C>T | p.S368L | MISSENSE |
| c.2162G>A | p.G721D | MISSENSE |
| c.994C>T | p.L332F | MISSENSE |
| c.448C>G | p.L150V | MISSENSE |
| c.1006C>T | p.L336F | MISSENSE |
| c.1147G>A | p.V383M | MISSENSE |
| c.314C>T | p.P105L | MISSENSE |
| c.479G>A | p.R160H | MISSENSE |
| c.718C>T | p.R240W | MISSENSE |
| c.1201G>A | p.V401I | MISSENSE |
| c.1035G>A | p.T345T | SYNONYMOUS |
| c.1521C>T | p.C507C | SYNONYMOUS |
| c.606G>A | p.G202G | SYNONYMOUS |
| c.1967G>A | p.R656H | MISSENSE |
| c.933A>C | p.T311T | SYNONYMOUS |
| c.881G>A | p.G294E | MISSENSE |
| c.572G>A | p.S191N | MISSENSE |
| c.256G>A | p.G86R | MISSENSE |
| c.1333C>T | p.R445C | MISSENSE |
| c.130G>A | p.G44R | MISSENSE |
| c.3063G>A | p.G1021G | SYNONYMOUS |
| c.985C>T | p.R329C | MISSENSE |
| c.1618G>A | p.A540T | MISSENSE |
| UTR+2T>A | 3'UTR | 3'UTR |
| c.3520G>A | p.E1177K | MISSENSE |
| c.184G>T | p.D62Y | MISSENSE |
| c.3218C>T | p.P1073L | MISSENSE |
| c.296G>A | p.G99D | MISSENSE |
| c.2492C>T | p.A831V | MISSENSE |
| c.663G>A | p.G221G | SYNONYMOUS |
| c.72C>T | p.D24D | SYNONYMOUS |
| c.365G>A | p.G122E | MISSENSE |
| c.577G>A | p.A193T | MISSENSE |
| c.706C>T | p.P236S | MISSENSE |
| c.2082G>A | p.R694R | SYNONYMOUS |
| c.5841C>T | p.S1947S | SYNONYMOUS |
| c.1297G>A | p.E433K | MISSENSE |
| c.609C>T | p.H203H | SYNONYMOUS |
| c.219G>A | p.W73X | NONSENSE |
| c.1667G>A | p.R556K | MISSENSE |

FIG. 10
CONTINUED

| | | | |
|---|---|---|---|
| SOX8 | CCDS10428.1 | Br27P | g.chr16:973886C>T |
| SP100 | CCDS2477.1 | Br25X | g.chr2:231194445A>T |
| SPACA4 | CCDS12725.1 | Br13X | g.chr19:53802290C>T |
| SPAG1 | NM_003114 | Br27P | g.chr8:101306708G>A |
| SPAG5 | NM_006461 | Br27P | g.chr17:23943830G>A |
| SPAG7 | NM_004890 | Br27P | g.chr17:4804840G>A |
| SPATA1 | CCDS697.1 | Br27P | g.chr1:84710633G>A |
| SPATA2 | CCDS13422.1 | Br27P | g.chr20:47958148G>A |
| SPATC1 | CCDS6413.1 | Br27P | g.chr8:145167826C>T |
| Spc25 | CCDS2229.1 | Br27P | g.chr2:169559318G>A |
| SPEG | ENST00000265327 | Br27P | g.chr2:220170269G>A |
| SPEN | CCDS164.1 | Br27P | g.chr1:15944675G>A |
| SPG3A | CCDS9700.1 | Br27P | g.chr14:50157167C>T |
| SPI1 | CCDS7933.1 | Br27P | g.chr11:47333534C>T |
| SPIN3 | NM_001010862 | Br20P | g.chrX:56904355C>T |
| SPIRE2 | NM_032451 | Br27P | g.chr16:88463485C>T |
| SPN | CCDS10650.1 | Br27P | g.chr16:29583027G>A |
| SPOCK3 | NM_016950 | Br27P | g.chr4:168050575T>A |
| SPON2 | CCDS3347.1 | Br27P | g.chr4:1154911G>A |
| SPRED2 | NM_181784 | Br25X | 5452553insCGACTCCCTGAGAACTTGCA |
| SPTB | NM_001024858 | Br27P | g.chr14:64311795C>T |
| SPTBN1 | NM_178313 | Br27P | g.chr2:54767929C>T |
| SPTBN1 | NM_178313 | Br27P | g.chr2:54770045C>T |
| SPTBN2 | CCDS8150.1 | Br27P | g.chr11:66231778C>T |
| SPTBN4 | CCDS12559.1 | Br13X | g.chr19:45670480G>A (HOMOZYGOUS) |
| SPTBN5 | NM_016642 | Br15X | g.chr15:39936447G>A |
| SREBF2 | CCDS14023.1 | Br27P | g.chr22:40596166G>A |
| SRGAP1 | CCDS8967.1 | Br14X | g.chr12:62777286A>T |
| SRPK2 | CCDS5735.1 | Br27P | g.chr7:104377559G>A |
| SRRM2 | NM_016333 | Br27P | g.chr16:2751609G>A |
| SSFA2 | CCDS2284.1 | Br27P | g.chr2:182591112A>G |
| ST14 | CCDS8487.1 | Br9PT | g.chr11:129565700C>G |
| ST8SIA4 | CCDS4091.1 | Br25X | g.chr5:100219999G>T |
| STAB1 | NM_015136 | Br20P | g.chr3:52516997C>G |
| STAP2 | CCDS12128.1 | Br02X | g.chr19:4279780A>C |
| STIM2 | CCDS3440.1 | Br02X | g.chr4:26686687G>T |
| STK33 | CCDS7789.1 | Br27P | g.chr11:8391759G>A |
| STK39 | NM_013233 | Br10P | g.chr2:168843809T>C |
| STRA6 | CCDS10261.1 | Br08X | g.chr15:72274725C>T |
| STS | CCDS14127.1 | Br27P | g.chrX:7035338G>A |
| STS-1 | NM_032873 | Br15X | g.chr11:122177146C>T |
| STX11 | CCDS5205.1 | Br25X | g.chr6:144550027C>T (HOMOZYGOUS) |
| STX12 | CCDS310.1 | Br27P | g.chr1:27830323G>A |
| STXBP2 | CCDS12181.1 | Br9PT | g.chr19:7613394C>T |
| STXBP3 | CCDS790.1 | Br27P | g.chr1:109037111G>A |
| STYK1 | CCDS8629.1 | Br27P | g.chr12:10666525C>T |
| SUCLA2 | CCDS9406.1 | Br27P | g.chr13:47440869C>T |
| SUCLG2 | NM_003848 | Br27P | g.chr3:67628971G>A |
| SULT6B1 | NM_001032377 | Br03X | g.chr2:37310339T>A |
| SUNC1 | NM_152782 | Br27P | g.chr7:47820016C>T |

FIG. 10
CONTINUED

| | | |
|---|---|---|
| c.580C>T | p.P194S | MISSENSE |
| c.1805A>T | p.Q602L | MISSENSE |
| c.243C>T | p.G81G | SYNONYMOUS |
| c.1820G>A | p.G607E | MISSENSE |
| c.559G>A | p.A187T | MISSENSE |
| c.117G>A | p.E39E | SYNONYMOUS |
| c.680G>A | p.G227E | MISSENSE |
| c.287G>A | p.G96D | MISSENSE |
| c.863C>T | p.P288L | MISSENSE |
| c.283G>A | p.E95K | MISSENSE |
| c.5244G>A | p.L1748L | SYNONYMOUS |
| c.142G>A | p.A48T | MISSENSE |
| c.963C>T | p.T321T | SYNONYMOUS |
| c.615C>T | p.H205H | SYNONYMOUS |
| c.47C>T | p.T16M | MISSENSE |
| c.1816C>T | p.P606S | MISSENSE |
| c.477G>A | p.E159E | SYNONYMOUS |
| c.754T>A | p.S252T | MISSENSE |
| c.414G>A | p.A138A | SYNONYMOUS |
| T990insCGACTCCCTGAGAACTTGCATCCGCCGG | INDEL | INDEL |
| c.4643C>T | p.A1548V | MISSENSE |
| c.1968C>T | p.D656D | SYNONYMOUS |
| c.3171C>T | p.D1057D | SYNONYMOUS |
| c.1438C>T | p.R480W | MISSENSE |
| c.112G>A | p.A38T | MISSENSE |
| c.8704G>A | p.A2902T | MISSENSE |
| c.1324G>A | p.A442T | MISSENSE |
| IVS14-2A>T | SPLICE SITE | SPLICE SITE |
| c.950G>A | p.G317D | MISSENSE |
| c.1079G>A | p.G360D | MISSENSE |
| c.687A>G | p.V229V | SYNONYMOUS |
| c.776C>G | p.T259S | MISSENSE |
| c.504G>T | p.R168S | MISSENSE |
| c.2063C>G | p.P688R | MISSENSE |
| c.482A>C | p.E161A | MISSENSE |
| c.1544G>T | p.R515L | MISSENSE |
| c.1203G>A | p.W401X | NONSENSE |
| c.623T>C | p.I208T | MISSENSE |
| c.568C>T | p.Q190X | NONSENSE |
| c.370G>A | p.D124N | MISSENSE |
| c.1491C>T | p.P497P | SYNONYMOUS |
| c.570C>T | p.S190S | SYNONYMOUS |
| c.670G>A | p.E224K | MISSENSE |
| c.874C>T | p.R292C | MISSENSE |
| c.835G>A | p.E279K | MISSENSE |
| c.946C>T | p.L316F | MISSENSE |
| c.664C>T | p.L222F | MISSENSE |
| c.859G>A | p.G287S | MISSENSE |
| c.556T>A | p.F186I | MISSENSE |
| c.478C>T | p.P160S | MISSENSE |

FIG. 10
CONTINUED

| | | | |
|---|---|---|---|
| SUSD5 | ENST00000309558 | Br27P | g.chr3:33230444G>A |
| SV2B | CCDS10370.1 | Br23X | g.chr15:89633801dupT |
| SWAP70 | NM_015055 | Br27P | g.chr11:9710759G>A |
| SYDE2 | ENST00000234668 | Br06X | g.chr1:85360243C>T |
| SYN2 | NM_133625 | Br27P | g.chr3:12186278C>T |
| SYNE1 | CCDS5236.1 | Br27P | g.chr6:152744768C>T |
| SYNE1 | CCDS5236.1 | Br27P | g.chr6:152723692C>T |
| SYNE1 | CCDS5237.1 | Br07X | g.chr6:152655536_152655534delATC |
| SYNE1 | CCDS5236.1 | Br27P | g.chr6:152780625G>A |
| SYNE1 | CCDS5236.1 | Br27P | g.chr6:152775573G>A |
| SYNE2 | CCDS9761.1 | Br27P | g.chr14:636698738G>A |
| SYT15 | NM_181519 | Br27P | g.chr10:46385078C>T |
| SYT16 | NM_031914 | Br27P | g.chr14:61617332C>T |
| SYT6 | CCDS871.1 | Br27P | g.chr1:114358340C>T |
| TAAR9 | ENST00000340640 | Br27P | g.chr6:132901206C>T |
| TACC2 | CCDS7626.1 | Br20P | g.chr10:123836918G>A |
| TACC3 | CCDS3352.1 | Br23X | g.chr4:1708936G>A |
| TAF1L | NM_153809 | Br27P | g.chr9:32622684G>A |
| TAF4B | ENST00000269142 | Br08X | g.chr18:22169166G>T |
| TAF6 | CCDS5686.1 | Br04X | g.chr7:99350752G>A |
| TANC1 | NM_033394 | Br27P | g.chr2:159912250C>T |
| TAOK1 | NM_020791 | Br17X | g.chr17:24873431A>G |
| TARBP2 | CCDS8861.1 | Br27P | g.chr12:52183775C>T |
| TAS1R2 | CCDS187.1 | Br17X | g.chr1:18926367C>T |
| TAS2R3 | CCDS5867.1 | Br27P | g.chr7:140917650C>T |
| TBC1D20 | CCDS13002.1 | Br13X | g.chr20:367925C>T |
| TBC1D4 | NM_014832 | Br27P | g.chr13:74759159G>A |
| TBCD | NM_001033052 | Br27P | g.chr17:78303503G>A |
| TBX20 | CCDS5445.1 | Br26X | g.chr7:35044358G>C |
| TBX22 | CCDS14445.1 | Br9PT | g.chrX:79083947G>A |
| TBX22 | CCDS14445.1 | Br13X | g.chrX:79089707C>T |
| TCF7L1 | CCDS1971.1 | Br27P | g.chr2:85444157C>T |
| TCF8 | CCDS7169.1 | Br27P | g.chr10:31850182C>T |
| TCHH | ENST00000290632 | Br13X | g.chr1:148898499C>T |
| TCN2 | CCDS13881.1 | Br27P | g.chr22:29336279C>T |
| TDRD5 | CCDS1332.1 | Br05X | g.chr1:176391563G>A |
| TDRD9 | CCDS9987.1 | Br03X | g.chr14:103558360C>T |
| TEAD2 | CCDS12761.1 | Br27P | g.chr19:54537527G>A |
| TEAD2 | CCDS12761.1 | Br27P | g.chr19:54552343G>A |
| TEPP | CCDS10790.1 | Br15X | g.chr16:56575722G>A |
| TERF2IP | NM_018975 | Br27P | g.chr16:74239592C>T |
| TFE3 | CCDS14315.1 | Br27P | g.chrX:48653042G>A |
| TGFBRAP1 | CCDS2067.1 | Br27P | g.chr2:105347941C>T |
| TGM1 | CCDS9622.1 | Br27P | g.chr14:23799722G>A |
| TGM1 | CCDS9622.1 | Br04X | .chr14:23798998_23798990delGAACTACG |
| TGM5 | NM_004245 | Br29P | g.chr15:41332273G>A |
| THAP9 | CCDS3598.1 | Br03X | 4:84195390_84195404delAAGTATGCCTCT |
| THBS1 | NM_003246 | Br02X | g.chr15:37666845G>A |
| THEA | CCDS592.1 | Br27P | g.chr1:54762516G>A |
| THOP1 | CCDS12095.1 | Br27P | g.chr19:2756027G>A |

FIG. 10
CONTINUED

| | | |
|---|---|---|
| c.687G>A | p.W229X | NONSENSE |
| c.1755dupT | fs | INDEL |
| c.1006G>A | p.E336K | MISSENSE |
| c.1620C>T | p.D540D | SYNONYMOUS |
| c.1180C>T | p.L394L | SYNONYMOUS |
| c.13166C>T | p.A4389V | MISSENSE |
| c.16972C>T | p.P5658S | MISSENSE |
| c.3418_3420delATC | p.I1140del | INDEL |
| c.9814G>A | p.V3272M | MISSENSE |
| IVS61-1G>A | SPLICE SITE | SPLICE SITE |
| c.5445G>A | p.Q1815Q | SYNONYMOUS |
| c.873C>T | p.Y291Y | SYNONYMOUS |
| c.961C>T | p.P321S | MISSENSE |
| c.862C>T | p.P288S | MISSENSE |
| c.85C>T | p.P29S | MISSENSE |
| c.4913G>A | p.R1638K | MISSENSE |
| c.2038G>A | p.E680K | MISSENSE |
| c.2894G>A | p.C965Y | MISSENSE |
| c.2298G>T | p.Q766H | MISSENSE |
| c.1347G>A | p.R449R | SYNONYMOUS |
| c.4806C>T | p.G1602G | SYNONYMOUS |
| c.1916A>G | p.N639S | MISSENSE |
| c.338C>T | p.P113L | MISSENSE |
| c.903C>T | p.S301S | SYNONYMOUS |
| c.508C>T | p.H170Y | MISSENSE |
| c.783C>T | p.R261R | SYNONYMOUS |
| c.3670G>A | p.A1224T | MISSENSE |
| c.145G>A | p.G49S | MISSENSE |
| c.888G>C | p.E296D | MISSENSE |
| c.34G>A | p.V12M | MISSENSE |
| c.936C>T | p.G312G | SYNONYMOUS |
| c.962C>T | p.P321L | MISSENSE |
| c.1913C>T | p.S638L | MISSENSE |
| c.267C>T | p.L89L | SYNONYMOUS |
| c.891C>T | p.N297N | SYNONYMOUS |
| c.2774G>A | p.R925H | MISSENSE |
| c.1691C>T | p.S564F | MISSENSE |
| c.1210G>A | p.E404K | MISSENSE |
| c.338G>A | p.R113K | MISSENSE |
| c.403G>A | p.A135T | MISSENSE |
| c.311C>T | p.A104V | MISSENSE |
| c.373G>A | p.A125T | MISSENSE |
| c.1861C>T | p.L621L | SYNONYMOUS |
| c.531G>A | p.K177K | SYNONYMOUS |
| c.864_872delGAACTACGG | INDEL | INDEL |
| c.592G>A | p.V198I | MISSENSE |
| c.846_860delAAGTATGCCTCTCAA | INDEL | INDEL |
| c.1126G>A | p.D376N | MISSENSE |
| c.201G>A | p.G67G | SYNONYMOUS |
| c.603G>A | p.E201E | SYNONYMOUS |

FIG. 10
CONTINUED

| | | | |
|---|---|---|---|
| THRAP3 | ENST00000354618 | Br08x | g.chr3:31471061C>T |
| THSD7B | ENST00000272643 | Br27P | g.chr2:137706467C>T |
| THSD7B | ENST00000272643 | Br16X | g.chr2:137824412C>T |
| TIMP2 | CCDS11758.1 | Br27P | g.chr17:74381568G>A |
| TINAG | CCDS4955.1 | Br17X | g.chr6:54294093A>T |
| TJP3 | NM_014428 | Br27P | g.chr19:3691579C>T |
| TLL1 | CCDS3811.1 | Br9PT | g.chr4:167293224C>T |
| TLN1 | NM_006289 | Br14X | g.chr9:35707211G>A |
| TLX3 | NM_021025 | Br25X | g.chr5:170669954C>G |
| TM4SF14 | CCDS7369.1 | Br27P | g.chr10:82259144C>T |
| TM4SF3 | CCDS8999.1 | Br27P | g.chr12:69824205C>T |
| TM9SF4 | CCDS13196.1 | Br29P | g.chr20:30206600A>G |
| TMED1 | CCDS12249.1 | Br27P | g.chr19:10806724G>A |
| TMEM131 | ENST00000186436 | Br27P | g.chr2:97889046C>T |
| TMEM131 | ENST00000186436 | Br17X | g.chr2:97835650G>A |
| TMEM132C | ENST00000315208 | Br02X | g.chr12:127715233C>A |
| TMEM16B | NM_020373 | Br08X | g.chr12:5592348G>A |
| TMEM16C | NM_031418 | Br9PT | g.chr11:26515535G>A |
| TMEM16E | NM_213599 | Br27P | g.chr11:22233570G>A |
| TMEM16G | NM_001001891 | Br27P | g.chr2:241864319G>A |
| TMEM16J | NM_001012302 | Br27P | g.chr11:423872G>A |
| TMEM16J | NM_001012302 | Br23X | g.chr11:410714C>T |
| TMEM38A | CCDS12349.1 | Br27P | g.chr19:16651821C>T |
| TMEM38A | CCDS12349.1 | Br27P | g.chr19:16652313G>A |
| TMEM46 | NM_001007538 | Br27P | g.chr13:25518984C>T |
| TMEM63B | NM_018426 | Br27P | g.chr6:44215211G>A |
| TMEM8 | CCDS10407.1 | Br27P | g.chr16:365425G>A |
| TMEM8 | CCDS10407.1 | Br27P | g.chr16:366366G>A |
| TMPRSS2 | NM_005656 | Br27P | g.chr21:41762253C>T |
| TMPRSS4 | NM_019894 | Br26X | g.chr11:117489205A>T |
| TNC | CCDS6811.1 | Br27P | g.chr9:114924560G>A |
| TNFAIP2 | CCDS9979.1 | Br17X | g.chr14:102662727G>A |
| TNFSF18 | CCDS1305.1 | Br9PT | g.chr1:169742463G>A |
| TNFSF4 | CCDS1306.1 | Br27P | g.chr1:169887356C>T |
| TNFSF9 | CCDS12169.1 | Br9PT | g.chr19:6486005C>T |
| TNIP1 | NM_006058 | Br27P | g.chr5:150398977C>T |
| TNIP2 | CCDS3362.1 | Br15X | g.chr4:2786718C>T |
| TNK1 | NM_003985 | Br27P | g.chr17:7228135C>T |
| TNMD | CCDS14469.1 | Br23X | g.chrX:99658721G>T |
| TNN | NM_022093 | Br27P | g.chr1:171778440G>A |
| TNPO1 | CCDS4016.1 | Br27P | g.chr5:72221442G>A |
| TNR | CCDS1318.1 | Br27P | g.chr1:172107441G>A |
| TNRC15 | NM_015575 | Br27P | g.chr2:233530088C>T |
| TNRC15 | NM_015575 | Br27P | g.chr2:233534273C>T |
| TNRC4 | CCDS1002.1 | Br13X | g.chr1:148493426G>A |
| TNRC6C | NM_018996 | Br27P | g.chr17:73599140T>C |
| TOE1 | CCDS521.1 | Br27P | g.chr1:45478074C>T |
| TOP2A | NM_001067 | Br11P | g.chr17:358820923A>G |
| TOR1A | CCDS6930.1 | Br03X | g.chr9:129660704C>A |
| TOSO | CCDS1473.1 | Br27P | g.chr1:203471565C>T |

FIG. 10
CONTINUED

| | | |
|---|---|---|
| c.1453C>T | p.R485X | NONSENSE |
| c.1241C>T | p.S414F | MISSENSE |
| c.2127C>T | p.H709H | SYNONYMOUS |
| c.159G>A | p.K53K | SYNONYMOUS |
| c.459A>T | p.V153V | SYNONYMOUS |
| c.1760C>T | p.A587V | MISSENSE |
| c.949C>T | p.R317C | MISSENSE |
| c.2390G>A | p.R797H | MISSENSE |
| c.617C>G | p.T206R | MISSENSE |
| c.387C>T | p.S129S | SYNONYMOUS |
| c.116C>T | p.S39F | MISSENSE |
| c.1228A>G | p.I410V | MISSENSE |
| c.351G>A | p.K117K | SYNONYMOUS |
| c.1181C>T | p.S394F | MISSENSE |
| c.4690G>A | p.V1564I | MISSENSE |
| c.1688C>A | p.T563N | MISSENSE |
| c.1969G>A | p.D657N | MISSENSE |
| c.983G>A | p.R328H | MISSENSE |
| c.1258G>A | p.E420K | MISSENSE |
| c.1101G>A | p.V367V | SYNONYMOUS |
| c.147G>A | p.R49R | SYNONYMOUS |
| IVS18+4C>T | SPLICE SITE | SPLICE SITE |
| c.151C>T | p.P51S | MISSENSE |
| c.387G>A | p.K129K | SYNONYMOUS |
| c.555C>T | p.A185A | SYNONYMOUS |
| c.437G>A | p.G146D | MISSENSE |
| c.1236G>A | p.R412R | SYNONYMOUS |
| c.995G>A | p.S332N | MISSENSE |
| c.1254C>T | p.N418N | SYNONYMOUS |
| c.755A>T | p.D252V | MISSENSE |
| c.2212G>A | p.A738T | MISSENSE |
| c.180G>A | p.A60A | SYNONYMOUS |
| c.235G>A | p.V79M | MISSENSE |
| c.508C>T | p.L170L | SYNONYMOUS |
| c.693C>T | p.G231G | SYNONYMOUS |
| c.1137C>T | p.T379T | SYNONYMOUS |
| c.437C>T | p.S146F | MISSENSE |
| c.705C>T | p.Y235Y | SYNONYMOUS |
| c.499G>T | p.D167Y | MISSENSE |
| c.229G>A | p.E77K | MISSENSE |
| c.1579G>A | p.V527I | MISSENSE |
| c.67G>A | p.G23S | MISSENSE |
| c.2791C>T | p.Q931X | NONSENSE |
| c.2902C>T | p.Q968X | NONSENSE |
| c.545G>A | p.R182H | MISSENSE |
| c.3827T>C | p.V1276A | MISSENSE |
| c.1140C>T | p.T380T | SYNONYMOUS |
| c.1167A>G | p.G389G | SYNONYMOUS |
| c.494C>A | p.S165Y | MISSENSE |
| c.885C>T | p.A295A | SYNONYMOUS |

FIG. 10
CONTINUED

| | | | |
|---|---|---|---|
| TP53 | CCDS11118.1 | Br9PT | g.chr17:7520254G>A |
| TP53 | CCDS11118.1 | Br23X | g.chr17:7519128G>T(HOMOZYGOUS) |
| TP53 | CCDS11118.1 | Br29P | g.chr17:7518988C>T |
| TP53 | CCDS11118.1 | Br13X | g.chr17:7518984T>A |
| TP53 | CCDS11118.1 | Br27P | g.chr17:7518957delT |
| TP53 | CCDS11118.1 | Br9PT | g.chr17:7518948_7518947delGA |
| TP53 | CCDS11118.1 | Br04X | g.chr17:7518273G>A (HOMOZYGOUS) |
| TP53 | CCDS11118.1 | Br12P | g.chr17:7518272G>A |
| TP53 | CCDS11118.1 | Br07X | g.chr17:7518264C>T |
| TP53 | CCDS11118.1 | Br10P | g.chr17:7517846C>T |
| TP53 | CCDS11118.1 | Br11P | g.chr17:7517845G>A |
| TP53 | CCDS11118.1 | Br03X | g.chr17:7517819C>T(HOMOZYGOUS) |
| TP53 | CCDS11118.1 | Br11P | g.chr17:7625707delG |
| TPH2 | NM_173353 | Br13X | g.chr12:70702490G>A |
| TPR | NM_003292 | Br27P | g.chr1:183064235G>A |
| TPST2 | CCDS13839.1 | Br02X | g.chr22:25261698G>A (HOMOZYGOUS) |
| TRAM1L1 | CCDS3707.1 | Br08X | g.chr4:183363316G>A |
| TRAPPC3 | CCDS404.1 | Br07X | g.chr1:36272641C>G |
| TREML2 | CCDS4853.1 | Br03x | g.chr6:41276676G>A |
| TREML3 | ENST00000332842 | Br9PT | g.chr6:41292883G>A |
| TRIM14 | CCDS6734.1 | Br27P | g.chr9:97936784C>T |
| TRIM42 | CCDS3113.1 | Br26X | g.chr3:141884298G>A |
| TRIM45 | CCDS893.1 | Br15X | g.chr1:117370353C>G |
| TRIM46 | CCDS1097.1 | Br27P | g.chr1:151969718G>A |
| TRIM55 | CCDS6186.1 | Br15X | g.chr8:67249339G>A |
| TRIM56 | NM_030961 | Br27P | g.chr7:100325094C>T |
| TRIM58 | CCDS1636.1 | Br11P | g.chr1:243365813T>C |
| TRIO | CCDS3883.1 | Br04X | g.chr5:14340101_14340102insCCC |
| TRIOBP | NM_007032 | Br27P | g.chr22:36479751C>T |
| TRIP12 | NM_004238 | Br07x | g.chr2:230549372A>G |
| TRIP6 | CCDS5708.1 | Br27P | g.chr7:100115547C>T |
| TRMT5 | NM_020810 | Br27P | g.chr14:60512237G>A |
| TRMT5 | NM_020810 | Br27P | g.chr14:60512083G>A |
| TRPC4AP | CCDS13246.1 | Br27P | g.chr20:33095976C>A |
| TRPC6 | CCDS8311.1 | Br27P | g.chr11:100880259C>T |
| TRPM2 | CCDS13710.1 | Br27P | g.chr21:44635733C>T |
| TRPM3 | CCDS6634.1 | Br10P | g.chr9:70447878G>C |
| TRPM4 | NM_017636 | Br03X | g.chr19:54363651C>T (HOMOZYGOUS) |
| TRPM5 | NM_014555 | Br29P | g.chr11:2382782G>A |
| TRPM6 | CCDS6647.1 | Br27P | g.chr9:74607488C>T |
| TRPM7 | NM_017672 | Br27P | g.chr15:48662577G>A |
| TRPV5 | CCDS5875.1 | Br15X | g.chr7:142139519G>A |
| TRPV5 | CCDS5875.1 | Br14X | g.chr7:142139507G>A |
| TRRAP | CCDS5659.1 | Br27P | g.chr7:98232807C>T |
| TSAP6 | CCDS2125.1 | Br27P | g.chr2:119728523G>A |
| TSAP6 | CCDS2125.1 | Br20P | g.chr2:119736998G>A |
| TSC2 | CCDS10458.1 | BR27P | g.chr16:2046664G>A |
| TSCOT | CCDS6786.1 | Br27P | g.chr9:112732030G>A |
| TSGA10 | CCDS2037.1 | Br27P | g.chr2:99110332A>C |
| TC12T | CCDS8360.1 | Br27P | g.chr11:112720256C>T |

FIG. 10
CONTINUED

| | | |
|---|---|---|
| c.158G>A | p.W53X | NONSENSE |
| c.527G>T | p.C176F | MISSENSE |
| c.586C>T | p.R196X | NONSENSE |
| c.590T>A | p.V197E | MISSENSE |
| c.617delT | fs | INDEL |
| c.626_627delGA | fs | INDEL |
| c.733G>A | p.G245S | MISSENSE |
| c.734G>A | p.G245D | MISSENSE |
| c.742C>T | p.R248W | MISSENSE |
| c.817C>T | p.R273C | MISSENSE |
| c.818G>A | p.R273H | MISSENSE |
| c.844C>T | p.R282W | MISSENSE |
| c.1045delG | fs | INDEL |
| c.1113G>A | p.G371G | SYNONYMOUS |
| IVS4-1G>A | SPLICE SITE | SPLICE SITE |
| c.453G>A | p.P151P | SYNONYMOUS |
| c.837G>A | p.S279S | SYNONYMOUS |
| c.272C>G | p.P91R | MISSENSE |
| c.226G>A | p.V76I | MISSENSE |
| c.306G>A | p.T102T | SYNONYMOUS |
| c.620C>T | p.P207L | MISSENSE |
| c.638G>A | p.R213H | MISSENSE |
| c.1353C>G | p.S451R | MISSENSE |
| c.2259G>A | p.G753G | SYNONYMOUS |
| c.683G>A | p.R228H | MISSENSE |
| c.1066C>T | p.P356S | MISSENSE |
| c.1442T>C | p.V481A | MISSENSE |
| c.469_470insCCC | p.A156_L157insP | INDEL |
| c.1165C>T | p.P389S | MISSENSE |
| c.522A>G | p.K174K | SYNONYMOUS |
| c.1402C>T | p.L468F | MISSENSE |
| c.1153G>A | p.V385I | MISSENSE |
| c.1307G>A | p.G436E | MISSENSE |
| c.858C>A | p.I286I | SYNONYMOUS |
| c.651C>T | p.S217S | SYNONYMOUS |
| c.1591C>T | p.L531L | SYNONYMOUS |
| c.2271G>C | p.W757C | MISSENSE |
| c.642C>T | p.R214R | SYNONYMOUS |
| c.3459G>A | p.W1153X | NONSENSE |
| c.3653C>T | p.T1218I | MISSENSE |
| c.4555G>A | p.V1519I | MISSENSE |
| c.1064G>A | p.R355H | MISSENSE |
| c.1076G>A | p.R359H | MISSENSE |
| c.9595C>T | p.P3199S | MISSENSE |
| c.1054G>A | p.E352K | MISSENSE |
| c.1321G>A | p.V441I | MISSENSE |
| c.667G>A | p.D223N | MISSENSE |
| c.487G>A | p.G163S | MISSENSE |
| c.1493A>C | p.Q498P | MISSENSE |
| c.1038C>T | p.A346A | SYNONYMOUS |

FIG. 10
CONTINUED

| | | | |
|---|---|---|---|
| TTC18 | CCDS7324.1 | Br27P | g.chr10:74739980G>A |
| TTC6 | NM_001007795 | Br15X | g.chr14:37335842G>T |
| TTLL2 | CCDS5301.1 | Br27P | g.chr6:167724715G>A |
| TTLL5 | NM_015072 | Br16X | g.chr14:75199303G>A |
| TTN | NM_133378 | Br15X | g.chr2:179417362G>A |
| TTN | NM_133378 | Br27P | g.chr2:179413114G>A |
| TTN | NM_133378 | Br27P | g.chr2:179314846G>A |
| TTN | NM_133432 | Br07x | g.chr2:179259759G>T |
| TTN | NM_133432 | Br27P | g.chr2:179258095C>T |
| TUBGCP3 | CCDS9525.1 | Br05X | g.chr13:112248141A>G |
| TUBGCP6 | CCDS14087.1 | Br27P | g.chr22:48959592C>A |
| TUBGCP6 | CCDS14087.1 | Br27P | g.chr22:48959587T>G |
| TULP1 | CCDS4807.1 | Br27P | g.chr6:355586617G>A |
| TXNDC3 | CCDS5452.1 | Br20P | g.chr7:37674978C>T |
| TYR | CCDS8284.1 | Br03X | g.chr11:88551006G>A |
| UBAP2L | CCDS1063.1 | Br27P | g.chr1:151020282G>A |
| UBE2G2 | CCDS13714.1 | Br27P | g.chr21:45032421C>T |
| UCHL1 | CCDS3462.1 | Br27P | g.chr4:41103715G>A |
| UGCGL2 | CCDS9480.1 | Br27P | g.chr13:95473926C>T |
| UGDH | CCDS3455.1 | Br23X | g.chr4:39328607T>C |
| UGT1A6 | CCDS2510.1 | Br02X | g.chr2:234451438G>T |
| ULK1 | CCDS9274.1 | Br27P | g.chr12:131058307G>A |
| UNQ2446 | CCDS10850.1 | Br04X | g.chr16:66477589C>T |
| UNQ3030 | CCDS3319.1 | Br17X | g.chr3:197875921C>T |
| UNQ689 | CCDS3542.1 | Br13X | g.chr4:71571406G>T |
| UPK3B | CCDS5588.1 | Br12P | g.chr7:75784626delG |
| URB1 | ENST00000270201 | Br13X | g.chr21:32660798C>T |
| USH2A | CCDS1516.1 | Br20P | g.chr1:212761551G>T |
| USP11 | CCDS14277.1 | Br27P | g.chrX:46860526G>A |
| USP26 | CCDS14635.1 | Br27P | g.chrX:131886308dupT |
| USP8 | CCDS10137.1 | Br27P | g.chr15:48520970C>T |
| VANGL1 | CCDS883.1 | Br27P | g.chr1:115918753C>T |
| VCAM1 | CCDS773.1 | Br27P | g.chr1:100906938G>A |
| VCIP135 | CCDS6192.1 | Br27P | g.chr8:67709358G>A |
| VCL | CCDS7340.1 | Br27P | g.chr10:75524051C>T |
| VDP | NM_003715 | Br27P | g.chr4:77065503C>T |
| VDR | CCDS8757.1 | Br27P | g.chr12:46524945C>T |
| VGCNL1 | CCDS9498.1 | Br27P | g.chr13:100557861G>A |
| VGLL2 | CCDS5115.1 | Br17X | 98780delGGCGCCCGGCCCGCCTCGCAA |
| VIPR2 | CCDS5950.1 | Br27P | g.chr7:158329069G>A |
| VMD2 | NM_004183 | Br27P | g.chr11:61482304C>T |
| VN2R1P | ENST00000312652 | Br27P | g.chr3:157237662C>T |
| VPS11 | NM_021729 | Br02X | g.chr11:118445239A>C |
| VPS13A | CCDS6655.1 | Br27P | g.chr9:77195897G>A |
| VPS24 | NM_001005753 | Br27P | g.chr2:86644694C>T |
| VPS41 | CCDS5457.1 | Br27P | g.chr7:38565112G>A |
| VPS45A | CCDS944.1 | Br27P | g.chr1:146862067G>A |
| VSIG2 | CCDS8452.1 | Br27P | .chr11:124124879_124124873delAGCCAG |
| VWF | CCDS8539.1 | Br26X | g.chr12:5929291C>T |
| WBSCR17 | CCDS5540.1 | Br27P | g.chr7:70480944C>T |

FIG. 10
CONTINUED

| | | |
|---|---|---|
| c.1408G>A | p.E470K | MISSENSE |
| c.161G>T | p.R54I | MISSENSE |
| c.916G>A | p.G306R | MISSENSE |
| c.58G>A | p.E20K | MISSENSE |
| c.16504G>A | p.A5502T | MISSENSE |
| c.18286G>A | p.V6096I | MISSENSE |
| c.36963G>A | p.G12321G | SYNONYMOUS |
| c.49787G>T | p.G16596V | MISSENSE |
| c.51451C>T | p.P17151S | MISSENSE |
| c.1208A>G | p.Y403C | MISSENSE |
| c.4818C>A | p.Y1606X | NONSENSE |
| IVS21+2T>G | SPLICE SITE | SPLICE SITE |
| c.498G>A | p.R166R | SYNONYMOUS |
| c.379C>T | p.R127X | NONSENSE |
| c.237G>A | p.S79S | SYNONYMOUS |
| c.422G>A | p.G141E | MISSENSE |
| c.61C>T | p.P21S | MISSENSE |
| c.298G>A | p.A100T | MISSENSE |
| c.330C>T | p.F110F | SYNONYMOUS |
| c.1259T>C | p.F420S | MISSENSE |
| c.505G>T | p.V169L | MISSENSE |
| IVS5+1G>A | SPLICE SITE | SPLICE SITE |
| c.424C>T | p.L142F | MISSENSE |
| c.1097C>T | p.T366M | MISSENSE |
| c.262G>T | p.G88W | MISSENSE |
| c.6delG | fs | INDEL |
| c.1266C>T | p.N422N | SYNONYMOUS |
| c.3624G>T | p.W1208C | MISSENSE |
| c.2164G>A | p.V722M | MISSENSE |
| c.1461dupT | fs | INDEL |
| c.237C>T | p.F79F | SYNONYMOUS |
| c.634C>T | p.R212W | MISSENSE |
| c.1183G>A | p.G395R | MISSENSE |
| c.3601G>A | p.E1201K | MISSENSE |
| c.1369C>T | p.P457S | MISSENSE |
| c.965C>T | p.A322V | MISSENSE |
| c.1135C>T | p.L379F | MISSENSE |
| c.2557G>A | p.V853M | MISSENSE |
| 6_773delGGCGCCCGGCCCGCCTCGCAACCGC | fs | INDEL |
| c.598G>A | p.V200M | MISSENSE |
| c.825C>T | p.V275V | SYNONYMOUS |
| c.1753C>T | p.P585S | MISSENSE |
| c.310A>C | p.K104Q | MISSENSE |
| c.7400G>A | p.G2467D | MISSENSE |
| c.362C>T | p.A121V | MISSENSE |
| c.1830G>A | p.Q610Q | SYNONYMOUS |
| c.370G>A | p.E124K | MISSENSE |
| c.521_527delAGCCAGT | fs | INDEL |
| c.8175C>T | p.N2725N | SYNONYMOUS |
| c.986C>T | p.S329L | MISSENSE |

FIG. 10
CONTINUED

| | | | |
|---|---|---|---|
| WBSCR27 | CCDS5561.1 | Br27P | g.chr7:72700151C>T |
| WDFY3 | CCDS3609.1 | Br27P | g.chr4:86099881C>T |
| WDR21 | CCDS9809.1 | Br27P | g.chr14:72490871C>T |
| WDR22 | NM_003861 | Br04X | g.chr14:68689345G>A |
| WDR24 | CCDS10420.1 | Br06x | g.chr16:677287C>T |
| WDR27 | NM_182552 | Br27P | g.chr6:169675358G>A |
| WDR32 | CCDS6613.1 | Br27P | g.chr9:37851206C>T |
| WDR34 | CCDS6906.1 | Br27P | g.chr9:128475704C>T |
| WDR34 | CCDS6906.1 | Br27P | g.chr9:128478821G>A |
| WDR42B | ENST00000329763 | Br14X | g.chrX:27525350T>A (HOMOZYGOUS) |
| WDR52 | CCDS2972.1 | Br27P | g.chr3:114580980G>A |
| WDR6 | CCDS2782.1 | Br27P | g.chr3:49025141C>T |
| WDR70 | NM_018034 | Br27P | g.chr5:37432400G>A |
| WDTC1 | CCDS296.1 | Br27P | g.chr1:27308633C>T |
| WEE1 | CCDS7800.1 | Br27P | g.chr11:9554199G>A |
| WFS1 | CCDS3386.1 | Br27P | g.chr4:6406941G>A |
| WFS1 | CCDS3386.1 | Br27P | g.chr4:6411108G>A |
| WNK1 | CCDS8506.1 | Br27P | g.chr12:866660G>A |
| WNK2 | CCDS6704.1 | Br06X | g.chr9:93109685G>A |
| WNT9A | NM_003395 | Br27P | g.chr1:224419937C>T |
| XAB2 | NM_020196 | Br04X | g.chr19:7595305C>A |
| XDH | CCDS1775.1 | Br04X | g.chr2:31535799C>A |
| XPO1 | NM_003400 | Br27P | g.chr2:61632778G>A |
| XPO7 | NM_015024 | Br23X | g.chr8:21896149G>A |
| XR_016172.1 | ENST00000355015 | Br17X | g.chr11:1145657C>T |
| XR_017335.1 | ENST00000314295 | Br03X | g.chr5:79663421C>T |
| YN004_HUMAN | ENST00000281581 | Br27P | g.chr14:59104832C>T |
| YTHDC2 | CCDS4113.1 | Br27P | g.chr5:112896581C>T |
| YWHAH | CCDS13901.1 | Br14X | g.chr22:30676761C>T |
| ZAN | NM_173059 | Br27P | g.chr7:100010258T>A |
| ZAN | NM_173059 | Br27P | g.chr7:100034691G>A |
| ZBTB16 | CCDS8367.1 | Br27P | g.chr11:113439645C>T |
| ZBTB24 | NM_014797 | Br27P | g.chr6:109893955C>T |
| ZBTB4 | CCDS11107.1 | Br27P | g.chr17:7306183C>T |
| ZBTB9 | NM_006772 | Br27P | g.chr6:33513799G>A |
| ZC3H6 | NM_198581 | Br11P | g.chr2:112804980G>T |
| ZFPM1 | NM_153813 | Br05X | g.chr16:87079931G>T |
| ZFYVE9 | CCDS563.1 | Br20P | g.chr1:52415353C>T |
| ZFYVE9 | CCDS563.1 | Br27P | g.chr1:52416058G>A |
| ZIC1 | CCDS3136.1 | Br08x | g.chr3:148610654G>A |
| ZIK1 | NM_001010879 | Br20P | g.chr19:62794168A>G |
| ZMAT4 | NM_024645 | Br26X | g.chr8:40802277G>A |
| ZNF10 | CCDS9283.1 | Br27P | g.chr12:132343082G>A |
| ZNF160 | CCDS12859.1 | Br07X | g.chr19:58265291C>T |
| ZNF17 | NM_006959 | Br27P | g.chr19:62623041G>A |
| ZNF18 | NM_144680 | Br27P | g.chr17:11822490C>T |
| ZNF183L1 | CCDS9486.1 | Br27P | g.chr13:97626966C>T |
| ZNF189 | CCDS6754.1 | Br27P | g.chr9:101251158G>A |
| ZNF25 | CCDS7195.1 | Br03X | g.chr10:38285976A>G |
| ZNF286 | CCDS11172.1 | Br27P | g.chr17:15552269C>T |

FIG. 10 CONTINUED

| | | |
|---|---|---|
| c.152C>T | p.P51L | MISSENSE |
| c.1126C>T | p.H376Y | MISSENSE |
| c.932C>T | p.T311I | MISSENSE |
| c.104G>A | p.R35K | MISSENSE |
| c.790C>T | p.R264C | MISSENSE |
| c.2649G>A | p.L883L | SYNONYMOUS |
| c.940C>T | p.L314L | SYNONYMOUS |
| c.1133C>T | p.T378I | MISSENSE |
| c.124G>A | p.A42T | MISSENSE |
| c.552T>A | p.H184Q | MISSENSE |
| c.2161G>A | p.E721K | MISSENSE |
| c.1170C>T | p.F390F | SYNONYMOUS |
| c.463G>A | p.E155K | MISSENSE |
| c.1118C>T | p.A373V | MISSENSE |
| c.765G>A | p.K255K | SYNONYMOUS |
| c.282G>A | p.R94R | SYNONYMOUS |
| c.573G>A | p.K191K | SYNONYMOUS |
| c.5293G>A | p.G1765S | MISSENSE |
| c.3799G>A | p.A1267T | MISSENSE |
| c.114C>T | p.P38P | SYNONYMOUS |
| c.849C>A | p.I283I | SYNONYMOUS |
| c.244C>A | p.H82N | MISSENSE |
| c.1147G>A | p.E383K | MISSENSE |
| c.1157G>A | p.R386Q | MISSENSE |
| c.345C>T | p.Y115Y | SYNONYMOUS |
| c.627C>T | p.Y209Y | SYNONYMOUS |
| c.375C>T | p.R125R | SYNONYMOUS |
| c.782C>T | p.A261V | MISSENSE |
| c.169C>T | p.R57X | NONSENSE |
| c.5014T>A | p.Y1672N | MISSENSE |
| c.7725G>A | p.W2575X | NONSENSE |
| c.413C>T | p.A138V | MISSENSE |
| c.1886C>T | p.P629L | MISSENSE |
| c.2842C>T | p.L948F | MISSENSE |
| c.1094G>A | p.G365E | MISSENSE |
| c.2254G>T | p.G752X | NONSENSE |
| c.124G>T | p.A42S | MISSENSE |
| c.243C>T | p.T81T | SYNONYMOUS |
| c.948G>A | p.G316G | SYNONYMOUS |
| c.57G>A | p.A19A | SYNONYMOUS |
| c.1177A>G | p.T393A | MISSENSE |
| c.76G>A | p.E26K | MISSENSE |
| c.900G>A | p.K300K | SYNONYMOUS |
| c.308C>T | p.P103L | MISSENSE |
| c.369G>A | p.E123E | SYNONYMOUS |
| c.1159C>T | p.L387F | MISSENSE |
| c.526C>T | p.P176S | MISSENSE |
| c.1553G>A | p.G518E | MISSENSE |
| c.216A>G | p.E72E | SYNONYMOUS |
| c.317C>T | p.P106L | MISSENSE |

FIG. 10
CONTINUED

| | | | |
|---|---|---|---|
| ZNF294 | NM_015565 | Br27P | g.chr21:29238660C>T |
| ZNF295 | CCDS13678.1 | Br26X | g.chr21:42286277G>A |
| ZNF30 | NM_194325 | Br27P | g.chr19:40126094C>T |
| ZNF31 | NM_145238 | Br27P | g.chr1:33629817G>A |
| ZNF313 | NM_018683 | Br27P | g.chr20:47986403G>A |
| ZNF318 | CCDS4895.1 | Br27P | g.chr6:43413696_43413694delAAA |
| ZNF333 | CCDS12316.1 | Br27P | g.chr19:146880011G>A |
| ZNF339 | CCDS13132.1 | Br29P | g.chr20:17953443C>T |
| ZNF343 | CCDS13028.1 | Br27P | g.chr20:2412002C>T |
| ZNF358 | NM_018083 | Br27P | g.chr19:7491396G>A |
| ZNF366 | CCDS4015.1 | Br05X | g.chr5:71792658G>A |
| ZNF406 | NM_001029939 | Br27P | g.chr8:135684102G>A |
| NF440L | NM_001012753 | Br14X | g.chr19:11950903G>A(HOMOZYGOUS) |
| ZNF473 | NM_015428 | Br27P | g.chr19:55234262C>T |
| ZNF487 | ENST00000315429 | Br05x | g.chr7:4939760G>A |
| ZNF496 | CCDS1631.1 | Br27P | g.chr1:243790270G>A |
| ZNF497 | CCDS12977.1 | Br03x | g.chr19:63559516A>T |
| ZNF497 | CCDS12977.1 | BR02X | g.chr19:63559982G>A |
| ZNF507 | NM_014910 | Br03X | g.chr19:37537093G>C |
| ZNF545 | CCDS12493.1 | Br04X | g.chr19:41575660C>T |
| ZNF547 | NM_173631 | Br27P | g.chr19:62580926C>T |
| ZNF558 | CCDS12208.1 | Br27P | g.chr19:8783719G>A |
| NF585A | CCDS12499.1 | Br27P | g.chr19:42335256G>A |
| ZNF628 | NM_033113 | Br27P | g.chr19:60687304C>T |
| ZNF67 | ENST00000323012 | Br20P | g.chrX:66377878T>G |
| ZNF79 | CCDS6871.1 | Br27P | g.chr9:127287027G>A |
| ZP2 | CCDS10596.1 | Br27P | g.chr16:21118396G>A |
| ZSCAN2 | CCDS10329.1 | Br15X | g.chr15:82966044C>G |
| ZSWIM4 | NM_023072 | Br04X | g.chr19:13797479C>T |
| ZSWIM4 | NM_023072 | Br27P | g.chr19:13771646C>T |
| ZW10 | CCDS8363.1 | Br27P | g.chr11:113112631C>T |

GENOMIC POSITIONS ARE COORDINATES IN THE MAY 2004, HG17 35.1 UCSC SANTA CRUZ RELEASE OF THE HUMAN GENOME. GENOMIC COORDINATES AND SEQUENCES OF MUTATIONS ARE ON THE CODING STRAND. ARE HETEROZYGOUS UNLESS MARKED AS HOMOZYGOUS. g., GENOMIC SEQUENCE; c., cDNA SEQUENCE; p., PROTEIN SEQUENCE; del, DELETION; dup, DUPLICATION; ins, INSERTION.

FIG. 10
CONTINUED

| | | |
|---|---|---|
| c.3898C>T | p.P1300S | MISSENSE |
| c.997G>A | p.G333S | MISSENSE |
| c.141C>T | p.T47T | SYNONYMOUS |
| c.2582G>A | p.G861E | MISSENSE |
| c.47G>A | p.G16E | MISSENSE |
| c.5478_5480delAAA | p.K1827del | INDEL |
| c.688G>A | p.D230N | MISSENSE |
| c.665C>T | p.T222M | MISSENSE |
| c.1605C>T | p.T535T | SYNONYMOUS |
| c.1007G>A | p.G336D | MISSENSE |
| c.422G>A | p.S141N | MISSENSE |
| c.1006G>A | p.V336M | MISSENSE |
| c.1173G>A | p.A391A | SYNONYMOUS |
| c.42C>T | p.D14D | SYNONYMOUS |
| c.171G>A | p.L57L | SYNONYMOUS |
| c.1356G>A | p.G452G | SYNONYMOUS |
| c.1298A>T | p.Q433L | MISSENSE |
| c.832G>A | p.D278N | MISSENSE |
| c.1517G>C | p.R506T | MISSENSE |
| c.1422C>T | p.G474G | SYNONYMOUS |
| c.770C>T | p.T257I | MISSENSE |
| c.447G>A | p.V149V | SYNONYMOUS |
| c.1220G>A | p.G407E | MISSENSE |
| c.2899C>T | p.R967C | MISSENSE |
| c.1111T>G | p.Y371D | MISSENSE |
| c.1494G>A | p.E498E | SYNONYMOUS |
| c.1923G>A | p.R641R | SYNONYMOUS |
| c.1611C>G | p.S537R | MISSENSE |
| c.1980C>T | p.A660A | SYNONYMOUS |
| c.266C>T | p.P89L | MISSENSE |
| c.2140C>T | p.P714S | MISSENSE |

FIG. 10
CONTINUED

| LS-MUT SCORES |
| --- |
| 0.802 |
| 0.892 |
| - |
| - |
| 0.688 |
| - |
| - |
| - |
| - |
| - |
| 0.876 |
| - |
| - |
| 0.594 |
| - |
| - |
| 0.688 |
| - |
| 0.866 |
| - |
| - |
| - |
| - |
| 0.892 |
| - |
| - |
| - |
| - |
| - |
| - |
| - |
| - |
| 0.842 |
| - |
| - |
| - |
| - |
| - |
| - |
| - |

```
           -
        0.748
           -
           -
           -
           -
           -
        0.916
           -
           -
        0.982
           -
           -
           -
           -
           -
        0.894
        0.932
        0.788
           -
           -
           -
           -
           -
           -
           -
        0.962
           -
           -
           -
        ─────────
        ALL CHANGES
```

FIG. 10
CONTINUED

TABLE S4. SOMATIC MUTATIONS IDENTIFIED IN GBM PREVALENCE SCREEN

| GENE | TRANSCRIPT ACCESSION ID | TUMOR | NUCLEOTIDE (GENOMIC)# | NUCLEOTIDE (cDNA)§ | AMINO ACID (PROTEIN)¶ | MUTATION TYPE |
|---|---|---|---|---|---|---|
| ARNT2 | NM_014862 | Br132X | g.chr15:78642607T>A | c.1288T>A | p.Y430N | MISSENSE |
| C21orf29 | CCDS13712.1 | Br248T | g.chr21:44812132G>A | c.268G>A | p.V90I | MISSENSE |
| DSG4 | CCDS11897.1 | Br148X | g.chr18:27237386G>T | c.1427G>T | p.G476V | MISSENSE |
| DSG4 | CCDS11897.1 | Br148X | g.chr18:27237484C>T | c.1525C>T | p.P509S | MISSENSE |
| DSG4 | CCDS11897.1 | Br116X | g.chr18:27237528G>A | c.1569G>A | p.P523P | SYNONYMOUS |
| EGFR | CCDS5514.1 | Br112X | g.chr7:54994483C>T | c.664C>T | p.R222C | MISSENSE |
| EGFR | CCDS5514.1 | Br124X | g.chr7:54996031C>T | c.866C>T | p.A289V | MISSENSE |
| EGFR | CCDS5514.1 | Br140X | g.chr7:54996031C>T | c.866C>T | p.A289V | MISSENSE |
| EGFR | CCDS5514.1 | Br306T | g.chr7:54996031C>T | c.866C>T | p.A289V | MISSENSE |
| EGFR | CCDS5514.1 | Br116X | g.chr7:54997745G>A | c.903G>A | p.V301V | SYNONYMOUS |
| EGFR | CCDS5514.1 | Br229T | g.chr7:54997773T>A | c.931T>A | p.C311S | MISSENSE |
| EGFR | CCDS5514.1 | Br215T | g.chr7:54997813G>T | c.971G>T | p.R324L | MISSENSE |
| EGFR | CCDS5514.1 | Br213T | g.chr7:55007252G>T | c.1793G>T | p.G598V | MISSENSE |
| EGFR | CCDS5514.1 | Br230T | g.chr7:55007252G>T | c.1793G>T | p.G598V | MISSENSE |
| EGFR | CCDS5514.1 | Br001X | g.chr7:55007263G>C (HOMOZYGOUS) | c.1804G>C | p.E602Q | MISSENSE |
| EGFR | CCDS5515.1 | Br143X | g.chr7:55012285A>T | c.1957A>T | p.S653C | MISSENSE |
| EGFR | CCDS5515.1 | Br143X | g.chr7:55012293C>T | c.1965C>T | p.S655S | SYNONYMOUS |
| EGFR | CCDS5514.1 | Br247T | g.chr7:55013103G>A | c.1907G>A | p.C636Y | MISSENSE |
| EGFR | CCDS5514.1 | Br302T | g.chr7:55042273C>G | c.2904C>G | p.F968L | MISSENSE |
| FRMPD4 | NM_014728 | Br230T | g.chrX:12276556C>T (HOMOZYGOUS) | c.142C>T | p.R48X | NONSENSE |
| FRMPD4 | NM_014728 | Br148X | g.chrX:12461363G>A | c.573G>A | p.S191S | SYNONYMOUS |
| FRMPD4 | NM_014728 | Br104X | g.chrX:12472154G>A | c.857G>A | p.R286Q | MISSENSE |
| IDH1 | CCDS2381.1 | Br104X | g.chr2:208938619C>A | c.394C>A | p.R132S | MISSENSE |
| IDH1 | CCDS2381.1 | Br129X | g.chr2:208938619C>A | c.394C>A | p.R132S | MISSENSE |
| IDH1 | CCDS2381.1 | Br106X | g.chr2:208938618G>A | c.395G>A | p.R132H | MISSENSE |
| IDH1 | CCDS2381.1 | Br122X | g.chr2:208938618G>A | c.395G>A | p.R132H | MISSENSE |
| IDH1 | CCDS2381.1 | Br123X | g.chr2:208938618G>A | c.395G>A | p.R132H | MISSENSE |
| IDH1 | CCDS2381.1 | Br211T | g.chr2:208938618G>A | c.395G>A | p.R132H | MISSENSE |
| IDH1 | CCDS2381.1 | Br237T | g.chr2:208938618G>A | c.395G>A | p.R132H | MISSENSE |

FIG. 10
CONTINUED

| Gene | Accession | Sample | Genomic | cDNA | Protein | Type |
|---|---|---|---|---|---|---|
| IRX6 | NM_024335 | Br112X | g.chr16:53918999G>C | c.414G>C | p.R138R | SYNONYMOUS |
| IRX6 | NM_024335 | Br306T | g.chr16:53920595G>C | c.1204G>C | p.E402Q | MISSENSE |
| MYO1B | CCDS2311.1 | Br103X | g.chr2:192071732C>T | c.1224C>T | p.N408N | SYNONYMOUS |
| MYO1B | CCDS2311.1 | Br118X | g.chr2:192082380G>A | c.2023G>A | p.V675M | MISSENSE |
| MYO1B | CCDS2311.1 | Br232T | g.chr2:192099399C>T | c.2581C>T | p.H861Y | MISSENSE |
| NF1 | CCDS11264.1 | Br132X | g.chr17:26532606G>T | c.627G>T | p.Q209H | MISSENSE |
| NF1 | CCDS11264.1 | Br132X | g.chr17:26532608T>A | c.629T>A | p.L210X | NONSENSE |
| NF1 | CCDS11264.1 | Br232T | g.chr17:26532635T>C | IVS6+2T>C | SPLICE SITE | SPLICE SITE |
| NF1 | CCDS11264.1 | Br018X | g.chr17:26583315A>T (HOMOZYGOUS) | c.3296A>T | p.K1099I | MISSENSE |
| NF1 | CCDS11264.1 | Br149X | g.chr17:26583948C>A (HOMOZYGOUS) | c.3419C>A | p.S1140X | NONSENSE |
| NF1 | CCDS11264.1 | Br21PT | g.chr17:26678814_26678832delCACCAGGAGTGTGAAGCCA | c.5377_5395delCACCAGGAGTGTGAAGCCA | fs | INDEL |
| NF1 | CCDS11264.1 | Br139X | g.chr17:26678895C>T | c.5458C>T | | NONSENSE |
| NF1 | CCDS11264.1 | Br21PT | g.chr17:26681564_26681567delAGTA | c.5671_5674delAGTA | fs | INDEL |
| NF1 | CCDS11264.1 | Br303T | g.chr17:26686071C>T | c.5839C>T | p.R1947X | NONSENSE |
| NF1 | CCDS11264.1 | Br232T | g.chr17:26688661_26688662delGA | c.6514_6515delGA | fs | INDEL |
| NF1 | CCDS11264.1 | Br113X | g.chr17:26689880_26689883delTTAC | 6789_6792delTTAC | fs | INDEL |
| NF1 | CCDS11264.1 | Br121X | g.chr17:26689880_26689883delTTAC | 6789_6792delTTAC | fs | INDEL |
| NF1 | CCDS11264.1 | Br22PT | g.chr17:26689880_26689883delTTAC | 6789_6792delTTAC | fs | INDEL |
| NF1 | CCDS11264.1 | Br227T | g.chr17:26916648G>C | IVS45-1G>C | SPLICE SITE | SPLICE SITE |
| NF1 | CCDS11264.1 | Br107X | g.chr17:26708187_26708188insT | 7759_7760insT | fs | INDEL |
| NF1 | CCDS11264.1 | Br141X | g.chr17:26709710_26709711delAG | 7994_7995delAG | fs | INDEL |
| NGEF | CCDS2500.1 | Br232T | g.chr2:233665017T>C | c.89T>C | p.V30A | MISSENSE |
| PIK3CA | NM_006218 | Br130X | hr3:180399339_180399371delTGAACTGTGGGCATCCACTTGATGCCCC | A4_56delTGAACTGTGGGCATCCACTTGATGCCCCA | INDEL | INDEL |
| PIK3CA | NM_006218 | Br118X | g.chr3:180399427C>G | c.112C>G | p.R38G | MISSENSE |
| PIK3CA | NM_006218 | Br238T | g.chr3:180399538C>G | c.223C>G | p.Q75E | MISSENSE |
| PIK3CA | NM_006218 | Br001X | g.chr3:180399638G>A | c.323G>A | p.R108H | MISSENSE |
| PIK3CA | NM_006218 | Br401X | g.chr3:180405065T>C | c.1132T>C | p.C378R | MISSENSE |
| PIK3CA | NM_006218 | Br21PT | g.chr3:180434755T>C | c.3128T>C | p.M1043T | MISSENSE |
| PIK3CA | NM_006218 | Br122X | g.chr3:180434787A>G | c.3140A>G | p.H1047R | MISSENSE |
| PIK3CA | NM_006218 | Br129X | g.chr3:180434787A>G | c.3140A>G | p.H1047R | MISSENSE |
| PIK3R1 | CCDS3993.1 | Br140X | g.chr5:67624894G>A | c.1126G>A | p.G376R | MISSENSE |

FIG. 10 CONTINUED

| Gene | Transcript | Sample | Genomic | Coding | Protein | Type |
|---|---|---|---|---|---|---|
| PIK3R1 | CCDS3993.1 | Br223T | g.chr5:67624494G>A | c.1126G>A | p.G376R | MISSENSE |
| PIK3R1 | CCDS3993.1 | Br102X | g.chr5:67625368A>G | c.1375A>G | p.K459E | MISSENSE |
| PIK3R1 | CCDS3993.1 | Br103X | g.chr5:67625383G>C | c.1390G>C | p.D464H | MISSENSE |
| PIK3R1 | CCDS3993.1 | Br019X | g.chr5:67626872T>C | c.1709T>C | p.L570P | MISSENSE |
| PIK3R1 | CCDS85933.1 | Br107X | g.chr5:67627003G>C | IVS12-1G>C | SPLICE SITE | SPLICE SITE |
| PTEN | NM_000314 | Br128X | g.chr10:89614223A>T | c.17A>T | p.K6I | MISSENSE |
| PTEN | NM_000314 | Br141X | g.chr10:89614260_89614261delGG | 54_55delGG | fs | INDEL |
| PTEN | NM_000314 | Br301T | g.chr10:89614281G>C | c.75G>C | p.L25F | MISSENSE |
| PTEN | NM_000314 | Br243T | g.chr10:89643840_89643842delTAG | c.158_160delTAG | fs | INDEL |
| PTEN | NM_000314 | Br223T | g.chr10:89643847delG | IVS2+1G>T | SPLICE SITE | SPLICE SITE |
| PTEN | NM_000314 | Br248T | g.chr10:89643847delG | IVS2+1delG | SPLICE SITE | INDEL |
| PTEN | NM_000314 | Br215T | g.chr10:89675298A>T | IVS3+4A>T | SPLICE SITE | SPLICE SITE |
| PTEN | NM_000314 | Br148X | g.chr10:89680827G>A | IVS4+1G>A | SPLICE SITE | SPLICE SITE |
| PTEN | NM_000314 | Br117X | g.chr10:89682759A>G | c.263A>G | p.Y88C | MISSENSE |
| PTEN | NM_000314 | Br227T | g.chr10:89682767G>T | c.271G>T | p.E91X | NONSENSE |
| PTEN | NM_000314 | Br245X | g.chr10:89682783C>T | c.287C>T | p.P96L | MISSENSE |
| PTEN | NM_000314 | Br136X | g.chr10:89682881G>T | c.355G>T | p.V119F | MISSENSE |
| PTEN | NM_000314 | Br217T | g.chr10:89682881G>T | c.385G>T | p.G129X | NONSENSE |
| PTEN | NM_000314 | Br203T | g.chr10:89682884C>G | c.388C>G | p.R130G | MISSENSE |
| PTEN | NM_000314 | Br134X | g.chr10:89682885C>C | c.389G>C | p.R130P | MISSENSE |
| PTEN | NM_000314 | Br22PT | g.chr10:89682957delT | 457delT | fs | INDEL |
| PTEN | NM_000314 | Br302T | g.chr10:89682957delT | 461delT | fs | INDEL |
| PTEN | NM_000314 | Br138X | g.chr10:89710779_89710782delTACT | c.950_953delTACT | fs | INDEL |
| PTEN | NM_000314 | Br145X | g.chr10:89710780_89710783delACTT | 951_954delACTT | fs | INDEL |
| PTEN | NM_000314 | Br019X | g.chr10:89710832C>T (HOMOZYGOUS) | c.1003C>T (HOMOZYGOUS) | p.R335X | NONSENSE |
| PTEN | NM_000314 | Br101X | g.chr10:89715023G>A | IVS8-1G>A | SPLICE SITE | SPLICE SITE |
| PTEN | NM_000314 | Br121X | g.chr10:89715130_89715133delGATA | c.1133_1136delGATA | fs | INDEL |
| PTEN | NM_000314 | Br111X | g.chr3:47779046G>A | c.225G>A | p.W75X | NONSENSE |
| PTEN | NM_000314 | Br126X | g.chr3:47814735G>A | IVS2-1G>A | SPLICE SITE | SPLICE SITE |
| RB1 | NM_000321 | Br149X | g.chr13:47849164delG | 1325delG | fs | INDEL |
| RB1 | NM_000321 | Br019X | g.chr13:47851744delG | 1346delG | fs | INDEL |
| RB1 | NM_000321 | Br131X | g.chr13:47935944A>C (HOMOZYGOUS) | c.2183A>G (HOMOZYGOUS) | p.Y728C | MISSENSE |
| RB1 | NM_000321 | Br232T | g.chr13:47937134G>A | IVS21-1G>A | SPLICE SITE | SPLICE SITE |
| SCN9A | NM_002977 | Br115X | g.chr2:166987916T>C | c.489T>C | p.Y163Y | SYNONYMOUS |
| SCN9A | NM_002977 | Br238T | g.chr2:166963030C>T | c.640C>T | p.R214X | NONSENSE |
| SCN9A | NM_002977 | Br403P | g.chr2:166915404A>G | c.3844A>G | p.R1282G | MISSENSE |
| TP53 | CCDS11118.1 | Br133X | g.chr17:7520031A>G | IVS2-2A>G | SPLICE SITE | SPLICE SITE |
| TP53 | CCDS11118.1 | Br133X | g.chr17:7520234C>G (HOMOZYGOUS) | c.178C>G | p.P60A | MISSENSE |
| TP53 | CCDS11118.1 | Br148X | g.chr17:7520233C>G | c.179C>G | p.P60R | MISSENSE |

FIG. 10
CONTINUED

| Gene | CCDS | Sample | Genomic Position | cDNA | Protein | Type |
|---|---|---|---|---|---|---|
| TP53 | CCDS11118.1 | Br211T | g.chr17:7520207delG (HOMOZYGOUS) | c.205delG | fs | INDEL |
| TP53 | CCDS11118.1 | Br237T | g.chr17:7520080T>C | c.332T>C | p.L111P | MISSENSE |
| TP53 | CCDS11118.1 | Br403P | g.chr17:7520037G>A | c.375G>A | p.T125T | SYNONYMOUS |
| TP53 | CCDS11118.1 | Br203T | g.chr17:7519275C>T | c.380C>T | p.S127F | MISSENSE |
| TP53 | CCDS11118.1 | Br237T | g.chr17:7519200C>T | c.455C>T | p.P152L | MISSENSE |
| TP53 | CCDS11118.1 | Br246T | g.chr17:7519200C>T | c.455C>T | p.P152L | MISSENSE |
| TP53 | CCDS11118.1 | Br232T | g.chr17:7519182G>A | c.473G>A | p.R158H | MISSENSE |
| TP53 | CCDS11118.1 | Br141X | g.chr17:7519147_7519141delACGGAGG | c.508_514delACGGAGG | fs | INDEL |
| TP53 | CCDS11118.1 | Br241T | g.chr17:7519131G>A | c.524G>A | p.R175H | MISSENSE |
| TP53 | CCDS11118.1 | Br123X | g.chr17:7519056delC | 569delC | fs | INDEL |
| TP53 | CCDS11118.1 | Br131X | g.chr17:7518988C>T | c.586C>T | p.R196X | NONSENSE |
| TP53 | CCDS11118.1 | Br113X | g.chr17:7518948_7518947delGA | 626_627delGA | fs | INDEL |
| TP53 | CCDS11118.1 | Br104X | g.chr17:7518305A>G (HOMOZYGOUS) | c.701A>G | p.Y234C | MISSENSE |
| TP53 | CCDS11118.1 | Br018X | g.chr17:7518273G>A | c.733G>A | p.G245S | MISSENSE |
| TP53 | CCDS11118.1 | Br143X | g.chr17:7518273G>A | c.733G>A | p.G245S | MISSENSE |
| TP53 | CCDS11118.1 | Br240T | g.chr17:7518273G>A | c.733G>A | p.G245S | MISSENSE |
| TP53 | CCDS11118.1 | Br303T | g.chr17:7518273G>A | c.733G>A | p.G245S | MISSENSE |
| TP53 | CCDS11118.1 | Br232T | g.chr17:7518264C>T | c.742C>T | p.R248W | MISSENSE |
| TP53 | CCDS11118.1 | Br233T | g.chr17:7518264C>T | c.742C>T | p.R248W | MISSENSE |
| TP53 | CCDS11118.1 | Br105X | g.chr17:7518263G>A | c.743G>A | p.R248Q | MISSENSE |
| TP53 | CCDS11118.1 | Br146X | g.chr17:7517864C>T | c.799C>T | p.R267W | MISSENSE |
| TP53 | CCDS11118.1 | Br109X | g.chr17:7517846C>T (HOMOZYGOUS) | c.817C>T | p.R273C | MISSENSE |
| TP53 | CCDS11118.1 | Br146X | g.chr17:7517845G>A | c.818G>A | p.R273H | MISSENSE |
| TP53 | CCDS11118.1 | Br115X | g.chr17:7517819C>T | c.844C>T | p.R282W | MISSENSE |
| TP53 | CCDS11118.1 | Br106X | g.chr17:7514737G>T (HOMOZYGOUS) | c.1015G>T | p.E339X | NONSENSE |

*GENOMIC POSITIONS ARE COORDINATES IN THE MAY 2004, HG17 35.1 UCSC SANTA CRUZ RELEASE OF THE HUMAN GENOME. GENOMIC COORDINATES AND SEQUENCES OF MUTATIONS ARE ON THE CODING STRAND. ALL CHANGES ARE HETEROZYGOUS UNLESS MARKED AS HOMOZYGOUS. g., GENOMIC SEQUENCE; c., cDNA SEQUENCE; p., PROTEIN SEQUENCE; del, DELETION; dup, DUPLICATION; INS, INSERTION.
§MUTATIONS IN NON-CODING SEQUENCES ARE ANNOTATED BY INTRON NUMBER PRECEDED BY "IVS", WITH POSITIVE NUMBERS STARTING FROM THE G OF THE GT SPLICE DONOR SITE AND NEGATIVE NUMBERS STARTING FROM THE G OF THE AG SPLICE ACCEPTOR SITE.
¶fs, FRAMESHIFT MUTATION; UTR, MUTATION IN 5' OR 3' UNTRANSLATED REGION; INDEL, IN FRAME INSERTION, DELETION OR DUPLICATION CHANGE AFFECTING MORE THAN A SINGLE CODON. NO MUTATIONS WERE IDENTIFIED IN 5 GENES THAT WERE ANALYZED IN THE PREVALENCE SCREEN (ASTN, KIAA0133, KIAA0774, SERPINA12, TRPV5).

FIG. 10
CONTINUED

TABLE S5. AMPLIFICATIONS DETECTED BY ILLUMINA ARRAYS

| SAMPLE | CHROMOSOME | LEFT BOUNDARY (bp) | RIGHT BOUNDARY (bp) | CANDIDATE TARGET OF AMPLIFICATION | CANDIDATE EVIDENCE* | OTHER GENES† |
|---|---|---|---|---|---|---|
| Br02X | 1 | 6,553,906 | 6,618,080 | PHF13 | | |
| Br02X | 1 | 6,637,977 | 6,652,336 | UNKNOWN | | |
| Br02X | 1 | 6,850,339 | 6,914,512 | UNKNOWN | | |
| Br02X | 1 | 7,159,397 | 7,164,110 | UNKNOWN | | |
| Br02X | 1 | 7,356,659 | 7,458,825 | UNKNOWN | | |
| Br02X | 1 | 7,475,206 | 7,578,989 | UNKNOWN | | |
| Br02X | 1 | 8,121,850 | 8,123,277 | UNKNOWN | | |
| Br03X | 1 | 37,961,327 | 37,961,374 | UNKNOWN | | |
| Br02X | 1 | 87,579,388 | 87,550,940 | UNKNOWN | | |
| Br02X | 1 | 94,246,433 | 94,246,484 | UNKNOWN | | |
| Br02X | 1 | 156,991,818 | 156,992,011 | UNKNOWN | | |
| Br07X | 1 | 199,264,981 | 199,292,305 | UNKNOWN | | |
| Br07X | 1 | 199,313,698 | 199,318,935 | UNKNOWN | | |
| Br05X | 1 | 202,698,859 | 203,429,680 | MDM4 | 1 | KLHL21, THAP3, ZBTB48 |
| Br06X | 1 | 242,284,342 | 242,287,212 | UNKNOWN | | |
| Br07X | 2 | 14,851,412 | 15,181,861 | UNKNOWN | | |
| Br07X | 2 | 15,198,595 | 16,235,845 | MYCN | 1 | CNTN2, LRRN2, NFASC, RBBP5, TMEM81 |
| Br02X | 2 | 20,688,139 | 20,688,199 | UNKNOWN | | |
| Br20P | 2 | 36,263,684 | 36,263,904 | UNKNOWN | | |
| Br20P | 2 | 118,777,060 | 118,778,863 | UNKNOWN | | |
| Br06X | 2 | 162,858,374 | 162,860,597 | UNKNOWN | | |
| Br25X | 2 | 166,230,991 | 166,231,208 | UNKNOWN | | |
| Br03X | 2 | 203,469,116 | 203,474,001 | UNKNOWN | | |
| Br02X | 2 | 219,141,517 | 219,141,633 | UNKNOWN | | |
| Br13X | 2 | 228,948,389 | 228,949,477 | UNKNOWN | | |
| Br03X | 3 | 101,817,778 | 101,926,422 | UNKNOWN | | DDX1, MYCNOS, NAG |
| Br03X | 3 | 102,096,686 | 102,100,370 | UNKNOWN | | |
| Br03X | 3 | 124,127,994 | 124,129,518 | UNKNOWN | | |
| Br03X | 3 | 125,527,639 | 125,531,454 | UNKNOWN | | |

FIG. 10 CONTINUED

| | | | | |
|---|---|---|---|---|
| B07X | 3 | 127,461,108 | 127,470,614 | UNKNOWN |
| B03X | 3 | 150,242,015 | 150,250,820 | UNKNOWN |
| B03X | 3 | 198,254,194 | 198,255,951 | UNKNOWN |
| B06X | 4 | 1,769,100 | 1,774,46 | UNKNOWN |
| B08X | 4 | 19,130,834 | 19,131,054 | UNKNOWN |
| B20P | 4 | 58,417,022 | 58,418,102 | UNKNOWN |
| B20P | 4 | 84,789,971 | 84,790,081 | UNKNOWN |
| B05X | 4 | 134,352,228 | 134,352,498 | UNKNOWN |
| B02X | 4 | 189,587,179 | 189,597,490 | UNKNOWN |
| B02X | 4 | 189,938,594 | 190,111,703 | UNKNOWN |
| B02X | 4 | 190,132,589 | 190,276,106 | UNKNOWN |
| B02X | 4 | 190,308,979 | 190,759,195 | UNKNOWN |
| B06X | 5 | 276,117 | 286,572 | UNKNOWN |
| B06X | 5 | 1,187,166 | 1,188,834 | UNKNOWN |
| B06X | 5 | 11,227,960 | 11,230,291 | UNKNOWN |
| B06X | 5 | 16,954,752 | 16,957,555 | UNKNOWN |
| B03X | 5 | 67,625,312 | 67,630,080 | UNKNOWN |
| B02X | 5 | 122,710,233 | 122,710,267 | UNKNOWN |
| B02X | 5 | 162,857,364 | 162,890,889 | MAT2B |
| B02X | 5 | 163,030,420 | 163,036,004 | UNKNOWN |
| B02X | 5 | 165,817,804 | 165,911,472 | UNKNOWN |
| B02X | 5 | 166,443,764 | 166,599,221 | UNKNOWN |
| B02X | 5 | 166,982,050 | 167,030,901 | UNKNOWN |
| B02X | 6 | 44,463,433 | 44,468,511 | UNKNOWN |
| B03X | 6 | 122,814,813 | 122,814,850 | UNKNOWN |
| B02X | 6 | 167,659,759 | 167,664,399 | UNKNOWN |
| B15X | 7 | 11,817,948 | 11,819,533 | UNKNOWN |
| B05X | 7 | 12,990,992 | 12,997,659 | UNKNOWN |
| B05X | 7 | 13,405,074 | 13,412,371 | UNKNOWN |
| B20P | 7 | 14,153,728 | 14,155,893 | UNKNOWN |
| B03X | 7 | 28,036,836 | 28,042,110 | UNKNOWN |
| B25X | 7 | 29,097,237 | 29,097,478 | UNKNOWN |
| B03X | 7 | 33,031,627 | 33,036,700 | UNKNOWN |
| B20P | 7 | 48,557,329 | 48,623,277 | UNKNOWN |

FIG. 10
CONTINUED

| | | | | | |
|---|---|---|---|---|---|
| Br20P | 7 | 50,058,516 | 50,114,484 | UNKOWN | |
| Br20P | 7 | 50,332,228 | 50,741,036 | GRB10 | |
| Br04X | 7 | 50,693,179 | 50,701,856 | UNKOWN | |
| Br26X | 7 | 54,222,123 | 56,113,498 | EGFR | DDC, FIGNL1 |
| Br25X | 7 | 54,602,061 | 55,501,341 | EGFR | CCT6A, ECOP, GBAS, LANCL2, MRPS17, PSPH, SEC61G, VSTM2A, ZNF713 |
| Br05X | 7 | 54,619,020 | 55,276,919 | EGFR | LANCL2, SEC61G |
| Br20P | 7 | 54,760,596 | 55,358,484 | EGFR | SEC61G |
| Br09P | 7 | 54,830,325 | 55,413,112 | EGFR | SEC61G |
| Br26X | 7 | 56,325,293 | 56,337,310 | UNKOWN | |
| Br13X | 7 | 73,272,823 | 73,289,679 | UNKOWN | |
| Br03X | 7 | 75,457,886 | 75,459,458 | UNKOWN | |
| Br05X | 7 | 78,936,881 | 78,951,653 | UNKOWN | |
| Br03X | 7 | 101,704,241 | 101,708,009 | UNKOWN | |
| Br13X | 7 | 156,031,360 | 156,063,977 | UNKOWN | |
| Br06X | 8 | 49,118,225 | 49,125,050 | UNKOWN | |
| Br02X | 8 | 49,125,003 | 49,125,041 | UNKOWN | |
| Br03X | 8 | 49,125,012 | 49,125,050 | UNKOWN | |
| Br26X | 8 | 141,189,636 | 141,189,852 | UNKOWN | |
| Br27P | 8 | 145,056,944 | 145,064,850 | UNKOWN | |
| Br03X | 9 | 105,936,630 | 105,941,327 | UNKOWN | |
| Br11P | 10 | 18,437,571 | 18,448,955 | UNKOWN | |
| Br11P | 10 | 19,484,188 | 19,507,088 | UNKOWN | |
| Br11P | 10 | 25,061,733 | 25,077,869 | UNKOWN | |
| Br08X | 10 | 45,010,196 | 45,071,698 | UNKOWN | |
| Br08X | 10 | 45,224,720 | 45,350,649 | UNKOWN | MARCH8 |
| Br02X | 11 | 1,737,423 | 1,739,140 | UNKOWN | |
| Br06X | 11 | 113,673,352 | 113,673,398 | UNKOWN | |
| Br11P | 11 | 125,123,118 | 125,124,437 | UNKOWN | |
| Br27P | 12 | 43,353,545 | 43,859,887 | CDK4 | DBX2, PLEKHA9 |
| Br16X | 12 | 56,170,068 | 57,559,240 | CDK4 | MARCH9, AVIL, B4GALNT1, CENTG1, CTDSP2, CYP27B1, DCTN2, DDIT3, DTX3, FAM119B, GEFT, KIF5A, MBD6, METTL1, OS9, PIP4K2C, Q8WYW9_HUMAN, SLC26A10, TSFM, TSPAN31, XR_016180.1, XRCC6BP1 |
| Br27P | 12 | 56,313,053 | 56,731,426 | CDK4 | MARCH9, AVIL, CENTG1, CTDSP2, CYP27B1, FAM119B, METTL1, OS9, Q8WYW9_HUMAN, TSFM, TSPAN31, XRCC6BP1 |
| Br09P | 12 | 56,354,655 | 56,496,029 | CDK4 | MARCH9, CENTG1, CYP27B1, FAM119B, METTL1, OS9, TSFM, TSPAN31 |

FIG. 10
CONTINUED

| ID | Chr | Start | End | Gene | | Notes |
|---|---|---|---|---|---|---|
| Br09P | 12 | 56,354,655 | 56,496,029 | CDK4 | | |
| Br09P | 12 | 56,505,948 | 56,745,675 | UNKOWN | | MARCH9, CENTG1, CYP27B1, FAM119B, METTL1, OS9, TSFM, TSPAN31 |
| Br16X | 12 | 61,104,748 | 61,250,710 | UNKOWN | | XRCC6BP1 |
| Br27P | 12 | 64,707,303 | 64,915,539 | UNKOWN | | |
| Br16X | 12 | 67,312,082 | 68,049,905 | RAP1B | | |
| Br27P | 12 | 123,395,187 | 123,955,485 | UNKOWN | | C12orf31, TMBIM4 |
| Br23X | 13 | 82,550,369 | 82,574,861 | UNKOWN | | CPM, CPSF6, LOC643752, LYZ, MDM2, ENST00000361329, NUP107, Q9P175_HUMAN, SLC35E3 |
| Br23X | 13 | 92,450,749 | 92,478,066 | UNKOWN | | SCARB1 |
| Br23X | 13 | 93,183,362 | 93,187,994 | UNKOWN | | |
| Br23X | 13 | 103,357,246 | 103,381,476 | UNKOWN | | |
| Br23X | 13 | 106,948,221 | 106,960,600 | UNKOWN | | |
| Br23X | 13 | 107,217,139 | 107,223,985 | UNKOWN | | |
| Br23X | 13 | 108,100,521 | 108,117,560 | UNKOWN | | |
| Br02X | 16 | 13,949,459 | 13,949,578 | UNKOWN | | |
| Br02X | 16 | 55,574,780 | 55,574,820 | UNKOWN | | |
| Br02X | 16 | 79,740,930 | 79,740,969 | UNKOWN | | |
| Br06X | 17 | 38,497,326 | 38,497,366 | UNKOWN | | |
| Br03X | 17 | 43,724,291 | 43,728,670 | UNKOWN | | |
| Br02X | 17 | 55,042,776 | 55,042,809 | UNKOWN | | |
| Br03X | 17 | 59,927,132 | 59,929,108 | UNKOWN | | |
| Br02X | 17 | 75,525,527 | 75,531,516 | UNKOWN | | |
| Br20P | 18 | 44,290,789 | 44,291,672 | UNKOWN | | |
| Br07X | 18 | 51,886,633 | 51,894,189 | UNKOWN | | |
| Br03X | 19 | 642,025 | 647,905 | UNKOWN | | |
| Br03X | 19 | 703,878 | 707,985 | UNKOWN | | |
| Br06X | 19 | 858,673 | 870,656 | UNKOWN | | |
| Br29P | 19 | 3,928,486 | 3,933,967 | UNKOWN | | |
| Br06X | 19 | 7,600,021 | 7,600,538 | UNKOWN | | |
| Br02X | 19 | 15,455,019 | 15,467,228 | UNKOWN | | |
| Br02X | 19 | 50,139,876 | 50,139,910 | UNKOWN | | |
| Br02X | 19 | 55,220,045 | 55,236,882 | UNKOWN | | |
| Br06X | 20 | 24,877,913 | 24,886,121 | UNKOWN | | |
| Br06X | X | 34,606,940 | 34,609,955 | UNKOWN | | |
| Br20P | X | 3,575,814 | 3,582,435 | UNKOWN | | |

FIG. 10 CONTINUED

| | | | |
|---|---|---|---|
| Br04X | | | |
| Br20P | X | 12,827,708 | 12,831,972 | UNKNOWN |
| Br04X | X | 16,305,623 | 16,306,395 | UNKNOWN |
| Br06X | X | 17,413,003 | 17,437,823 | UNKNOWN |
| Br03X | X | 20,187,346 | 20,187,385 | UNKNOWN |
| Br04X | X | 21,576,928 | 21,576,953 | UNKNOWN |
| Br29P | X | 38,365,465 | 38,400,112 | UNKNOWN |
| Br29P | X | 53,927,466 | 53,940,364 | UNKNOWN |
| Br29P | X | 58,276,219 | 58,292,688 | UNKNOWN |
| Br16X | X | 61,660,428 | 61,683,946 | UNKNOWN |
| Br02X | X | 63,988,007 | 63,988,941 | UNKNOWN |
| Br03X | X | 66,859,466 | 66,859,511 | UNKNOWN |
| Br20P | X | 68,752,130 | 68,752,682 | UNKNOWN |
| Br20P | X | 124,916,709 | 124,932,598 | UNKNOWN |
| Br29P | X | 130,099,706 | 130,113,107 | UNKNOWN |
| Br29P | X | 133,674,808 | 133,694,476 | UNKNOWN |
| Br20P | X | 144,110,845 | 144,113,003 | UNKNOWN |
| Br02X | X | 150,561,266 | 150,564,832 | UNKNOWN |
| Br02X | X | 150,642,155 | 150,645,024 | UNKNOWN |
| Br16X | X | 154,429,838 | 154,431,317 | UNKNOWN |

*CLASSES OF EVIDENCE FOR CANDIDATE TARGETS OF AMPLIFICATION: 1, COMPARED TO NORMAL TISSUE, CANDIDATE WAS ≥2 FOLD OVEREXPRESSED IN THE TUMOR IN WHICH IT WAS AMPLIFIED AS WELL AS IN OTHER TUMORS; 2, CANDIDATE WAS MUTATED IN A TUMOR IN WHICH IT WAS NOT AMPLIFIED AND ≥2 FOLD OVEREXPRESSED IN OTHER TUMORS; 3, CANDIDATE WAS ≥2 FOLD OVEREXPRESSED IN OTHER TUMORS. †INDICATES GENES WITHIN THE AMPLICON IN ADDITION TO THE PRESUMPTIVE TARGET GENE

FIG. 10 CONTINUED

TABLE S6. HOMOZYGOUS DELETIONS DETECTED BY ILLUMINA ARRAYS

| SAMPLE | CHROMOSOME | LEFT BOUNDARY (bp) | RIGHT BOUNDARY (bp) | CANDIDATE TARGET OF DELETION | CANDIDATE EVIDENCE* | OTHER GENES † |
|---|---|---|---|---|---|---|
| Br04X | 1 | 3,500,493 | 4,562,392 | MEGF6 | 1 | C1orf174, CCDC27, DFFB, KIAA0495, KIAA0562, LRRC47, TP73 |
| Br17X | 1 | 86,174,832 | 86,176,913 | UNKNOWN | | |
| Br16X | 1 | 108,535,014 | 108,538,635 | UNKNOWN | | SLC25A24 |
| Br08X | 1 | 147,305,744 | 147,448,972 | UNKNOWN | | |
| Br13X | 1 | 167,493,526 | 167,507,362 | UNKNOWN | | |
| Br25X | 1 | 173,064,490 | 173,068,262 | UNKNOWN | | |
| Br27P | 2 | 36,263,684 | 36,263,904 | UNKNOWN | | |
| Br06P | 2 | 52,614,242 | 52,637,176 | UNKNOWN | | |
| Br25X | 2 | 123,197,294 | 123,198,771 | UNKNOWN | | |
| Br25X | 2 | 141,180,656 | 141,267,820 | LRP1B | 1 | |
| Br03X | 2 | 141,432,018 | 141,610,364 | LRP1B | 1 | |
| Br25X | 2 | 141,735,396 | 141,751,756 | UNKNOWN | | |
| Br15X | 2 | 159,667,833 | 159,669,697 | UNKNOWN | | |
| Br25X | 2 | 208,061,364 | 208,066,083 | UNKNOWN | | |
| Br05X | 3 | 26,407,350 | 26,414,475 | UNKNOWN | | |
| Br02X | 3 | 133,194,645 | 133,195,707 | UNKNOWN | | |
| Br23X | 3 | 191,220,845 | 191,221,750 | UNKNOWN | | |
| Br16X | 4 | 42,392,310 | 42,404,178 | UNKNOWN | | |
| Br07X | 4 | 64,378,106 | 64,392,223 | UNKNOWN | | |
| Br14X | 4 | 64,380,191 | 64,386,602 | UNKNOWN | | |
| Br13X | 4 | 69,129,446 | 69,153,720 | UNKNOWN | | |
| Br20P | 4 | 115,398,433 | 115,401,739 | UNKNOWN | | |
| Br23X | 4 | 115,398,433 | 115,401,739 | UNKNOWN | | |
| Br03X | 4 | 122,504,713 | 122,508,095 | UNKNOWN | | |
| Br07X | 4 | 153,010,030 | 153,012,241 | UNKNOWN | | |
| Br07X | 4 | 157,183,142 | 157,186,835 | UNKNOWN | | |
| Br07X | 4 | 181,751,048 | 181,969,740 | UNKNOWN | | |
| Br11P | 5 | 15,772,769 | 15,773,478 | UNKNOWN | | |
| Br07X | 5 | 101,503,405 | 101,550,575 | UNKNOWN | | |
| Br03X | 5 | 155,410,444 | 155,421,495 | UNKNOWN | | |
| Br02X | 5 | 167,925,074 | 167,933,033 | UNKNOWN | | |
| Br04X | 5 | 170,062,869 | 170,063,768 | UNKNOWN | | |
| Br08X | 6 | 19,151,979 | 19,156,771 | UNKNOWN | | |
| Br14X | 6 | 29,967,496 | 30,007,126 | UNKNOWN | | |
| Br08X | 6 | 31,373,715 | 31,385,967 | UNKNOWN | | PANK3 |
| Br06X | 6 | 32,061,446 | 32,096,483 | UNKNOWN | | |
| Br27P | 6 | 32,563,460 | 32,567,928 | UNKNOWN | | |

FIG. 10 CONTINUED

| Col1 | Col2 | Col3 | Col4 | Col5 | Col6 |
|---|---|---|---|---|---|
| Br06X | 6 | 32,592,346 | 32,628,250 | HLA-DRB5 | |
| Br29P | 6 | 32,643,872 | 32,550,112 | UNKNOWN | |
| Br14X | 6 | 58,714,934 | 58,715,776 | UNKNOWN | |
| Br04X | 6 | 100,422,887 | 100,630,860 | UNKNOWN | |
| Br06X | 6 | 139,645,437 | 139,648,424 | UNKNOWN | MCHR2 |
| Br04X | 6 | 159,236,418 | 159,237,500 | UNKNOWN | |
| Br12P | 7 | 141,412,174 | 141,439,888 | UNKNOWN | |
| Br07X | 8 | 15,828,545 | 15,831,260 | UNKNOWN | |
| Br08X | 8 | 72,378,104 | 72,380,244 | UNKNOWN | |
| Br14X | 8 | 115,703,454 | 115,711,712 | TSNARE1 | |
| Br07X | 8 | 142,830,192 | 143,494,054 | UNKNOWN | |
| Br07X | 8 | 143,897,019 | 143,916,095 | UNKNOWN | GML |
| Br07X | 8 | 144,236,804 | 144,246,305 | UNKNOWN | |
| Br17X | 9 | 1,437,011 | 1,440,428 | UNKNOWN | |
| Br27P | 9 | 6,691,130 | 6,695,824 | UNKNOWN | C9orf93 |
| Br07X | 9 | 6,691,130 | 6,695,824 | UNKNOWN | ASAH3L, SLC24A2 |
| Br14X | 9 | 14,964,080 | 15,013,765 | UNKNOWN | SLC24A2 |
| Br25X | 9 | 15,539,731 | 15,761,541 | UNKNOWN | SLC24A2, KIAA1797, MLLT3 |
| Br17X | 9 | 19,409,446 | 19,540,684 | UNKNOWN | SLC24A2, KIAA1797, MLLT3 |
| Br05X | 9 | 19,507,795 | 19,540,684 | UNKNOWN | MLLT3, KIAA1797, IFNB1, SLC24A2, IFNA4, IFNW1, PTPLAD2 |
| Br13X | 9 | 19,660,630 | 19,836,444 | UNKNOWN | KIAA1797, C9orf53, CDKN2B, IFNA1, IFNA10, IFNA13, IFNA14, IFNA16, IFNA2, IFNA21, IFNA4, IFNA5, IFNA6, IFNA7, IFNA8, IFNB1, IFNE1, IFNW1, KHL9, MTAP, PTPLAD2, Q8WTY6_HUMAN, MLLT3, KIAA1797 |
| Br17X | 9 | 19,702,170 | 20,892,081 | UNKNOWN | IFNB1, KIAA1797, PTPLAD2, IFNA1, C9orf53, IFNA8, CDKN2B, IFNA2, IFNE1, MTAP, Q8WTY6_HUMAN, DMRTA1, ELAVL2, TUSC1 |
| Br05X | 9 | 19,702,170 | 21,186,356 | UNKNOWN | IFNA21, IFNA1, IFNW1, IFNA2, IFNA8, KHL9, IFNA4, IFNA13, IFNA6, IFNA5, IFNE1, Q8WTY6_HUMAN, CDKN2B |
| Br26X | 9 | 19,892,822 | 20,015,247 | UNKNOWN | IFNA1, IFNA13, IFNA2, IFNA6, IFNA8, IFNE1, Q8WTY6_HUMAN, C9orf53, CDKN2B |
| Br26X | 9 | 20,134,936 | 22,206,506 | CDKN2A | |
| Br02X | 9 | 20,830,838 | 26,141,961 | CDKN2A | |
| Br15X | 9 | 21,088,843 | 22,356,889 | CDKN2A | |
| Br13X | 9 | 21,337,828 | 21,993,367 | CDKN2A | |
| Br17X | 9 | 21,337,828 | 21,995,330 | CDKN2A | IFNA1, IFNA13, IFNA2, IFNA6, IFNA8, IFNE1, Q8WTY6_HUMAN, CDKN2B |
| Br05X | 9 | 21,360,864 | 22,421,172 | CDKN2A | IFNA2, IFNA1, C9orf53, IFNA8, IFNE1, MTAP, Q8WTY6_HUMAN |
| Br20P | 9 | 21,391,106 | 21,398,857 | UNKNOWN | |
| Br14X | 9 | 21,523,610 | 21,993,367 | CDKN2A | Q8WTY6_HUMAN, C9orf53, CDKN2B |
| Br25X | 9 | 21,762,064 | 22,663,444 | CDKN2A | MTAP, CDKN2B |

| Sample | Chr | Start | End | Annotation | # | Genes |
|--------|-----|-------|-----|------------|---|-------|
| Br06X | 9 | 21,792,469 | 21,981,016 | CDKN2A | | |
| Br20P | 9 | 21,851,557 | 21,917,327 | UNKNOWN | 1 | MTAP, C9orf53 |
| Br08X | 9 | 21,965,561 | 23,315,027 | CDKN2 | 1 | MTAP |
| Br20P | 9 | 22,019,547 | 22,206,506 | UNKNOWN | | CDKN2B, DMRTA1 |
| Br13X | 9 | 22,122,076 | 22,326,954 | UNKNOWN | | |
| Br17X | 9 | 22,122,076 | 22,436,828 | UNKNOWN | | |
| Br14X | 9 | 22,148,398 | 22,998,119 | UNKNOWN | | |
| Br06X | 9 | 22,318,194 | 22,336,105 | UNKNOWN | | |
| Br26X | 9 | 22,596,575 | 22,598,275 | UNKNOWN | | |
| Br17X | 9 | 22,824,703 | 22,956,660 | UNKNOWN | | |
| Br26X | 9 | 22,862,408 | 24,123,577 | UNKNOWN | | |
| Br14X | 9 | 23,102,398 | 22,954,237 | UNKNOWN | | |
| Br06X | 9 | 23,469,588 | 23,297,377 | UNKNOWN | | |
| Br08X | 9 | 23,628,686 | 23,507,989 | UNKNOWN | | |
| Br13X | 9 | 23,628,686 | 23,727,408 | UNKNOWN | | |
| Br15X | 9 | 23,722,000 | 23,813,399 | UNKNOWN | | |
| Br14X | 9 | 23,968,172 | 23,765,449 | UNKNOWN | | ELAVL2 |
| Br14X | 9 | 24,492,737 | 24,282,583 | UNKNOWN | | ELAVL2 |
| Br15X | 9 | 25,145,167 | 25,277,180 | UNKNOWN | | |
| Br25X | 9 | 25,386,115 | 24,505,111 | UNKNOWN | | |
| Br25X | 9 | 25,386,115 | 25,277,180 | UNKNOWN | | |
| Br06X | 9 | 27,988,125 | 25,417,205 | UNKNOWN | | |
| Br25X | 9 | 31,973,460 | 26,570,067 | UNKNOWN | | TUSC1 |
| Br02X | 9 | 113,693,260 | 29,151,218 | UNKNOWN | | LINGO2 |
| Br13X | 9 | 128,560,616 | 32,261,795 | UNKNOWN | | |
| Br04X | 9 | 134,941,052 | 113,693,505 | UNKNOWN | | |
| Br15X | 10 | 56,280,721 | 128,561,879 | UNKNOWN | | |
| Br23X | 10 | 58,567,923 | 134,944,131 | UNKNOWN | | |
| Br10P | 10 | 58,880,806 | 56,361,311 | PTEN | 2 | PAPSS2, ATAD1, KILLIN |
| Br04X | 10 | 89,468,496 | 58,606,559 | UNKNOWN | | |
| Br07X | 11 | 5,741,599 | 58,881,704 | UNKNOWN | | |
| Br05X | 11 | 41,774,842 | 89,627,047 | UNKNOWN | | |
| Br27P | 12 | 39,161,618 | 5,755,246 | UNKNOWN | | |
| Br07X | 12 | 39,161,962 | 41,775,435 | UNKNOWN | | |
| Br07X | 12 | 98,319,260 | 39,162,250 | TMEM132B | 1 | ITM2B |
| Br04X | 13 | 124,316,922 | 39,162,250 | RB1 | 2 | |
| Br07X | 13 | 47,684,077 | 47,862,826 | UNKNOWN | | |
| Br04X | 13 | 57,491,658 | 57,497,032 | UNKNOWN | | |

101/120

| | | | | |
|---|---|---|---|---|
| B04X | 13 | 82,763,946 | 82,812,014 | UNKNOWN |
| B04X | 13 | 86,013,322 | 86,241,525 | UNKNOWN |
| B20P | 13 | 99,378,354 | 99,379,711 | UNKNOWN |
| Br17X | 14 | 40,679,974 | 40,698,108 | UNKNOWN |
| Br13X | 14 | 98,574,125 | 98,574,712 | UNKNOWN |
| B03X | 15 | 27,686,508 | 27,690,054 | UNKNOWN |
| B04X | 15 | 32,509,517 | 32,595,161 | ZNF280D | 1 | MNS1, TEX9, TCF12 |
| B03X | 15 | 54,329,515 | 55,246,412 | A2BP1 |
| Br17X | 15 | 54,579,805 | 54,582,930 | IL4 | 1 | Q8WZ91_HUMAN |
| B03X | 16 | 6,612,412 | 6,757,376 | TP53 |
| B03X | 16 | 27,248,560 | 27,258,188 | UNKNOWN | 1 |
| B02X | 17 | 7,470,627 | 7,598,047 | UNKNOWN | 2 | ATP1B2, DNAH2, SHBG, SAT2, EFNB3, WDR79 |
| B06X | 18 | 36,514,524 | 36,518,476 | UNKNOWN |
| B07X | 20 | 40,694,858 | 40,702,735 | UNKNOWN |
| B03X | 21 | 22,576,805 | 22,583,018 | UNKNOWN |
| B04X | 21 | 22,576,805 | 22,583,706 | UNKNOWN |
| B04X | 22 | 21,808,695 | 21,809,273 | UNKNOWN |
| Br13X | 22 | 36,078,340 | 36,079,559 | UNKNOWN | 1 | Q8N7Q6_HUMAN |
| Br25X | 22 | 37,693,776 | 37,708,598 | UNKNOWN | 1 | APOBEC3B |
| Br25X | 22 | 45,878,213 | 46,554,514 | UNKNOWN | 2 | TBC1D22A, U6126_HUMAN |
| B02X | X | 33,964,391 | 33,978,251 | UNKNOWN | | ATRX |
| Br12P | X | 76,774,818 | 76,824,354 | UNKNOWN |
| Br16X | X | 84,750,960 | 84,753,048 | UNKNOWN |
| B25X | X | 154,049,748 | 154,070,562 | UNKNOWN |

* CLASSES OF EVIDENCE FOR CANDIDATE TARGETS OF HOMOZYGOUS DELETION: 1. COMPARED TO NORMAL TISSUE, CANDIDATE WAS NOT EXPRESSED IN THE TUMOR IN WHICH IT WAS DELETED AND WAS EXPRESSED AT >5 FOLD LOWER LEVELS IN OTHER TUMORS; 2. CANDIDATE WAS MUTATED IN A TUMOR IN WHICH IT WAS NOT DELETED AND WAS EXPRESSED AT >5 FOLD LOWER LEVELS IN OTHER TUMORS.
† INDICATES GENES WITHIN THE DELETION IN ADDITION TO THE PRESUMPTIVE TARGET GENE

FIG. 10
CONTINUED

TABLE S7. GBM *CAN*-GENES*

| GENE | NUMBER OF MUTATIONS | NUMBER OF AMPLIFICATIONS | NUMBER OF DELETIONS | PASSENGER PROBABILITY LOW |
|---|---|---|---|---|
| TP53 | 13 | 0 | 1 | <0.001 |
| CDKN2A | 0 | 0 | 11 | <0.001 |
| PTEN | 5 | 0 | 1 | <0.001 |
| EGFR | 2 | 5 | 0 | <0.001 |
| IDH1 | 5 | 0 | 0 | <0.001 |
| CDK4 | 0 | 3 | 0 | <0.001 |
| GML | 1 | 0 | 1 | 0.005 |
| RB1 | 2 | 0 | 1 | 0.004 |
| ENST00000355324 | 2 | 0 | 0 | 0.004 |
| NF1 | 3 | 0 | 0 | 0.009 |
| SKP2 | 2 | 0 | 0 | 0.009 |
| COL3A1 | 3 | 0 | 0 | 0.009 |
| ARNT2 | 2 | 0 | 0 | 0.009 |
| KIAA1804 | 2 | 0 | 0 | 0.009 |
| Q8NDH2_HUMAN | 2 | 0 | 0 | 0.009 |
| C6orf170 | 2 | 0 | 0 | 0.030 |
| IMP4 | 2 | 0 | 0 | 0.030 |
| IRX6 | 3 | 0 | 0 | 0.030 |
| KIAA1441 | 2 | 0 | 0 | 0.030 |
| LRP2 | 4 | 0 | 0 | 0.030 |
| OR2L13 | 2 | 0 | 0 | 0.030 |
| PIK3CA | 2 | 0 | 0 | 0.030 |
| PIK3R1 | 2 | 0 | 0 | 0.030 |
| RBM27 | 2 | 0 | 0 | 0.030 |
| SERPINA12 | 2 | 0 | 0 | 0.030 |
| PKHD1 | 3 | 0 | 0 | 0.053 |
| C21orf29 | 2 | 0 | 0 | 0.057 |
| LMX1A | 2 | 0 | 0 | 0.057 |
| ZNF497 | 2 | 0 | 0 | 0.057 |
| LRRC7 | 2 | 0 | 0 | 0.057 |
| KIAA0133 | 2 | 0 | 0 | 0.087 |
| MYO1B | 2 | 0 | 0 | 0.087 |
| TRPV5 | 2 | 0 | 0 | 0.087 |
| DSG4 | 2 | 0 | 0 | 0.107 |
| KIAA0774 | 2 | 0 | 0 | 0.107 |
| NGEF | 2 | 0 | 0 | 0.107 |
| PHIP | 2 | 0 | 0 | 0.108 |
| ASTN | 2 | 0 | 0 | 0.108 |
| FRMPD4 | 2 | 0 | 0 | 0.108 |
| SCN9A | 2 | 0 | 0 | 0.108 |
| GRM3 | 2 | 0 | 0 | 0.263 |

FIG. 10
CONTINUED

| CACNA1H | 2 | 0 | 0 | 0.303 |

*CAN-GENES WERE DEFINED AS THOSE HAVING AT LEAST TWO ALTERATIONS IN THE DISCOVERY SCREEN SAMPLES ALTERATIONS PER MB SEQUENCE ANALYZED. PASSENGER PROBABILITIES WERE CALCULATED AS DESCRIBED IN THE SUPPORTING ONLINE MATERIAL.

FIG. 10
CONTINUED

| PASSENGER PROBABILITY MID | PASSENGER PROBABILITY HIGH |
| --- | --- |
| <0.001 | <0.001 |
| <0.001 | <0.001 |
| <0.001 | <0.001 |
| <0.001 | <0.001 |
| <0.001 | <0.001 |
| <0.001 | <0.001 |
| 0.016 | 0.017 |
| 0.017 | 0.025 |
| 0.035 | 0.066 |
| 0.040 | 0.174 |
| 0.040 | 0.174 |
| 0.040 | 0.174 |
| 0.070 | 0.174 |
| 0.070 | 0.174 |
| 0.070 | 0.188 |
| 0.097 | 0.188 |
| 0.097 | 0.316 |
| 0.097 | 0.188 |
| 0.097 | 0.188 |
| 0.097 | 0.344 |
| 0.097 | 0.188 |
| 0.097 | 0.188 |
| 0.097 | 0.316 |
| 0.097 | 0.188 |
| 0.097 | 0.316 |
| 0.097 | 0.366 |
| 0.097 | 0.344 |
| 0.097 | 0.344 |
| 0.097 | 0.344 |
| 0.163 | 0.344 |
| 0.307 | 0.391 |
| 0.307 | 0.391 |
| 0.307 | 0.391 |
| 0.321 | 0.391 |
| 0.321 | 0.391 |
| 0.321 | 0.391 |
| 0.379 | 0.646 |
| 0.445 | 0.646 |
| 0.445 | 0.646 |
| 0.445 | 0.646 |
| 0.445 | 0.772 |

FIG. 10
CONTINUED

| 0.445 | 0.772 |
|---|---|

(EXCLUDING Br27P) AND AT LEAST TEN
MATERIALS AND METHODS SECTION OF THE

FIG. 10
CONTINUED

| TABLE S8. CANDIDATE GENE SETS ENRICHED FOR GENETIC ALTERATIONS IN GBMs | | | |
|---|---|---|---|
| GENE SET | PATHWAY DATABASE | SET SIZE | NUMBER OF MUTATIONS IN SET |
| ion transport | GO | 55 | 5 |
| negative regulation of cell-matrix adhesion | GO | 6 | 5 |
| calcium ion transport | GO | 121 | 18 |
| Cell adhesion_Cell-matrix interactions | GG | 185 | 23 |
| Cell adhesion_Integrin priming | GG | 130 | 23 |
| Cell adhesion_ECM remodeling | MA | 70 | 13 |
| Cytoskeleton remodeling_Cytoskeleton remodeling | MA | 159 | 23 |
| synaptic transmission | GO | 239 | 22 |
| positive regulation of epithelial cell proliferation | GO | 33 | 7 |
| Neurophysiological process_Transmission of nerve impulse | GG | 262 | 26 |
| Signal transduction_PTEN pathway | MA | 56 | 25 |
| Development_EGFR signaling via PIP3 | MA | 27 | 12 |
| Translation _Non-genomic (rapid) action of Androgen Receptor | MA | 70 | 15 |
| Apoptosis and survival_DNA-damage-induced apoptosis | MA | 18 | 15 |
| Transcription_P53 signaling pathway | MA | 48 | 18 |
| negative regulation of neuroblast proliferation | GO | 6 | 15 |
| Cell adhesion_Chemokines and adhesion | MA | 152 | 21 |
| somatic stem cell division | GO | 6 | 1 |
| regulation of protein stability | GO | 6 | 5 |
| response to chemical stimulus | GO | 20 | 16 |
| Muscle contraction | GG | 320 | 27 |
| B cell lineage commitment | GO | 6 | 13 |

FIG. 10
CONTINUED

| | | |
|---|---|---|
| Cell adhesion_Attractive and repulsive receptors | GG | 193 | 20 |
| cell migration | GO | 64 | 12 |
| Transport_Sodium transport | GG | 150 | 15 |
| Cytoskeleton remodeling_FAK signaling | MA | 66 | 14 |
| Transport_Calcium transport | GG | 182 | 19 |
| response to retinoic acid | GO | 7 | 15 |
| G1/S transition of mitotic cell cycle | GO | 55 | 7 |
| Cell adhesion_Platelet-endothelium-leucocyte interactions | GG | 184 | 20 |
| Cytoskeleton remodeling_TGF, WNT and cytoskeletal remodeling | MA | 184 | 28 |
| Development_Neurogenesis:Axonal guidance | GG | 236 | 21 |
| response to cytokine stimulus | GO | 15 | 16 |
| Proteolysis_ECM remodeling | GG | 110 | 13 |
| cell adhesion | GO | 589 | 38 |
| positive regulation of cell cycle | GO | 8 | 12 |
| Signal transduction_NOTCH signaling | GG | 219 | 36 |
| Cell adhesion_Integrin-mediated cell-matrix adhesion | GG | 248 | 23 |
| Reproduction_GnRH signaling pathway | GG | 233 | 23 |
| Development_PIP3 signaling in cardiac myocytes | MA | 76 | 14 |
| negative regulation of cell cycle | GO | 139 | 30 |
| Cell cycle_G0-G1 | GG | 95 | 18 |
| Cardiac development_FGF_ErbB signaling | GG | 143 | 16 |
| response to drug | GO | 162 | 24 |
| negative regulation of apoptosis | GG | 131 | 28 |
| Cell cycle_G1-S | GG | 217 | 26 |
| potassium ion transport | GO | 177 | 14 |
| Inflammation_IL-2 signaling | GG | 103 | 15 |
| DNA damage_Brca1 as a transcription regulator | MA | 30 | 16 |
| response to X-ray | GO | 20 | 16 |

FIG. 10
CONTINUED

| | | | |
|---|---|---|---|
| aging | GO | 58 | 18 |
| negative regulation of cell growth | GO | 73 | 18 |
| ER overload response | GO | 10 | 12 |
| Apoptosis and survival_p53-dependent apoptosis | MA | 31 | 13 |
| DNA damage_DNA-damage-induced responses | MA | 10 | 13 |
| response to organic substance | GO | 59 | 6 |
| wound healing | GO | 45 | 20 |
| Signal transduction_AKT signaling | MA | 61 | 22 |
| protein amino acid phosphorylation | GO | 575 | 36 |
| transmembrane receptor protein tyrosine kinase signaling pathway | GO | 105 | 10 |
| DNA damage_ATM/ATR regulation of G1/S checkpoint | MA | 45 | 14 |
| positive regulation of neuron apoptosis | GO | 11 | 15 |
| protein tetramerization | GO | 11 | 14 |
| Proliferation_Positive regulation cell proliferation | GG | 235 | 18 |
| Cell cycle_G1-S Interleukin regulation | GG | 109 | 9 |
| Cytoskeleton_Regulation of cytoskeleton rearrangement | GG | 269 | 21 |
| Development_Blood vessel morphogenesis | GG | 356 | 25 |
| cell proliferation | GO | 357 | 36 |
| cell-cell adhesion | GO | 80 | 13 |
| response to gamma radiation | GO | 22 | 14 |
| response to organic cyclic substance | GO | 50 | 18 |
| response to metal ion | GO | 12 | 13 |
| DNA damage_Checkpoint | GG | 148 | 20 |
| heart development | GO | 151 | 19 |
| Cardiac development_Wnt_beta-catenin, Notch, VEGF, IP3 and integrin signaling | GG | 205 | 18 |
| positive regulation of apoptosis | GO | 99 | 20 |
| response to inorganic substance | GO | 13 | 13 |
| Cell cycle_G1-S Growth factor regulation | GG | 177 | 14 |

FIG. 10
CONTINUED

| | | |
|---|---|---|
| Apoptosis and survival_Role of CDK5 in neuronal death and survival | MA | 40 | 17 |
| Proliferation_Negative regulation of cell proliferation | GG | 198 | 25 |
| proteolysis | GO | 487 | 27 |
| Development_Regulation of angiogenesis | GG | 300 | 20 |
| regulation of cell cycle | GO | 127 | 20 |
| nucleotide-excision repair | GO | 28 | 14 |
| central nervous system development | GO | 131 | 26 |
| Proteolysis_Putative SUMO-1 pathway | MA | 28 | 13 |
| Immune response _PIP3 signaling in B lymphocytes | MA | 59 | 11 |
| Development_Neurotrophin family signaling | MA | 45 | 17 |
| DNA damage_BER-NER repair | GG | 97 | 18 |
| Signal transduction_Androgen receptor signaling cross-talk | GG | 99 | 9 |
| response to organic nitrogen | GO | 17 | 12 |
| cell cycle checkpoint | GO | 17 | 2 |

*THE SETS LISTED WERE GENETICALLY ALTERED IN AT LEAST 50% OF THE GBMs, CONTAINED >5 AND <600 GENES, AND HAD A Q-VALUE <0.20. SEE SUP

FIG. 10
CONTINUED

| NUMBER OF DELETIONS IN SET | NUMBER OF AMPLIFICATIONS IN SET | NUMBER OF ALTERED SAMPLES | STATISTICAL SIGNIFICANCE OF ALTERED GENES IN SET |
|---|---|---|---|
| 0 | 0 | 82% | <0.001 |
| 11 | 0 | 64% | <0.001 |
| 0 | 3 | 55% | <0.001 |
| 0 | 5 | 64% | <0.001 |
| 1 | 0 | 64% | <0.001 |
| 0 | 5 | 55% | <0.001 |
| 1 | 0 | 59% | <0.001 |
| 0 | 1 | 55% | <0.001 |
| 0 | 5 | 50% | <0.001 |
| 0 | 0 | 55% | <0.001 |
| 2 | 6 | 82% | 0.001 |
| 1 | 5 | 59% | 0.001 |
| 1 | 6 | 64% | 0.001 |
| 1 | 0 | 55% | 0.001 |
| 2 | 1 | 68% | 0.001 |
| 1 | 0 | 55% | 0.002 |
| 1 | 0 | 55% | 0.002 |
| 11 | 0 | 50% | 0.002 |
| 12 | 0 | 64% | 0.002 |
| 1 | 0 | 59% | 0.002 |
| 0 | 0 | 59% | 0.002 |
| 1 | 0 | 50% | 0.003 |

FIG. 10
CONTINUED

| | | | |
|---|---|---|---|
| 0  | 0 | 50% | 0.004 |
| 1  | 0 | 50% | 0.004 |
| 0  | 0 | 50% | 0.005 |
| 1  | 0 | 50% | 0.005 |
| 0  | 0 | 50% | 0.005 |
| 1  | 0 | 59% | 0.005 |
| 12 | 3 | 68% | 0.006 |
| 0  | 5 | 64% | 0.006 |
| 1  | 1 | 77% | 0.006 |
| 0  | 1 | 55% | 0.006 |
| 1  | 0 | 59% | 0.009 |
| 0  | 0 | 50% | 0.009 |
| 0  | 3 | 73% | 0.013 |
| 1  | 3 | 55% | 0.013 |
| 3  | 5 | 91% | 0.013 |
| 0  | 0 | 59% | 0.014 |
| 0  | 5 | 59% | 0.015 |
| 1  | 0 | 50% | 0.018 |
| 14 | 5 | 95% | 0.019 |
| 13 | 4 | 91% | 0.028 |
| 1  | 5 | 68% | 0.032 |
| 12 | 1 | 95% | 0.033 |
| 2  | 0 | 77% | 0.034 |
| 13 | 4 | 95% | 0.035 |
| 0  | 0 | 50% | 0.037 |
| 2  | 3 | 59% | 0.043 |
| 2  | 0 | 59% | 0.045 |
| 1  | 0 | 64% | 0.045 |

FIG. 10
CONTINUED

| | | | |
|---|---|---|---|
| 12 | 1 | 91% | 0.045 |
| 13 | 0 | 86% | 0.046 |
| 1 | 1 | 55% | 0.046 |
| 12 | 1 | 91% | 0.046 |
| 1 | 0 | 50% | 0.046 |
| 11 | 0 | 55% | 0.048 |
| 1 | 0 | 68% | 0.049 |
| 2 | 1 | 77% | 0.051 |
| 0 | 8 | 82% | 0.051 |
| 0 | 5 | 50% | 0.051 |
| 1 | 4 | 59% | 0.051 |
| 1 | 0 | 55% | 0.051 |
| 1 | 0 | 59% | 0.052 |
| 0 | 6 | 50% | 0.052 |
| 13 | 3 | 73% | 0.053 |
| 1 | 2 | 55% | 0.054 |
| 0 | 5 | 59% | 0.056 |
| 1 | 6 | 95% | 0.062 |
| 0 | 5 | 50% | 0.068 |
| 1 | 0 | 50% | 0.073 |
| 12 | 0 | 86% | 0.073 |
| 1 | 0 | 55% | 0.076 |
| 2 | 4 | 73% | 0.077 |
| 1 | 0 | 55% | 0.083 |
| 1 | 0 | 55% | 0.084 |
| 1 | 1 | 59% | 0.091 |
| 1 | 0 | 55% | 0.095 |
| 12 | 8 | 77% | 0.101 |

FIG. 10
CONTINUED

| | | | |
|---|---|---|---|
| 1 | 0 | 68% | 0.113 |
| 3 | 2 | 77% | 0.113 |
| 0 | 1 | 68% | 0.116 |
| 0 | 0 | 59% | 0.122 |
| 2 | 4 | 73% | 0.152 |
| 1 | 0 | 55% | 0.155 |
| 2 | 0 | 77% | 0.158 |
| 1 | 1 | 59% | 0.161 |
| 1 | 0 | 50% | 0.166 |
| 1 | 0 | 68% | 0.177 |
| 1 | 0 | 68% | 0.195 |
| 0 | 6 | 50% | 0.199 |
| 12 | 0 | 86% | 0.199 |
| 12 | 0 | 55% | 0.199 |

PORTING ONLINE MATERIAL, STATISTICAL SECTION, FOR DETAILS.

FIG. 10
CONTINUED

TABLE S9. GBM OVEREXPRESSED GENES*

| | NORMAL BRAIN 1 | NORMAL BRAIN 2 | Br01X | Br02X | Br05X | Br07X | Br10PT | Br13X | Br14X | Br15X | Br16X | Br17X | Br18X | Br19X | Br20PT | Br23PT | Br25x | Br26X |
|---|---|---|---|---|---|---|---|---|---|---|---|---|---|---|---|---|---|---|
| NUMBER OF TAGS SEQUENCED | 5319813 | 5374760 | 3193979 | 7971888 | 4585886 | 4692463 | 2656151 | 6017541 | 2688881 | 6036214 | 4852790 | 6046592 | 7686292 | 7884769 | 2995314 | 3716605 | 3256355 | 9644975 |
| NUMBER OF HIGH QUALITY SEQUENCE TAGS | 3890781 | 3811603 | 2998803 | 3846546 | 1914626 | 1603509 | 2268438 | 5609235 | 2560845 | 5409160 | 3054466 | 4109053 | 3002707 | 1517919 | 2566499 | 3246601 | 5595470 | 3311260 |
| NUMBER OF TAGS MATCHING KNOWN TRANSCRIPTS | 2539767 | 2539721 | 2210496 | 2626761 | 1253622 | 1124729 | 1127330 | 3445010 | 1300996 | 3880894 | 1951194 | 2996841 | 1816665 | 1032974 | 1779688 | 1987225 | 2410107 | 429245 |

| GENE | NORMAL BRAIN 1 | NORMAL BRAIN 2 | Br01X | Br02X | Br05X | Br07X | Br10PT | Br13X | Br14X | Br15X | Br16X | Br17X | Br18X | Br19X | Br20PT | Br23PT | Br25x | Br26X | OVEREXPRESSED† |
|---|---|---|---|---|---|---|---|---|---|---|---|---|---|---|---|---|---|---|---|
| ANXA1 | 11 | 13 | 76 | 40 | 200 | 626 | 30 | 433 | 449 | 152 | 253 | 254 | 303 | 17 | 41 | 264 | 37 | 389 | |
| ANXA5 | 38 | 43 | 83 | 666 | 679 | 668 | 10 | 730 | 602 | 341 | 594 | 271 | 443 | 647 | 194 | 429 | 24 | 865 | + |
| ASF1B | 0 | 0 | 29 | 62 | 3 | 36 | 0 | 19 | 50 | 46 | 33 | 42 | 23 | 23 | 10 | 13 | 7 | 0 | + |
| ASPM | 0 | 0 | 36 | 62 | 98 | 189 | 26 | 53 | 46 | 68 | 40 | 133 | 67 | 138 | 60 | 18 | 0 | 7 | + |
| ATAD2 | 2 | 9 | 219 | 187 | 276 | 229 | 35 | 96 | 240 | 467 | 296 | 426 | 220 | 365 | 96 | 215 | 97 | 203 | + |
| ATAD5 | 10 | 0 | 12 | 7 | 5 | 7 | 7 | 2 | 3 | 8 | 0 | 10 | 0 | 5 | 30 | 9 | 153 | 2 | + |
| AURKA | 0 | 3 | 81 | 54 | 49 | 93 | 0 | 39 | 57 | 52 | 32 | 74 | 43 | 34 | 60 | 34 | 0 | 77 | + |
| AURKB | 1 | 0 | 81 | 16 | 10 | 6 | 0 | 6 | 30 | 46 | 19 | 49 | 28 | 6 | 22 | 16 | 9 | 2 | + |
| BLM | 0 | 0 | 2 | 16 | 22 | 7 | 0 | 8 | 22 | 5 | 4 | 17 | 0 | 3 | 9 | 2 | 0 | 12 | + |
| BUB1 | 0 | 0 | 24 | 45 | 16 | 70 | 0 | 5 | 11 | 8 | 12 | 28 | 34 | 27 | 0 | 5 | 9 | 12 | + |
| BUB1B | 0 | 0 | 22 | 44 | 41 | 124 | 4 | 17 | 20 | 50 | 1 | 75 | 46 | 73 | 4 | 11 | 28 | 144 | + |
| C13orf3 | 0 | 0 | 12 | 7 | 4 | 12 | 0 | 3 | 8 | 7 | 1 | 11 | 0 | 2 | 9 | 6 | 8 | 0 | + |
| C14orf22 | 0 | 0 | 1 | 13 | 18 | 2 | 152 | 4 | 7 | 25 | 19 | 6 | 11 | 12 | 20 | 37 | 0 | 26 | + |
| CASC5 | 0 | 0 | 54 | 68 | 333 | 203 | 0 | 55 | 122 | 178 | 97 | 263 | 129 | 112 | 100 | 54 | 10 | 47 | + |
| CBX2 | 2 | 3 | 41 | 17 | 0 | 14 | 0 | 4 | 12 | 87 | 58 | 58 | 10 | 37 | 13 | 13 | 84 | 7 | + |
| CCDC99 | 0 | 1 | 14 | 23 | 37 | 44 | 0 | 13 | 12 | 12 | 19 | 13 | 22 | 38 | 20 | 9 | 0 | 2 | + |
| CCNB2 | 0 | 0 | 53 | 29 | 59 | 58 | 18 | 16 | 41 | 52 | 12 | 66 | 31 | 32 | 20 | 9 | 17 | 5 | + |
| CDC14A | 1 | 0 | 5 | 6 | 6 | 7 | 3 | 13 | 16 | 6 | 22 | 10 | 0 | 51 | 0 | 9 | 0 | 9 | + |
| CDC2 | 0 | 3 | 306 | 270 | 335 | 525 | 0 | 67 | 262 | 465 | 184 | 297 | 140 | 145 | 31 | 65 | 117 | 42 | + |
| CDC25A | 2 | 1 | 29 | 39 | 61 | 57 | 3 | 6 | 23 | 78 | 28 | 67 | 2 | 103 | 0 | 43 | 22 | 16 | + |
| CDC45L | 0 | 0 | 66 | 25 | 33 | 28 | 0 | 13 | 48 | 31 | 23 | 66 | 47 | 18 | 0 | 5 | 0 | 84 | + |
| CDCA8 | 1 | 1 | 13 | 15 | 9 | 27 | 0 | 17 | 14 | 15 | 7 | 8 | 6 | 16 | 2 | 10 | 10 | 0 | + |

| Gene | + | + | + | + | + | + | + | + | + | + | + | + | + | + | + | + |
|---|---|---|---|---|---|---|---|---|---|---|---|---|---|---|---|---|
| CDK6 | 6 | 3 | 24 | 352 | 277 | 71 | 12 | 121 | 387 | 17 | 53 | 608 | 60 | 158 | 124 | 13 |
| CDKN2C | 6 | 12 | 10 | 353 | 350 | 268 | 0 | 80 | 125 | 144 | 152 | 133 | 99 | 253 | 124 | 47 |
| CDKN3 | 2 | 2 | 46 | 49 | 58 | 72 | 0 | 64 | 29 | 56 | 14 | 103 | 30 | 15 | 9 | 28 |
| CDT1 | 2 | 1 | 87 | 30 | 15 | 18 | 0 | 11 | 60 | 44 | 22 | 23 | 6 | 7 | 39 | 31 |
| CENPA | 0 | 0 | 65 | 58 | 30 | 67 | 10 | 20 | 34 | 42 | 22 | 71 | 23 | 24 | 19 | 34 |
| CENPE | 1 | 0 | 23 | 19 | 27 | 37 | 0 | 12 | 13 | 12 | 13 | 23 | 0 | 16 | 23 | 0 |
| CENPF | 0 | 0 | 57 | 83 | 41 | 42 | 0 | 28 | 69 | 89 | 50 | 101 | 46 | 64 | 71 | 48 |
| CENPK | 6 | 0 | 98 | 89 | 647 | 317 | 4 | 33 | 144 | 152 | 85 | 174 | 97 | 149 | 213 | 113 |
| CEP55 | 0 | 0 | 67 | 38 | 40 | 96 | 56 | 38 | 45 | 87 | 9 | 44 | 43 | 25 | 6 | 30 |
| CHEK1 | 2 | 0 | 33 | 45 | 39 | 101 | 12 | 0 | 36 | 11 | 20 | 41 | 1 | 47 | 9 | 18 |
| CHRNA5 | 1 | 1 | 15 | 6 | 9 | 14 | 9 | 1 | 27 | 13 | 7 | 6 | 8 | 15 | 7 | 1 |
| CHST9 | 0 | 0 | 3 | 0 | 0 | 0 | 10 | 38 | 32 | 2 | 10 | 4 | 0 | 15 | 8 | 8 |
| CKAP2L | 0 | 0 | 16 | 43 | 48 | 38 | 6 | 19 | 20 | 32 | 25 | 45 | 14 | 38 | 0 | 12 |
| CKS1B | 9 | 1 | 263 | 152 | 132 | 245 | 0 | 158 | 71 | 91 | 96 | 192 | 192 | 258 | 31 | 80 |
| CNTLN | 0 | 8 | 6 | 4 | 2 | 12 | 5 | 4 | 2 | 13 | 2 | 19 | 14 | 8 | 0 | 9 |
| CRISPLD1 | 3 | 0 | 18 | 142 | 0 | 13 | 9 | 269 | 53 | 84 | 103 | 34 | 15 | 44 | 20 | 19 |
| DEPDC1B | 0 | 2 | 27 | 15 | 11 | 22 | 16 | 7 | 14 | 11 | 10 | 13 | 7 | 21 | 0 | 11 |
| DLG7 | 0 | 0 | 45 | 38 | 34 | 65 | 0 | 11 | 8 | 40 | 5 | 41 | 6 | 11 | 0 | 0 |
| DNAH11 | 0 | 0 | 3 | 22 | 18 | 4 | 0 | 8 | 5 | 9 | 12 | 11 | 8 | 3 | 15 | 33 |
| DNAH9 | 0 | 0 | 28 | 5 | 7 | 4 | 2 | 6 | 34 | 19 | 26 | 7 | 10 | 1 | 0 | 30 |
| DTL | 2 | 0 | 43 | 34 | 34 | 32 | 10 | 21 | 13 | 61 | 15 | 59 | 22 | 61 | 31 | 0 |
| E2F2 | 0 | 0 | 9 | 12 | 10 | 15 | 10 | 5 | 27 | | 15 | 15 | 0 | 11 | 6 | 8 |

FIG. 10 CONTINUED

| | | | | | | | | | | | | | | | | | | | | | |
|---|---|---|---|---|---|---|---|---|---|---|---|---|---|---|---|---|---|---|---|---|---|
| | + | + | + | + | + | + | + | + | + | + | + | + | + | + | + | + | + | + | + | + | + |
| E2F7 | 0 | 0 | 80 | 129 | 165 | 62 | 0 | 5 | 10 | 31 | 113 | 3 | 60 | 121 | 44 | 35 | 48 | 50 | 164 |
| EPR1 | 1 | 1 | 118 | 124 | 30 | 131 | 5 | 0 | 42 | 86 | 69 | 14 | 76 | 48 | 26 | 39 | 45 | 72 | 84 |
| ESCO2 | 0 | 0 | 12 | 14 | 16 | 26 | 11 | 5 | 3 | 11 | 15 | 0 | 22 | 12 | 15 | 0 | 5 | 7 | 5 |
| ESPL1 | 0 | 0 | 28 | 20 | 27 | 29 | 0 | 11 | 21 | 23 | 41 | 25 | 49 | 9 | 22 | 0 | 9 | 30 | 0 |
| EXO1 | 0 | 0 | 28 | 56 | 22 | 59 | 0 | 0 | 6 | 7 | 10 | 6 | 30 | 1 | 35 | 55 | 4 | 0 | 5 |
| EZH2 | 11 | 7 | 357 | 418 | 589 | 172 | 35 | 1 | 147 | 456 | 690 | 476 | 888 | 297 | 375 | 7 | 374 | 172 | 54 |
| FAM111B | 0 | 0 | 3 | 17 | 34 | 36 | 1 | 0 | 19 | 55 | 33 | 16 | 36 | 9 | 31 | 28 | 32 | 0 | 0 |
| FAM152A | 4 | 0 | 28 | 47 | 76 | 122 | 0 | 10 | 67 | 46 | 53 | 49 | 62 | 53 | 90 | 61 | 24 | 0 | 5 |
| FAM64A | 0 | 3 | 41 | 105 | 227 | 92 | 0 | 0 | 46 | 240 | 168 | 159 | 458 | 51 | 96 | 38 | 163 | 0 | 37 |
| FAM72B | 5 | 0 | 83 | 88 | 152 | 146 | 1 | 0 | 39 | 53 | 98 | 90 | 142 | 94 | 159 | 0 | 102 | 0 | 19 |
| FAM83D | 1 | 6 | 55 | 6 | 22 | 50 | 0 | 1 | 22 | 35 | 35 | 22 | 33 | 12 | 44 | 23 | 3 | 0 | 0 |
| FBXO5 | 3 | 1 | 37 | 72 | 119 | 128 | 1 | 0 | 28 | 49 | 254 | 56 | 93 | 142 | 288 | 121 | 68 | 147 | 35 |
| FOXM1 | 2 | 3 | 108 | 98 | 78 | 36 | 0 | 73 | 90 | 135 | 114 | 76 | 159 | 70 | 21 | 8 | 181 | 0 | 70 |
| GALR1 | 0 | 0 | 0 | 0 | 6 | 0 | 1 | 0 | 3 | 7 | 26 | 9 | 24 | 0 | 66 | 7 | 10 | 6 | 151 |
| GEN1 | 0 | 0 | 4 | 10 | 37 | 12 | 2 | 17 | 10 | 22 | 12 | 27 | 11 | 16 | 6 | 39 | 6 | 17 | 2 |
| GINS1 | 0 | 0 | 51 | 20 | 86 | 67 | 0 | 0 | 29 | 68 | 58 | 75 | 60 | 71 | 56 | 0 | 39 | 0 | 156 |
| H3F3B | 0 | 2 | 6 | 20 | 92 | 37 | 0 | 0 | 206 | 304 | 20 | 100 | 31 | 68 | 69 | 0 | 0 | 0 | 398 |
| HBG1 | 0 | 0 | 198 | 119 | 19 | 172 | 0 | 0 | 346 | 372 | 525 | 36 | 26 | 8 | 90 | 7 | 15 | 5 | 172 |
| HELLS | 0 | 0 | 38 | 21 | 1024 | 77 | 106 | 0 | 19 | 40 | 73 | 34 | 41 | 50 | 18 | 531 | 1404 | 225 | 2294 |
| HIF1A | 1 | 6 | 634 | 6439 | 69 | 3963 | 0 | 0 | 1072 | 678 | 1252 | 3346 | 2460 | 2537 | 1237 | 7 | 39 | 11 | 9 |
| HJURP | 0 | 0 | 67 | 37 | 38 | 31 | 0 | 0 | 35 | 58 | 63 | 34 | 157 | 78 | 57 | 48 | 27 | 0 | 0 |
| HMMR | 0 | 0 | 95 | 6 | 0 | 23 | 0 | 0 | 34 | 29 | 97 | 38 | 104 | 24 | 29 | 0 | 9 | 4 | 16 |
| HNF4G | 0 | 1 | 5 | 32 | 38 | 11 | 0 | 0 | 19 | 6 | 0 | 1 | 10 | 0 | 8 | 187 | 1 | 44 | 133 |
| HOXB3 | 0 | 0 | 188 | 377 | 31 | 175 | 0 | 0 | 66 | 92 | 0 | 6 | 120 | 159 | 27 | 0 | 2 | 1719 | 0 |
| HOXB4 | 0 | 0 | 30 | 61 | 6 | 27 | 1 | 0 | 28 | 11 | 4 | 4 | 1 | 36 | 0 | 38 | 13 | 20 | 33 |
| HOXB7 | 0 | 0 | 7 | 57 | 10 | 47 | 0 | 0 | 72 | 55 | 0 | 34 | 45 | 59 | 53 | 0 | 1 | 10 | 0 |
| HOXD10 | 0 | 1 | 0 | 16 | 5 | 52 | 1 | 0 | 26 | 3 | 0 | 22 | 47 | 16 | 0 | 46 | 2 | 2 | 123 |
| HOXD3 | 0 | 0 | 0 | 0 | 5 | 0 | 0 | 6 | 21 | 5 | 29 | 5 | 42 | 1 | 26 | 0 | 49 | 16 | 147 |

| | | | | | | | | | | | | | | | | | | | | | | |
|---|---|---|---|---|---|---|---|---|---|---|---|---|---|---|---|---|---|---|---|---|---|---|
| | | | | | | | | | | | | | | | | | | | | + | + | + | |
| | | | | | | | | | | | | | | | | | | | | | | + | + |
| MMP16 | | | 1 | 0 | 86 | 40 | 49 | 9 | 32 | 1 | 15 | 26 | 24 | 71 | 37 | 32 | 18 | 3 | 0 | 2 | | | |
| MYBL2 | | | 0 | 0 | 57 | 20 | 10 | 17 | 0 | 13 | 74 | 35 | 11 | 19 | 4 | 15 | 0 | 14 | 0 | 2 | | | |
| N4BP2_HUMAN | | | 0 | 3 | 41 | 347 | 171 | 48 | 0 | 19 | 34 | 74 | 82 | 144 | 41 | 65 | 7 | 20 | 0 | 19 | | | |
| NCAPG | | | 0 | 1 | 27 | 26 | 34 | 27 | 5 | 7 | 32 | 31 | 11 | 41 | 12 | 17 | 37 | 10 | 6 | 77 | | | |
| NCAPH | | | 1 | 0 | 52 | 39 | 25 | 17 | 0 | 17 | 20 | 23 | 14 | 54 | 0 | 39 | 19 | 30 | 22 | 212 | | | |
| NDC80 | | | 0 | 0 | 3 | 6 | 7 | 28 | 0 | 19 | 22 | 29 | 32 | 60 | 24 | 67 | 0 | 35 | 0 | 200 | | | |
| NEK2 | | | 1 | 0 | 21 | 34 | 32 | 54 | 9 | 28 | 27 | 21 | 18 | 52 | 9 | 39 | 0 | 32 | 15 | 2 | | | |
| NUF2 | | | 0 | 0 | 65 | 45 | 34 | 96 | 7 | 26 | 56 | 49 | 6 | 84 | 20 | 40 | 28 | 90 | 25 | 98 | | | |
| NUSAP1 | | | 1 | 0 | 120 | 164 | 250 | 315 | 3 | 68 | 145 | 239 | 51 | 222 | 82 | 133 | 137 | 76 | 53 | 121 | | | |
| ORC1L | | | 0 | 0 | 61 | 61 | 84 | 84 | 0 | 21 | 47 | 50 | 31 | 46 | 108 | 90 | 0 | 55 | 29 | 42 | | | |
| PBK | | | 1 | 0 | 246 | 165 | 93 | 63 | 0 | 75 | 132 | 182 | 93 | 149 | 52 | 126 | 30 | 61 | 19 | 61 | | | |
| PLOD2 | | | 0 | 1 | 124 | 489 | 124 | 1278 | 0 | 413 | 73 | 229 | 52 | 71 | 359 | 422 | 7 | 6 | 18 | 182 | | | |
| POLQ | | | 1 | 0 | 12 | 18 | 12 | 32 | 28 | 6 | 5 | 7 | 6 | 19 | 6 | 27 | 19 | 29 | 15 | 2 | | | |
| PRKD1 | | | 0 | 1 | 4 | 19 | 57 | 36 | 81 | 21 | 18 | 31 | 33 | 32 | 10 | 24 | 0 | 1536 | 100 | 426 | | | |
| PTN | | | 0 | 0 | 1107 | 2319 | 1027 | 558 | 742 | 2139 | 2147 | 2748 | 2824 | 1412 | 431 | 1924 | 516 | 3044 | 912 | 4067 | | | |
| PTPRZ1 | | | 2 | 2 | 1281 | 12076 | 18775 | 2474 | 38 | 3442 | 11129 | 2842 | 13668 | 5833 | 3492 | 16273 | 2415 | 353 | 37 | 44 | | | |
| PTTG1 | | | 88 | 86 | 385 | 62 | 125 | 248 | 0 | 140 | 258 | 483 | 251 | 338 | 89 | 134 | 308 | 4 | 33 | 135 | | | |
| Q69GN2_HUMAN | | | 139 | 58 | 14 | 29 | 20 | 56 | 0 | 53 | 90 | 12 | 14 | 9 | 19 | 10 | 0 | 233 | 131 | 242 | | | |
| RRM2 | | | 10 | 13 | 494 | 1154 | 790 | 953 | 0 | 229 | 328 | 659 | 191 | 667 | 284 | 583 | 89 | 24 | 9 | 2 | | | |
| SAMD9 | | | 1 | 1 | 0 | 8 | 13 | 9 | 0 | 35 | 19 | 4 | 6 | 17 | 47 | 35 | 8 | 16 | 63 | 2 | | | |
| SGOL1 | | | 0 | 0 | 22 | 29 | 16 | 13 | 5 | 5 | 17 | 18 | 7 | 42 | 9 | 19 | 2 | 3 | 0 | 12 | | | |
| SHOX2 | | | 0 | 1 | 3 | 7 | 10 | 36 | 0 | 12 | 11 | 33 | 13 | 10 | 20 | 15 | 34 | 367 | 1046 | 387 | | | |
| SMC4 | | | 6 | 0 | 404 | 795 | 1242 | 3397 | 17 | 342 | 609 | 658 | 405 | 1056 | 817 | 445 | 176 | 41 | 7 | 121 | | | |
| SOX11 | | | 0 | 1 | 100 | 21 | 26 | 28 | 0 | 18 | 84 | 241 | 75 | 209 | 21 | 85 | 10 | 27 | 65 | 0 | | | |
| STC1 | | | 2 | 1 | 69 | 41 | 2 | 34 | 6 | 25 | 4 | 96 | 44 | 48 | 112 | 15 | 7 | 86 | 4 | 35 | | | |
| TACC3 | | | 2 | 1 | 64 | 124 | 79 | 229 | 0 | 23 | 27 | 82 | 15 | 109 | 61 | 54 | 12 | | | | | | |

FIG. 10
CONTINUED

| | | | | | | | | | | | | | | | | | |
|---|---|---|---|---|---|---|---|---|---|---|---|---|---|---|---|---|---|
| TBC1D8B | 1 | 2 | 23 | 33 | 100 | 41 | 109 | 14 | 19 | 25 | 33 | 12 | 52 | 18 | 12 | 2 | 14 | 0 |
| tcag7.929 | 1 | 0 | 5 | 3 | 27 | 3 | 90 | 10 | 8 | 6 | 28 | 7 | 19 | 5 | 14 | 2 | 0 | 0 |
| TPI | 4 | 4 | 197 | 102 | 238 | 57 | 12 | 183 | 45 | 21 | 66 | 118 | 90 | 23 | 120 | 37 | 53 | 95 | + |
| TGIF1 | 2 | 0 | 24 | 16 | 23 | 15 | 61 | 54 | 44 | 18 | 50 | 89 | 10 | 64 | 106 | 51 | 11 | 28 | + |
| TMEM45A | 4 | 8 | 0 | 23 | 2 | 667 | 13 | 94 | 52 | 343 | 139 | 46 | 987 | 449 | 277 | 134 | 0 | 676 | + |
| TMSL8 | 2 | 1 | 37 | 33 | 0 | 118 | 48 | 8 | 1 | 1 | 113 | 360 | 28 | 190 | 79 | 864 | 24 | 0 | + |
| TNC | 3 | 9 | 9 | 110 | 61 | 368 | 12 | 148 | 104 | 100 | 200 | 214 | 398 | 155 | 15 | 61 | 536 | 12 | + |
| TNFAIP6 | 6 | 9 | 10 | 332 | 162 | 152 | 0 | 2126 | 140 | 51 | 511 | 181 | 569 | 1039 | 405 | 46 | 29 | 347 | + |
| TNFRSF19 | 2 | 12 | 51 | 163 | 969 | 287 | 0 | 70 | 125 | 69 | 319 | 640 | 326 | 58 | 176 | 43 | 907 | 135 | + |
| TOP2A | 0 | 0 | 1650 | 1614 | 1792 | 2866 | 183 | 541 | 1746 | 2243 | 1546 | 3011 | 787 | 1919 | 1477 | 1273 | 47 | 894 | + |
| TPX2 | 2 | 1 | 131 | 69 | 25 | 108 | 4 | 53 | 137 | 81 | 51 | 97 | 35 | 22 | 61 | 62 | 96 | 5 | + |
| TROAP | 0 | 0 | 97 | 50 | 2 | 15 | 5 | 21 | 58 | 55 | 67 | 68 | 54 | 25 | 43 | 44 | 32 | 2 | + |
| TSKU | 1 | 2 | 17 | 41 | 2 | 54 | 20 | 62 | 16 | 12 | 14 | 22 | 4 | 25 | 14 | 14 | 108 | 9 | + |
| TMS | 2 | 11 | 448 | 228 | 457 | 832 | 13 | 130 | 232 | 251 | 147 | 483 | 77 | 291 | 87 | 91 | 57 | 282 | + |
| UBE2C | 2 | 0 | 131 | 32 | 14 | 22 | 59 | 25 | 92 | 75 | 39 | 76 | 18 | 11 | 25 | 37 | 8599 | 12 | + |
| VIM | 457 | 1297 | 22980 | 21254 | 19283 | 25798 | 1231 | 15975 | 2114 | 12460 | 11290 | 20530 | 12515 | 4386 | 4184 | 14662 | 0 | 18626 | + |
| WRN | 1 | 1 | 1 | 29 | 49 | 11 | 4 | 12 | 8 | 2 | 25 | 33 | 29 | 59 | 40 | 28 | 0 | 5 | + |
| ZNF700 | 1 | 1 | 4 | 12 | 17 | 28 | 0 | 24 | 8 | 2 | 28 | 19 | 51 | 23 | 0 | 30 | 0 | 158 | + |
| ZNF93 | 0 | 0 | 4 | 15 | 14 | 9 | 8 | 6 | 17 | 10 | 10 | 8 | 8 | 11 | 4 | 9 | 0 | 0 | + |

* NUMBERS INDICATED FOR EACH GENE CORRESPOND TO SAGE TAGS NORMALIZED PER MILLION TAGS. THE TOTAL NUMBER OF TAGS ANALYZED FOR EACH SAMPLE IS INDICATED ABOVE EACH SAMPLE NAME.
† GENES WERE CONSIDERED "OVEREXPRESSED" IF THE TUMOR EXPRESSION VALUES WERE MORE THAN TEN FOLD GREATER THAN THE HIGHEST NORMAL EXPRESSION VALUE FOR MOR THAN EIGHT TUMORS.
‡ GENES ARE INDICATED AS "EXTRACELLULAR" USING ANNOTATION FROM GENE ONTOLOGY CELLULAR COMPONENT NUMBERS RELATED TO THE EXTRACELLULAR COMPARTMENT, PLASMA MEMBRANE, AND CELL SURFACE. THIS INCLUDES GO:0016324, GO:0016327, GO:0016328, GO:0019867, GO:0019897, GO:0019898, GO:00310, GO:0031232, GO:0031233, GO:0031234, GO:0033162, GO:0044420, GO:0044421, GO:0044459, GO:0046658, AND GO:0045196.

FIG. 10
CONTINUED

| EXTRACELLULAR ‡ |
| --- |
| Y |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| N |
| Y |
| N |
| N |
| N |
| N |
| Y |
| N |
| N |
| N |
| N |
| N |
| N |

TABLE S10. GBM OVEREXPRESSED EXTRACELLULAR GENES*

| | NORMAL BRAIN 1 | NORMAL BRAIN 2 | Br01X | Br02X | Br05X | Br07X | Br10PT | Br13X | Br14X | Br15X | Br16X | Br17X | Br18X | Br19X | Br20PT | Br23PT | Br25x | Br26X |
|---|---|---|---|---|---|---|---|---|---|---|---|---|---|---|---|---|---|---|
| NUMBER OF TAGS SEQUENCED | 5319813 | 5374760 | 3193979 | 7971688 | 4558896 | 4692453 | 2656151 | 6017541 | 2688881 | 6036214 | 4852790 | 6046592 | 7686292 | 7884769 | 2935314 | 3716505 | 6256355 | 9644975 |
| NUMBER OF HIGH QUALITY SEQUENCE | 3890781 | 3811603 | 2996803 | 3846546 | 1914626 | 1603509 | 2284388 | 5608235 | 2600945 | 5409160 | 3054466 | 4109053 | 3002707 | 1517919 | 2566499 | 3248601 | 5595470 | 3311260 |
| NUMBER OF TAGS MATCHING KNOWN | 2539767 | 2539721 | 2210496 | 2626761 | 1253622 | 1124729 | 1127330 | 3445010 | 1330996 | 3680894 | 1951184 | 2996841 | 1816665 | 1032974 | 1779688 | 1987225 | 2410107 | 429345 |

| GENE | NORMAL BRAIN 1 | NORMAL BRAIN 2 | Br01X | Br02X | Br05X | Br07X | Br10PT | Br13X | Br14X | Br15X | Br16X | Br17X | Br18X | Br19X | Br20PT | Br23PT | Br25x | Br26X | OVEREXPRESSED† | EXTRACELLULAR‡ |
|---|---|---|---|---|---|---|---|---|---|---|---|---|---|---|---|---|---|---|---|---|
| ANXA1 | 11 | 13 | 76 | 40 | 200 | 626 | 30 | 433 | 449 | 152 | 253 | 254 | 303 | 17 | 41 | 264 | 37 | 389 | + | Y |
| CHRNA5 | 1 | 0 | 15 | 6 | 9 | 14 | 10 | 1 | 27 | 13 | 7 | 6 | 8 | 15 | 7 | 1 | 10 | 14 | + | Y |
| CRISPLD1 | 3 | 2 | 18 | 142 | 0 | 13 | 16 | 269 | 53 | 84 | 103 | 34 | 15 | 44 | 20 | 19 | 60 | 242 | + | Y |
| GALR1 | 0 | 0 | 0 | 0 | 82 | 0 | 0 | 3 | 7 | 26 | 43 | 24 | 0 | 66 | 8 | 10 | 0 | 151 | | Y |
| HMMR | 0 | 0 | 95 | 6 | 38 | 23 | 9 | 34 | 29 | 97 | 38 | 104 | 24 | 29 | 48 | 27 | 1153 | 0 | + | Y |
| IGFBP2 | 19 | 39 | 1097 | 2401 | 290 | 142 | 37 | 1725 | 518 | 1179 | 145 | 1087 | 527 | 171 | 409 | 482 | 14 | 26 | + | Y |
| IL1RAP | 7 | 3 | 90 | 11 | 1027 | 437 | 0 | 224 | 202 | 115 | 123 | 396 | 287 | 156 | 242 | 33 | 0 | 533 | + | Y |
| LEPRE1 | 1 | 0 | 9 | 8 | 15 | 25 | 32 | 12 | 3 | 4 | 17 | 11 | 76 | 12 | 0 | 16 | 0 | 0 | | Y |
| MMP16 | 1 | 1 | 66 | 40 | 49 | 9 | 28 | 1 | 15 | 26 | 33 | 7 | 37 | 24 | 18 | 3 | 1 | 2 | + | Y |
| PRKD1 | 2 | 2 | 4 | 19 | 57 | 36 | 81 | 21 | 18 | 31 | 23 | 32 | 10 | 32 | 0 | 29 | 100 | 12 | + | Y |
| PTN | 86 | 88 | 1107 | 2319 | 1027 | 558 | 742 | 2139 | 2147 | 2748 | 2824 | 1412 | 431 | 1924 | 516 | 1536 | 100 | 426 | + | Y |
| PTPRZ1 | 58 | 139 | 1281 | 12076 | 18775 | 2474 | 0 | 3442 | 11129 | 2842 | 13668 | 5833 | 3492 | 16273 | 2415 | 3044 | 912 | 4067 | + | Y |
| STC1 | 1 | 2 | 69 | 41 | 2 | 34 | 12 | 25 | 4 | 96 | 44 | 48 | 112 | 15 | 7 | 27 | 65 | 0 | + | Y |
| TPI | 4 | 4 | 197 | 102 | 238 | 57 | 0 | 183 | 45 | 21 | 66 | 118 | 90 | 23 | 120 | 37 | 24 | 95 | + | Y |
| TNC | 3 | 9 | 9 | 110 | 61 | 368 | 12 | 148 | 104 | 100 | 200 | 214 | 398 | 155 | 15 | 61 | 24 | 12 | + | Y |
| TNFAIP6 | 6 | 9 | 10 | 332 | 162 | 152 | 0 | 2126 | 140 | 51 | 544 | 181 | 569 | 1039 | 405 | 46 | 536 | 347 | + | Y |

*NUMBERS INDICATED FOR EACH GENE CORRESPOND TO SAGE TAGS NORMALIZED PER MILLION TAGS. THE TOTAL NUMBER OF TAGS ANALYZED FOR EACH SAMPLE IS INDICATED ABOVE EACH SAMPLE NAME.
† GENES WERE CONSIDERED "OVEREXPRESSED" IF THE TUMOR EXPRESSION VALUES WERE MORE THAN TEN FOLD GREATER THAN THE HIGHEST NORMAL EXPRESSION VALUE FOR MORE THAN EIGHT TUMORS.
‡ GENES ARE INDICATED AS "EXTRACELLULAR" USING ANNOTATION FROM GENE ONTOLOGY CELLULAR COMPONENT NUMBERS RELATED TO THE EXTRACELLULAR COMPARTMENT, PLASMA MEMBRANE, AND CELL SURFACE. THIS INCLUDES GO:0016324, GO:0016327, GO:0016328, GO:0019897, GO:0019898, GO:0031012, GO:0031226, GO:0031232, GO:0031233, GO:0031234, GO:0031362, GO:0044420, GO:0044421, GO:0044459, GO:0046658, AND GO:0048196.

Summary of genetic and clinical characteristics of brain tumors analyzed

| Tumor Classification | Tumors analyzed | Median age | Male (%) | Median survival (months) | Tumors with IDH1 mutations | Tumors with IDH2 mutations | Percent of tumors with IDH mutations | Median age of patients with IDH mutation | Median age of patients with wild type IDH | Percent of tumors with p53 mutations | Percent of tumors with 1p and 19q loss | Percent of tumors with PTEN mutations | Percent of tumors with EGFR amplification | Percent of tumors with CDKN2A/B loss |
|---|---|---|---|---|---|---|---|---|---|---|---|---|---|---|
| Diffuse astrocytoma | 31 | 33 | 55% | 132 | 26 | 1 | 84% | 35 | 10 | 50% | NA | NA | 0% | 0% |
| Anaplastic astrocytoma | 61 | 38 | 56% | 42 | 41 | 2 | 70% | 35 | 47 | 63% | 11% | 8% | 2% | 10% |
| Secondary GBM | 13 | 33 | 70% | 16 | 11 | 0 | 85% | 32 | 62 | 60% | NA | NA | 0% | 22% |
| Primary Adult GBM | 150 | 58.5 | 59% | 12 | 7 | NA | 5% | 32 | 59 | 24% | NA | 25% | 39% | 44% |
| Primary Pediatric GBM | 15 | 5 | 60% | 8 | 0 | NA | 0% | ND | 5 | 33% | NA | NA | NA | 20% |
| Oligodendroglioma | 51 | 37 | 63% | 135 | 41 | 2 | 84% | 37 | 19 | 16% | 60% | 0% | 0% | 3% |
| Anaplastic oligodendroglioma | 36 | 45 | 64% | 84 | 31 | 3 | 94% | 45 | 32 | 10% | 84% | 0% | 0% | 14% |
| Oligoastrocytoma | 3 | 38 | 67% | ND | 3 | NA | 100% | 38 | ND | NA | NA | NA | 0% | 0% |
| Anaplastic Oligoastrocytoma | 7 | 30 | 57% | ND | 7 | NA | 100% | 30 | ND | NA | NA | NA | 0% | 0% |
| Pleomorphic xanthoastrocytoma | 7 | 11 | 14% | 44 | 1 | NA | 14% | 20 | 11 | NA | NA | NA | 0% | NA |
| Pilocytic astrocytoma | 21 | 5 | 48% | ND | 0 | NA | 0% | NA | NA | NA | NA | NA | NA | NA |
| Subependymal giant cell astrocytoma | 2 | 16 | NA | ND | 0 | NA | 0% | NA | NA | NA | NA | NA | NA | NA |
| Ependymoma | 30 | 5.5 | 45% | ND | 0 | NA | 0% | NA | NA | NA | NA | NA | NA | NA |
| Medulloblastoma | 55 | 7 | 65% | 27 | 0 | NA | 0% | NA | NA | NA | NA | NA | NA | NA |

*Patient age refers to age at which the study sample was obtained. "Secondary GBM designates a GBM which was resected > 1 year after a prior diagnosis of a lower grade glioma (WHO I-III). Abbreviations: WHO (World Health Organization), M (male), NA (not analyzed), ND (not determined due to limited sample size and data censoring status). Of the indicated tumors, six secondary and 50 primary GBMs used previously described in Parsons et al. (16). Copy number changes of EGFR and CDKN2A/B were determined by quantitative real time PCR (Q-PCR). For Q-PCR, copy number levels >8 or <0.3 were considered amplifications or losses, respectively.

Fig. 12

Evaluation of the frequency of common genetic alterations in IDH1/2 mutated and wildtype gliomas.

| Tumor type | IDH1/2 mutation status | Total number of patients | TP53 mutated (%) | PTEN mutated (%) | EGFR amplified (%) | CDKN2A/B deleted (%) | 1p/19q LOH (%) |
|---|---|---|---|---|---|---|---|
| Oligodendroglioma | mut | 43 | 5/24 (21%) | 0/20 (0%) | 0/43 (0%) | 2/40 (5%) | 18/23 (78%) |
| | wt | 8 | 0/8 (0%) | 0/4 (0%) | 0/8 (0%) | 0/8 (0%) | 0/7 (0%) |
| | total | 51 | 5/32 (16%) | 0/24 (0%) | 0/51 (0%) | 2/48 (4%) | 18/30 (60%) |
| Anaplastic oligodendroglioma | mut | 34 | 3/30 (10%) | 0/28 (0%) | 0/33 (0%) | 3/33 (9%) | 27/30 (90%) |
| | wt | 2 | 0/2 (0%) | 0/2 (0%) | 0/2 (0%) | 2/2 (100%) | 0/2 (0%) |
| | total | 36 | 3/32 (10%) | 0/30 (0%) | 0/35 (0%) | 5/35 (14%) | 27/32 (84%) |
| Anaplastic astrocytoma | mut | 43 | 24/29 (83%) | 1/29 (3%) | 0/40 (0%) | 0/36 (0%) | 0/15 (0%) |
| | wt | 18 | 2/12 (17%) | 2/7 (29%) | 1/16 (6%) | 5/16 (31%) | 1/3 (33%) |
| | total | 61 | 26/41 (63%) | 3/36 (8%) | 1/56 (2%) | 5/52 (10%) | 1/18 (6%) |
| Secondary GBM | mut | 11 | 6/8 (75%) | nd | 0/9 (0%) | 1/7 (14%) | nd |
| | wt | 2 | 0/2 (0%) | nd | 0/2 (0%) | 1/2 (50%) | nd |
| | total | 13 | 6/10 (60%) | nd | 0/11 (0%) | 2/9 (22%) | nd |
| Primary GBM | mut | 7 | 6/7 (86%) | 0/7 (0%) | 0/8 (0%) | 0/8 (0%) | nd |
| | wt | 143 | 30/140 (21%) | 19/96 (20%) | 28/102 (28%) | 33/107 (31%) | nd |
| | total | 150 | 36/147 (24%) | 19/103 (19%) | 28/102 (28%) | 33/107 (31%) | nd |

US 8,685,660 B2

GENETIC ALTERATIONS IN ISOCITRATE DEHYDROGENASE AND OTHER GENES IN MALIGNANT GLIOMA

This application was made using funds from the United States government. Therefore the U.S. government retains certain rights in the invention under the terms of NIH grants CA 43460, CA 57345, CA 62924, R01CA118822, NS20023-21, R37CA11898-34, and CA 121113.

TECHNICAL FIELD OF THE INVENTION

This invention is related to the area of cancer diagnostics, prognostics, drug screening, and therapeutics. In particular, it relates to brain tumors in general, and glioblastoma multiforme, in particular.

BACKGROUND OF THE INVENTION

Gliomas, the most common type of primary brain tumors, are classified as Grade I to Grade IV using histopathological and clinical criteria established by the World Health Organization (WHO)[1]. This group of tumors includes a number of specific histologies, the most common of which are astrocytomas, oligodendrogliomas, and ependymomas. Grade I gliomas, often considered to be benign lesions, are generally curable with complete surgical resection and rarely, if ever, evolve into higher-grade lesions[2]. However, tumors of Grades II and III are malignant tumors that grow invasively, progress to higher-grade lesions, and carry a correspondingly poor prognosis. Grade IV tumors (glioblastoma multiforme, GBM) are the most invasive form and have a dismal prognosis[3, 4]. Using histopathologic criteria, it is impossible to distinguish a secondary GBM, defined as one which occurs in a patient previously diagnosed with a lower grade glioma, from a primary GBM which has no known antecedent tumor[5, 6].

A number of genes are known to be genetically altered in gliomas, including TP53, PTEN, CDKN2A, and EGFR[7-12]. These alterations tend to occur in a defined order in the progression to high grade tumors. TP53 mutation appears to be a relatively early event during astrocytoma development, while loss or mutation of PTEN and amplification of EGFR are characteristic of higher-grade tumors[6,13,14]. In oligodendrogliomas, allelic losses of 1p and 19q occur in many Grade II tumors while losses of 9p21 are largely confined to Grade III tumors[15].

There is a continuing need in the art to identify the causes, identifiers, and remedies for glioblastomas and other brain tumors.

SUMMARY OF THE INVENTION

According to one aspect of the invention a method is provided of characterizing a glioblastoma multiforme (GBM) tumor in a human subject. A GBM tumor is analyzed to identify the presence or absence of a somatic mutation at codon 132 in isocitrate dehydrogenase 1 (IDH1) or at codon 172 in isocitrate dehydrogenase 2 (IDH2) in a GBM tumor of a human subject.

Also provided as another aspect of the invention is an isolated antibody which specifically binds R132H IDH1, or R132C IDH1, or R132S IDH1, or R132L IDH1, or R132G IDH1, but not R132 IDH1; or R172M IDH2, R172G IDH2, or R172K IDH2, but not R172; i.e., mutant forms of IDH1 or IDH2 which are found in GBM. Also provided is an isolated antibody which specifically binds R132 IDH1 or R172 IDH2, i.e., wild-type active sites of IDH1 or IDH2.

Another aspect of the invention is a method of immunizing a mammal. An IDH1 mutant polypolypeptide comprising at least 8 contiguous amino acid residues of a human IDH1 protein or an IDH2 mutant polypolypeptide comprising at least 8 contiguous amino acid residues of a human IDH2 protein found in a human tumor is administered to a mammal. The at least 8 contiguous amino acid residues comprise residue 132 or IDH1 or residue 172 of IDH2. Residue 132 or residue 172 is not arginine. Antibodies and/or T cells which are immunoreactive with epitopes found on the IDH1 or IDH2 mutant polypeptide but not found on normal IDH1 or IDH2 are produced.

Also provided as another aspect of the invention is an IDH1 or IDH2 mutant polypeptide comprising at least 8 but less than 200 contiguous amino acid residues of a human IDH1 or IDH2 protein found in a human tumor. The at least 8 contiguous amino acid residues comprise residue 132 of IDH1 or residue 172 of IDH2. Residues 132 or 172 are not R.

An additional aspect of the invention is an isolated polynucleotide comprising at least 18 but less than 600 contiguous nucleotide residues of a coding sequence of a human IDH1 or human IDH2 protein found in a human tumor. The at least 18 contiguous amino acid residues comprise nucleotides 394 and/or 395 of IDH1 or nucleotide 515 or IDH2. Nucleotides 394 and/or 395 of IDH1 are not C and/or G, respectively. Residue 515 of IDH2 is not G.

Another aspect of the invention is a method of immunizing a mammal. An IDH1 polypeptide comprising at least 8 contiguous amino acid residues of a human IDH1 protein or an IDH2 polypeptide comprising at least 8 contiguous amino acid residues of a human IDH2 protein is administered to a mammal. The at least 8 contiguous amino acid residues comprise residue 132 of IDH1 or residue 172 of IDH2. Residue 132 or residue 172 is arginine. Antibodies and/or T cells which are immunoreactive with epitopes found on the IDH1 or IDH2 polypeptide are produced.

Also provided as another aspect of the invention is an IDH1 or IDH2 polypeptide comprising at least 8 but less than 200 contiguous amino acid residues of a human IDH1 or IDH2 protein. The at least 8 contiguous amino acid residues comprise residue 132 of IDH1 or residue 172 of IDH2. Residues 132 or 172 are R.

Still another aspect of the invention is a method of detecting or diagnosing glioblastoma multiforme (GBM) or minimal residual disease of GBM or molecular relapse of GBM in a human. A somatic mutation in a gene or its encoded mRNA or protein is determined in a test sample relative to a normal sample of the human. The gene is selected from the group consisting of those listed in FIG. 10, Table S7. The human is identified as likely to have glioblastoma multiforme, minimal residual disease, or molecular relapse of GBM when the somatic mutation is determined.

Yet another aspect of the invention is a method of characterizing a glioblastoma multiforme in a human. A CAN-gene mutational signature for a glioblastoma multiforme is determined by determining in a test sample relative to a normal sample of the human, a somatic mutation in at least one gene or its encoded cDNA or protein. The gene is selected from the group consisting of those listed in FIG. 10, Table S7. The glioblastoma multiforme is assigned to a first group of glioblastoma multiforme tumors that have the CAN-gene mutational signature.

Another method provided by the invention is for characterizing a glioblastoma multiforme tumor in a human. A mutated pathway selected from the group consisting of TP53, RB1, and PI3K/PTEN is identified in a glioblastoma multiforme tumor by determining at least one somatic mutation in a test sample relative to a normal sample of the human. The at least one somatic mutation is in one or more genes selected from the group consisting of TP53, MDM2, MDM4, RB1, CDK4, CDKN2A, PTEN, PIK3CA, PIK3R1, and IRS1. The glioblastoma multiforme is assigned to a first group of glioblastoma multiforme tumors that have a mutation in one of said pathways. The first group is heterogeneous with respect to the genes in the pathway that have a somatic mutation and homogeneous with respect to the pathway that has a somatic mutation.

Also provided is a method to detect or diagnose glioblastoma multiforme, or minimal residual disease of GBM or molecular relapse of GBM in a human. Expression is determined in a clinical sample of one or more genes listed in FIG. 10, Table S5 or S9 (brain overexpressed genes from SAGE). The expression of the one or more genes in the clinical sample is compared to expression of the one or more genes in a corresponding sample of a control human or control group of humans. A clinical sample with elevated expression relative to a control is identified as likely to have glioblastoma multiforme, or minimal residual disease of GBM or molecular relapse of GBM in a human.

Another aspect of the invention is a method to monitor glioblastoma multiforme burden. Expression in a clinical sample is determined of one or more genes listed in FIG. 10, Table S5 or S9 (brain overexpressed genes from SAGE). The step of determining is repeated one or more times. An increase, decrease or stable level of expression over time is identified.

Yet another aspect of the invention is a method to monitor glioblastoma multiforme burden. A somatic mutation is determined in a clinical sample of one or more genes listed in FIG. 10, Table S7. The step of determining is repeated one or more times. An increase, decrease or stable level of said somatic mutation over time is identified.

Still another aspect of the invention relates to a method to detect or diagnose gliobastoma multiforme. Expression in a clinical sample of one or more genes listed in FIG. 10, Table S6 (homozygous deletions) is determined. Expression of the one or more genes in the clinical sample is compared to expression of the one or more genes in a corresponding sample of a control human or control group of humans. A clinical sample with reduced expression relative to a control is identified as likely to have gliobastoma multiforme.

A further aspect of the invention is a method to monitor glioblastoma multiforme burden. Expression in a clinical sample of one or more genes listed in FIG. 10, Table S6 (homozygous deletions) is determined. The step of determining is repeated one or more times. An increase, decrease or stable level of expression over time is identified.

These and other embodiments which will be apparent to those of skill in the art upon reading the specification provide the art with new tools for analyzing, detecting, stratifying and treating GBM.

BRIEF DESCRIPTION OF THE DRAWINGS

FIG. 4A. Schematic diagram of mutations at codon R132 in IDH1 (bottom) and R172 in IDH2 (top) identified in human gliomas. Codons 130 to 134 of IDH1 and 170 to 174 of IDH2 are shown. The number of patients with each mutation (n) is listed at the right of the figure. FIG. 4B. Number and frequency of IDH1 and IDH2 mutations in human gliomas and other tumor types. The non-CNS cancers included 35 lung cancers, 57 gastric cancers, 27 ovarian cancers, 96 breast cancers, 114 colorectal cancers, 95 pancreatic cancers, seven prostate cancers, and peripheral blood specimens from 4 chronic myelogenous leukemias, 7 chronic lymphocytic leukemias, seven acute lymphoblastic leukemias, and 45 acute myelogenous leukemias.

FIG. 7. Sequence alterations in IDH1 and IDH2. Representative examples of somatic mutations at codon 132 of the IDH1 gene (top) and codon 172 of the IDH2 gene (bottom). In each case, the top sequence chromatogram was obtained from analysis of DNA from normal tissue while the lower chromatograms were obtained from the indicated tumor samples. Arrows indicate the location of the missense mutations and resulting amino acid changes in IDH1 in tumor TB2604 (anaplastic astrocytoma), 640 (anaplastic astrocytoma), and 1088 (anaplastic oligodendroglioma), and in IDH2 in tumor H883 (anaplastic astrocytoma) and H476 (anaplastic oligodendroglioma).

FIG. 11. Summary of genetic and clinical characteristics of brain tumors.

FIG. 12. Evaluation of frequency of common genetic alterations in IDH1/IDH2 mutated and wildtype gliomas.

Figure 1:
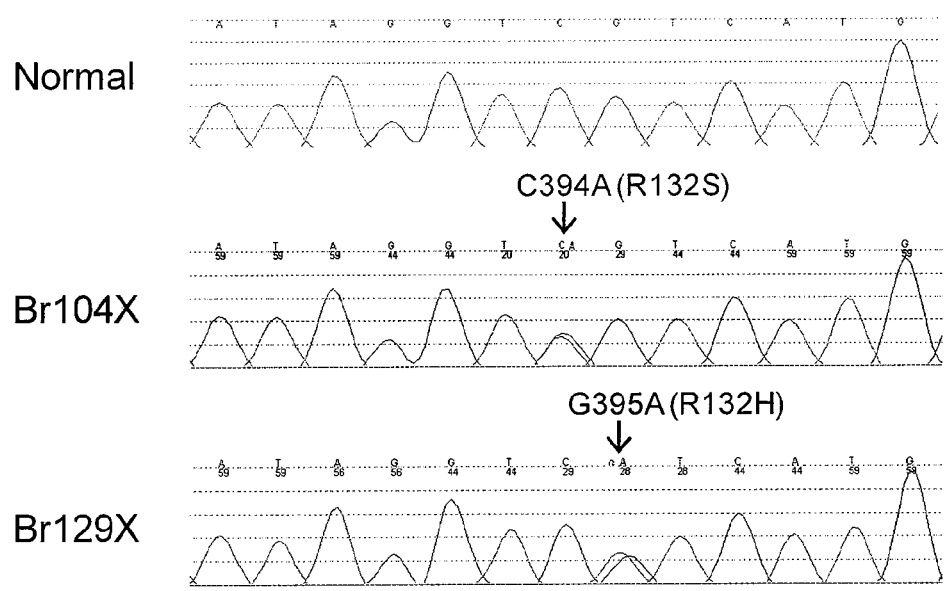
FIG. 1. Sequence alterations in IDH1. Representative examples of somatic mutations at codon 132 of the IDH1 gene. The top sequence chromatogram was obtained from analysis of DNA from normal tissue while the lower chromatograms were obtained from the indicated GBM samples. Arrows indicate the location of the recurrent heterozygous missense mutations C394A (in tumor Br104X) and G395A (in tumor Br129X) resulting in the indicated amino acid changes.

A sequence listing is part of this application.

DETAILED DESCRIPTION OF THE INVENTION

In a genome-wide analysis of GBMs, we identified somatic mutations of codon 132 of the isocitrate dehydrogenase 1 gene (IDH1) in ~12% of GBMs analyzed[16]. These mutations were found at higher frequency in secondary GBMs (5 of 6 patients evaluated). One interpretation of these data is that IDH1 mutations occur in a subset of lower-grade gliomas, driving them to progress to GBMs. To evaluate this possibility, we have analyzed a large number of gliomas of various types. Remarkably, we found IDH1 mutations in the majority of early malignant gliomas. Furthermore, many of the gliomas without IDH1 mutations had analogous mutations in the closely related IDH2 gene. These results suggest that IDH mutations play an early and essential role in malignant glioma development.

Somatic mutations are mutations which occur in a particular clone of somatic cells during the lifetime of the individual organism. The mutation is thus not inherited or passed on. The mutation will appear as a difference relative to other cells, tissues, organs. When testing for a somatic mutation in a brain tissue suspected of being cancerous, a comparison can be made to normal brain tissue that appears to be non-neoplastic, or to a non-brain sample, such as blood cells, or to a sample from an unaffected individual.

The common amino acid at codon 132 of IDH1 and codon 172 of IDH2 in healthy tissues is arginine (R). Mutant codons have been found with substitutions of histidine (H), serine (S), and cysteine (C), leucine (L), and glycine (G) of IDH1 codon 132 and of methionine (M), lysine (K), and glycine (G) of codon 172 of IDH2. The mutations at codon 132 and codon 172 can be detected using any means known in the art, including at the DNA, mRNA, or protein levels. Antibodies which specifically bind to the arginine-132 form of the enzyme, the histidine-132 form of the enzyme, the serine-132 form of the enzyme, leucine-132 form of the enzyme, glycine-132 form of the enzyme, or the cysteine-132 form of the enzyme can be used in assays for mutation detection. Likewise antibodies which specifically bind to the arginine-172, methionine-172, lysine-172, or glycine-172 forms of IDH2 can be used in assays for mutation detection. Similarly, probes which contain codons for these amino acid residues in the context of the coding sequence of IDH1 or IDH2 can be used for detecting the gene or mRNA of the different forms. Primers which contain all or part of these codons can also be used for allele-specific amplification or extension. Primers hybridizing to regions surrounding these codons can be used to amplify the codons, followed by subsequent analysis of the amplified region containing codon 132 of IDH1 or codon 172 of IDH2.

Interestingly, the codon 132 mutations of IDH1 and codon 172 mutations of IDH2 have been found to be strongly associated with secondary GBM and with a favorable prognosis. Drugs can be tested against groups of glioblastoma patients that are stratified with regard to the $132^{nd}$ amino acid residue of IDH1 and/or the $172^{nd}$ amino acid residue of IDH2. The groups may comprise wild-type (arginine) and variants (combined) or variants (each separately). Drug sensitivity can be determined for each group to identify drugs which will or will not be efficacious relative to a particular mutation or wild-type (arginine). Both sensitivity and resistance information are useful to guide treatment decisions.

Once a codon 132 or 172 mutation is identified in a tumor, inhibitors of IDH1 or IDH2 may be used therapeutically. Such inhibitors may be specific for a mutation in the tumor or may simply be an inhibitor of IDH1 or IDH2. Small molecule inhibitors as well as antibodies and antibody-derivatives can be used. Such antibodies include monoclonal and polyclonal antibodies, ScFv antibodies, and other constructs which comprise one or more antibody Fv moieties. Antibodies can be humanized, human, or chimeric, for example. Antibodies may be armed or unarmed. Armed antibodies may be conjugated to toxins or radioactive moieties, for example. Unarmed antibodies may function to bind to tumor cells and participate in host immunological processes, such as antibody-dependent cell-mediated cytotoxicity. Antibodies may preferentially bind to mutant versus wild-type IDH1 or IDH2, specifically bind to mutant versus wild-type IDH1 or IDH2, or bind equally to both mutant and wild-type IDH1 or IDH2. Preferably the antibodies will bind to an epitope in the active site which may include codon 132 or codon 172. Epitopes may be continuous or discontinuous along the primary sequence of the protein. Inhibitors may include alpha-methyl isocitrate, aluminum ions, or oxalomalate. Other inhibitors may be used and optionally identified using enzyme assays known in the art, including spectrophotometric assays (Kornberg, A., 1955) and bioluminescent assays (Raunio, R. et al., 1985). Inhibitors may be alternatively identified by binding tests, for example by in vitro or in vivo binding assays. Peptides and proteins which bind to IDH1 or IDH2 may also be used as inhibitors.

Inhibitory RNA molecules may be used to inhibit expression. These may be, for example, siRNA, microRNA or antisense oligonucleotides or constructs. These can be used to inhibit the expression of IDH1 or IDH2 as appropriate in a human.

Potential therapeutic efficacy can be tested for an antibody, polynucleotide, protein, small molecule, or antibody by contacting with cells, tissues, whole animals, or proteins. Indications of efficacy include modulation of enzyme activity, inhibition of cancer cell growth, prolongation of life expectancy, inhibition of cancer cell proliferation, stimulation of cancer cell apoptosis, and inhibition or retardation of tumor growth. Any assays known in the art can be used, without limitation. Combinations of candidates and combinations of candidates with known agents can be assessed as well. Known agents may include, for example, chemotherapeutic anti-cancer agents, biological anti-cancer agents, such as antibodies and hormones, radiation.

In order to raise or increase an immune response to a glioblastoma in a person or mammal with a tumor, in a person with a likelihood of developing a tumor, or in an apparently healthy individual, a polypeptide can be administered to the person or mammal. The polypeptide will typically comprise at least 6, at least 8, at least 10, at least 12, or at least 14 contiguous amino acid residues of human IDH1 protein including residue 132 or IDH2 including residue 172. Typically but not always, the polypeptide will contain a residue other than arginine at residue 132 of IDH1 or residue 172 or IDH2. In the situation where the person or mammal already has a tumor, the amino acid at residue 132 can be matched to the residue in the tumor. The polypeptide may comprise the whole of IDH1, but can comprise less than 200, less than 150, less than 100, less than 50, less than 30 amino acid residues. Although applicants do not wish to be bound by any mechanism of action, the polypeptide immunization may act though an antibody and/or T cell response. Polypeptides can be administered with immune adjuvants or conjugated to moieties which stimulate an immune response. These are well known in the art, and can be used as appropriate.

Antibodies which specifically bind to an epitope on IDH1 or IDH2 do so with a higher avidity or a higher association rate than they bind to other proteins. Preferably the higher avidity or rate of association is at least about 2-fold, 5-fold, 7-fold, or 10-fold relative to other proteins that do not contain the epitope.

An isolated polynucleotide can be used to encode and deliver the polypeptide for immunization. The polynucleotide can be used to manufacture the polypeptide in a host cell in culture, or may be used in a gene therapy context to raise an immune response in vivo upon expression in the vaccine recipient. Polynucleotides can also be used as primers or probes, which may or may not be labeled with a detectable label. Primers can be used for primer extension, for example, using a primer that is complementary to nucleotides adjacent to but not including either nt 394 or nt 395 of IDH1 or nucleotide 515 of IDH2. Products can be detected and distinguished using labeled nucleotides as reagents. Different labels may be used on different nucleotides so that the identity of the analyte can be readily determined. Typically the polynucleotide for use as a primer or probe will comprise at least 10, at least 12, at least 14, at least 16, at least 18, at least 20 contiguous nucleotides of IDH1 or IDH2 coding sequence. Typically the polynucleotide will comprise less than 600, less than 500, less than 400, less than 300, less than 200, less than 100 nucleotides of IDH1 or IDH2 coding sequence.

Our data identified IDH1 as a major target of genetic alteration in patients with GBM. All mutations in this gene resulted in amino acid substitutions at position 132, an evolutionarily conserved residue located within the isocitrate binding site (42). In addition, the only previously-reported mutation of IDH1 was another missense mutation affecting this same residue in a colorectal cancer patient (10). The functional effect of these IDH1 mutations is unclear. The recurrent nature of the mutations is reminiscent of activating alterations in other oncogenes such as BRAF, KRAS, and PIK3CA. The prediction that this mutation would be activating is strengthened by the lack of observed inactivating changes (i.e. frameshift or stop mutations, splice site alterations), the lack of alterations in other key residues of the active site, and by the fact that all mutations observed to date were heterozygous (without any evidence of loss of the second allele through LOH). Interestingly, enzymatic studies have shown that substitution of arginine at residue 132 with glutamate results in a catalytically inactive enzyme suggesting that this residue plays a critical role in IDH1 activity (46). However, the nature of the substitutions observed in GBMs is qualitatively different, with arginine changed to histidine or serine. Histidine forms hydrogen bonding interactions, with carboxylate as part of the catalytic activity of many enzymes (47), and could serve an analogous function to the known interaction of Arg132 and the α-carboxylate of isocitrate. It is conceivable that R132H alterations may lead to higher overall catalytic activity. Increased activity of IDH1 would be expected to result in higher levels of NADPH, providing additional cellular defenses against reactive oxygen species, preventing apoptosis and increasing cellular survival and tumor growth. Further biochemical and molecular analyses will be needed to determine the effect of alterations of IDH1 on enzymatic activity and cellular phenotypes.

Regardless of the specific molecular consequences of IDH1 and IDH2 alterations, it is clear that detection of mutations in IDH1 and IDH2 will be clinically useful. Although significant effort has focused on the identification of characteristic genetic lesions in primary and secondary GBMs, the altered genes identified to date are far from perfect for this purpose. For example, in comparing primary versus secondary GBMs, TP53 is mutated in ~30% vs. 65%, respectively, EFGR amplification is present in ~35% vs. 5-10%, and PTEN mutation is present in ~25% vs. ~5% (5). Our study revealed IDH1 mutation to be a novel and significantly more specific marker for secondary GBM, with 5 of the 6 (83%) secondary GBM samples analyzed having a mutation in this gene, while only 7 of 99 (7%) primary GBM patients had such alterations (P<0.001, binomial test). The sole secondary GBM patient sample that did not have an IDH1 mutation was both genetically and clinically unusual, harboring mutations of PTEN but not TP53, and occurring in an older patient (age 56 years) with a prior diagnosis of ganglioglioma (which is rarely known to undergo malignant transformation) (48). It is possible that this patient had two distinct CNS tumors which were completely unrelated, and that the GBM in this case was actually a primary tumor.

One intriguing hypothesis is that IDH1 alterations identify a biologically-specific subgroup of GBM patients, including both patients who would be classified as having secondary GBMs as well as a subpopulation of primary GBM patients with a similar tumor biology and more protracted clinical course (Table 4). Interestingly, patients with IDH1 mutations had a very high frequency of TP53 mutation and a very low frequency of mutations in other commonly-altered GBM genes. For example, such patients had TP53 mutation without any detected mutation of EGFR, PTEN, RB1, or NF1 in 83% of cases (10 of 12 patients); in contrast, only 12% of patients with wildtype IDH1 (11 of 93) had the same mutation pattern (FIG. 12) (P<0.001, binomial test). In addition to this relative genetic uniformity, the patients with mutated IDH1 had distinct clinical characteristics, including younger age and a significantly improved clinical prognosis (Table 4) even after adjustment for age and TP53 mutation status (both of which are associated with improved survival). Perhaps most surprisingly, they all shared mutation of a single amino acid residue of IDH1, a protein that previously had no genetic link to GBMs or other cancers. This unforeseen result clearly validates the utility of genome-wide screening for genetic alterations in the study of human cancers.

Figure 10:
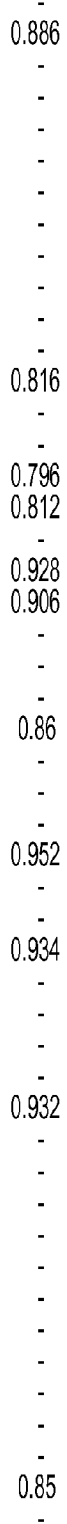
FIG. 10. Compendium of Tables S3-S10. Table S3 (somatic mutations identified in GBM discovery screen). Tables S4 (somatic mutations in prevalence screen), Table S5 (amplified genes), Table S6 (homozygously deleted genes), Table S7 (top CAN-candidate genes), Table S8 (candidate gene sets enriched for genetic alterations in GBM), Table S9 (overexpressed genes in SAGE), and Table S10 (extracellular subset of overexpressed genes in SAGE).
Figure 13:
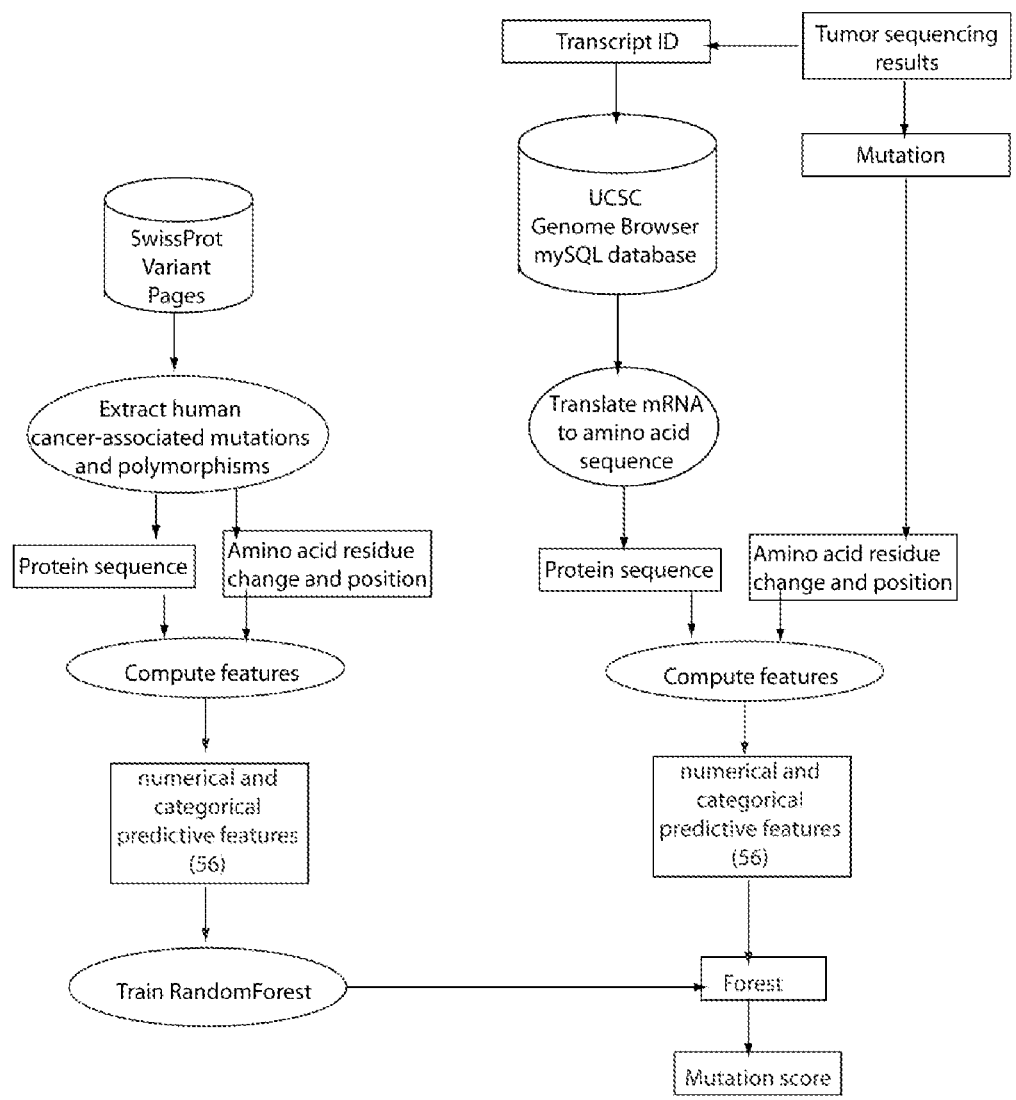
FIG. 13 shows the bioinformatics software pipeline to compute mutation scores. A supervised machine learning prediction algorithm (RandomForest) is trained on ~22,000 annotated variants (cancer-associated mutations and polymorphism) from the SwissProt variant pages. At total of 56 numeric and categorical predictive features are calculated for each variant.

Mutations that have been found in GBM tumors are shown in FIG. 10, Table S7. These mutations can be detected in test samples, such as suspected tumor tissue samples, blood, CSF, urine, saliva, lymph etc. A somatic mutation is typically determined by comparing a sequence in the test sample to a sequence in a normal control sample, such as from healthy brain tissue. One or more mutations can be used for this purpose. If the patient has undergone surgery, detection of the mutation in tumor margin or remaining tissue can be used to detect minimal residual disease or molecular relapse. If GBM has been previously undiagnosed, the mutation may serve to help diagnose, for example in conjunction with other physical findings or laboratory results, including but not limited to biochemical markers and radiological findings.

CAN-gene signatures can be determined in order to characterize a GBM. A signature is a set of one or more somatic mutations in a CAN gene. The CAN genes for GBM are listed in FIG. 10, Table S7. Once such a signature has been determined, a GBM can be assigned to a group of GBMs sharing the signature. The group can be used to assign a prognosis, to assign to a clinical trial group, to assign to a treatment regimen, and/or to assign for further characterization and studies. In a clinical trial group, drugs can be assessed for the ability to differentially affect GBMs with and without the signature. Once a differential effect is determined, the signature can be used to assign patients to drug regimens, or to avoid unnecessarily treating patients in whom the drug will not have a beneficial effect. The drug in a clinical trial can be one which is previously known for another purpose, previously known for treating GBM, or previously unknown as a therapeutic. A CAN-gene signature may comprise at least 1, at least 2, at least 3, at least 4, at least 5, at least 6, at least 7, at least 8, at least 9. at least 10 genes. The number of genes or mutations in a particular signature may vary depending on the identity of the CAN genes in the signature. Standard statistical analyses can be used to achieve desired sensitivity and specificity of a CAN gene signature.

Analysis of the mutated genes in the analyzed GBM tumors has revealed interesting involvement of pathways. Certain pathways frequently carry mutations in GBMs. A single gene mutation appears to exclude the presence of a mutation in another gene in that pathway in a particular tumor. Frequently mutated pathways in GBMs are the TP53, RB1, PI3K/PTEN pathways. Pathways can be defined using any of the standard reference databases, such as MetaCore Gene Ontology (GO) database, MetaCore canonical gene pathway maps (MA) database, MetaCore GeneGo (GG) database, Panther, TRMP, KEGG, and SPAD databases. Groups can be formed based on the presence or absence of a mutation in a certain pathway. Such groups will be heterogeneous with respect to mutated gene but homogeneous with respect to mutated pathway. As with CAN gene signatures, these groups can be used to characterize a GBM. Once a mutation in a pathway has been determined, a GBM can be assigned to a group of GBMs sharing the mutated pathway. The group can be used to assign a prognosis, to assign to a clinical trial group, to assign to a treatment regimen, and/or to assign for further characterization and studies. In a clinical trial group, drugs can be assessed for the ability to differentially affect GBMs with and without the mutated pathway. Once a differential effect is determined, the pathway can be used to assign patients to drug regimens, or to avoid unnecessarily treating patients in whom the drug will not have a beneficial effect. The drug in a clinical trial can be one which is previously known for another purpose, previously known for treating GBM, or previously unknown as a therapeutic. Among the genes in the pathways which may be found mutant are: TP53, MDM2, MDM4, RB1, CDK4, CDKN2A, PTEN, PIK3CA, PIK3RI, and IRS 1. This list is not necessarily exhaustive.

Expression levels can be determined and overexpression may be indicative of a new GBM tumor, molecular relapse, or minimal residual disease of GBM. Highly increased expression found in GBM tumors are shown in FIG. 10, Table S5 and FIG. 10, Table S9. These overexpressed genes can be detected in test samples, such as suspected tumor tissue samples, blood, CSF, urine, saliva, lymph etc. Elevated expression is typically determined by comparing expression of a gene in the test sample to expression of a gene in a normal control sample, such as from healthy brain tissue. Elevated expression of one or more genes can be used for this purpose. If the patient has undergone surgery, detection of the elevated expression in tumor margin or remaining tissue can be used to detect minimal residual disease or molecular relapse. If GBM has been previously undiagnosed, the elevated expression may serve to help diagnose, for example in conjunction with other physical findings or laboratory results, including but not limited to biochemical markers and radiological findings. For these purposes, any means known in the art for quantitating expression can be used, including SAGE or microarrays for detecting elevated mRNA, and antibodies used in various assay formats for detecting elevated protein expression. For detecting protein expression, the genes listed in FIG. 10, Table S10 are particularly useful.

Tumor burden can be monitored using the mutations listed in FIG. 10, Table S7. This may be used in a watchful waiting mode, or during therapy to monitor efficacy, for example. Using a somatic mutation as a marker and assaying for level of detectable DNA, mRNA, or protein over time, can indicate tumor burden. The level of the mutation in a sample may increase, decrease or remain stable over the time of analysis. Therapeutic treatments and timing may be guided by such monitoring.

Analysis of the GBMs revealed certain genes which are homozygously deleted. These are listed in FIG. 10, Table S6. Determining loss of expression of one or more of these genes can be used as a marker of GBM. This may be done in a sample of blood or lymph node or in a brain tissue sample. Expression of one or more of these genes may be tested. Techniques such as ELISA or IHC may be used to detect diminution or loss of protein expression in a sample. Similarly the homozygously deleted genes listed in FIG. 10, Table S6 may be used to monitor tumor burden over time. Expression can be repeatedly monitored so that in increase, decrease, or stable level of expression can be ascertained.

The data resulting from this integrated analysis of mutations and copy number alterations have provided a novel view of the genetic landscape of glioblastomas. The combination of different types of genetic data, including point mutations, amplifications, and deletions allows for identification of individual CAN-genes as well as groups of genes that may be preferentially affected in complex cellular pathways and processes in GBMs. Identification of virtually all genes previously shown to be affected in GBMs by mutation, amplification, or deletion validates the comprehensive genomic approach we have employed.

It should be noted, however, that our approach, like all genome-wide studies, has limitations. First we did not assess chromosomal translocations, which is one type of genetic alteration that could play an important role in tumorigenesis. However, observations of recurrent chromosomal translocations have only rarely been reported in cytogenetic studies of GBM. We also did not assess epigenetic alterations, though our large scale expression studies should have identified any genes that were differentially expressed through this mechanism (FIG. 10, Table S9). Additionally, for copy number changes we focused on regions that were truly amplified or homozygously deleted as these have historically been most useful in identifying cancer genes. The SNP array data we have generated for these samples, however, contains information that can be analyzed to determine loss of heterozygosity (LOH) or small copy number gains due to duplications rather than true amplification events. Analysis of such data for known cancer genes, such as CDKN2A or NF1, identified additional tumors that had LOH in these regions, but given the substantial fraction of the genome that undergoes LOH in GBMs, such observations are in general not likely to be helpful in pinpointing new candidate cancer genes. Finally, the primary tumors used in our analysis contained small amounts of contaminating normal tissue, as is the rule for this sample type, which limited our ability to detect homozygous deletions and to a lesser extent, somatic mutations, in those specific tumors. This was true even though we carefully selected these tumors to contain a minimal stromal component by histological and molecular biologic criteria. This observation serves as an important reminder of the value of early passage xenografts and cell lines for such large scale genomic studies.

Despite these limitations, our studies provide a number of important genetic and clinical insights into GBMs. The first of these is that the pathways known to be altered in GBMs affect a larger fraction of gene members and patients than previously anticipated. A majority of the tumors analyzed had alterations in members of each of the TP53, RB1, and PI3K pathways. The fact that all but one of the cancers with mutations in members of a pathway did not have alterations in other members of the same pathway is significant and suggests that such alterations are functionally equivalent in tumorigenesis. These observations also point to distinct opportunities for potential therapeutic intervention in these pathways in GBMs. The second observation is that a variety of new genes and pathways not previously implicated in GBMs were identified. Among the new pathways detected, a number of these appear to be involved in brain specific ion transport and signaling processes and represent interesting and potentially useful aspects of GBM biology.

These data immediately raise questions with important implications for the treatment and counseling of patients with GBMs as well as those with lower-grade gliomas. For example, are mutations in IDH also present in a subset of patients diagnosed with lower-grade gliomas (WHO grades I-III)? If IDH1 mutations are indeed found to be a relatively early genetic event in glioma progression, are these patients at increased risk of progression to GBM? Given the significant clinical difficulty of deciding which low grade glioma patients will receive adjuvant radiation therapy or chemotherapy (and how aggressive treatment should be), the knowledge that a patient is at increased risk for malignant progression would significantly alter the risk-benefit analysis of such treatment decisions. For pediatric patients, in whom radiation therapy can have particularly devastating effects on neurocognitive development and function, these decisions are particularly difficult and any additional risk-classification would be especially useful. IDH mutations may also provide one biological explanation for the occasional long-term GBM survivor, and could help to identify patients that would receive particular benefit from specific currently-available therapies. The utility of IDH as a clinical marker is likely to be enhanced by the fact that only a single codon of the gene needs to be examined to determine mutation status. Finally, it is conceivable that new treatments may be designed to take advantage of these IDH alterations, either as monotherapy or in combination with other agents. Along these lines, inhibition of mitochondrial IDH2 has recently been shown to result in increased sensitivity of tumor cells to a variety of chemotherapeutic agents (49). In summary, this finding of IDH mutations in a subset of GBM patients and in at least one other cancer type opens a new avenue of research that could illuminate a previously unappreciated aspect of human tumorigenesis.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods

DNA was extracted from primary tumor and xenograft samples and patient-matched normal blood lymphocytes obtained from the Tissue Bank at the Preston Robert Tisch Brain Tumor Center at Duke and collaborating centers, as previously described[17]. All brain tumors analyzed were subjected to consensus review by two neuropathologists. The panel of brain tumors consisted of 21 pilocytic astrocytomas and 2 subependymal giant cell gliomas (WHO Grade I); 31 diffuse astrocytomas, 51 oligodendrogliomas, three oligoastrocytomas, 30 ependymomas, and seven pleomorphic xanthoastrocytomas (WHO Grade II); 43 anaplastic astrocytomas, 36 anaplastic oligodendrogliomas, and seven anaplastic oligoastrocytomas (WHO Grade III); 178 GBMs and 55 medulloblastomas (WHO Grade IV). The GBM samples included 165 primary and 13 secondary cases. Fifteen of the GBMs were from patients <20 years old). Secondary GBMs were defined as those that were resected >1 year after a prior diagnosis of a lower grade glioma (WHO Grades Sixty-six of the 178 GBMs, but none of the lower grade tumors, had been analyzed in our prior genome-wide mutation analysis of GBMs[16]. In addition to the brain tumors, 494 non-CNS cancers were examined: 35 lung cancers, 57 gastric cancers, 27 ovarian cancers, 96 breast cancers, 114 colorectal cancers, 95 pancreatic cancers, seven prostate cancers, 4 chronic myelogenous leukemias, 7 chronic lymphocytic leukemias, 7 acute lymphoblastic leukemias, and 45 acute myelogenous leukemias. All samples were obtained in accordance with the Health Insurance Portability and Accountability Act. Acquisition of tissue specimens was approved by the Duke University Health System Institutional Review Board and the corresponding IRBs at collaborating institutions.

Exon 4 of the IDH1 gene was PCR-amplified and sequenced in the matched tumor and normal DNAs for each patient as previously described[16]. In selected patients without an R132 IDH1 mutation (those with Grade II or III lesions or secondary GBM), the remaining seven exons of IDH1 and all 11 exons of IDH2 were sequenced and analyzed for mutations. All coding exons of TP53 and PTEN were also sequenced in the panel of oligodendrogliomas, anaplastic oligodendrogliomas, anaplastic astrocytomas, and GBMs. EGFR amplification and CDKN2A/CDKN2B deletion were analyzed by quantitative real-time PCR in the same tumors[18]. Oligodendroglioma and anaplastic oligodendroglioma samples were evaluated for loss of heterozygosity (LOH) at 1p and 19q as previously described[15, 19].

Clinical information included date of birth, date the study sample was obtained, date of pathologic diagnosis, date and pathology of any preceding diagnosis of a lower grade glioma, administration of radiation therapy and/or chemotherapy prior to the date that the study sample was obtained, date of last patient contact, and patient status at last contact. Clinical information for survival analysis was available for all 482 primary brain tumor patients. Kaplan-Meier survival curves were plotted and the survival distributions were compared by the Mantel Cox log-rank test and the Wilcoxon test. Overall survival was calculated by using date of GBM diagnosis and date of death or last patient contact. The correlations between the occurrence of IDH1/IDH2 mutations and other genetic alterations were examined using Fisher's exact test.

Example 2

High Frequency Alterations of IDH1 in Young GBM Patients

The top CAN-gene list included a number of individual genes which had not previously been linked to GBMs. The most frequently mutated of these genes, IDH1, encodes isocitrate dehydrogenase 1, which catalyzes the oxidative carboxylation of isocitrate to α-ketoglutarate, resulting in the production of NADPH. Five isocitrate dehydrogenase genes are encoded in the human genome, with the products of three (IDH3 alpha, IDH3 beta, IDH3 gamma) forming a heterotetramer ($\alpha_2\beta\gamma$ in the mitochondria and utilizing NAD(+) as an electron acceptor to catalyze the rate-limiting step of the tricarboxylic acid cycle. The fourth isocitrate dehydrogenase (IDH2) is also localized to the mitochondria, but like IDH1, uses NADP(+) as an electron acceptor. The IDH1 product, unlike the rest of the IDH proteins, is contained within the cytoplasm and peroxisomes (41). The protein forms an asymmetric homodimer (42), and is thought to function to regenerate NADPH and α-ketoglutarate for intraperoxisomal and cytoplasmic biosynthetic processes. The production of cytoplasmic NADPH by IDH1 appears to play a significant role in cellular control of oxidative damage (43) (44). None of the other IDH genes, other genes involved in the tricarboxylic acid cycle, or other peroxisomal proteins were found to be genetically altered in our analysis.

Figure 2:
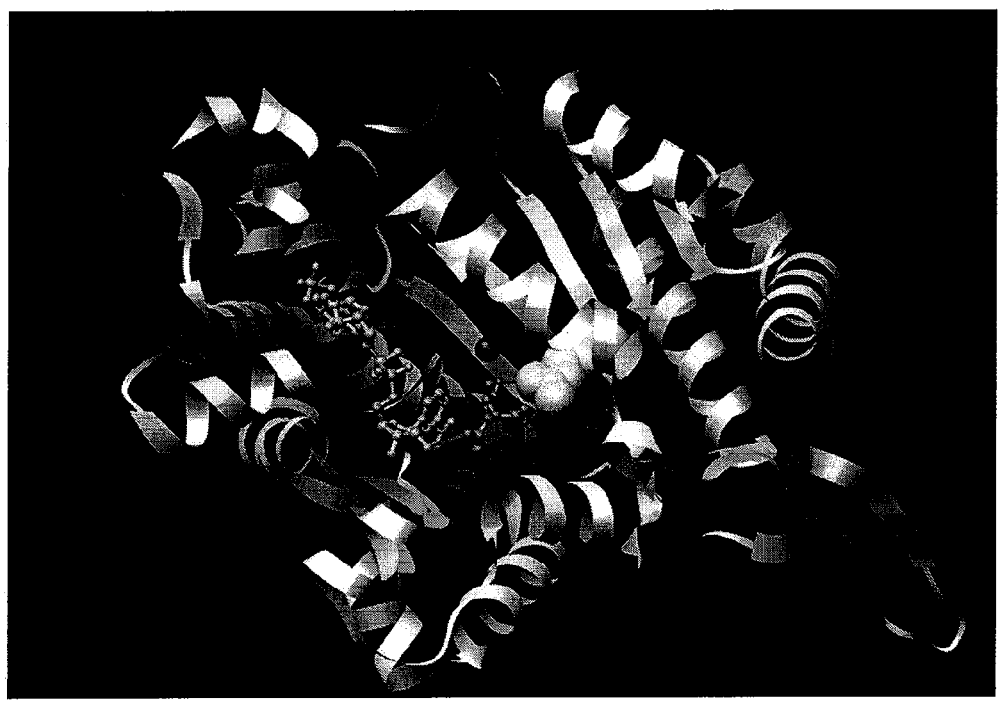
FIG. 2. Structure of the active site of IDH1. The crystal structure of the human cytosolic NADP(+)-dependent IDH is shown in ribbon format (PDBID: 1T0L) (42). The active cleft of IDH1 consists of a NADP-binding site and the isocitrate-metal ion-binding site. The alpha-carboxylate oxygen and the hydroxyl group of isocitrate chelate the Ca2+ ion. NADP is colored in orange, isocitrate in purple and Ca2+ in blue. The Arg132 residue, displayed in yellow, forms hydrophilic interactions, shown in red, with the alpha-carboxylate of isocitrate.

IDH1 was found to be somatically mutated in five GBM tumors in the Discovery Screen. Surprisingly, all five had the same heterozygous point mutation, a change of a guanine to an adenine at position 395 of the IDH1 transcript (G395A), leading to a replacement of an arginine with a histidine at amino acid residue 132 of the protein (R132H). In our prior study of colorectal cancers, this same codon had been found to be mutated in a single case through alteration of the adjacent nucleotide, resulting in a R132C amino acid change (10). Five additional GBMs evaluated in our Prevalence Screen were found to have heterozygous R132H mutations, and an additional two tumors had a third distinct mutation affecting the same amino acid residue, R132S (FIG. 1; Table 4). The R132 residue is conserved in all known species and is localized to the substrate binding site, forming hydrophilic interaction with the alpha-carboxylate of isocitrate (FIG. 2) (42, 45).

Figure 3:
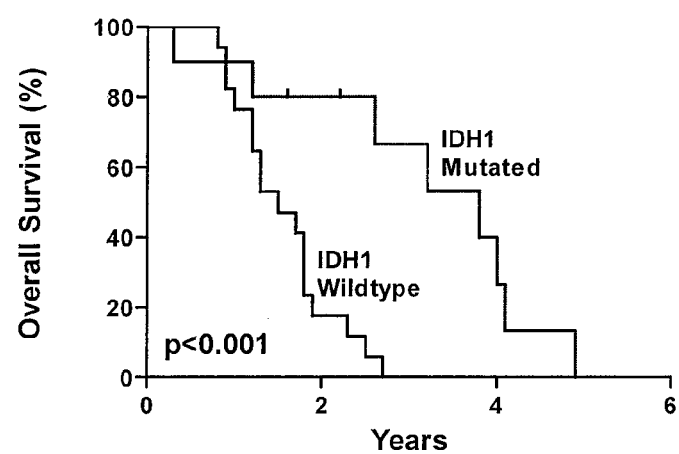
FIG. 3. Overall survival among patients <45 years old according to IDH1 mutation status. The hazard ratio for death among patients with mutated IDH1, as compared to those with wildtype IDH1, was 0.19 (95 percent confidence interval, 0.08 to 0.49; P<0.001). The median survival was 3.8 years for patients with mutated IDH1, as compared to 1.5 years for patients with wildtype IDH1.

Several important observations were made about IDH1 mutations and their potential clinical significance. First, mutations in IDH1 preferentially occurred in younger GBM patients, with a mean age of 33 years for IDH1-mutated patients, as opposed to 53 years for patients with wildtype IDH1 ($P<0.001$, t-test, Table 4. In patients under 35 years of age, nearly 50% (9 of 19) had mutations in IDH1. Second, mutations in IDH1 were found in nearly all of the patients with secondary GBMs (mutations in 5 of 6 secondary GBM patients, as compared to 7 of 99 patients with primary GBMs, $P<0.001$, binomial test), including all five secondary GBM patients under 35 years of age. Third, patients with IDH1 mutations had a significantly improved prognosis, with a median overall survival of 3.8 years as compared to 1.1 years for patients with wildtype IDH1 ($P<0.001$, log-rank test). Although younger age and mutated TP53 are known to be positive prognostic factors for GBM patients, this association between IDH1 mutation and improved survival was noted even in patients <45 years old (FIG. 3, $P<0.001$, log-rank test), as well as in the subgroup of young patients with TP53 mutations ($P<0.02$, log-rank test).

Example 3

Glioblastoma Multiforme (GBM) DNA Samples

Tumor DNA was obtained from GBM xenografts and primary tumors, with matched normal DNA for each case obtained from peripheral blood samples, as previously described (1). All samples were given the histologic diagnosis of glioblastoma multiforme (GBM; World Health Organization Grade IV), except for two Discovery Screen samples who were recorded as "high grade glioma, not otherwise specified". Samples were classified as recurrent for patients in whom a GBM had been diagnosed at least 3 months prior to the surgery when the study GBM sample was obtained. There were 3 recurrent GBMs in the Discovery Screen, and 15 in the Prevalence Screen. Samples were classified as secondary for patients in whom a lower grade glioma (WHO grade I-III) had been histologically confirmed at least 1 year prior to the surgery when the study GBM sample was obtained. One Discovery Screen sample and 5 Prevalence Screen samples were classified as secondary.

Pertinent clinical information, including date of birth, date study GBM sample obtained, date of original GBM diagnosis (if different than the date that the GBM sample was obtained, as in the case of recurrent GBMs), date and pathology of preceding diagnosis of lower grade glioma (in cases of secondary GBMs), the administration of radiation therapy and/or chemotherapy prior to the date that the GBM sample was obtained, date of last patient contact, and patient status at last contact. All samples were obtained in accordance with the Health Insurance Portability and Accountability Act (HIPAA). All samples were obtained in accordance with the Health Insurance Portability and Accountability Act (HIPAA). As previously described, tumor-normal pair matching was confirmed by typing nine STR loci using the PowerPlex 2.1 System (Promega, Madison, Wis.) and sample identities checked throughout the Discovery and Prevalence screens by sequencing exon 3 of the HLA-A gene. PCR and sequencing was carried out as described in (1).

Example 4

Statistical Analysis of Clinical Data

Paired normal and malignant tissue from 105 GBM patients were used for genetic analysis. Complete clinical information (i.e. all pertinent clinical information such as date of initial GBM diagnosis, date of death or last contact) was available for 91 of the 105 patients. Of these 91 patients, five (all IDH1-wildtype) died within the first month after surgery and were excluded from analysis (Br308T, Br246T, Br23X, Br301T, Br139X), as was a single patient (Br119X) with a presumed surgical cure (also IDH1-wildtype) who was alive at last contact ~10 years after diagnosis. Kaplan Meier survival curves were compared using the Mantel Cox log-rank test. Hazard ratios were computed using the Mantel-Haenszel method. The following definitions were used in the GBM patient grouping and survival analysis computations: 1) Patient age referred to the age at which the patient GBM sample was obtained. 2) Recurrent GBM designates a GBM which was resected >3 months after a prior diagnosis of GBM. 3) Secondary GBM designates a GBM which was resected >1 year after a prior diagnosis of a lower grade glioma (WHO I-III). 4) Overall survival was calculated using date of GBM diagnosis and date of death or last patient contact. All confidence intervals were calculated at the 95% level.

Example 5

IDH 1 and IDH2 Mutations

Figure 4A:
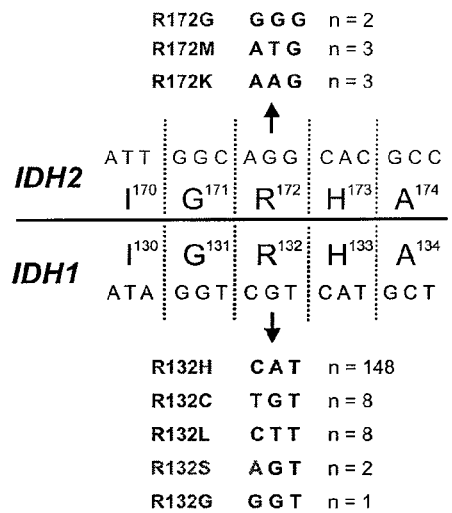
FIG. 4A-4B. IDH1 and IDH2 mutations in human gliomas.
Figure 4B:
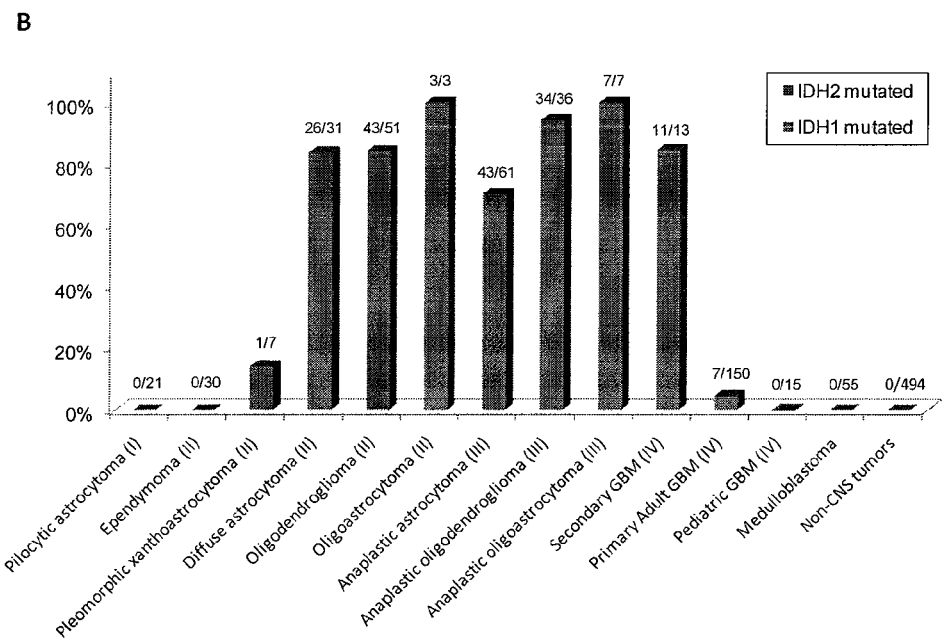

Sequence analysis of IDH1 in 976 tumor samples revealed a total of 167 somatic mutations at residue R132, including R132H (148 tumors), R132C (8 tumors), R132S (2 tumors), R132L (8 tumors) and R132G (1 tumor) (FIG. 4A, FIG. 7). Tumors with somatic R132 mutations included 25 of 31 (81%) diffuse astrocytomas (WHO Grade II), 41 of 51 (80%) oligodendrogliomas (WHO Grade II), 3 of 3 (100%) oligoastrocytomas (WHO Grade II), one of 7 (14%) pleomorphic xanthoastrocytomas (WHO Grade II), 41 of 61 (67%) anaplastic astrocytomas (WHO Grade III), 31 of 36 (86%) anaplastic oligodendrogliomas (WHO Grade III), 7 of 7 (100%) anaplastic oligoastrocytomas (WHO grade III), 11 of 13 (85%) secondary GBMs, and 7 of 165 (4%) primary GBMs (FIG. 1B, FIG. 11). In contrast, no R132 mutations were observed in 21 pilocytic astrocytomas (WHO Grade I), two subependymal giant cell astrocytomas (WHO Grade I), 30 ependymomas (WHO Grade II), 55 medulloblastomas, or in any of the 494 non-CNS tumor samples. Sequence analysis of the remaining IDH1 exons revealed no other somatic mutations of IDH1 in the R132-negative tumors.

If IDH1 were critical to the development or progression of oligodendrogliomas and astrocytomas, we reasoned that alterations in other genes with similar functions to IDH1 might be found in those in those tumors without IDH1 mutations. We therefore analyzed the IDH2 gene, which encodes the only human protein homologous to IDH1 that utilizes NADP+ as an electron acceptor. Sequence evaluation of all IDH2 exons in these samples, revealed eight somatic mutations, all at residue R172: R172M in three tumors, R172K in three tumors, and R172G in two tumors (FIG. 1A, FIG. 7). The R172 residue in IDH2 is the exact analogue of the R132 residue of IDH1, which is located in the active site of the enzyme and forms hydrogen bonds with the isocitrate substrate.

Figure 8:
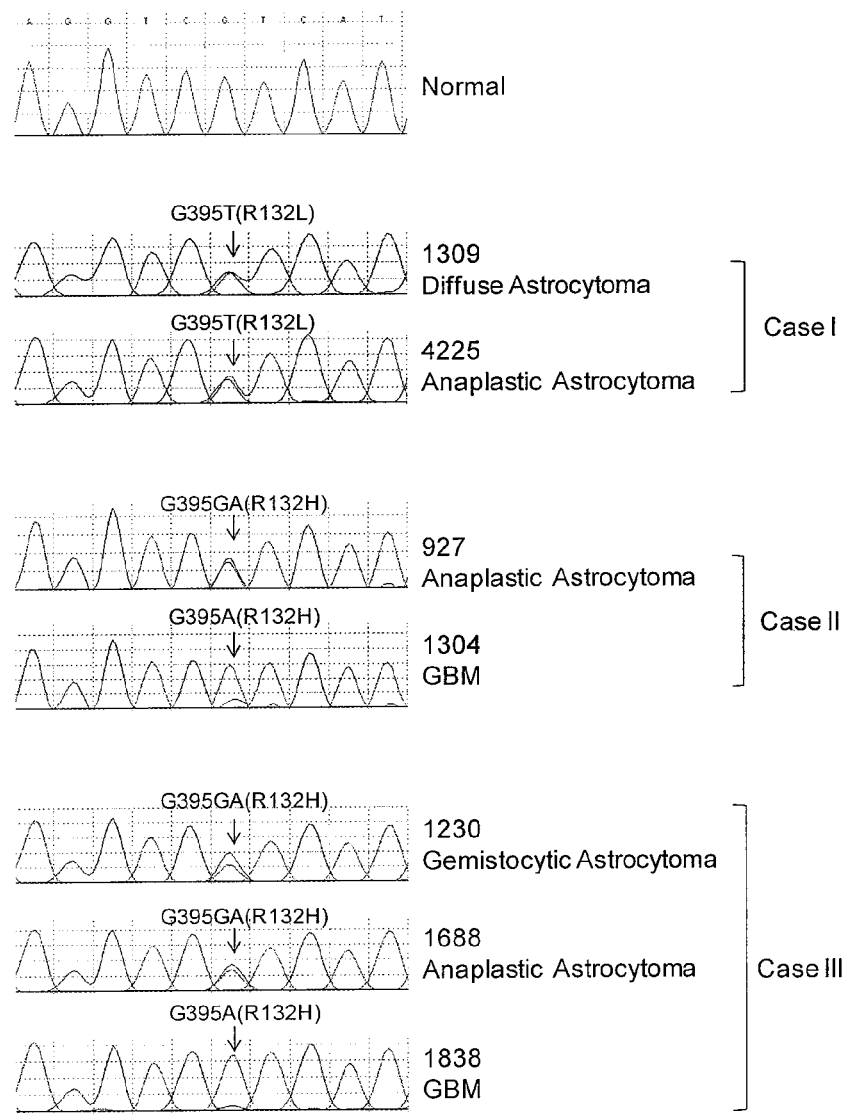
FIG. 8. Sequence alterations in IDH1 in progressive gliomas. Representative examples of somatic mutations at codon 132 of the IDH1 are indicated in three representative cases. The top sequence chromatogram was obtained from analysis of DNA from normal tissue while the lower chromatograms were obtained from the indicated brain tumor samples. Arrows indicate the location of the mutations and the resulting amino acid changes in IDH1. In all cases, the identical IDH1 mutations were found in the lower- and higher-grade tumors from each patient.

To further evaluate the timing of IDH alterations in glioma progression, we assessed IDH1 mutations in seven patients with progressive gliomas in which both low- and high-grade tumor samples were available. Sequence analysis identified IDH1 mutations in both the low and high-grade tumors in all seven cases (FIG. 8, Table 4). These results unambiguously demonstrate that IDH1 alterations occur in low-grade tumors and that subsequent cancers in such patients are directly derived from these early lesions.

We also examined the oligodendrogliomas, anaplastic oligodendrogliomas, anaplastic astrocytomas, and a subset of GBMs for mutations of TP53 and PTEN, amplification of EGFR, deletion of CDKN2A/CDKN2B, and LOH of 1p/19q (FIG. 12). TP53 mutations were much more common in anaplastic astrocytomas (63%) and secondary GBMs (60%) than in oligodendrogliomas (16%) or anaplastic oligodendrogliomas (10%) (p<0.001, Fisher's exact test). Conversely, deletions of 1p and 19q were found more often in oligodendrocytic than astrocytic tumors, as expected 15.

Comparison of these alterations with those in IDH1 and IDH2 revealed several striking correlations. Nearly all of the anaplastic astrocytomas and GBMs with mutated IDH1/IDH2 also had mutation of TP53 (82%), but only 5% had any alteration of PTEN, EGFR, or CDKN2A/CDKN2B (FIG. 12). Conversely, anaplastic astrocytomas and GBMs with wild-type IDH1 had few TP53 mutations (21%) and more frequent alterations of PTEN, EGFR, or CDKN2A/CDKN2B (40%) (p<0.001, Fisher's exact test). Loss of 1p/19q was observed in 85% (45/53) of the oligodendrocytic tumors with mutated IDH1 or IDH2 but in none (0/9) of the patients with wild-type IDH genes (p<0.001, Fisher's exact test).

Figure 9A:
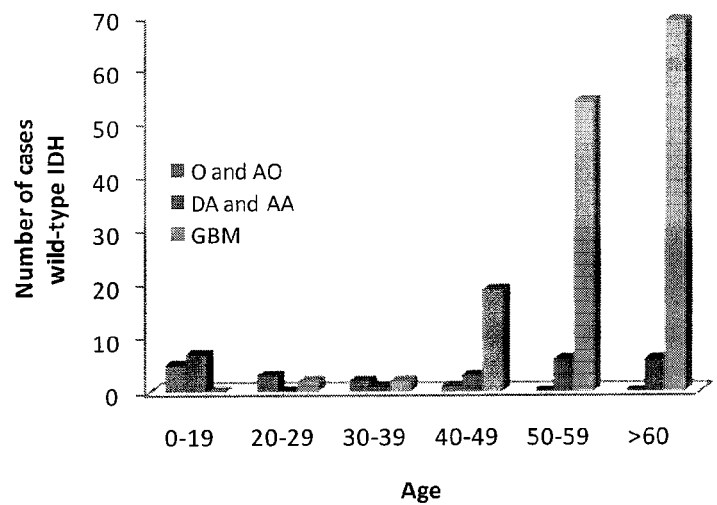
FIG. 9A-9B. Age distribution of glioma patients with mutated and wild-type IDH. Age distribution of oligodendroglioma (O), anaplastica oligodendroglioma (AO), diffuse astrocytoma (DA), anaplastic astrocytoma (AA), and glioblastoma multiforme (GBM) in patients with wild-type IDH genes (FIG. 9A) or mutated IDH genes (FIG. 9 B).
Figure 9B:
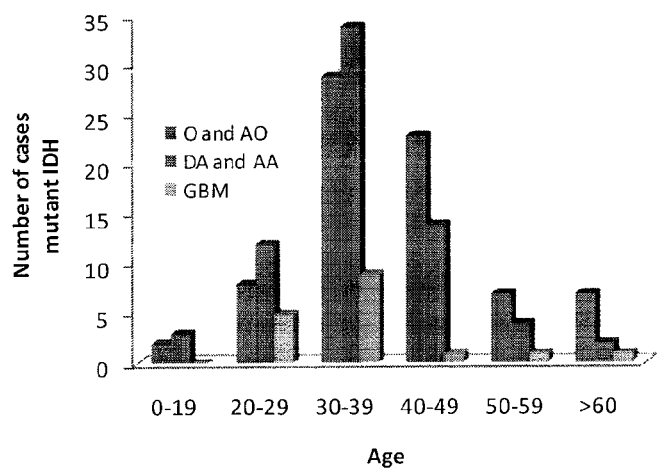

Patients with anaplastic astrocytomas and GBMs with IDH1 or IDH2 mutations were significantly younger than those with wild-type IDH1 and IDH2 genes (median age of 34 years vs. 58 years, p<0.001, Student's t-test). Interestingly, despite the lower median age of patients with IDH1 or IDH2 mutations, no mutations were identified in GBM from patients who were less than 20 years old (0 of 18 patients, FIG. 9). In patients with oligodendrogliomas and anaplastic oligodendrogliomas, the median age of the patients with IDH1 or IDH2 mutation was 39 years, with IDH1 mutations identified in two teenagers (14 and 16 yrs), but not in younger patients (0 of 4).

Figure 5A:
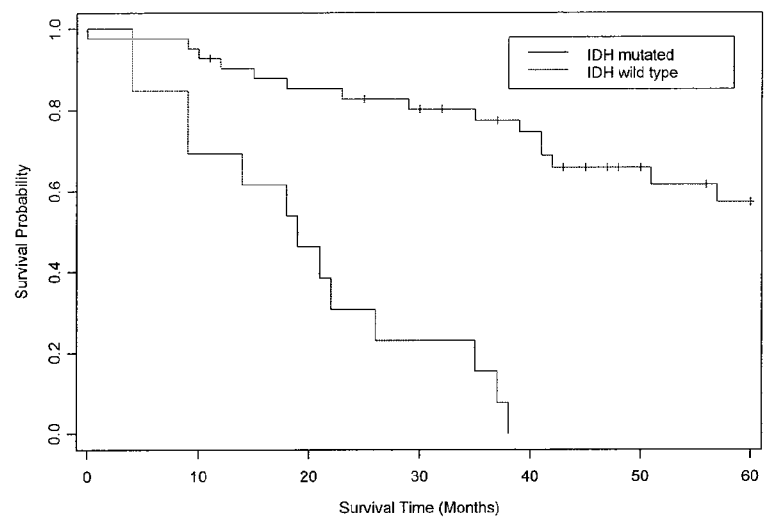
FIG. 5A-5B. Survival for patients with malignant gliomas according to IDH1 and IDH2 mutation status. For patients with anaplastic astrocytomas (FIG. 5A), the median survival was 65 months for patients with mutated IDH1 or IDH2, as compared to 19 months for patients with wildtype IDH1 and IDH2. For patients with GBM (FIG. 5B), the median survival was 39 months for patients with mutated IDH1 or IDH2, as compared to 13.5 months for patients with wildtype IDH1 and IDH2.
Figure 5B:
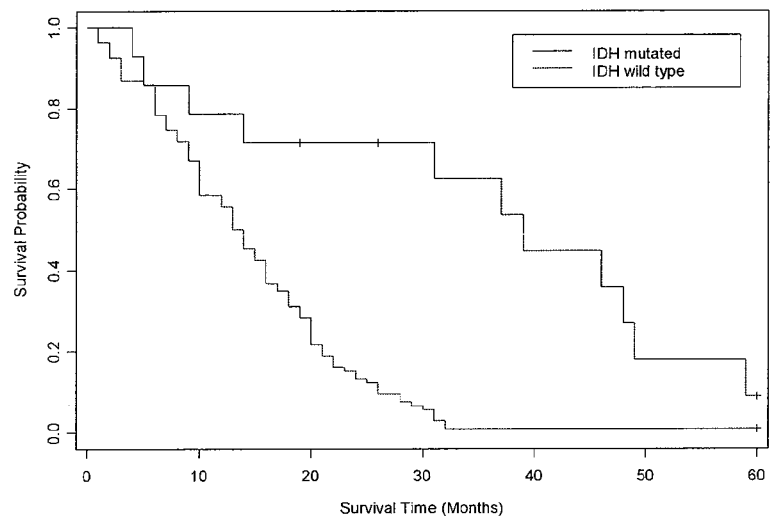
Figure 6:
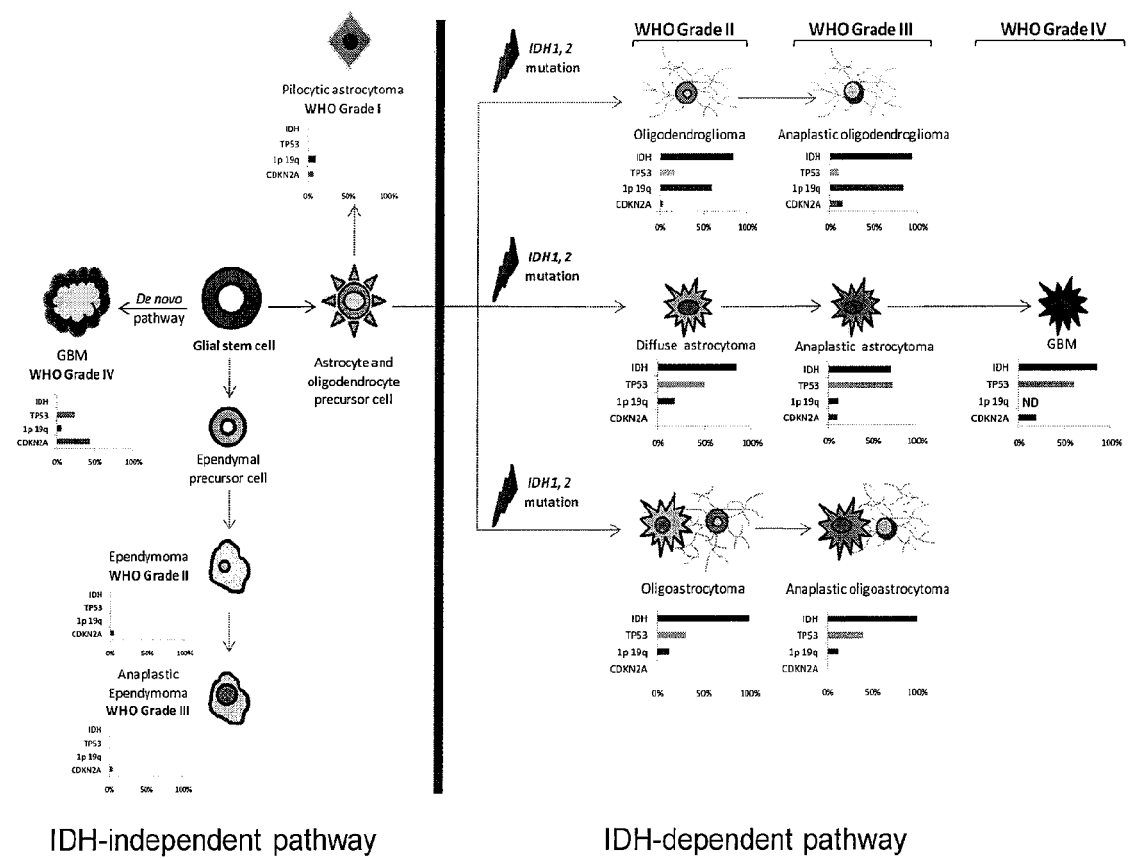
FIG. 6. Model of malignant glioma development. For each tumor type common genetic alterations (IDH1/IDH2 mutation, TP53 mutation, 1p 19q loss, and CDKN2A loss) are indicated. Detailed frequencies of genetic alterations are contained in Table 1 and 2 or reference[1]. In general, tumors on the right acquire IDH alterations, while those on the left do not.

Our prior observation of improved prognosis for GBM patients with mutated IDH1 16 was confirmed in this larger data set and extended to include patients with mutations in IDH2. Patients with IDH1 or IDH2 mutations had a median overall survival of 39 months, significantly longer than the 13.5 month survival in patients with wild-type IDH1 (FIG. 5, p<0.001, log-rank test). Mutations of IDH genes were also associated with improved prognosis in patients with anaplastic astrocytomas (WHO Grade III), with median overall survival of 65 months for patients with mutations and 19 months for those without (p<0.001, log-rank test). Differential survival analyses could not be performed in patients with diffuse astrocytomas, oligodendrogliomas, or anaplastic oligodendrogliomas because there were so few tumors of these types without IDH gene mutations.

REFERENCES

The disclosure of each reference cited is expressly incorporated herein. The references in the following list are cited in the text with superscript reference numerals.

1. Louis D N, Ohgaki, H., Wiestler, O. D., Cavenee, W. K, ed. WHO Classification of Tumours of the Central Nervous System. 4th ed. Lyon: International Agency for Research on Cancer; 2007.
2. Burger P C S B, Paulus W. Pilocytic astrocytoma. In: Kleihues P C W, ed. Pathology and Genetics of Tumours of the Nervous System. Lyon, France: International Agency for Research on Cancer; 2000:45-51.
3. Stupp R, Mason W P, van den Bent M J, et al. Radiotherapy plus concomitant and adjuvant temozolomide for glioblastoma. The New England Journal of Medicine 2005; 352 (10):987-96.
4. Wen P Y, Kesari S. Malignant gliomas in adults. The New England Journal of Medicine 2008; 359(5):492-507.
5. Ohgaki H, Dessen P, Jourde B, et al. Genetic pathways to glioblastoma: a population-based study. Cancer Research 2004; 64(19):6892-9.
6. Ohgaki H, Kleihues P. Genetic pathways to primary and secondary glioblastoma. The American Journal of Pathology 2007; 170(5):1445-53.

7. The Cancer Genome Atlas Research Network. Comprehensive genomic characterization defines human glioblastoma genes and core pathways. Nature 2008 Sep. 4. [Epub ahead of print].
8. Li J, Yen C, Liaw D, et al. PTEN, a putative protein tyrosine phosphatase gene mutated in human brain, breast, and prostate cancer. Science 1997; 275(5308):1943-7.
9. Nigro J M, Baker S J, Preisinger A C, et al. Mutations in the p53 gene occur in diverse human tumour types. Nature 1989; 342(6250):705-8.
10. Ueki K, Ono Y, Henson J W, Efird J T, von Deimling A, Louis D N. CDKN2/p16 or RB alterations occur in the majority of glioblastomas and are inversely correlated. Cancer Research 1996; 56(1):150-3.
11. Wong A J, Bigner S H, Bigner D D, Kinzler K W, Hamilton S R, Vogelstein B. Increased expression of the epidermal growth factor receptor gene in malignant gliomas is invariably associated with gene amplification. Proceedings of the National Academy of Sciences of the United States of America 1987; 84(19):6899-903.
12. Wong A J, Ruppert J M, Bigner S H, et al. Structural alterations of the epidermal growth factor receptor gene in human gliomas. Proceedings of the National Academy of Sciences of the United States of America 1992; 89(7):2965-9.
13. Furnari F B, Fenton T, Bachoo R M, et al. Malignant astrocytic glioma: genetics, biology, and paths to treatment. Genes & development 2007; 21(21):2683-710.
14. Weber R G, Sabel M, Reifenberger J, et al. Characterization of genomic alterations associated with glioma progression by comparative genomic hybridization. Oncogene 1996; 13(5):983-94.
15. Bigner S H, Matthews M R, Rasheed B K, et al. Molecular genetic aspects of oligodendrogliomas including analysis by comparative genomic hybridization. The American journal of pathology 1999; 155(2):375-86.
16. Parsons D W, Jones S, Zhang X, et al. An Integrated Genomic Analysis of Human Glioblastoma Multiforme. Science 2008 Sep. 4. [Epub ahead of print].
17. Sjoblom T, Jones S, Wood L D, et al. The consensus coding sequences of human breast and colorectal cancers. Science 2006; 314(5797):268-74.
18. Wang T L, Diaz L A, Jr., Romans K, et al. Digital karyotyping identifies thymidylate synthase amplification as a mechanism of resistance to 5-fluorouracil in metastatic colorectal cancer patients. Proceedings of the National Academy of Sciences of the United States of America 2004; 101(9):3089-94.
19. Reifenberger J, Reifenberger G, Liu L, James C D, Wechsler W, Collins V P. Molecular genetic analysis of oligodendroglial tumors shows preferential allelic deletions on 19q and 1p. The American Journal of Pathology 1994; 145(5):1175-90.
20. Xu X, Zhao J, Xu Z, et al. Structures of human cytosolic NADP-dependent isocitrate dehydrogenase reveal a novel self-regulatory mechanism of activity. The Journal of Biological Chemistry 2004; 279(32):33946-57.

The references in the following list are cited in the text with reference numerals in parentheses. The disclosure of each is expressly incorporated herein.

REFERENCES

1. D. N. Louis et al., *Acta Neuropathol* 114, 97 (2007).
2. R. Stupp et al., *N Engl J Med* 352, 987 (2005).
3. H. Scherer, *American Journal of Cancer* 40, 159 (1940).
4. P. Kleihues, H. Ohgaki, *Neuro Oncol* 1, 44 (1999).
5. H. Ohgaki, P. Kleihues, *Am J Pathol* 170, 1445 (2007).
6. H. Ohgaki et al., *Cancer Res* 64, 6892 (2004).
7. I. K. Mellinghoff et al., *N Engl J Med* 353, 2012 (2005).
8. E. A. Maher et al., *Cancer Res* 66, 11502 (2006).
9. C. L. Tso et al., *Cancer Res* 66, 159 (2006).
10. T. Sjoblom et al., *Science* 314, 268 (2006).
11. L. D. Wood et al., *Science* 318, 1108 (2007).
12. See Supporting Online Material for Science 26 Sep. 2008: vol. 321. no. 5897, pp. 1807-1812
13. D. P. Cahill et al., *Clin Cancer Res* 13, 2038 (2007).
14. C. Hunter et al., *Cancer Res* 66, 3987 (2006).
15. J. M. Winter, J. R. Brody, S. E. Kern, *Cancer Biol Ther* 5, 360 (2006).
16. S. Jones et al., *Proc Natl Acad Sci USA* 105, 4283 (2008).
17. S. Jones, co-submitted to *Science* (2008).
18. R. Kraus-Ruppert, J. Laissue, H. Burki, N. Odartchenko, *J Comp Neurol* 148, 211 (1973).
19. P. C. Ng, S. Henikoff, *Nucleic Acids Res* 31, 3812 (2003).
20. R. Karchin. (2008). Structural models of mutants identified in glioblastomas. Available on the karchinlab.org website as a html file at the directory GBM, at the subdirectory Mutants, at the subsub directory CAN-genes, at the subsubsub directory brain
21. F. J. Steemers et al., *Nat Methods* 3, 31 (2006).
22. R. J. Leary, *Submitted* (2008).
23. P. Cairns et al., *Nat Genet* 11, 210 (1995).
24. J. M. Nigro et al., *Nature* 342, 705 (1989).
25. J. Li et al., *Science* 275, 1943 (1997).
26. K. Ueki et al., *Cancer Res* 56, 150 (1996).
27. A. J. Wong et al., *Proc Natl Acad Sci USA* 84, 6899 (1987).
28. A. J. Wong et al., *Proc Natl Acad Sci USA* 89, 2965 (1992).
29. L. Frederick, X. Y. Wang, G. Eley, C. D. James, *Cancer Res* 60, 1383 (2000).
30. Y. Li et al., *Cell* 69, 275 (1992).
31. G. Thiel et al., *Anticancer Res* 15, 2495 (1995).
32. Y. Samuels et al., *Science* 304, 554 (2004).
33. D. K. Broderick et al., *Cancer Res* 64, 5048 (2004).
34. G. L. Gallia et al., *Mol Cancer Res* 4, 709 (2006).
35. S. Ekins, Y. Nikolsky, A. Bugrim, E. Kirillov, T. Nikolskaya, *Methods Mol Biol* 356, 319 (2007).
36. V. E. Velculescu, L. Zhang, B. Vogelstein, K. W. Kinzler, *Science* 270, 484 (1995).
37. M. Sultan et al., *Science* (2008).
38. R. Lister et al., *Cell* 133, 523 (2008).
39. A. Mortazavi, B. A. Williams, K. McCue, L. Schaeffer, B. Wold, *Nat Methods* 5, 621 (2008).
40. R. Morin et al., *Biotechniques* 45, 81 (2008).
41. B. V. Geisbrecht, S. J. Gould, *J Biol Chem* 274, 30527 (1999).
42. X. Xu et al., *J Biol Chem* 279, 33946 (2004).
43. S. M. Lee et al., *Free Radic Biol Med* 32, 1185 (2002).
44. S. Y. Kim et al., *Mol Cell Biochem* 302, 27 (2007).
45. A. Nekrutenko, D. M. Hillis, J. C. Patton, R. D. Bradley, R. J. Baker, *Mol Biol Evol* 15, 1674 (1998).
46. G. T. Jennings, K. I. Minard, L. McAlister-Henn, *Biochemistry* 36, 13743 (1997).
47. D. Christianson, R. Alexander, *J Am Chem Soc* 111, 6412 (1989).
48. C. Luyken et al., *Cancer* 101, 146 (2004).
49. I. S. Kil, S. Y. Kim, S. J. Lee, J. W. Park, *Free Radic Biol Med* 43, 1197 (2007).

Example 6

Sequencing Strategy

We extended our previously-developed sequencing strategy for identification of somatic mutations to include 23,219 transcripts from 20,583 genes. These included 2783 additional genes from the Ensembl databases that were not present in the CCDS or RefSeq databases analyzed in previous studies (10, 11). In addition, we redesigned PCR primers for regions of the genome that (i) were difficult to PCR amplify and had been sub-optimally analyzed in prior studies; or (ii) were found to share significant identity with other human or mouse sequences. The combination of these new, redesigned, and existing primers sequences resulted in a total of 208,311 primer pairs (table S1; available on-line at Science 26 Sep. 2008: Vol. 321. no. 5897, pp. 1807-1812) that were successfully used for sequence analysis of the coding exons of these genes.

Twenty-two GBM samples (FIG. 10, Table S2) were selected for PCR sequence analysis, consisting of 7 samples extracted directly from patient tumors and 15 tumor samples passaged in nude mice as xenografts. One tumor (Br27P) was a secondary GBM obtained from a patient who had previously been treated with both radiation therapy and chemotherapy, including temozolomide. All other tumors were categorized as primary GBMs and had not received tumor-directed treatment prior to the acquisition of the studied tumor sample.

In the first stage of this analysis, called the Discovery Screen, the primer pairs were used to amplify and sequence 175,471 coding exons and adjacent intronic splice donor and acceptor sequences in the 22 GBM samples and in one matched normal sample. The data were assembled for each amplified region and evaluated using stringent quality criteria, resulting in successful amplification and sequencing of 95.0% of targeted amplicons and 93.0% of targeted bases in the 22 tumors. A total of 689 Mb of sequence data were generated through this approach. The amplicon traces were analyzed using automated approaches to identify changes in the tumor sequences that were not present in the reference sequences of each gene, then alterations present in the normal control sample and in single nucleotide polymorphism (SNP) databases were removed from further analyses. The remaining sequence traces of potential alterations were visually inspected to remove false-positive mutation calls generated through our automated software. All exons containing putative mutations were then re-amplified and sequenced in the affected tumor and matched normal DNA samples. This process allowed confirmation of the mutation in the tumor sample and determined whether the alteration was somatic (i.e. tumor-specific) or was present in the germline. All putative somatic mutations were examined computationally and experimentally to confirm that the alterations did not arise through the aberrant co-amplification of related gene sequences (12).

TABLE 1

Summary of genomic analyses of GBM

Sequencing analysis

| | |
|---|---|
| Number of genes analyzed | 20,583 |
| Number of transcripts analyzed | 23,781 |
| Number of exons analyzed | 184,292 |
| Primer pairs designed for amplification | 219,229 |
| Fraction of passing amplicons* | 95.0% |
| Total number of nucleotides sequenced | 689,071,123 |
| Fraction of passing amplicon sequences successfully analyzed# | 98.4% |
| Fraction of targeted bases sucessfully analyzed# | 93.0% |
| Number of somatic mutations identified (n = 22 samples) | 2,328 |
| Number of somatic mutations (excluding Br27P) | 996 |
| Missense | 870 |

TABLE 1-continued

Summary of genomic analyses of GBM

| | |
|---|---|
| Nonsense | 43 |
| Insertion | 3 |
| Deletion | 46 |
| Duplication | 7 |
| Splice site or UTR | 27 |
| Average number of sequence alterations per sample | 47.4 |
| Copy number analysis | |
| Total number of SNP loci assessed for copy number changes | 1,069,688 |
| Number of copy number alterations identified (n = 22 samples) | 281 |
| Amplifications | 147 |
| Homozygous deletions | 134 |
| Average number of amplifications per sample | 6.7 |
| Average number of homozygous deletions per sample | 6.1 |

*Passing amplicons were defined as having PHRED20 scores or better over 90% of the target sequence in 75% of samples analyzed.
Fraction of nucleotides having PHRED20 scores or better (see Supporting Online Materials for additional information).

Example 7

Analysis of Sequence Alterations

We found that 2043 genes (10% of the 20,661 genes analyzed) contained at least one somatic mutation that would be expected to alter the protein sequence. The vast majority of these alterations were single-base substitutions (94%), while the others were small insertions, deletions, or duplications. The tumor sample Br27P obtained from the patient previously treated with radiation therapy and chemotherapy (including temozolomide), had 1332 total somatic mutations, 17-fold higher than any of the other 21 patients (FIG. 10, Table S3). The mutation spectrum of this sample, comprising an excess of C>T transitions in the 5' cytosine of CpC dinucleotides, was dramatically different from those of the other GBM patients, but was consistent with previous observations of a hypermutation phenotype in glioma samples of patients treated with temozolomide (13, 14). In the previously-reported patients, the hypermutability was thought to occur due to prolonged exposure of an akylating agent in the presence of MSH6 mismatch repair deficiency; however, in BR27P, no somatic alterations were observed in MSH6 or in any of the other mismatch repair genes (MSH2, MLH1, MLH3, PMS1, PMS2). In contrast to BR27P, none of the other 21 tumor samples analyzed in the Discovery Screen were known to have received prior radiation or chemotherapeutic treatment, and none had the characteristic CpC mutation spectrum that has been found in such pre-treated tumors.

After removing Br27P from consideration, the remaining 993 mutations were observed to be distributed relatively evenly among the 21 remaining tumors (FIG. 10, Table S3). The number of somatic mutations identified in each tumor ranged between 17 and 79 with a mean of 47 mutations per tumor, or 1.51 mutations per Mb of GBM tumor genome sequenced. Six DNA samples extracted from primary tumors had somewhat smaller numbers of mutations than those obtained from xenografts, likely because of the masking effect of non-neoplastic cells in the former. It has previously been shown that cell lines and xenografts provide the optimal template DNA for cancer genome sequencing analyses (15) and that they faithfully represent the alterations present in primary tumors (16).

Both the total number and frequency of sequence alterations in GBMs were substantially smaller than the number and frequency of such alterations observed in cancers of the colon or breast, and slightly less than in pancreas (10, 11, 17). The most likely explanation for this difference is the reduced number of cell generations in glial cells prior to the onset of neoplasia. It has been suggested that up to half of the somatic mutations observed in colorectal cancers occur in epithelial stem cells during the normal cell renewal processes (16). As normal glial stem cells turn over much less frequently than mammary or colon epithelial cells, they would be expected to contain many fewer mutations when the tumor-initiating mutation occurred (18).

We further evaluated a set of 20 mutated genes identified in the Discovery Screen in a second screen, called a Prevalence Screen, comprising an additional 83 GBMs with well-documented clinical histories (table S2, available on line at *Science* 26 Sep. 2008: Vol. 321. no. 5897, pp. 1807-1812). These genes were mutated in at least two tumors and had mutation frequencies >10 mutations per Mb of tumor DNA sequenced. Nonsilent somatic mutations were identified in 15 of these 20 genes in the additional tumor samples (FIG. 10, Table S4). The mutation frequency of all analyzed genes in the Prevalence Screen was 24 mutations per Mb of tumor DNA, markedly increased from the overall mutation frequency in the Discovery Screen of 1.5 mutations per Mb (p<0.001, binomial test). Additionally, the observed ratio of nonsilent to silent mutations (NS:S) among mutations in the Prevalence Screen was 14.8:1, substantially higher than the 3.1:1 ratio that was observed in the Discovery Screen (P<0.001, binomial test). The increased mutation frequency and higher number of nonsilent mutations suggested that genes mutated in the Prevalence Screens were enriched for genes that actively contributed to tumorigenesis.

In addition to the frequency of mutations in a gene, the type of mutation can provide information useful for evaluating its potential role in disease (19). Nonsense mutations, out-of-frame insertions or deletions, and splice site changes generally lead to inactivation of the protein products. The likely effect of missense mutations can be assessed through evaluation of the mutated residue by evolutionary or structural means. To evaluate missense mutations, we developed a new algorithm that employs machine learning of 56 predictive features based on the physical-chemical properties of amino acids involved in the substation and their evolutionary conservation at equivalent positions of conserved proteins (12). Approximately 15% of the missense mutations identified in this study were predicted to have a statistically significant effect on protein function when assessed by this method (FIG. 10, Table S3). We were also able to make structural models of 244 of the 870 missense mutations identified in this study (20). In each case, the model was based on x-ray crystallography or nuclear magnetic resonance spectroscopy of the normal protein or a closely related homolog. This analysis showed that 35 of the missense mutations were located close to a domain interface or substrate-binding site and were likely to impact function (links to structural models available in (12)).

Example 8

Analysis of Copy Number Changes

The same tumors were then evaluated for copy number alterations through genomic hybridization of DNA samples to Illumina high density oligonucleotide arrays containing ~1 million SNP loci probes (21). We have recently developed a sensitive and specific approach for the identification of focal amplifications resulting in 12 or more copies per nucleus (6-fold or greater amplification compared to the diploid genome) as well as deletions of both copies of a gene (homozygous deletions) using such arrays (22). Such focused alterations can be used to identify underlying candidate genes in these regions. It is impossible to reliably identify such candidate genes in regions with larger chromosomal aberrations, such as those involving gains or losses of entire chromosomal arms, which occur frequently in tumors and are of unknown significance.

We identified a total of 147 amplifications (FIG. 10, Table S5) and 134 homozygous deletions (FIG. 10, Table S6) in the 22 samples used in the Discovery Screen, with 0 to 34 amplifications and 0 to 14 deletions found per tumor sample. Although the number of amplifications was similar between primary samples and those tumors that had been passaged as xenografts, the latter samples allowed detection of a larger number of homozygous deletions (average of 8.0 deletions per xenograft versus 2.2 per primary sample). These observations are consistent with previous reports documenting the difficulty of identifying homozygous deletions in samples containing contaminating normal DNA (23) and highlight the importance of using purified human tumor cells, such as those present in xenografts or cell lines, for genomic analyses.

Example 9

Integration of Sequencing, Copy Number and Expression Analyses

Mutations that arise during tumorigenesis may provide a selective advantage to the tumor cell (driver mutations) or have no net effect on tumor growth (passenger mutations). The mutational data obtained from sequencing and analysis of copy number alterations were integrated in order to identify GBM candidate cancer genes (CAN-genes) that would be most likely to be drivers and therefore worthy of further investigation. The bioinformatic approach employed to determine if a gene was likely to harbor driver mutations involved comparison of the number and type of mutations observed in each gene to the number that would be expected due to the passenger mutation rates. For sequence alterations, we calculated upper and lower bounds of passenger rates. The upper bound was conservatively calculated as the total number of observed alterations minus those mutations occurring in known cancer genes divided by the amount of tumor DNA sequenced, while the lower bound was determined on the basis of the observed silent mutations and estimates of expected NS:S ratios (12). For copy number changes, we made the very conservative assumption that all amplifications and deletions were passengers when determining the background rate. For analysis of each gene, all types of alterations (sequence changes, amplifications and homozygous deletions), were then combined to estimate the passenger probability for that gene (see (12) for a more detailed description of the statistical methods).

The top-ranked CAN-genes, together with their passenger probabilities, are listed in FIG. 10, Table S7. The CAN-genes included a number of genes that had been well established with respect to their involvement in gliomas, including TP53, PTEN, CDKN2A, RB1, EGFR, NF1, PIK3CA and PIK3R1 (24-34). The most frequently altered of these genes in our analyses included CDKN2A (altered in 50% of GBMs), TP53, EGFR, and PTEN (altered in 30-40%), NF1, CDK4 and RB1 (altered in 12-15%), and PIK3CA and PIK3R1 (altered in 8-10%). Overall, these frequencies, which are similar to or in some cases higher than those previously reported, validate the sensitivity of our approach for detection of somatic alterations.

TABLE 2

Most frequently altered GBM CAN-genes

| Gene | Point mutations& Number of tumors | Point mutations& Fraction of tumors | Amplifications& Number of tumors | Amplifications& Fraction of tumors | Homozygous deletions& Number of tumors | Homozygous deletions& Fraction of tumors | Fraction of tumors with any alteration | Passenger Probability* |
|---|---|---|---|---|---|---|---|---|
| CDKN2A | 0/22 | 0% | 0/22 | 0% | 11/22 | 50% | 50% | 0.00 |
| TP53 | 37/105 | 35% | 0/22 | 0% | 1/22 | 5% | 40% | 0.00 |
| EGFR | 15/105 | 14% | 5/22 | 23% | 0/22 | 0% | 37% | 0.00 |
| PTEN | 27/105 | 26% | 0/22 | 0% | 1/22 | 5% | 30% | 0.00 |
| NF1 | 16/105 | 15% | 0/22 | 0% | 0/22 | 0% | 15% | 0.04 |
| CDK4 | 0/22 | 0% | 3/22 | 14% | 0/22 | 0% | 14% | 0.00 |
| RB1 | 8/105 | 8% | 0/22 | 0% | 1/22 | 5% | 12% | 0.01 |
| IDH1 | 12/105 | 11% | 0/22 | 0% | 0/22 | 0% | 11% | 0.00 |
| PIK3CA | 10/105 | 10% | 0/22 | 0% | 0/22 | 0% | 10% | 0.10 |
| PIK3R1 | 8/105 | 8% | 0/22 | 0% | 0/22 | 0% | 8% | 0.14 |

The most frequently-altered CAN-genes are listed; all CAN-genes are listed in Table S7.
^Fraction of tumors with point mutations indicates the fraction of mutated GBMs out of the 105 samples in the Discovery and Prevalence Screens.
CDKN2A and CDK4 were not analyzed for point mutations in the Prevalence Screen because no sequence alterations were detected in these genes in the Discovery Screen.
&Fraction of tumors with amplifications and deletions indicates the number of tumors with these types of alterations in the 22 Discovery Screen samples.
*Passenger probability indicates the Passenger probability-Mid (12).

Analysis of additional gene members within pathways affected by these genes identified alterations of critical genes in the TP53 pathway (TP53, MDM2, MDM4), the RB1 pathway (RB1, CDK4, CDKN2A), and the PI3K/PTEN pathway (PIK3CA, PIK3R1, PTEN, IRS1). These alterations resulted in aberrant pathways in a majority of tumors (64%, 68%, and 50%, respectively) and in all cases but one, mutations within each tumor affected only a single member of each pathway in a mutually exclusive manner (P<0.05) (Table 3). Systematic analyses of functional gene groups and pathways contained within the well-annotated MetaCore database (35) identified enrichment of mutated genes in additional members of the TP53 and PI3K/PTEN pathways as well as in a variety of other cellular processes, including those regulating cell adhesion as well as brain specific cellular pathways such those involving synaptic transmission, transmission of nerve impulses, and channels involved in transport of sodium, potassium and calcium ions (FIG. 10, Table S8). Interestingly, none of these latter pathways were observed as being enriched in large-scale studies on pancreatic cancers (17) and may represent a subversion of normal glial cell processes to promote dysregulated growth and invasion. Many members of the detected pathways had not been appreciated to have any role in GBMs or any other human cancer, and substantial effort will be required to determine their role in tumorigenesis.

TABLE 3

Mutations of the TP53, PI3K, and RB1 pathways in GBM

| Tumor sample | TP53 | | | | PI3K Pathway | | | | | RB1 | | | |
|---|---|---|---|---|---|---|---|---|---|---|---|---|---|
| | TP53 | MDM2 | MDM4 | All genes | PTEN | PIK3CA | PIK3R1 | IRS1 | All genes | RB1 | CDK4 | CDKN2A | All genes |
| Br02 | | | Del | Alt | | | | Mu | Alt | | | Del | Alt |
| Br03 | Mu | | | Alt | Mu | | | | Alt | | | | |
| Br04 | Mu | | | Alt | Mu | | | | Alt | Mu | | | Alt |
| Br05 | | | Amp | Alt | | Mu | | | Alt | | | Del | Alt |
| Br06 | | | | | | | | | | | | Del | Alt |
| Br07 | Mu | | | Alt | Mu | | | | Alt | Del | | | Alt |
| Br08 | | | | | | | | | | | | Del | Alt |
| Br09P | Mu | | | Alt | | | | | | | Amp | | Alt |
| Br10P | Mu | | | Alt | | | | | | | | | |
| Br11P | Mu | | | Alt | | | | | | | | | |
| Br12P | Mu | | | Alt | | | Mu | | Alt | | | | |
| Br13 | Mu | | | Alt | | | | | | | | Del | Alt |
| Br14 | | | | | | | Mu | | Alt | Mu | | Del | Alt |
| Br15 | | | | | | | | | | Mu | | Del | Alt |
| Br16 | | Amp | | Alt | | | | | | | Amp | | Alt |
| Br17 | | | | | Mu | | | | Alt | | | Del | Alt |
| Br20P | | | | | | | | | | | | | |
| Br23 | Mu | | | Alt | Del | | | | Alt | | | | |
| Br25 | | | | | | Mu | | | Alt | | | Del | Alt |
| Br26 | | | | | | | Mu | | Alt | | | Del | Alt |
| Br27P | Mu | | | Alt | | | | | | | Amp | | Alt |
| Br29P | Mu | | | Alt | | | | | | | | | |

TABLE 3-continued

Mutations of the TP53, PI3K, and RB1 pathways in GBM

| Tumor sample | TP53 | | | | PI3K Pathway | | | | | RB1 | | | |
|---|---|---|---|---|---|---|---|---|---|---|---|---|---|
| | TP53 | MDM2 | MDM4 | All genes | PTEN | PIK3CA | PIK3R1 | IRS1 | All genes | RB1 | CDK4 | CDKN2A | All genes |
| Fraction of tumors with altered gene/pathway# | 0.55 | 0.05 | 0.05 | 0.64 | 0.27 | 0.09 | 0.09 | 0.05 | 0.50 | 0.14 | 0.14 | 0.45 | 0.68 |

*Mut, mutated;
Amp, amplified;
Del, deleted;
Alt, altered
Fraction of affected tumors in 22 Discovery Screen samples Gene expression patterns can inform the analysis of pathways because they can reflect epigenetic alterations not detectable by sequencing or copy number analyses. They can also point to downstream effects on gene expression resulting from the altered pathways described above. To analyze the transcriptome of GBMs, we performed SAGE (serial analysis of gene expression) (36) on all GBM samples used for mutation analysis for which RNA was available (total of 18 samples) as well as two independent normal brain RNA controls. When combined with massively parallel sequencing-by-synthesis methods (37-40), SAGE provides a highly quantitative and sensitive measure of gene expression.

The transcript analysis was first used to help identify target genes from the amplified and deleted regions that were identified in this study. Though some of these regions contained a known tumor suppressor gene or oncogene, many contained several genes that had not previously been implicated in cancer. In tables S5 and S6, a candidate target gene could be identified within several of these regions through the use of the mutational as well as transcriptional data.

Second, we attempted to identify genes that were differentially expressed in GBMs compared to normal brain. There was a high number (143) of genes that were expressed at an average 10-fold higher level in 18 GBMs analyzed (compared to normal brain samples). Among the 143 over-expressed genes, there were 16 that were secreted or expressed on the cell surface. Many of these were over expressed in the xenografts as well as in the primary brain tumors, suggesting new opportunities for diagnostic and therapeutic applications.

Example 10

High Frequency Alterations of IDH 1 in Young GBM Patients

The top CAN-gene list (FIG. 10, Table S7) included a number of individual genes which had not previously been linked to GBMs. The most frequently mutated of these genes, IDH1, encodes isocitrate dehydrogenase 1, which catalyzes the oxidative carboxylation of isocitrate to α-ketoglutarate, resulting in the production of NADPH. Five isocitrate dehydrogenase genes are encoded in the human genome, with the products of three (IDH3 alpha, IDH3 beta, IDH3 gamma) forming a heterotetramer (2 in the mitochondria and utilizing NAD(+) as an electron acceptor to catalyze the rate-limiting step of the tricarboxylic acid cycle. The fourth isocitrate dehydrogenase (IDH2) is also localized to the mitochondria, but like IDH1, uses NADP(+) as an electron acceptor. The IDH1 product, unlike the rest of the IDH proteins, is contained within the cytoplasm and peroxisomes (41). The protein forms an asymmetric homodimer (42), and is thought to function to regenerate NADPH and -ketoglutarate for intraperoxisomal and cytoplasmic biosynthetic processes. The production of cytoplasmic NADPH by IDH1 appears to play a significant role in cellular control of oxidative damage (43) (44). None of the other IDH genes, other genes involved in the tricarboxylic acid cycle, or other peroxisomal proteins were found to be genetically altered in our analysis.

IDH1 was found to be somatically mutated in five GBM tumors in the Discovery Screen. Surprisingly, all five had the same heterozygous point mutation, a change of a guanine to an adenine at position 395 of the IDH1 transcript (G395A), leading to a replacement of an arginine with a histidine at amino acid residue 132 of the protein (R132H). In our prior study of colorectal cancers, this same codon had been found to be mutated in a single case through alteration of the adjacent nucleotide, resulting in a R132C amino acid change (10). Five additional GBMs evaluated in our Prevalence Screen were found to have heterozygous R132H mutations, and an additional two tumors had a third distinct mutation affecting the same amino acid residue, R132S (FIG. 1; Table 4). The R132 residue is conserved in all known species and is localized to the substrate binding site, forming hydrophilic interaction with the alpha-carboxylate of isocitrate (FIG. 2) (42, 45).

TABLE 4

Characteristics of GBM patients with IDHI mutations

| Patient ID | Patient age (years)* | Sex | Recurrent GBM# | Secondary GBM^ | Overall survival (years)& | IDH1 Mutation | | Mutation of TP53 | Mutation of PTEN, RB1, EGFR, or NF1 |
|---|---|---|---|---|---|---|---|---|---|
| | | | | | | Nucleotide | Amino acid | | |
| Br10P | 30 | F | No | No | 2.2 | G395A | R132H | Yes | No |
| Br11P | 32 | M | No | No | 4.1 | G395A | R132H | Yes | No |
| Br12P | 31 | M | No | No | 1.6 | G395A | R132H | Yes | No |
| Br104X | 29 | F | No | No | 4.0 | C394A | R132S | Yes | No |
| Br106X | 36 | M | No | No | 3.8 | G395A | R132H | Yes | No |

TABLE 4-continued

Characteristics of GBM patients with IDHI mutations

| Patient ID | Patient age (years)* | Sex | Recurrent GBM# | Secondary GBM^ | Overall survival (years)& | IDH1 Mutation Nucleotide | IDH1 Mutation Amino acid | Mutation of TP53 | Mutation of PTEN, RB1, EGFR, or NF1 |
|---|---|---|---|---|---|---|---|---|---|
| Br122X | 53 | M | No | No | 7.8 | G395A | R132H | No | No |
| Br123X | 34 | M | No | Yes | 4.9 | G395A | R132H | Yes | No |
| Br237T | 26 | M | No | Yes | 2.6 | G395A | R132H | Yes | No |
| Br211T | 28 | F | No | Yes | 0.3 | G395A | R132H | Yes | No |
| Br27P | 32 | M | Yes | Yes | 1.2 | G395A | R132H | Yes | No |
| Br129X | 25 | M | Yes | Yes | 3.2 | C394A | R132S | No | No |
| Br29P | 42 | F | Yes | Unknown | Unknown | G395A | R132H | Yes | No |
| IDH1 mutant patients (n = 12) | 33.2 | 67% M | 25% | 42% | 3.8 | 100% | 100% | 83% | 0% |
| IDH1 wildtype patients (n = 93) | 53.3 | 65% M | 16% | 1% | 1.5 | 0% | 0% | 27% | 60% |

*Patient age refers to age at which patent GBM sample was obtained.
Recurrent GBM designates a GBM which was resected >3 months after a prior diagnosis of GBM.
^Secondary GBM designates a GBM which was resected >1 year after a prior diagnosis of a lower grade glioma (WHO I-III).
&Overall survival was calculated using date of GBM diagnosis and date of death or last patient contact: patients Br10P and Br11P were alive at last contact. Median survival for IDH1 mutant patients and IDH1 wildtype patients was calculated using logrank test. Previous pathologic diagnoses in secondary GBM patients were oligodendroglioma (WHO grade II) in Br123X, low grade glioma (WHO grade I-II) in Br237T and B211T, anaplastic astrocytoma (WHO grade III) in Br27P, and anaplastic oligodendroglioma (WHO grade III) in Br129X.
Abbreviations: GBM (glioblastoma multiforme, WHO grade IV), WHO (World Health Organization), M (male), F (female), mut (mutant).
Mean age and median survival are listed for the groups of IDH1-mutated and IDH1-wildtype patients.

Several important observations were made about IDH1 mutations and their potential clinical significance. First, mutations in IDH1 preferentially occurred in younger GBM patients, with a mean age of 33 years for IDH1-mutated patients, as opposed to 53 years for patients with wildtype IDH1 (P<0.001, t-test, Table 4). In patients under 35 years of age, nearly 50% (9 of 19) had mutations in IDH1. Second, mutations in IDH1 were found in nearly all of the patients with secondary GBMs (mutations in 5 of 6 secondary GBM patients, as compared to 7 of 99 patients with primary GBMs, P<0.001, binomial test), including all five secondary GBM patients under 35 years of age. Third, patients with IDH1 mutations had a significantly improved prognosis, with a median overall survival of 3.8 years as compared to 1.1 years for patients with wildtype IDH1 (P<0.001, log-rank test). Although younger age and mutated TP53 are known to be positive prognostic factors for GBM patients, this association between IDH1 mutation and improved survival was noted even in patients <45 years old (FIG. 3, P<0.001, log-rank test), as well as in the subgroup of young patients with TP53 mutations (P<0.02, log-rank test).

REFERENCES AND NOTES

The disclosure of each reference cited is expressly incorporated herein.
1. D. N. Louis et al., Acta Neuropathol 114, 97 (2007).
2. R. Stupp et al., N Engl J Med 352, 987 (2005).
3. F L Scherer, American Journal of Cancer 40, 159 (1940).
4. P. Kleihues, H. Ohgaki, Neuro Oncol 1, 44 (1999).
5. H. Ohgaki, P. Kleihues, Am J Pathol 170, 1445 (2007).
6. H. Ohgaki et al., Cancer Res 64, 6892 (2004).
7. I. K. Mellinghoff et al., N Engl J Med 353, 2012 (2005).
8. E. A. Maher et al., Cancer Res 66, 11502 (2006).
9. C. L. Tso et al., Cancer Res 66, 159 (2006).
10. T. Sjoblom et al., Science 314, 268 (2006).
11. L. D. Wood et al., Science 318, 1108 (2007).
12. See Supporting Online Material Science 26 Sep. 2008: Vol. 321. no. 5897, pp. 1807-1812.
13. D. P. Cahill et al., Clin Cancer Res 13, 2038 (2007).
14. C. Hunter et al., Cancer Res 66, 3987 (2006).
15. J. M. Winter, J. R. Brody, S. E. Kern, Cancer Biol Ther 5, 360 (2006).
16. S. Jones et al., Proc Natl Acad Sci USA 105, 4283 (2008).
17. S. Jones, co-submitted to Science (2008).
18. R. Kraus-Ruppert, J. Laissue, F L Burk, N. Odartchenko, J Comp Neurol 148, 211 (1973).
19. P. C. Ng, S. Henikoff, Nucleic Acids Res 31, 3812 (2003).
20. R. Karchin. (2008). Structural models of mutants identified in glioblastomas. (available at the website of the Karchin Laboratory)
21. F. J. Steemers et al., Nat Methods 3, 31 (2006).
22. R. J. Leary, Submitted (2008).
23. P. Cairns et al., Nat Genet 11, 210 (1995).
24. J. M. Nigro et al., Nature 342, 705 (1989).
25. J. Li et al., Science 275, 1943 (1997).
26. K. Ueki et al., Cancer Res 56, 150 (1996).
27. A. J. Wong et al., Proc Natl Acad Sci USA 84, 6899 (1987).
28. A. J. Wong et al., Proc Natl Acad Sci USA 89, 2965 (1992).
29. L. Frederick, X. Y. Wang, G. Eley, C. D. James, Cancer Res 60, 1383 (2000).
30. Y. Li et al., Cell 69, 275 (1992).
31. G. Thiel et al., Anticancer Res 15, 2495 (1995).
32. Y. Samuels et al., Science 304, 554 (2004).
33. D. K. Broderick et al., Cancer Res 64, 5048 (2004).
34. G. L. Gallia et al., Mol Cancer Res 4, 709 (2006).
35. S. Ekins, Y. Nikolsky, A. Bugrim, E. Kirillov, T. Nikolskaya, Methods Mol Biol 356, 319 (2007).
36. V. E. Velculescu, L. Zhang, B. Vogelstein, K. W. Kinzler, Science 270, 484 (1995).
37. M. Sultan et al., Science (2008).
38. R. Lister et al., Cell 133, 523 (2008).
39. A. Mortazavi, B. A. Williams, K. McCue, L. Schaeffer, B. Wold, Nat Methods 5, 621 (2008).
40. R. Morin et al., Biotechniques 45, 81 (2008).
41. B. V. Geisbrecht, S. J. Gould, J Biol Chem 274, 30527 (1999).
42. X. Xu et al., J Biol Chem 279, 33946 (2004).
43. S. M. Lee et al., Free Radic Biol Med 32, 1185 (2002).
44. S. Y. Kim et al., Mol Cell Biochem 302, 27 (2007).
45. A. Nekrutenko, D. M. Hillis, J. C. Patton, R. D. Bradley, R. J. Baker, Mol Biol Evol 15, 1674 (1998).

46. G. T. Jennings, K. I. Minard, L. McAlister-Henn, Biochemistry 36, 13743 (1997).
47. D. Christianson, R. Alexander, J Am Chem Soc 111, 6412 (1989).
48. C. Luyken et al., Cancer 101, 146 (2004).
49. I. S. Kil, S. Y. Kim, S. J. Lee, J. W. Park, Free Radic Biol Med 43, 1197 (2007).

Example 11

Materials and Methods

Gene Selection

The protein coding exons from 23,781 transcripts representing 20,735 unique genes were targeted for sequencing. This set comprised 14,554 transcripts from the highly curated Consensus Coding Sequence (CCDS) database (available at the NIH website) a further 6,019 transcripts from the Reference Sequence (RefSeq) database (available at the NIH website) and an additional 3,208 transcripts with intact open reading frames from the Ensembl database. We excluded transcripts from genes that were located on the Y chromosome or were precisely duplicated within the genome. As detailed below, 23,219 transcripts representing 20,661 genes were successfully sequenced.

Bioinformatic Resources

Consensus Coding Sequence (Release 1), RefSeq (release 16, March 2006) and Ensembl (release 31) gene coordinates and sequences were acquired from the UCSC Santa Cruz Genome Bioinformatics Site. The positions listed in the Supplementary Tables correspond to UCSC Santa Cruz hg17, build 35.1. The single nucleotide polymorphisms used to filter-out known SNPs were those present in dbSNP (release 125) that had been validated by the HapMap project. BLAT and In Silico PCR (UCSC Santa Cruz Genome Bioinformatics Site) were used to perform homology searches in the human and mouse genomes.

Primer Design

Primer 3 software (available at frodo at MIT) was used to generate primers no closer than 50 bp to the target boundaries, producing products of 300 to 600 bp. Exons exceeding 350 bp were divided into several overlapping amplicons. In silico PCR and BLAT were used to select primer pairs yielding a single PCR product from a unique genomic position. Primer pairs for duplicated regions giving multiple in silico PCR or BLAT hits were redesigned at positions that were maximally different between the target and duplicated sequences. A universal primer (M13F, 5'-GTAAAACGACGGCCAGT-3'; SEQ ID NO: 136) was added to the 5' end of the primer with the smallest number of mono- or dinucleotide repeats between itself and the target region. The primer sequences used in this study are listed in table S1 available on line at Science 26 Sep. 2008: Vol. 321. no. 5897, pp. 1807-1812.

Glioblastoma Multiforme (GBM) DNA Samples

Tumor DNA was obtained from GBM xenografts and primary tumors, with matched normal DNA for each case obtained from peripheral blood samples, as previously described (1). The Discovery Screen consisted of 22 tumor samples (15 xenografts and 7 primary tumors), with the Prevalence screen including another 83 samples (53 xenografts and 30 primary tumors). Additional clinical information regarding Discovery and Prevalence Screen samples is available in table S2, available on line at *Science* 26 Sep. 2008: Vol. 321. no. 5897, pp. 1807-1812. All samples were given the histologic diagnosis of glioblastoma multiforme (GBM; World Health Organization Grade IV), except for two Discovery Screen samples who were recorded as "high grade glioma, not otherwise specified". Samples were classified as recurrent for patients in whom a GBM had been diagnosed at least 3 months prior to the surgery when the study GBM sample was obtained. There were 3 recurrent GBMs in the Discovery Screen, and 15 in the Prevalence Screen. Samples were classified as secondary for patients in whom a lower grade glioma (WHO grade I-III) had been histologically confirmed at least 1 year prior to the surgery when the study GBM sample was obtained. One Discovery Screen sample and 5 Prevalence Screen samples were classified as secondary.

TABLE 5

Overview of GBM samples used in the Prevalence and Discovery Screens:

|  | Discovery | Validation | Total |
|---|---|---|---|
| Number of samples | 22 | 83 | 105 |
| Patient age | | | |
| Mean age (years) | 48.6 | 51.7 | 51.0 |
| Median age (years) | 45 | 53 | 52 |
| Patient sex | | | |
| Male | 14 | 55 | 69 |
| Female | 8 | 28 | 36 |
| Sample source | | | |
| Xenograft | 15 | 53 | 68 |
| Primary tumor | 7 | 30 | 37 |
| GBM subclasses | | | |
| Recurrent | 3 | 15 | 18 |
| Recurrent with prior chemotherapy | 1 | 10 | 11 |
| Secondary | 1 | 5 | 6 |

Pertinent clinical information, including date of birth, date study GBM sample obtained, date of original GBM diagnosis (if different than the date that the GBM sample was obtained, as in the case of recurrent GBMs), date and pathology of preceding diagnosis of lower grade glioma (in cases of secondary GBMs), the administration of radiation therapy and/or chemotherapy prior to the date that the GBM sample was obtained, date of last patient contact, and patient status at last contact. All samples were obtained in accordance with the Health Insurance Portability and Accountability Act (HIPAA). All samples were obtained in accordance with the Health Insurance Portability and Accountability Act (HIPAA). As previously described, tumor-normal pair matching was confirmed by typing nine STR loci using the PowerPlex 2.1 System (Promega, Madison, Wis.) and sample identities checked throughout the Discovery and Prevalence screens by sequencing exon 3 of the HLA-A gene. PCR and sequencing was carried out as described in (1).

Statistical Analysis of Clinical Data

Paired normal and malignant tissue from 105 GBM patients were used for genetic analysis. Complete clinical information (i.e. all pertinent clinical information such as date of initial GBM diagnosis, date of death or last contact) was available for 91 of the 105 patients. Of these 91 patients, five (all IDH1-wildtype) died within the first month after surgery and were excluded from analysis (Br308T, 8r246T, Br23X, Br301T, Br139X), as was a single patient (Br119X) with a presumed surgical cure (also IDH 1—wildtype) who was alive at last contact ~10 years after diagnosis. Kaplan Meier survival curves were compared using the Mantel Cox log-rank test. Hazard ratios were computed using the Mantel-Haenszel method. The following definitions were used in the GBM patient grouping and survival analysis computations: 1) Patient age referred to the age at which the patient GBM sample was obtained. 2) Recurrent GBM designates a GBM which was resected >3 months after a prior diagnosis of GBM. 3) Secondary GBM designates a GBM which was resected >1 year after a prior diagnosis of a lower grade glioma (WHO 4) Overall survival was calculated using date of GBM diagnosis and date of death or last patient contact. All confidence intervals were calculated at the 95% level.

Mutation Discovery Screen

CCDS, RefSeq and Ensembl genes were amplified in 22 GBM samples and one control samples from normal tissues of one of the GBM patients. All coding sequences and the flanking 4 bp were analyzed using Mutations Surveyor (Softgenetics, State College, Pa.) coupled to a relational database (Microsoft SQL Server). For an amplicon to be further analyzed, at least three quarters of the tumors were required to have 90% or more of bases in the region of interest with a Phred quality score of 20. In the amplicons that passed this quality control, mutations identical to those observed in the normal sample as well as known single nucleotide polymorphisms were removed. The sequencing chromatogram of each detected mutation was then visually inspected to remove false positive calls by the software. Every putative mutation was re-amplified and sequenced in tumor DNA to eliminate artifacts. DNA from normal tissues of the same patient in which the mutation was identified was amplified and sequenced to determine whether the mutations were somatic. When a mutation was found, BLAT was used to search the human and mouse genomes for related exons to ensure that putative mutations were the result of amplification of homologous sequences. When there was a similar sequence with 90% identity over 90% of the target region, additional steps were performed. Mutations potentially arising from human duplications were re-amplified using primers designed to distinguish between the two sequences. Mutations not observed using the new primer pair were excluded. The remainder were included as long as the mutant base was not present in the homologous sequence identified by BLAT. Mutations originally observed in mouse xenografts were re-amplified in DNA from primary tumors and included either if the mutation was present in the primary tumors or if the mutant was not identified in the homologous mouse sequence identified by BLAT.

Mutation Prevalence Screen

We further evaluated a set of 20 mutated genes that had been identified in the Discover Screen in a second (Prevalence) screen, which included an additional 83 GBMs (tabl S2). The genes selected were mutated in at least two tumors and had mutatio frequencies >10 mutations per Mb of tumor DNA sequenced. The primers used (table S1, available on line at Science 26 Sep. 2008: Vol. 321. no. 5897, pp. 1807-1812) and methods of analysis and duration of potential mutations were the same as in the Discovery screen. All somatic mutations observed in the Prevalence screen are reported in FIG. 10, Table S4.

Copy Number Analysis

The Illumina Infinium II Whole Genome Genotyping Assay employing the BeadChip platform was used to analyze tumor samples at 1,072,820 (1M) SNP loci. All SNP positions were based on the hg18 (NCBI Build 36, March 2006) version of the human genome reference sequence. The genotyping assay begins with hybridization to a 50 nucleotide oligo, followed by a two-color fluorescent single base extension. Fluorescence intensity image files were processed using Illumina BeadStation software to provide normalized intensity values (R) for each SNP position. For each SNP, the normalized experimental intensity value (R) was compared to the intensity values for that SNP from a training set of normal samples and represented as a ratio (called the "Log R Ratio") of log 2(Rexperimental/Rtraining set).

The SNP array data were analyzed using modifications of a previously described method (2). Homozygous deletions (HDs) were defined as three or more consecutive SNPs with a Log R Ratio value of −2. The first and last SNPs of the HD region were considered to be the boundaries of the alteration for subsequent analyses. To eliminate chip artifacts and potential copy number polymorphisms, we removed all HDs that were included in copy number polymorphism databases. Adjacent homozygous deletions separated by three or fewer SNPs were considered to be part of the same deletion, as were HDs within 100,000 bp of each other. To identify the target genes affected by HDs, we compared the location of coding exons in the RefSeq, CCDS and Ensembl databases with the genomic coordinates of the observed HDs. Any gene with a portion of its coding region contained within a homozygous deletion was considered to be affected by the deletion.

As outlined in (2), amplifications were defined by regions containing three SNPs with an average LogR ratio 0.9, with at least one SNP having a LogR ratio 1.4. As with HDs, we excluded all putative amplifications that had identical boundaries in multiple samples. As focal amplifications are more likely to be useful in identifying specific target genes, a second set of criteria were used to remove complex amplifications, large chromosomal regions or entire chromosomes that showed copy number gains. Amplifications >3 Mb in size and groups of nearby amplifications (within 1 Mb) that were also >3 Mb in size were considered complex. Amplifications or groups of amplifications that occurred at a frequency of 4 distinct amplifications in a 10 Mb region or 5 amplifications per chromosome were deemed to be complex. The amplifications remaining after these filtering steps were considered to be focal amplifications and were the only ones included in subsequent statistical analyses. To identify protein coding genes affected by amplifications, we compared the location of the start and stop positions of each gene within the RefSeq, CCDS and Ensmbl databases with the genomic coordinates of the observed amplifications. As amplifications containing only a fraction of a gene are less likely to have a functional consequence, we only considered genes whose entire coding regions were included in the observed amplifications.

Estimation of Passenger Mutation Rates

From the synonymous mutations observed in the Discovery Screen, we estimated a lower bound of the passenger rate. The lower bound was defined as the product of the synonymous mutation rate and the NS:S ratio (1.02) observed in the HapMap database of human polymorphisms. The calculated rate of 0.38 mutations/Mb successfully sequenced is likely an underestimate because selection against nonsynonymous mutations may be more stringent in the germline than in somatic cells. An upper bound was calculated from the total observed number of non-synonymous mutations/Mb after excluding the most highly mutated genes known to be drivers from previous studies (TP53, PTEN, and RB1). The resultant passenger mutation rate of 1.02 non-synonymous mutations/Mb represents an over-estimate of the background rate as some of the mutations in genes other than TP53, PTEN, and RB1 were likely to be drivers. A "Mid" measure of 0.70 mutations/Mb was obtained from the average of the lower and upper bound rates. For comparisons of the number and type of somatic mutations identified in the Discovery and Prevalence Screens, two sample t-tests between percents were used.

Expression Analysis

SAGE tags were generated using a Digital Gene Expression-Tag Profiling preparation kit (Illumina, San Diego, Calif.) as recommended by the manufacturer. In brief, RNA was purified using guianidine isothiocyanate and reverse transcription with oligo-dT magnetic beads was performed on ~1 ug of total RNA from each sample. Second strand synthesis was accomplished through RNAse H nicking and DNA polymerase I extension. The double-stranded cDNA was digested with the restriction enonuclease Nla III and ligated to an adapter containing a Mme I restriction site. After Mme I digestion, a second adapter was ligated, and the adapter-ligated cDNA construct was enriched by 18 cycles of PCR and fragments of 85 bp were purified from a polyacrylamide gel. The library size was estimated using real-time PCR and the tags sequenced on a Genome Analyzer System (Illumina, San Diego, Calif.).

Statistical Analysis

Overview of Statistical Analysis

The statistical analyses focused on quantifying the evidence that the mutations in a gene or a biologically defined set of genes reflect an underlying mutation rate that is higher than the passenger rate. In both cases, the analysis integrates data on point mutations with data on copy number alterations (CNA). The methodology for the analysis of point mutations is based on that described in (3) while the methodology for integration across point mutations and CNA's is based on (2). We provide a self-contained summary herein, as several modifications to the previously described methods were required.

Statistical Analyses of CAN-Genes

The mutation profile of a gene refers to the number of each of the twenty-five context-specific types of mutations defined earlier (3). The evidence on mutation profiles is evaluated using an Empirical Bayes analysis (4) comparing the experimental results to a reference distribution representing a genome composed only of passenger genes. This is obtained by simulating mutations at the passenger rate in a way that precisely replicates the experimental plan. Specifically, we consider each gene in turn and simulate the number of mutations of each type from a binomial distribution with success probability equal to the context-specific passenger rate. The number of available nucleotides in each context is the number of successfully sequenced nucleotides for that particular context and gene in the samples studied. When considering nonsynonymous mutations other than indels, we focus on nucleotides at risk, as defined previously (3).

Using these simulated datasets, we evaluated the passenger probabilities for each of the genes that were analyzed in this study. These passenger probabilities represent statements about specific genes rather than about groups of genes. Each passenger probability is obtained via a logic related to that of likelihood ratios: the likelihood of observing a particular score in a gene if that gene is a passenger is compared to the likelihood of observing it in the real data. The gene-specific score used in our analysis is based on the Likelihood Ratio Test (LRT) for the null hypothesis that, for the gene under consideration, the mutation rate is the same as the passenger mutation rate. To obtain a score, we simply transform the LRT to $s=\log(LRT)$. Higher scores indicate evidence of mutation rates above the passenger rates. This general approach for evaluating passenger probabilities follows that described by Efron and Tibshirani (4). Specifically, for any given score s, F(s) represents the proportion of simulated genes with scores higher than s in the experimental data, F0 is the corresponding proportion in the simulated data, and p0 is the estimated overall proportion of passenger genes (discussed below). The variation across simulations is small but nonetheless we generated and collated 100 datasets to estimate F0. We then numerically estimated the density functions f and f0 corresponding to F and F0 and calculated, for each score s, the ratio p0·f0(s)/f(s), also known as "local false discovery rate" (4). Density estimation was performed using the function "density" in the R statistical programming language with default settings. The passenger probability calculations depend on an estimate of p0, the proportion of true passengers. Our implementation seeks to give an upper bound to p0 and thus provide conservatively high estimates of the passenger probability. To this end we set p0=1. We also constrained the passenger probability to change monotonically with the score by starting with the lowest values and recursively setting values that decrease in the next value to their right. We similarly constrain passenger probabilities to change monotonically with the passenger rate.

An open source package for performing these calculations in the R statistical environment, named CancerMutationAnalysis, is available at astor at JHMI. A detailed mathematical account of our specific implementation is provided in (5) and general analytic issues are discussed in (6).

Statistical Analysis of CNA. For each of the genes involved in amplifications or deletions, we further quantified the strength of the evidence that they drive tumorigenesis through estimations of their passenger probabilities. In each case, we obtain the passenger probability as an a posteriori probability that integrates information from the somatic mutation analysis of (3) with the data presented in this article. The passenger probabilities derived from the point mutation analysis serve as a priori probabilities. These are available for three different scenarios of passenger mutation rates and results are presented separately for each in FIG. 10, Table S3. Then, a likelihood ratio for "driver" versus "passenger" was evaluated using as evidence the number of samples in which a gene was found to be amplified (or deleted). The passenger term is the probability that the gene in question is amplified (or deleted) at the frequency observed. For each sample, we begin by computing the probability that the observed amplifications (and deletions) will include the gene in question by chance. Inclusion of all available SNPs is required for amplification, while any overlap of SNPs is sufficient for deletions. Specifically, if in a specific sample N SNPs are typed, and K amplifications are found, whose sizes, in terms of SNPs involved, are A1 ... AK, a gene with G SNPs will be included at random with probability $(A1-G+1)/N + \ldots + (AK-G+1)/N$ for amplifications and $(A1+G-1)/N + \ldots + (AK+G-1)/N$ for deletions. We then compute the probability of the observed number of amplifications (or deletions) assuming that the samples are independent but not identically distributed Bernoulli random variables, using the Thomas and Traub algorithm (7). Our approach to evaluating the likelihood under the null hypothesis is highly conservative, as it assumes that all the deletions and amplifications observed only include passengers. The driver term of the likelihood ratio was approximated as for the passenger term, after multiplying the sample-specific passenger rates above by a gene-specific factor reflecting the increase (alternative hypothesis) of interest. This increase is estimated by the ratio between the empirical deletion rate of the gene and the overall deletion rate.

This combination approach makes an approximating assumption of independence of amplifications and deletions. In reality, amplified genes cannot be deleted, so independence is technically violated. However, because of the relatively small number of amplification and deletion events, this assumption is tenable for the purposes of our analysis. Inspection of the likelihood, in a logarithmic scale, suggests that it is roughly linear in the overall number of events, supporting the validity of this approximation as a scoring system.

Analysis of Mutated Gene Pathways and Groups

Four types of data were obtained from the MetaCore database (GeneGo, Inc., St. Joseph, Mich.): pathway maps, Gene Ontology (GO) processes, GeneGo process networks, and protein-protein interactions. The memberships of each of the 23,781 transcripts in these categories were retrieved from the databases using RefSeq identifiers. In GeneGo pathway maps, 22,622 relations were identified, involving 4,175 transcripts and 509 pathways. For Gene Ontology processes, a total of 66,397 pairwise relations were identified, involving 12,373 transcripts and 4,426 GO groups. For GeneGo process networks, a total of 23,356 pairwise relationships, involving 6,158 transcripts and 127 processes, were identified. The predicted protein products of each mutated gene were also evaluated with respect to their physical interactions with proteins encoded by other mutated genes as inferred from the MetaCore database.

For each of the gene sets considered, we quantified the strength of the evidence that they included a higher-than-average proportion of drivers of carcinogenesis after consideration of set size. For this purpose, we sorted the genes by a score based on the combined passenger probability described above (taking into account mutations, homozygous deletions, and amplifications). We compared the ranking of the genes contained in the set with the ranking of those outside, using the Wilcoxon test, as implemented by the Limma package in Bioconductor (8), then corrected for multiplicity by the q-value method with an alpha of 0.2 (9).

Bioinformatic Analysis
Overview of Bioinformatic Analysis

We have developed a novel bioinformatics software pipeline (depicted below) to compute: (1) a score for ranking somatic missense mutations by the likelihood that they are passengers (LSMUT). The scores are based on properties derived from protein sequences, amino acid residue changes and positions within the proteins; and (2) qualitative annotations of each mutation, based on protein structure homology models.

Mutation Scores

We tested several supervised machine learning algorithms to identify one that would reliably distinguish between presumably neutral polymorphisms and cancer-associated mutations. The best algorithm was a Random Forest (12), which we trained on 2,840 cancer-associated mutations and 19,503 polymorphisms from the SwissProt Variant Pages (13) using parallel Random Forest software (PARF). Cancer-associated mutations were identified by parsing for the keywords "cancer", "carcinoma", "sarcoma", "blastoma", "melanoma", "lymphoma", "adenoma" and "glioma". For each mutation or polymorphism, we computed 58 numerical and categorical features (see table below). Two mutations present in the GBM tumor samples were found in the SwissProt Variant Pages and removed from the training data. Because the training set contained ~7 times as many polymorphisms as cancer-associated mutations, we used class weights to upweight the minority class (cancer-associated mutation weight was 5.0 and polymorphism weight was 1.0). The mtry parameter was set to 8 and the forest size to 500 trees. Missing feature values were filled in using the Random Forest proximity-based imputation algorithm (12) with six iterations. Full parameter settings and all data used to build the Random Forest are available upon request.

We then applied the trained forest to 594 GBM missense mutations and to a control set of 142 randomly generated missense mutations in transcripts of 78 genes that were found to be non-mutated in 11 colorectal cancers (5). For each mutation, the 58 predictive features were computed as described above and the trained forest was used to compute a predictive score for ranking the mutations. Specifically, the scores used are the fraction of trees that voted in favor of the "Polymorphic" class for each mutation.

To test the hypothesis that the scores of missense mutations in top-ranked CAN-genes were distributed differently than random missense mutations, we applied a modified Kolmogorov-Smirnov (KS) test, in which ties are broken by adding a very small random number to each score. The scores of missense mutations in the top 13 CAN genes were found to be significantly different from the mutations in the control set ($P<0.001$).

We estimate that mutations with scores <0.7 (~15% of the missense mutations) are unlikely to be passengers. The threshold is based on the putative similarity of passengers to the neutral polymorphisms in the SwissProt Variant set, of which only ~2% have scores <0.7. Scores of SwissProt Variants were obtained by randomly partitioning them into two folds, training a Random Forest on each (as described above) and then scoring each fold with the Random Forest trained on the other one.

Homology Models

The protein translations of mRNA transcripts found to have somatic missense mutations were input into ModPipe 1.0/MODELLER 9.1 homology model building software (14, 15). For each mutation, we identified all models that included the mutated position. If more than one model was produced for a mutation, we selected the model having the highest sequence identity with its template structure. The resulting model was used to compute the solvent accessibility of the wild type residue at the mutated position, using DSSP software (16). Accessibility values were normalized by dividing by the maximum residue solvent accessibility for each side chain type in a Gly-X-Gly tri-peptide (17). Solvent accessibilities greater than 36% were considered to be "exposed," those between 9% and 35% were considered "intermediate," and those <9% were considered "buried." DSSP was also used to compute the secondary structure of the mutated position. We used the LigBase (18) and PiBase (19) databases to identify mutated residue positions in the homology models that were close to ligands or domain interfaces in the equivalent positions of their template structures. Finally, for each mutation, we generated an image of the mutation mapped onto its homology model with UCSF Chimera (20). The images and associated information for each mutation are available at the website of the Karchin Laboratory. Model coordinates are available on request.

TABLE 6

The 58 numerical and categorical features used to train the Random Forest

| # | Feature | Description |
|---|---------|-------------|
| 1 | Net residue charge change | The change in formal charge resulting from the mutation. |
| 2 | Net residue volume change | The change in residue volume resulting from the mutation (18). |

TABLE 6-continued

The 58 numerical and categorical features used to train the Random Forest

| # | Feature | Description |
|---|---------|-------------|
| 3 | Net residue hydrophobicity change | The change in residue hydrophobicity resulting from the substitution (19). |
| 4 | Positional Hidden Markov model (HMM) conservation score | This feature is calculated based on the degree of conservation of the residue estimated from a multiple sequence alignment built with SAM-T2K software (20), using the protein in which the mutation occurred as the seed sequence (21). The SAM-T2K alignments are large, superfamily-level alignments that include distantly related homologs (as well as close homologs and orthologs) of the protein of interest. |
| 5 | Entropy of HMM alignment | The Shannon entropy calculated for the column of the SAM-T2K multiple sequence alignment, corresponding to the location of the mutation (21). |
| 6 | Relative entropy of HMM alignment | Difference in Shannon entropy calculated for the column of the SAM-T2K multiple sequence alignment (corresponding to the location of the mutation) and that of a background distribution of amino acid residues computed from a large sample of multiple sequence alignments (21). |
| 7 | Compatibility score for amino acid substitution in the column of a multiple sequence alignment of orthologs. | These multiple sequence alignments are calculated using groups of orthologous proteins from the OMA database (22), which are aligned with T-Coffee software (23). The compatibility score for the mutation in the column of interest is computed as: (P (most frequent residue in the column) − 2*P (wild type) + P (mutant) + P (Deletion) − 1)/(5 * number of unique amino acid residues in the column) |
| 8 | Grantham score | The Grantham substitution score for the wild type => mutant transition (24). |
| 9-11 | Predicted residue solvent accessibility | These features consist of the probability of the wild type residue being buried, intermediate or exposed as predicted by a neural network trained with Predict-2nd software (20) on a set of 1763 proteins with high resolution X-ray crystal structures sharing less than 30% homology (25). |
| 12-14 | Predicted contribution to protein stability | These features consist of the probability that the wild type residue contributes to overall protein stability in a manner that is highly stabilizing, average or destabilizing, as predicted by a neural network trained with Predict-2nd software (20) on a set of 1763 proteins with less than 30% homology. Stability estimates for the neural net training data were calculated using the FoldX force field (26). |
| 15-17 | Predicted flexibility (Bfactor) | These features consist of the probability that the wild type residue backbone is stiff, intermediate or flexible as predicted by a neural network trained with Predict-2nd software (20) on a set of 1763 proteins with less than 30% homology. Flexibilities for the neural net training data were estimated based on normalized temperature factors, computed using the method of (27) from the X-ray crystal structure files. |
| 18-20 | Predicted secondary structure | These features consist of the probability that the secondary structure of the region in which the wild type residue exists is helix, loop or strand as predicted by a neural net trained with Predict-2nd software (20) on a set of 1763 proteins with crystal structures and with less than 30% homology. |
| 21 | Change in hydrophobicity | Change in residue hydrophobicity due to the wild type → mutant transition. |
| 22 | Change in volume | Change in residue volume due to the wildtype → mutant transition. |
| 23 | Change in charge | Change in residue formal charge due to the wild type -> mutant transition. |
| 24 | Change in polarity | Change in residue polarity due to the wildtype → mutant transition. |
| 25 | EX substitution score | Amino acid substitution score from the EX matrix (28) |
| 26 | PAM250 substitution score | Amino acid substitution score from the PAM250 matrix (29) |
| 27 | BLOSUM 62 substitution score | Amino acid substitution score from the BLOSUM 62 matrix (30) |
| 28 | MJ substitution score | Amino acid substitution score from the Miyazawa-Jernigan contact energy matrix (28, 31) |
| 29 | HGMD2003 mutation count | Number of times that the wild type → mutant substitution occurs in the Human Gene Mutation Database, 2003 version (28, 32). |
| 30 | VB mutation count | Amino acid substitution score from the VB (Venkatarajan and Braun) matrix (28, 33) |
| 31-34 | Probability of seeing the wild type residue in the first, middle, or last position of an amino acid triple | Calculated by joint frequencies of amino acid triples in human proteins found in UniProtKB (11) |

TABLE 6-continued

The 58 numerical and categorical features used to train the Random Forest

| # | Feature | Description |
|---|---------|-------------|
| 35-37 | Probability of seeing the mutant residue in the first, middle, or last position of an amino acid triple | Calculated by joint frequencies of amino acid triples in human proteins found in UniProtKB (11) |
| 38-40 | Difference in probability of seeing the wildtype vs. the mutant residue in the first, middle, or last position of an amino acid triple | Calculated by joint frequencies of amino acid triples in human proteins found in UniProtKB (11) |
| 41 | Probability of seeing the wildtype at the center of a window of 5 amino acid residues | Calculated by a Markov chain of amino acid quintuples in human proteins found in UniProtKB (11) |
| 42 | Probability of seeing the mutant at the center of a window of 5 amino acid residues | Calculated by a Markov chain of amino acid quintuples in human proteins found in UniProtKB (11) |
| 43-56 | Binary categorical features from the UniProt KnowledgeBase feature table for the protein product of the transcript | These features give annotations, curated from the literature, of general binding sites, general active sites, lipid, metal, carbohydrate, DNA, phosphate and calcium binding sites, disulfides, seleno-cysteines, modified residues, propeptide residues, signal peptide residues, known mutagenic sites, transmembrane regions, compositionally biased regions, repeat regions, known motifs, and zinc fingers. The integer 1 indicates that a feature is present and the integer 0 indicates that it is absent at a mutated position. |

REFERENCES FOR EXAMPLE 11

1. T. Sjoblom et al., Science 314, 268 (2006).
2. R. J. Leary et al., Submitted (2008).
3. L. D. Wood et al., Science 318, 1108 (2007).
4. B. Efron, R. Tibshirani, Genet Epidemiol 23, 70 (2002).
5. G. Parmigiani et al., "Statistical Methods for the Analysis of Cancer Genome Sequencing Data" (Johns Hopkins University, 2006).
6. G. Parmigiani et al., Genomics in press (2008).
7. M. A. Thomas, A. E. Taub, Journal of Statistical Computation and Simulation 14, 125 (1982).
8. G. K. Smyth, in Bioinformatics and Computational Biology Solutions using R and Bioconductor V. Gentleman, S. Carey, R. Dudoit, W. H. Irizarry, Eds. (Springer, New York, 2005) pp. 397-420.
9. Y. Benjamini, Y. Hochberg, Journal of the Royal Statistical Society. Series B (Methodological) 57 289-300 (1995).
10. L. Breiman, Machine Learning, 5 (2001).
11. C. H. Wu et al., Nucleic Acids Res 34, D187 (2006).
12. R. Karchin et al., Bioinformatics 21, 2814 (2005).
13. A. Sali, T. L. Blundell, Journal of Molecular Biology 234, 779 (1993).
14. G. D. Rose, A. R. Geselowitz, G. J. Lesser, R. H. Lee, M. H. Zehfus, Science 229, 834 (1985).
15. A. C. Stuart, V. A. Ilyin, A. Sali, Bioinformatics 18, 200 (2002).
16. F. P. Davis, A. Sali, Bioinformatics 21, 1901 (2005).
17. E. F. Pettersen et al., J Comput Chem 25, 1605 (2004).
18. A. A. Zamyatnin, Prog Biophys Mol Biol, 107 (1972).
19. D. M. Engelman, T. A. Steitz, A. Goldman, Annu Rev Biophys Biophys Chem 15, 321 (1986).
20. K. Karplus et al., Proteins Suppl 5, 86 (2001).
21. S. Kullback, Information theory and statistics (Wiley, New York, 1959), pp.
22. A. Schneider, C. Dessimoz, G. H. Gonnet, Bioinformatics 23, 2180 (2007).
23. C. Notredame, D. G. Higgins, J. Heringa, J Mol Biol 302, 205 (2000).
24. R. Grantham, Science 185, 862 (1974).
25. G. Wang, R. L. Dunbrack, Jr., Bioinformatics 19, 1589 (2003).
26. J. Schymkowitz et al., Nucleic Acids Res 33, W382 (2005).
27. D. K. Smith, P. Radivojac, Z. Obradovic, A. K. Dunker, G. Zhu, Protein Sci 12, 1060 (2003).
28. L. Y. Yampolsky, A. Stoltzfus, Pac Symp Biocomput, 433 (2005).
29. R. M. Schwartz, M. O. Dayhoff, Science 199, 395 (1978).
30. S. Henikoff, J. G. Henikoff, Proc Natl Acad Sci USA 89, 10915 (1992).
31. S. Miyazawa, and Jernigan, R. L., Macromolecules, 534 (1985).
32. P. D. Stenson et al., Hum Mutat 21, 577 (2003).
33. M. S. Venkatarajan, and Braun, W., Journal of Molecular Modeling, 445 (2001).

The invention claimed is:

1. A method of characterizing a glioblastoma multiforme (GBM) tumor of a human subject, comprising:
assaying protein or nucleic acids of a GBM tumor of a human subject to identify the presence or absence of a somatic mutation at
codon 132 in isocitrate dehydrogenase 1 (IDH1); or
codon 172 in isocitrate dehydrogenase 2 (IDH2).

2. The method of claim 1 wherein the somatic mutation is selected from the group consisting of R132H in IDH1, R132S in IDH1, R132C in IDH1, R132L in IDH1, R132G in IDH1, R172M in IDH2, R172K in IDH2, and R172G in IDH2.

3. The method of claim 1 further comprising more than one step selected from the group consisting of:
identifying the tumor as likely to be a secondary GBM when the somatic mutation is present or a primary GBM when the somatic mutation is absent;
assigning a more favorable prognosis (longer life expectancy) when the somatic mutation is present or a less favorable prognosis (shorter life expectancy) when the somatic mutation is absent; and
assigning the subject to a clinical trial group based on presence or absence of the somatic mutation.

4. The method of claim 1 further comprising the step of:
prescribing an anti-cancer agent selected from the group consisting of a chemotherapeutic agent, a biological agent, and radiation to treat the GBM tumor.

5. The method of claim 1 wherein the step of assaying utilizes more than one technique selected from the group consisting of:
amplifying at least a portion of:
the IDH1 gene or cDNA of the IDH1 mRNA, said portion comprising codon 132 or nucleotide 394 or 395 of IDH1 transcript; or
the IDH2 gene or cDNA of the IDH2 mRNA, said portion comprising codon 172 or nucleotide 515 of IDH2 transcript;
employing an antibody which specifically binds to isocitrate dehydrogenase 1 (IDH1), to isocitrate dehydrogenase 2 (IDH2), or to both IDH1 and IDH2;
employing an antibody which preferentially binds to one or more of R132H, R132C, R132S, R132L, and R132G, of isocitrate dehydrogenase 1 (IDH1) and R172M, R172G, and R172K of IDH2, relative to R132 IDH1 or R172 IDH2;
hybridizing an oligonucleotide probe comprising:
IDH1 codon 132 or nucleotide 394 or 395 of IDH1 transcript plus sufficient adjacent nucleotides of IDH1 to achieve specific hybridization; or
IDH2 codon 172 or nucleotide 515 of IDH2 transcript plus sufficient adjacent nucleotides of IDH2 to achieve specific hybridization;
primer extending to generate a reaction product comprising at least a portion of:
IDH1 that includes codon 132 or nucleotide 394 or 395 of IDH1 transcript; or
IDH2 that includes codon 172 or nucleotide 515 of IDH2 transcript.

6. The method of claim 1 further comprising the step of:
identifying the tumor as likely to be a secondary GBM when the somatic mutation is present or a primary GBM when the somatic mutation is absent.

7. The method of claim 1 further comprising the step of:
assigning a more favorable prognosis (longer life expectancy) when the somatic mutation is present or a less favorable prognosis (shorter life expectancy) when the somatic mutation is absent.

8. The method of claim 1 further comprising the step of:
assigning the subject to a clinical trial group based on presence or absence of the somatic mutation.

9. The method of claim 1 wherein the step of assaying comprises:
amplifying at least a portion of:
the IDH1 gene or cDNA of the IDH1 mRNA, said portion comprising codon 132 or nucleotide 394 or 395 of IDH1 transcript; or
the IDH2 gene or cDNA of the IDH2 mRNA, said portion comprising codon 172 or nucleotide 515 of IDH2 transcript.

10. The method of claim 1 wherein the step of assaying comprises:
employing an antibody which specifically binds to isocitrate dehydrogenase 1 (IDH1), to isocitrate dehydrogenase 2 (IDH2), or to both IDH1 and IDH2.

11. The method of claim 1 wherein the step of assaying comprises:
employing an antibody which preferentially binds to one or more of R132H, R132C, R132S, R132L, and R132G, of isocitrate dehydrogenase 1 (IDH1) and R172M, R172G, and R172K of IDH2, relative to R132 IDH1 or R172 IDH2.

12. The method of claim 1 wherein the step of assaying comprises:
hybridizing an oligonucleotide probe comprising:
IDH1 codon 132 or nucleotide 394 or 395 of IDH1 transcript plus sufficient adjacent nucleotides of IDH1 to achieve specific hybridization; or IDH2 codon 172 or nucleotide 515 of IDH2 transcript plus sufficient adjacent nucleotides of IDH2 to achieve specific hybridization.

13. The method of claim 1 wherein the step of assaying comprises:
   primer extending to generate a reaction product comprising at least a portion of:
      IDH1 that includes codon 132 or nucleotide 394 or 395 of IDH1 transcript; or
      IDH2 that includes codon 172 or nucleotide 515 of IDH2 transcript.

14. The method of claim 1 further comprising the step of:
   administering an anti-cancer agent selected from the group consisting of a chemotherapeutic agent, a biological agent, and radiation to treat the GBM tumor.

* * * * *

UNITED STATES PATENT AND TRADEMARK OFFICE
CERTIFICATE OF CORRECTION

PATENT NO. : 8,685,660 B2
APPLICATION NO. : 13/060191
DATED : April 1, 2014
INVENTOR(S) : Vogelstein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 198 days.

Signed and Sealed this

Twenty-ninth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,685,660 B2
APPLICATION NO. : 13/060191
DATED : April 1, 2014
INVENTOR(S) : Bert Vogelstein et al.

Page 1 of 1

It is certified that error appears in the above-identified patent and that said Letters Patent is hereby corrected as shown below:

On Column 1, please replace the first paragraph as follows:
STATEMENT OF GOVERNMENTAL INTEREST
This invention was made with government support under grant numbers CA121113, CA062924, CA057345, CA043460, awarded by the National Institutes of Health. The government has certain rights in the invention.

Signed and Sealed this
Twentieth Day of March, 2018

Andrei Iancu
*Director of the United States Patent and Trademark Office*

SEQUENCE LISTING

<160> NUMBER OF SEQ ID NOS: 136

<210> SEQ ID NO 1
<211> LENGTH: 15
<212> TYPE: PRT
<213> ORGANISM: Homo sapiens

<400> SEQUENCE: 1

-continued

Lys Pro Ile Ile Ile Gly Arg His Ala Tyr Gly Asp Gln Tyr Arg
1               5                   10                  15

<210> SEQ ID NO 2
<211> LENGTH: 15
<212> TYPE: PRT
<213> ORGANISM: Homo sapiens

<400> SEQUENCE: 2

Lys Pro Ile Ile Ile Gly His His Ala Tyr Gly Asp Gln Tyr Arg
1               5                   10                  15

<210> SEQ ID NO 3
<211> LENGTH: 15
<212> TYPE: PRT
<213> ORGANISM: Homo sapiens

<400> SEQUENCE: 3

Lys Pro Ile Ile Ile Gly Cys His Ala Tyr Gly Asp Gln Tyr Arg
1               5                   10                  15

<210> SEQ ID NO 4
<211> LENGTH: 15
<212> TYPE: PRT
<213> ORGANISM: Homo sapiens

<400> SEQUENCE: 4

Lys Pro Ile Ile Ile Gly Leu His Ala Tyr Gly Asp Gln Tyr Arg
1               5                   10                  15

<210> SEQ ID NO 5
<211> LENGTH: 15
<212> TYPE: PRT
<213> ORGANISM: Homo sapiens

<400> SEQUENCE: 5

Lys Pro Ile Ile Ile Gly Ser His Ala Tyr Gly Asp Gln Tyr Arg
1               5                   10                  15

<210> SEQ ID NO 6
<211> LENGTH: 15
<212> TYPE: PRT
<213> ORGANISM: Homo sapiens

<400> SEQUENCE: 6

Lys Pro Ile Ile Ile Gly Gly His Ala Tyr Gly Asp Gln Tyr Arg
1               5                   10                  15

<210> SEQ ID NO 7
<211> LENGTH: 15
<212> TYPE: PRT
<213> ORGANISM: Homo sapiens

<400> SEQUENCE: 7

Lys Pro Ile Thr Ile Gly Arg His Ala His Gly Asp Gln Tyr Lys
1               5                   10                  15

<210> SEQ ID NO 8
<211> LENGTH: 15
<212> TYPE: PRT
<213> ORGANISM: Homo sapiens

<400> SEQUENCE: 8

Lys Pro Ile Thr Ile Gly Met His Ala His Gly Asp Gln Tyr Lys
1               5                   10                  15

<210> SEQ ID NO 9
<211> LENGTH: 15
<212> TYPE: PRT
<213> ORGANISM: Homo sapiens

<400> SEQUENCE: 9

Lys Pro Ile Thr Ile Gly Lys His Ala His Gly Asp Gln Tyr Lys
1               5                   10                  15

<210> SEQ ID NO 10
<211> LENGTH: 27
<212> TYPE: PRT
<213> ORGANISM: Homo sapiens

<400> SEQUENCE: 10

Ser Gly Trp Val Lys Pro Ile Ile Ile Gly His His Ala Tyr Gly Asp
1               5                   10                  15

Gln Tyr Arg Ala Thr Asp Phe Val Val Pro Gly
            20                  25

<210> SEQ ID NO 11
<211> LENGTH: 15
<212> TYPE: PRT
<213> ORGANISM: Homo sapiens

<400> SEQUENCE: 11

Gly Trp Val Lys Pro Ile Ile Ile Gly His His Ala Tyr Gly Asp
1               5                   10                  15

<210> SEQ ID NO 12
<211> LENGTH: 15
<212> TYPE: PRT
<213> ORGANISM: Homo sapiens

<400> SEQUENCE: 12

Ile Gly His His Ala Tyr Gly Asp Gln Tyr Arg Ala Thr Asp Phe
1               5                   10                  15

<210> SEQ ID NO 13
<211> LENGTH: 15
<212> TYPE: PRT
<213> ORGANISM: Homo sapiens

<400> SEQUENCE: 13

Ser Gly Trp Val Lys Pro Ile Ile Ile Gly His His Ala Tyr Gly
1               5                   10                  15

<210> SEQ ID NO 14
<211> LENGTH: 15
<212> TYPE: PRT
<213> ORGANISM: Homo sapiens

<400> SEQUENCE: 14

Lys Pro Ile Ile Ile Gly His His Ala Tyr Gly Asp Gln Tyr Arg
1               5                   10                  15

<210> SEQ ID NO 15
<211> LENGTH: 15
<212> TYPE: PRT
<213> ORGANISM: Homo sapiens

<400> SEQUENCE: 15

Gly Trp Val Lys Pro Ile Ile Ile Gly His His Ala Tyr Gly Asp
1               5                   10                  15

```
<210> SEQ ID NO 16
<211> LENGTH: 15
<212> TYPE: PRT
<213> ORGANISM: Homo sapiens

<400> SEQUENCE: 16

Val Lys Pro Ile Ile Ile Gly His His Ala Tyr Gly Asp Gln Tyr
 1               5                  10                  15

<210> SEQ ID NO 17
<211> LENGTH: 15
<212> TYPE: PRT
<213> ORGANISM: Homo sapiens

<400> SEQUENCE: 17

Pro Ile Ile Ile Gly His His Ala Tyr Gly Asp Gln Tyr Arg Ala
 1               5                  10                  15

<210> SEQ ID NO 18
<211> LENGTH: 8
<212> TYPE: PRT
<213> ORGANISM: Homo sapiens

<400> SEQUENCE: 18

Gly His His Ala Tyr Gly Asp Gln
 1               5

<210> SEQ ID NO 19
<211> LENGTH: 9
<212> TYPE: PRT
<213> ORGANISM: Homo sapiens

<400> SEQUENCE: 19

Lys Pro Ile Ile Ile Gly His His Ala
 1               5

<210> SEQ ID NO 20
<211> LENGTH: 9
<212> TYPE: PRT
<213> ORGANISM: Homo sapiens

<400> SEQUENCE: 20

Lys Pro Ile Ile Ile Gly His His Ala
 1               5

<210> SEQ ID NO 21
<211> LENGTH: 9
<212> TYPE: PRT
<213> ORGANISM: Homo sapiens

<400> SEQUENCE: 21

Pro Ile Ile Ile Gly His His Ala Tyr
 1               5

<210> SEQ ID NO 22
<211> LENGTH: 9
<212> TYPE: PRT
<213> ORGANISM: Homo sapiens

<400> SEQUENCE: 22

Gly His His Ala Tyr Gly Asp Gln Tyr
 1               5

<210> SEQ ID NO 23
<211> LENGTH: 10
```

```
<212> TYPE: PRT
<213> ORGANISM: Homo sapiens

<400> SEQUENCE: 23

Lys Pro Ile Ile Gly His His Ala Tyr
 1               5                   10

<210> SEQ ID NO 24
<211> LENGTH: 10
<212> TYPE: PRT
<213> ORGANISM: Homo sapiens

<400> SEQUENCE: 24

Ile Gly His His Ala Tyr Gly Asp Gln Tyr
 1               5                   10

<210> SEQ ID NO 25
<211> LENGTH: 11
<212> TYPE: PRT
<213> ORGANISM: Homo sapiens

<400> SEQUENCE: 25

Val Lys Pro Ile Ile Gly His His Ala Tyr
 1               5                   10

<210> SEQ ID NO 26
<211> LENGTH: 11
<212> TYPE: PRT
<213> ORGANISM: Homo sapiens

<400> SEQUENCE: 26

Ile Ile Gly His His Ala Tyr Gly Asp Gln Tyr
 1               5                   10

<210> SEQ ID NO 27
<211> LENGTH: 9
<212> TYPE: PRT
<213> ORGANISM: Homo sapiens

<400> SEQUENCE: 27

Ile Ile Ile Gly His His Ala Tyr Gly
 1               5

<210> SEQ ID NO 28
<211> LENGTH: 9
<212> TYPE: PRT
<213> ORGANISM: Homo sapiens

<400> SEQUENCE: 28

Ile Ile Gly His His Ala Tyr Gly Asp
 1               5

<210> SEQ ID NO 29
<211> LENGTH: 9
<212> TYPE: PRT
<213> ORGANISM: Homo sapiens

<400> SEQUENCE: 29

Pro Ile Ile Ile Gly His His Ala Tyr
 1               5

<210> SEQ ID NO 30
<211> LENGTH: 9
<212> TYPE: PRT
<213> ORGANISM: Homo sapiens
```

```
<400> SEQUENCE: 30

Trp Val Lys Pro Ile Ile Gly His
1               5

<210> SEQ ID NO 31
<211> LENGTH: 10
<212> TYPE: PRT
<213> ORGANISM: Homo sapiens

<400> SEQUENCE: 31

Ile Ile Ile Gly His His Ala Tyr Gly Asp
1               5                   10

<210> SEQ ID NO 32
<211> LENGTH: 10
<212> TYPE: PRT
<213> ORGANISM: Homo sapiens

<400> SEQUENCE: 32

Ile Ile Gly His His Ala Tyr Gly Asp Gln
1               5                   10

<210> SEQ ID NO 33
<211> LENGTH: 10
<212> TYPE: PRT
<213> ORGANISM: Homo sapiens

<400> SEQUENCE: 33

Val Lys Pro Ile Ile Ile Gly His His Ala
1               5                   10

<210> SEQ ID NO 34
<211> LENGTH: 10
<212> TYPE: PRT
<213> ORGANISM: Homo sapiens

<400> SEQUENCE: 34

His His Ala Tyr Gly Asp Gln Tyr Arg Ala
1               5                   10

<210> SEQ ID NO 35
<211> LENGTH: 9
<212> TYPE: PRT
<213> ORGANISM: Homo sapiens

<400> SEQUENCE: 35

Pro Ile Ile Ile Gly His His Ala Tyr
1               5

<210> SEQ ID NO 36
<211> LENGTH: 9
<212> TYPE: PRT
<213> ORGANISM: Homo sapiens

<400> SEQUENCE: 36

Trp Val Lys Pro Ile Ile Ile Gly His
1               5

<210> SEQ ID NO 37
<211> LENGTH: 9
<212> TYPE: PRT
<213> ORGANISM: Homo sapiens

<400> SEQUENCE: 37

Ile Ile Ile Gly His His Ala Tyr Gly
```

```
<210> SEQ ID NO 38
<211> LENGTH: 9
<212> TYPE: PRT
<213> ORGANISM: Homo sapiens

<400> SEQUENCE: 38

Gly His His Ala Tyr Gly Asp Gln Tyr
1               5

<210> SEQ ID NO 39
<211> LENGTH: 9
<212> TYPE: PRT
<213> ORGANISM: Homo sapiens

<400> SEQUENCE: 39

Ile Ile Gly His His Ala Tyr Gly Asp
1               5

<210> SEQ ID NO 40
<211> LENGTH: 9
<212> TYPE: PRT
<213> ORGANISM: Homo sapiens

<400> SEQUENCE: 40

Lys Pro Ile Ile Ile Gly His His Ala
1               5

<210> SEQ ID NO 41
<211> LENGTH: 10
<212> TYPE: PRT
<213> ORGANISM: Homo sapiens

<400> SEQUENCE: 41

Trp Val Lys Pro Ile Ile Ile Gly His His
1               5                   10

<210> SEQ ID NO 42
<211> LENGTH: 10
<212> TYPE: PRT
<213> ORGANISM: Homo sapiens

<400> SEQUENCE: 42

Ile Ile Ile Gly His His Ala Tyr Gly Asp
1               5                   10

<210> SEQ ID NO 43
<211> LENGTH: 10
<212> TYPE: PRT
<213> ORGANISM: Homo sapiens

<400> SEQUENCE: 43

Pro Ile Ile Ile Gly His His Ala Tyr Gly
1               5                   10

<210> SEQ ID NO 44
<211> LENGTH: 10
<212> TYPE: PRT
<213> ORGANISM: Homo sapiens

<400> SEQUENCE: 44

Lys Pro Ile Ile Ile Gly His His Ala Tyr
1               5                   10
```

```
<210> SEQ ID NO 45
<211> LENGTH: 10
<212> TYPE: PRT
<213> ORGANISM: Homo sapiens

<400> SEQUENCE: 45

Ile Gly His His Ala Tyr Gly Asp Gln Tyr
1               5                   10

<210> SEQ ID NO 46
<211> LENGTH: 10
<212> TYPE: PRT
<213> ORGANISM: Homo sapiens

<400> SEQUENCE: 46

Ile Ile Gly His His Ala Tyr Gly Asp Gln
1               5                   10

<210> SEQ ID NO 47
<211> LENGTH: 9
<212> TYPE: PRT
<213> ORGANISM: Homo sapiens

<400> SEQUENCE: 47

Trp Val Lys Pro Ile Ile Ile Gly His
1               5

<210> SEQ ID NO 48
<211> LENGTH: 10
<212> TYPE: PRT
<213> ORGANISM: Homo sapiens

<400> SEQUENCE: 48

Trp Val Lys Pro Ile Ile Ile Gly His His
1               5                   10

<210> SEQ ID NO 49
<211> LENGTH: 10
<212> TYPE: PRT
<213> ORGANISM: Homo sapiens

<400> SEQUENCE: 49

Gly His His Ala Tyr Gly Asp Gln Tyr Arg
1               5                   10

<210> SEQ ID NO 50
<211> LENGTH: 9
<212> TYPE: PRT
<213> ORGANISM: Homo sapiens

<400> SEQUENCE: 50

Pro Ile Ile Ile Gly His His Ala Tyr
1               5

<210> SEQ ID NO 51
<211> LENGTH: 9
<212> TYPE: PRT
<213> ORGANISM: Homo sapiens

<400> SEQUENCE: 51

Trp Val Lys Pro Ile Ile Ile Gly His
1               5

<210> SEQ ID NO 52
<211> LENGTH: 9
<212> TYPE: PRT
```

<213> ORGANISM: Homo sapiens

<400> SEQUENCE: 52

Gly His His Ala Tyr Gly Asp Gln Tyr
1               5

<210> SEQ ID NO 53
<211> LENGTH: 10
<212> TYPE: PRT
<213> ORGANISM: Homo sapiens

<400> SEQUENCE: 53

Trp Val Lys Pro Ile Ile Ile Gly His His
1               5                   10

<210> SEQ ID NO 54
<211> LENGTH: 10
<212> TYPE: PRT
<213> ORGANISM: Homo sapiens

<400> SEQUENCE: 54

Lys Pro Ile Ile Ile Gly His His Ala Tyr
1               5                   10

<210> SEQ ID NO 55
<211> LENGTH: 10
<212> TYPE: PRT
<213> ORGANISM: Homo sapiens

<400> SEQUENCE: 55

Ile Gly His His Ala Tyr Gly Asp Gln Tyr
1               5                   10

<210> SEQ ID NO 56
<211> LENGTH: 9
<212> TYPE: PRT
<213> ORGANISM: Homo sapiens

<400> SEQUENCE: 56

Trp Val Lys Pro Ile Ile Ile Gly His
1               5

<210> SEQ ID NO 57
<211> LENGTH: 9
<212> TYPE: PRT
<213> ORGANISM: Homo sapiens

<400> SEQUENCE: 57

Ile Ile Ile Gly His His Ala Tyr Gly
1               5

<210> SEQ ID NO 58
<211> LENGTH: 9
<212> TYPE: PRT
<213> ORGANISM: Homo sapiens

<400> SEQUENCE: 58

His His Ala Tyr Gly Asp Gln Tyr Arg
1               5

<210> SEQ ID NO 59
<211> LENGTH: 10
<212> TYPE: PRT
<213> ORGANISM: Homo sapiens

<400> SEQUENCE: 59

```
Pro Ile Ile Ile Gly His His Ala Tyr Gly
1               5                   10
```

<210> SEQ ID NO 60
<211> LENGTH: 9
<212> TYPE: PRT
<213> ORGANISM: Homo sapiens

<400> SEQUENCE: 60

```
Lys Pro Ile Ile Ile Gly His His Ala
1               5
```

<210> SEQ ID NO 61
<211> LENGTH: 10
<212> TYPE: PRT
<213> ORGANISM: Homo sapiens

<400> SEQUENCE: 61

```
Lys Pro Ile Ile Ile Gly His His Ala Tyr
1               5                   10
```

<210> SEQ ID NO 62
<211> LENGTH: 9
<212> TYPE: PRT
<213> ORGANISM: Homo sapiens

<400> SEQUENCE: 62

```
Trp Val Lys Pro Ile Ile Ile Gly His
1               5
```

<210> SEQ ID NO 63
<211> LENGTH: 9
<212> TYPE: PRT
<213> ORGANISM: Homo sapiens

<400> SEQUENCE: 63

```
Pro Ile Ile Ile Gly His His Ala Tyr
1               5
```

<210> SEQ ID NO 64
<211> LENGTH: 9
<212> TYPE: PRT
<213> ORGANISM: Homo sapiens

<400> SEQUENCE: 64

```
Trp Val Lys Pro Ile Ile Ile Gly His
1               5
```

<210> SEQ ID NO 65
<211> LENGTH: 9
<212> TYPE: PRT
<213> ORGANISM: Homo sapiens

<400> SEQUENCE: 65

```
Gly His His Ala Tyr Gly Asp Gln Tyr
1               5
```

<210> SEQ ID NO 66
<211> LENGTH: 10
<212> TYPE: PRT
<213> ORGANISM: Homo sapiens

<400> SEQUENCE: 66

```
Lys Pro Ile Ile Ile Gly His His Ala Tyr
1               5                   10
```

<210> SEQ ID NO 67
<211> LENGTH: 10
<212> TYPE: PRT
<213> ORGANISM: Homo sapiens

<400> SEQUENCE: 67

Ile Gly His His Ala Tyr Gly Asp Gln Tyr
1               5                   10

<210> SEQ ID NO 68
<211> LENGTH: 10
<212> TYPE: PRT
<213> ORGANISM: Homo sapiens

<400> SEQUENCE: 68

Trp Val Lys Pro Ile Ile Ile Gly His His
1               5                   10

<210> SEQ ID NO 69
<211> LENGTH: 9
<212> TYPE: PRT
<213> ORGANISM: Homo sapiens

<400> SEQUENCE: 69

His His Ala Tyr Gly Asp Gln Tyr Arg
1               5

<210> SEQ ID NO 70
<211> LENGTH: 9
<212> TYPE: PRT
<213> ORGANISM: Homo sapiens

<400> SEQUENCE: 70

Gly His His Ala Tyr Gly Asp Gln Tyr
1               5

<210> SEQ ID NO 71
<211> LENGTH: 9
<212> TYPE: PRT
<213> ORGANISM: Homo sapiens

<400> SEQUENCE: 71

Pro Ile Ile Ile Gly His His Ala Tyr
1               5

<210> SEQ ID NO 72
<211> LENGTH: 9
<212> TYPE: PRT
<213> ORGANISM: Homo sapiens

<400> SEQUENCE: 72

Gly His His Ala Tyr Gly Asp Gln Tyr
1               5

<210> SEQ ID NO 73
<211> LENGTH: 8
<212> TYPE: PRT
<213> ORGANISM: Homo sapiens

<400> SEQUENCE: 73

Ile Ile Ile Gly His His Ala Tyr
1               5

<210> SEQ ID NO 74

```
<211> LENGTH: 8
<212> TYPE: PRT
<213> ORGANISM: Homo sapiens

<400> SEQUENCE: 74

His His Ala Tyr Gly Asp Gln Tyr
1               5

<210> SEQ ID NO 75
<211> LENGTH: 9
<212> TYPE: PRT
<213> ORGANISM: Homo sapiens

<400> SEQUENCE: 75

Trp Val Lys Pro Ile Ile Ile Gly His
1               5

<210> SEQ ID NO 76
<211> LENGTH: 9
<212> TYPE: PRT
<213> ORGANISM: Homo sapiens

<400> SEQUENCE: 76

His His Ala Tyr Gly Asp Gln Tyr Arg
1               5

<210> SEQ ID NO 77
<211> LENGTH: 9
<212> TYPE: PRT
<213> ORGANISM: Homo sapiens

<400> SEQUENCE: 77

Val Lys Pro Ile Ile Ile Gly His His
1               5

<210> SEQ ID NO 78
<211> LENGTH: 9
<212> TYPE: PRT
<213> ORGANISM: Homo sapiens

<400> SEQUENCE: 78

Pro Ile Ile Ile Gly His His Ala Tyr
1               5

<210> SEQ ID NO 79
<211> LENGTH: 9
<212> TYPE: PRT
<213> ORGANISM: Homo sapiens

<400> SEQUENCE: 79

Gly His His Ala Tyr Gly Asp Gln Tyr
1               5

<210> SEQ ID NO 80
<211> LENGTH: 8
<212> TYPE: PRT
<213> ORGANISM: Homo sapiens

<400> SEQUENCE: 80

Val Lys Pro Ile Ile Ile Gly His
1               5

<210> SEQ ID NO 81
<211> LENGTH: 9
<212> TYPE: PRT
<213> ORGANISM: Homo sapiens
```

<400> SEQUENCE: 81

His His Ala Tyr Gly Asp Gln Tyr Arg
1               5

<210> SEQ ID NO 82
<211> LENGTH: 9
<212> TYPE: PRT
<213> ORGANISM: Homo sapiens

<400> SEQUENCE: 82

Gly His His Ala Tyr Gly Asp Gln Tyr
1               5

<210> SEQ ID NO 83
<211> LENGTH: 9
<212> TYPE: PRT
<213> ORGANISM: Homo sapiens

<400> SEQUENCE: 83

Val Lys Pro Ile Ile Ile Gly His His
1               5

<210> SEQ ID NO 84
<211> LENGTH: 9
<212> TYPE: PRT
<213> ORGANISM: Homo sapiens

<400> SEQUENCE: 84

Lys Pro Ile Ile Ile Gly His His Ala
1               5

<210> SEQ ID NO 85
<211> LENGTH: 9
<212> TYPE: PRT
<213> ORGANISM: Homo sapiens

<400> SEQUENCE: 85

Pro Ile Ile Ile Gly His His Ala Tyr
1               5

<210> SEQ ID NO 86
<211> LENGTH: 9
<212> TYPE: PRT
<213> ORGANISM: Homo sapiens

<400> SEQUENCE: 86

Gly His His Ala Tyr Gly Asp Gln Tyr
1               5

<210> SEQ ID NO 87
<211> LENGTH: 10
<212> TYPE: PRT
<213> ORGANISM: Homo sapiens

<400> SEQUENCE: 87

Lys Pro Ile Ile Ile Gly His His Ala Tyr
1               5                   10

<210> SEQ ID NO 88
<211> LENGTH: 10
<212> TYPE: PRT
<213> ORGANISM: Homo sapiens

<400> SEQUENCE: 88

```
Ile Gly His His Ala Tyr Gly Asp Gln Tyr
1               5                   10

<210> SEQ ID NO 89
<211> LENGTH: 9
<212> TYPE: PRT
<213> ORGANISM: Homo sapiens

<400> SEQUENCE: 89

Lys Pro Ile Ile Ile Gly His His Ala
1               5

<210> SEQ ID NO 90
<211> LENGTH: 9
<212> TYPE: PRT
<213> ORGANISM: Homo sapiens

<400> SEQUENCE: 90

Lys Pro Ile Ile Ile Gly His His Ala
1               5

<210> SEQ ID NO 91
<211> LENGTH: 9
<212> TYPE: PRT
<213> ORGANISM: Homo sapiens

<400> SEQUENCE: 91

Lys Pro Ile Ile Ile Gly His His Ala
1               5

<210> SEQ ID NO 92
<211> LENGTH: 8
<212> TYPE: PRT
<213> ORGANISM: Homo sapiens

<400> SEQUENCE: 92

Lys Pro Ile Ile Ile Gly His His
1               5

<210> SEQ ID NO 93
<211> LENGTH: 15
<212> TYPE: PRT
<213> ORGANISM: Homo sapiens

<400> SEQUENCE: 93

Gly Trp Val Lys Pro Ile Ile Ile Gly His His Ala Tyr Gly Asp
1               5                   10                  15

<210> SEQ ID NO 94
<211> LENGTH: 15
<212> TYPE: PRT
<213> ORGANISM: Homo sapiens

<400> SEQUENCE: 94

Lys Pro Ile Ile Ile Gly His His Ala Tyr Gly Asp Gln Tyr Arg
1               5                   10                  15

<210> SEQ ID NO 95
<211> LENGTH: 15
<212> TYPE: PRT
<213> ORGANISM: Homo sapiens

<400> SEQUENCE: 95

His His Ala Tyr Gly Asp Gln Tyr Arg Ala Thr Asp Phe Val Val
1               5                   10                  15
```

-continued

```
<210> SEQ ID NO 96
<211> LENGTH: 15
<212> TYPE: PRT
<213> ORGANISM: Homo sapiens

<400> SEQUENCE: 96

Ser Gly Trp Val Lys Pro Ile Ile Gly His His Ala Tyr Gly
1               5                   10                  15

<210> SEQ ID NO 97
<211> LENGTH: 15
<212> TYPE: PRT
<213> ORGANISM: Homo sapiens

<400> SEQUENCE: 97

Val Lys Pro Ile Ile Ile Gly His His Ala Tyr Gly Asp Gln Tyr
1               5                   10                  15

<210> SEQ ID NO 98
<211> LENGTH: 15
<212> TYPE: PRT
<213> ORGANISM: Homo sapiens

<400> SEQUENCE: 98

Trp Val Lys Pro Ile Ile Ile Gly His His Ala Tyr Gly Asp Gln
1               5                   10                  15

<210> SEQ ID NO 99
<211> LENGTH: 15
<212> TYPE: PRT
<213> ORGANISM: Homo sapiens

<400> SEQUENCE: 99

Ser Gly Trp Val Lys Pro Ile Ile Gly His His Ala Tyr Gly
1               5                   10                  15

<210> SEQ ID NO 100
<211> LENGTH: 15
<212> TYPE: PRT
<213> ORGANISM: Homo sapiens

<400> SEQUENCE: 100

Val Lys Pro Ile Ile Ile Gly His His Ala Tyr Gly Asp Gln Tyr
1               5                   10                  15

<210> SEQ ID NO 101
<211> LENGTH: 15
<212> TYPE: PRT
<213> ORGANISM: Homo sapiens

<400> SEQUENCE: 101

Trp Val Lys Pro Ile Ile Ile Gly His His Ala Tyr Gly Asp Gln
1               5                   10                  15

<210> SEQ ID NO 102
<211> LENGTH: 15
<212> TYPE: PRT
<213> ORGANISM: Homo sapiens

<400> SEQUENCE: 102

Lys Pro Ile Ile Ile Gly His His Ala Tyr Gly Asp Gln Tyr Arg
1               5                   10                  15

<210> SEQ ID NO 103
<211> LENGTH: 15
```

```
<212> TYPE: PRT
<213> ORGANISM: Homo sapiens

<400> SEQUENCE: 103

Gly His His Ala Tyr Gly Asp Gln Tyr Arg Ala Thr Asp Phe Val
1               5                   10                  15

<210> SEQ ID NO 104
<211> LENGTH: 15
<212> TYPE: PRT
<213> ORGANISM: Homo sapiens

<400> SEQUENCE: 104

Pro Ile Ile Ile Gly His His Ala Tyr Gly Asp Gln Tyr Arg Ala
1               5                   10                  15

<210> SEQ ID NO 105
<211> LENGTH: 15
<212> TYPE: PRT
<213> ORGANISM: Homo sapiens

<400> SEQUENCE: 105

His His Ala Tyr Gly Asp Gln Tyr Arg Ala Thr Asp Phe Val Val
1               5                   10                  15

<210> SEQ ID NO 106
<211> LENGTH: 15
<212> TYPE: PRT
<213> ORGANISM: Homo sapiens

<400> SEQUENCE: 106

Ser Gly Trp Val Lys Pro Ile Ile Ile Gly His His Ala Tyr Gly
1               5                   10                  15

<210> SEQ ID NO 107
<211> LENGTH: 15
<212> TYPE: PRT
<213> ORGANISM: Homo sapiens

<400> SEQUENCE: 107

Val Lys Pro Ile Ile Ile Gly His His Ala Tyr Gly Asp Gln Tyr
1               5                   10                  15

<210> SEQ ID NO 108
<211> LENGTH: 15
<212> TYPE: PRT
<213> ORGANISM: Homo sapiens

<400> SEQUENCE: 108

Pro Ile Ile Ile Gly His His Ala Tyr Gly Asp Gln Tyr Arg Ala
1               5                   10                  15

<210> SEQ ID NO 109
<211> LENGTH: 15
<212> TYPE: PRT
<213> ORGANISM: Homo sapiens

<400> SEQUENCE: 109

Gly Trp Val Lys Pro Ile Ile Ile Gly His His Ala Tyr Gly Asp
1               5                   10                  15

<210> SEQ ID NO 110
<211> LENGTH: 15
<212> TYPE: PRT
<213> ORGANISM: Homo sapiens
```

```
<400> SEQUENCE: 110

Trp Val Lys Pro Ile Ile Ile Gly His His Ala Tyr Gly Asp Gln
1               5                   10                  15

<210> SEQ ID NO 111
<211> LENGTH: 15
<212> TYPE: PRT
<213> ORGANISM: Homo sapiens

<400> SEQUENCE: 111

Ile Gly His His Ala Tyr Gly Asp Gln Tyr Arg Ala Thr Asp Phe
1               5                   10                  15

<210> SEQ ID NO 112
<211> LENGTH: 15
<212> TYPE: PRT
<213> ORGANISM: Homo sapiens

<400> SEQUENCE: 112

Gly His His Ala Tyr Gly Asp Gln Tyr Arg Ala Thr Asp Phe Val
1               5                   10                  15

<210> SEQ ID NO 113
<211> LENGTH: 15
<212> TYPE: PRT
<213> ORGANISM: Homo sapiens

<400> SEQUENCE: 113

Ser Gly Trp Val Lys Pro Ile Ile Ile Gly His His Ala Tyr Gly
1               5                   10                  15

<210> SEQ ID NO 114
<211> LENGTH: 15
<212> TYPE: PRT
<213> ORGANISM: Homo sapiens

<400> SEQUENCE: 114

Trp Val Lys Pro Ile Ile Ile Gly His His Ala Tyr Gly Asp Gln
1               5                   10                  15

<210> SEQ ID NO 115
<211> LENGTH: 15
<212> TYPE: PRT
<213> ORGANISM: Homo sapiens

<400> SEQUENCE: 115

Ile Ile Ile Gly His His Ala Tyr Gly Asp Gln Tyr Arg Ala Thr
1               5                   10                  15

<210> SEQ ID NO 116
<211> LENGTH: 15
<212> TYPE: PRT
<213> ORGANISM: Homo sapiens

<400> SEQUENCE: 116

Gly Trp Val Lys Pro Ile Ile Ile Gly His His Ala Tyr Gly Asp
1               5                   10                  15

<210> SEQ ID NO 117
<211> LENGTH: 15
<212> TYPE: PRT
<213> ORGANISM: Homo sapiens

<400> SEQUENCE: 117

His His Ala Tyr Gly Asp Gln Tyr Arg Ala Thr Asp Phe Val Val
```

```
                   1               5                  10                 15

<210> SEQ ID NO 118
<211> LENGTH: 15
<212> TYPE: PRT
<213> ORGANISM: Homo sapiens

<400> SEQUENCE: 118

Val Lys Pro Ile Ile Ile Gly His His Ala Tyr Gly Asp Gln Tyr
 1               5                  10                 15

<210> SEQ ID NO 119
<211> LENGTH: 15
<212> TYPE: PRT
<213> ORGANISM: Homo sapiens

<400> SEQUENCE: 119

His His Ala Tyr Gly Asp Gln Tyr Arg Ala Thr Asp Phe Val Val
 1               5                  10                 15

<210> SEQ ID NO 120
<211> LENGTH: 15
<212> TYPE: PRT
<213> ORGANISM: Homo sapiens

<400> SEQUENCE: 120

Trp Val Lys Pro Ile Ile Ile Gly His His Ala Tyr Gly Asp Gln
 1               5                  10                 15

<210> SEQ ID NO 121
<211> LENGTH: 15
<212> TYPE: PRT
<213> ORGANISM: Homo sapiens

<400> SEQUENCE: 121

Ser Gly Trp Val Lys Pro Ile Ile Ile Gly His His Ala Tyr Gly
 1               5                  10                 15

<210> SEQ ID NO 122
<211> LENGTH: 15
<212> TYPE: PRT
<213> ORGANISM: Homo sapiens

<400> SEQUENCE: 122

Gly Trp Val Lys Pro Ile Ile Ile Gly His His Ala Tyr Gly Asp
 1               5                  10                 15

<210> SEQ ID NO 123
<211> LENGTH: 15
<212> TYPE: PRT
<213> ORGANISM: Homo sapiens

<400> SEQUENCE: 123

Ser Gly Trp Val Lys Pro Ile Ile Ile Gly His His Ala Tyr Gly
 1               5                  10                 15

<210> SEQ ID NO 124
<211> LENGTH: 15
<212> TYPE: PRT
<213> ORGANISM: Homo sapiens

<400> SEQUENCE: 124

Val Lys Pro Ile Ile Ile Gly His His Ala Tyr Gly Asp Gln Tyr
 1               5                  10                 15
```

```
<210> SEQ ID NO 125
<211> LENGTH: 15
<212> TYPE: PRT
<213> ORGANISM: Homo sapiens

<400> SEQUENCE: 125

Lys Pro Ile Ile Ile Gly His His Ala Tyr Gly Asp Gln Tyr Arg
 1               5                  10                  15

<210> SEQ ID NO 126
<211> LENGTH: 15
<212> TYPE: PRT
<213> ORGANISM: Homo sapiens

<400> SEQUENCE: 126

Pro Ile Ile Ile Gly His His Ala Tyr Gly Asp Gln Tyr Arg Ala
 1               5                  10                  15

<210> SEQ ID NO 127
<211> LENGTH: 15
<212> TYPE: PRT
<213> ORGANISM: Homo sapiens

<400> SEQUENCE: 127

Ile Ile Gly His His Ala Tyr Gly Asp Gln Tyr Arg Ala Thr Asp
 1               5                  10                  15

<210> SEQ ID NO 128
<211> LENGTH: 9
<212> TYPE: PRT
<213> ORGANISM: Homo sapiens

<400> SEQUENCE: 128

Gly His His Ala Tyr Gly Asp Gln Tyr
 1               5

<210> SEQ ID NO 129
<211> LENGTH: 9
<212> TYPE: PRT
<213> ORGANISM: Homo sapiens

<400> SEQUENCE: 129

Pro Ile Ile Ile Gly His His Ala Tyr
 1               5

<210> SEQ ID NO 130
<211> LENGTH: 414
<212> TYPE: PRT
<213> ORGANISM: Homo sapiens

<400> SEQUENCE: 130

Met Ser Lys Lys Ile Ser Gly Gly Ser Val Val Glu Met Gln Gly Asp
 1               5                  10                  15

Glu Met Thr Arg Ile Ile Trp Glu Leu Ile Lys Glu Lys Leu Ile Phe
                20                  25                  30

Pro Tyr Val Glu Leu Asp Leu His Ser Tyr Asp Leu Gly Ile Glu Asn
            35                  40                  45

Arg Asp Ala Thr Asn Asp Gln Val Thr Lys Asp Ala Ala Glu Ala Ile
        50                  55                  60

Lys Lys His Asn Val Gly Val Lys Cys Ala Thr Ile Thr Pro Asp Glu
 65                  70                  75                  80

Lys Arg Val Glu Glu Phe Lys Leu Lys Gln Met Trp Lys Ser Pro Asn
                85                  90                  95
```

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 131
<211> LENGTH: 452
<212> TYPE: PRT
<213> ORGANISM: Homo sapiens

<400> SEQUENCE: 131

Met Ala Gly Tyr Leu Arg Val Val Arg Ser Leu Cys Arg Ala Ser Gly
1               5                   10                  15

Ser Arg Pro Ala Trp Ala Pro Ala Ala Leu Thr Ala Pro Thr Ser Gln
            20                  25                  30

Glu Gln Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
    50                  55                  60

```
Phe Ile Lys Glu Lys Leu Ile Leu Pro His Val Asp Ile Gln Leu Lys
 65                  70                  75                  80

Tyr Phe Asp Leu Gly Leu Pro Asn Arg Asp Gln Thr Asp Gln Val
                 85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
            115                 120                 125

Lys Lys Met Trp Lys Ser Pro Asn Gly Thr Ile Arg Asn Ile Leu Gly
            130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
            195                 200                 205

Val Tyr Asn Phe Pro Ala Gly Gly Val Gly Met Gly Met Tyr Asn Thr
210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
                245                 250                 255

Ala Tyr Asp Gly Arg Phe Lys Asp Ile Phe Gln Glu Ile Phe Asp Lys
                260                 265                 270

His Tyr Lys Thr Asp Phe Asp Lys Asn Lys Ile Trp Tyr Glu His Arg
            275                 280                 285

Leu Ile Asp Asp Met Val Ala Gln Val Leu Lys Ser Ser Gly Gly Phe
            290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335

Pro Asp Gly Lys Thr Ile Glu Ala Glu Ala Ala His Gly Thr Val Thr
                340                 345                 350

Arg His Tyr Arg Glu His Gln Lys Gly Arg Pro Thr Ser Thr Asn Pro
            355                 360                 365

Ile Ala Ser Ile Phe Ala Trp Thr Arg Gly Leu Glu His Arg Gly Lys
            370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                405                 410                 415

Gly Cys Ile His Gly Leu Ser Asn Val Lys Leu Asn Glu His Phe Leu
            420                 425                 430

Asn Thr Thr Asp Phe Leu Asp Thr Ile Lys Ser Asn Leu Asp Arg Ala
            435                 440                 445

Leu Gly Arg Gln
    450

<210> SEQ ID NO 132
<211> LENGTH: 45
<212> TYPE: DNA
<213> ORGANISM: Homo sapiens
```

```
<400> SEQUENCE: 132
aaacctatca tcataggtcg tcatgcttat ggggatcaat acaga                    45

<210> SEQ ID NO 133
<211> LENGTH: 45
<212> TYPE: DNA
<213> ORGANISM: Homo sapiens

<400> SEQUENCE: 133
aagcccatca ccattggcag gcacgcccat ggcgaccagt acaag                    45

<210> SEQ ID NO 134
<211> LENGTH: 2339
<212> TYPE: DNA
<213> ORGANISM: Homo sapiens

<400> SEQUENCE: 134
cctgtggtcc cgggtttctg cagagtctac ttcagaagcg gaggcactgg gagtccggtt    60
tgggattgcc aggctgtggt tgtgagtctg agcttgtgag cggctgtggc gccccaactc   120
ttcgccagca tatcatcccg gcaggcgata aactacattc agttgagtct gcaagactgg   180
gaggaactgg ggtgataaga aatctattca ctgtcaaggt ttattgaagt caaaatgtcc   240
aaaaaaatca gtggcggttc tgtggtagag atgcaaggga tgaaatgac acgaatcatt   300 tgggaattga ttaaagagaa actcattttt ccctacgtgg aattggatct acatagctat   360
gatttaggca tagagaatcg tgatgccacc aacgaccaag tcaccaagga tgctgcagaa   420
gctataaaga agcataatgt tggcgtcaaa tgtgccacta tcactcctga tgagaagagg   480
gttgaggagt tcaagttgaa acaaatgtgg aaatcaccaa atggcaccat acgaaatatt   540
ctgggtggca cggtcttcag agaagccatt atctgcaaaa atatcccccg gcttgtgagt   600
ggatgggtaa aacctatcat cataggtcgt catgcttatg gggatcaata cagagcaact   660
gattttgttg ttcctgggcc tggaaaagta gagataacct acacaccaag tgacggaacc   720
caaaaggtga catacctggt acataacttt gaagaaggtg gtggtgttgc catggggatg   780
tataatcaag ataagtcaat tgaagatttt gcacacagtt ccttccaaat ggctctgtct   840
aagggttggc ctttgtatct gagcaccaaa aacactattc tgaagaaata tgatgggcgt   900
tttaaagaca tctttcagga gatatatgac aagcagtaca agtcccagtt tgaagctcaa   960
aagatctggt atgagcatag gctcatcgac gacatggtgg cccaagctat gaaatcagag  1020
ggaggcttca tctgggcctg taaaaactat gatggtgacg tgcagtcgga ctctgtggcc  1080
caagggtatg gctctctcgg catgatgacc agcgtgctgg tttgtccaga tggcaagaca  1140
gtagaagcag aggctgccca cgggactgta acccgtcact accgcatgta ccagaaagga  1200
caggagacgt ccaccaatcc cattgcttcc atttttgcct ggaccagagg gttagcccac  1260
agagcaaagc ttgataacaa taagagcttg ccttctttg caaatgcttt ggaagaagtc  1320
tctattgaga caattgaggc tggcttcatg accaaggact tggctgcttg cattaaaggt  1380
ttacccaatg tgcaacgttc tgactacttg aatacatttg agttcatgga taaacttgga  1440
gaaaacttga agatcaaact agctcaggcc aaactttaag ttcatacctg agctaagaag  1500
gataattgtc ttttggtaac taggtctaca ggtttacatt tttctgtgtt acactcaagg  1560
ataaaggcaa aatcaatttt gtaatttgtt tagaagccag agtttatctt tctataagt   1620 ttacagcctt tttcttatat atacagttat tgccaccttt gtgaacatgg caagggactt  1680
ttttacaatt tttattttat tttctagtac cagcctagga attcggttag tactcatttg  1740
```

| | |
|---|---|
| tattcactgt cacttttct catgttctaa ttataaatga ccaaaatcaa gattgctcaa | 1800 |
| aagggtaaat gatagccaca gtattgctcc ctaaaatatg cataaagtag aaattcactg | 1860 |
| ccttcccctc ctgtccatga ccttgggcac agggaagttc tggtgtcata gatatcccgt | 1920 |
| tttgtgaggt agagctgtgc attaaacttg cacatgactg aacgaagta tgagtgcaac | 1980 |
| tcaaatgtgt tgaagatact gcagtcattt ttgtaaagac cttgctgaat gtttccaata | 2040 |
| gactaaatac tgtttaggcc gcaggagagt ttggaatccg gaataaatac tacctggagg | 2100 |
| tttgtcctct ccattttct ctttctcctc ctggcctggc ctgaatatta tactactcta | 2160 |
| aatagcatat ttcatccaag tgcaataatg taagctgaat cttttttgga cttctgctgg | 2220 |
| cctgttttat ttcttttata taatgtgat ttctcagaaa ttgatattaa acactatctt | 2280 |
| atcttctcct gaactgttga ttttaattaa aattaagtgc taattaccaa aaaaaaaa | 2339 |

<210> SEQ ID NO 135
<211> LENGTH: 1740
<212> TYPE: DNA
<213> ORGANISM: Homo sapiens

<400> SEQUENCE: 135

| | |
|---|---|
| ccagcgttag cccgcggcca ggcagccggg aggagcggcg cgcgctcgga cctctcccgc | 60 |
| cctgctcgtt cgctctccag cttgggatgg ccggctacct gcgggtcgtg cgctcgctct | 120 |
| gcagagcctc aggctcgcgg ccggcctggg cgccggcggc cctgacagcc cccacctcgc | 180 |
| aagagcagcc gcgcgccac tatgccgaca aaaggatcaa ggtggcgaag cccgtggtgg | 240 |
| agatggatgg tgatgagatg acccgtatta tctggcagtt catcaaggag aagctcatcc | 300 |
| tgccccacgt ggacatccag ctaaagtatt ttgacctcgg gctcccaaac cgtgaccaga | 360 |
| ctgatgacca ggtcaccatt gactctgcac tggccaccca gaagtacagt gtggctgtca | 420 |
| agtgtgccac catcaccct gatgaggcc gtgtggaaga gttcaagctg aagaagatgt | 480 |
| ggaaaagtcc caatggaact atccggaaca tcctgggggg gactgtcttc cgggagccca | 540 |
| tcatctgcaa aaacatccca cgcctagtcc ctggctggac caagcccatc accattggca | 600 |
| ggcacgccca tggcgaccag tacaaggcca cagactttgt ggcagaccgg gccggcactt | 660 |
| tcaaaatggt cttcacccca aaagatggca gtggtgtcaa ggagtgggaa gtgtacaact | 720 |
| tccccgcagg cggcgtgggc atgggcatgt acaacaccga cgagtccatc tcaggtttg | 780 |
| cgcacagctg cttccagtat gccatccaga agaaatggcc gctgtacatg agcaccaaga | 840 |
| acaccatact gaaagcctac gatgggcgtt tcaaggacat cttccaggag atctttgaca | 900 |
| agcactataa gaccgacttc gacaagaata agatctggta tgagcaccgg ctcattgatg | 960 |
| acatggtggc tcaggtcctc aagtcttcgg gtggctttgt gtgggcctgc aagaactatg | 1020 |
| acggagatgt gcagtcagac atcctggccc agggctttgg ctcccttggc ctgatgacgt | 1080 |
| ccgtcctggt ctgccctgat gggaagacga ttgaggctga ggccgctcat gggaccgtca | 1140 |
| cccgccacta cgggagcac agaaagggcc ggcccaccag caccaaccc atcgccagca | 1200 |
| tctttgcctg gacacgtggc ctggagcacc ggggaagct ggatgggaac caagacctca | 1260 |
| tcaggtttgc ccagatgctg gagaaggtgt gcgtggagac ggtggagagt ggagccatga | 1320 |
| ccaaggacct ggcgggctgc attcacggcc tcagcaatgt gaagctgaac gagcacttcc | 1380 |
| tgaacaccac ggacttcctc gacaccatca gagcaacct ggacagagcc ctgggcaggc | 1440 |
| agtagggggga ggcgccaccc atggctgcag tggaggggcc agggctgagc cggcgggtcc | 1500 |
| tcctgagcgc ggcagagggt gagcctcaca gcccctctct ggaggccttt ctaggggatg | 1560 |

```
tttttttata agccagatgt ttttaaaagc atatgtgtgt ttcccctcat ggtgacgtga    1620
ggcaggagca gtgcgtttta cctcagccag tcagtatgtt ttgcatactg taatttatat    1680
tgcccttgga acacatggtg ccatatttag ctactaaaaa gctcttcaca aaaaaaaaaa    1740

<210> SEQ ID NO 136
<211> LENGTH: 17
<212> TYPE: DNA
<213> ORGANISM: M13 virus

<400> SEQUENCE: 136
gtaaaacgac ggccagt                                                       17
```